US011993590B2

(12) United States Patent
Moghadam

(10) Patent No.: US 11,993,590 B2
(45) Date of Patent: May 28, 2024

(54) PYRANONE COMPOUNDS USEFUL TO MODULATE OMA1 PROTEASE

(71) Applicant: 712 North Inc., Oakland, CA (US)

(72) Inventor: Marcel Victor Alavi Khorassani Moghadam, Berkeley, CA (US)

(73) Assignee: 712 North Inc., Oakland, CA (US)

( * ) Notice: Subject to any disclaimer, the term of this patent is extended or adjusted under 35 U.S.C. 154(b) by 147 days.

(21) Appl. No.: 17/156,237

(22) Filed: Jan. 22, 2021

(65) Prior Publication Data

US 2021/0246125 A1 Aug. 12, 2021

Related U.S. Application Data

(63) Continuation-in-part of application No. 16/022,481, filed on Jun. 28, 2018, now Pat. No. 10,906,931, which is a continuation of application No. PCT/US2017/064195, filed on Dec. 1, 2017.

(60) Provisional application No. 63/041,292, filed on Jun. 19, 2020, provisional application No. 62/581,723, filed on Nov. 5, 2017, provisional application No. 62/481,392, filed on Apr. 4, 2017, provisional application No. 62/429,846, filed on Dec. 4, 2016.

(51) Int. Cl.

| | |
|---|---|
| ***C07D 405/12*** | (2006.01) |
| ***A61K 9/00*** | (2006.01) |
| ***A61P 25/28*** | (2006.01) |
| ***A61P 35/00*** | (2006.01) |

(52) U.S. Cl.

CPC .......... *C07D 405/12* (2013.01); *A61K 9/0043* (2013.01); *A61K 9/0073* (2013.01); *A61P 25/28* (2018.01); *A61P 35/00* (2018.01)

(58) Field of Classification Search

CPC ........ C07D 405/12; A61P 25/28; A61P 35/00; A61K 9/0043; A61K 9/0073

See application file for complete search history.

(56) References Cited

U.S. PATENT DOCUMENTS

| | | | | |
|---|---|---|---|---|
| 6,169,181 | B1 * | 1/2001 | Romines | C07D 311/74 544/298 |
| 10,906,931 | B2 | 2/2021 | Moghadam | |
| 2004/0101874 | A1 | 5/2004 | Ghosh | |
| 2005/0142094 | A1 | 6/2005 | Kumar | |
| 2009/0209615 | A1 | 8/2009 | Lipton | |
| 2010/0209436 | A1 | 8/2010 | Reichert | |
| 2012/0157386 | A1 | 6/2012 | Smith | |
| 2013/0052184 | A1 | 2/2013 | Chang | |
| 2017/0101679 | A1 | 4/2017 | Davezac | |
| 2018/0371007 | A1 | 12/2018 | Moghadam et al. | |

FOREIGN PATENT DOCUMENTS

| | | | |
|---|---|---|---|
| KR | 20180047397 | A | 5/2018 |
| WO | 0030656 | A1 | 6/2000 |
| WO | 2000030656 | A1 | 6/2000 |
| WO | 2005103716 | A2 | 11/2005 |
| WO | 2011053825 | A2 | 5/2011 |
| WO | 2018132662 | A1 | 7/2018 |

OTHER PUBLICATIONS

PubChem CID 54711517, created on Dec. 26, 2011, https://pubchem.ncbi.nlm.nih.gov/compound/54711517 (Year: 2011).*

Guo Y. et al., Association of OPA1 polymorphisms with NTG and HTG: a meta-analysis, PLoS one, (2012), 7:e4287, 12 pages.

Hackenbrock et al., Ultrastructural bases for metabolically linked mechanical activity in mitochondria, The Journal of Cell Biology, (1966), 30:269-297.

Hanahan et al., Hallmarks of cancer: the next generation, Cell, (2011), 144:646-674.

Head et al., Inducible proteolytic inactivation of OPA1 mediated by the OMA1 protease in mammalian cells, The Journal of Cell Biology, (2009), 187: 959-966.

Herlan, Alternative topogenesis of Mgm1 and mitochondrial morphology depend on ATP and a functional import motor, The Journal of Cell Biology, (2004), 165:167-173.

Hessenberger et al., Regulated membrane remodeling by Mic60 controls formation of mitochondrial crista junctions, Nature Communications, (2017), 8: 11 pages.

Hokama et al., Altered expression of diabetes-related genes in Alzheimer's disease brains: the Hisayama study, Cerebral Cortex, (2014), 24: 2476-2488.

Imaizumi et al., Mitochondrial dysfunction associated with increased oxidative stress and α-synuclein accumulation in PARK2 iPSC-derived neurons and postmortem brain tissue, Molecular Brain, (2012), 5: 13 pages.

Ishihara et al., Regulation of mitochondrial morphology through proteolytic cleavage of OPA1, The EMBO Journal, (2006), 25:2966-2977.

Jakobs et al., Spatial and temporal dynamics of budding yeast mitochondria lacking the division component Fis1, Journal of Cell Science, (2003), 116:2005-2014.

Jiang et al., Activation of mitochondrial protease OMA1 by Bax and Bak promotes cytochrome c release during apoptosis, Proceedings of the National Academy of Sciences, (2014), 111:14782-14787.

Ju et al., Intraocular Pressure Elevation Induces Mitochondrial Fission and Triggers OPA1 Release in Glaucomatous Optic Nerve, Investigative Ophthalmology and Visual Science, (2008), 49: 4903-4911.

(Continued)

*Primary Examiner* — Yih-Horng Shiao

(74) *Attorney, Agent, or Firm* — Collard & Roe, P.C.

(57) ABSTRACT

Pyranone compounds are disclosed herein, which were quite surprisingly found as having OMA1 and/or OPA1 modulatory properties. Compounds of present invention may provide useful for the treatment of certain conditions and diseases, which are amenable to OMA1 and/or OPA1-modulatory therapies. Such conditions may include conditions and diseases prevalent in the elderly, such as cancer and Alzheimer's disease. Pharmaceutical compositions comprising compounds of present invention may be combined with other treatments or further comprise other pharmaceutically active ingredients.

20 Claims, 31 Drawing Sheets

Specification includes a Sequence Listing.

(56) References Cited

OTHER PUBLICATIONS

Kandimalla et al., Reduced dynamin-related protein 1 protects against phosphorylated Tau-induced mitochondrial dysfunction and synaptic damage in Alzheimer's disease, Human Molecular Genetics, (2016), 25:4881-4897.
Karbowski et al., Spatial and temporal association of Bax with mitochondrial fission sites, Drp1, and Mfn2 during apoptosis, The Journal of Cell Biology, (2002), 159:931-938.
Kaser et al., OMA1, a novel membrane-bound metallopeptidase in mitochondia with activities overlapping with the m-AAA protease, The Journal of Biological Chemistry, (2003), 278:46414-46423.
Keeney et al., Parkinson's Disease Brain Mitochondrial Complex | Has Oxidatively Damaged Subunits and Is Functionally Impaired and Misassembled, The Journal of Neuroscience , (2006), 26:5256-5264.
Kim et al., DRP1 inhibition rescues retinal ganglion cells and their axons by preserving mitochondrial integrity in a mouse model of glaucoma, Cell Death and Disease, (2015), 6:e1839, 15 pages.
Kong et al., p53 is required for cisplatin-induced processing of the mitochondrial fusion protein L-Opa1 that is mediated by the mitochondrial metallopeptidase Oma1 in gynecologic cancers, The Journal of Biological Chemistry, The American Society for Biochemisty and Melecular Biology, (2014), 289:27134-27145.
Koob et al., The non-glycosylated isoform of MIC26 is a constituent of the mammalian MICOS complex and promotes formation of crista junctions, Biochimica et Biophysica Acta, (2015), 1853:1551-1563.
Koppen et al., Variable and Tissue-Specific Subunit Composition of Mitochondrial m-AAA Protease Complexes Linked to Hereditary Spastic Paraplegia, Molecular ad Cellular Biology, (2007), 27:758-767.
Korwitz et al., Loss of OMA1 delays neurodegeneration by preventing stress-induced OPA1 processing in mitochondria, The Journal of Cell Biology, (2016), 212:157-166.
Landes et al., The BH3-only Bnip3 binds to the dynamin Opa1 to promote mitochondrial fragmentation and apoptosis by distinct mechanisms, EMBO Reports, (2010), 11:459-465.
Le Page et al., Increase in Cardiac Ischemia-Reperfusion Injuries in Opa1 +/− Mouse Model, PLoS One, (2016), 11: e0164066, p. 19.
Lee et al., Roles of the mammalian mitochondrial fission and fusion mediators Fis1, Drp1, and Opa 1 in apoptosis, Molecular Biology of the Cell, (2004), 15:5001-5011.
Leonhard et al., Membrane protein degradation by AAA proteases in mitochondria: extraction of substrates from either membrane surface, Molecular Cell, (2000), 5:629-638.
Lesnick et al., A Genomic Pathway Approach to a Complex Disease: Axon Guidance and Parkinson Disease, PLoS Genetics, (2007), 3:984-995.
Li et al., Increased plaque burden in brains of APP mutant MnSOD heterozygous knockout mice, Journal of Neurochemistry, (2004), 89:1308-1312.
Li et al., The importance of Dendric Mitochondria in the Morphogenesis and Plasticity of Spines and Synapses, Cell, (2004), 119:873-887.
Lustbader et al., ABAD directly links Abeta to mitochondrial toxicity in Alzheirmer's disease, Science, (2004), 304:448-452.
Lutz et al., Loss of parkin or PINK1 function increases Drp1-dependent mitochondrial fragmentation, The Journal of Biological Chemistry, (2009), 284:22938-22951.
Lyamzaev et al., Selective elimination of mitochondrial from living cells induced by inhibitors of bioenergetic functions, Biochemical Society Transactions, (2004), 23:1070-1071.
Manczak et al., Mitochondria are a direct site of Aβ accumulation in Alzheimer's disease neurons: implications for free radical generation and oxidative damage in disease progression, Human Molecular Genetics, (2006), 15:1437-1449.
Manczak et al., Impaired mitochondrial dynamics and abnormal interaction of amyloid beta with motochondrial protein Drp1 in neurons from patients with Alzheirmer's disease: implications neuronal damage, Human Molecular Genetics, (2011), 20:2495-2509.
Manczak et al., Protective effects of reduced dynamin-related protein 1 against amyloid beta-induced mitochondrial dysfunction and synaptic damage in Alzheimer's disease, Human Molecular Genetics, (2016), 25:5148-5166.
Manczak et al., Abnormal interaction between the mitochondrial fission protein Drp1 and Hyperphosphorylated tau in Alzheimer's disease neurons: implications for mitochondrial dysfunction and neuronal damage, Human Molecular Genetics, (2012), 21:2538-2547.
Maraganore et al., High-resolution whole-genome association study of Parkinson disease, American Journal of Human genetics, (2005), 77:685-693.
Maresca et al., The Optic nerve: a mito-window on mitochondrial neurodegeneration, Molecular and Cell Neurosciences, (2013), 55:62-76.
Medja et al., Thiorphan, a neutral endopeptidase inhibitor used for diarrhoea, is neuroprotective in newborn mice, Brain, (2006), 129:3209-3223.
Merkwirth et al., Prohibitins control cell proliferation and apoptosis by regulating OPA1-dependent cristae morphogenesis in mitochondria, Genes & Development, (2008), 22:476-488.
Merz et al., The Protein Folding Problem and Tertiary Structure Prediction, Birkhauser Boston, (1994), p. 433-506.
Miller et al., Genes and pathways underlying regional and cell type changes in Alzheirmer's disease, Genome Medicine, (2013), 5: 17 pages.
Mukherjee et al., Parkinson's disease proteins: Novel mitochondrial targets for cardioprotection, Pharmacology & Therapeutics, (2015), 156:34-43.
Nakamura et al., α-Synuclein and Mitochondria: Partners in Crime?, Neurotherapeutics, (2013), 10:391-399.
Nakamura et al., Direct membrane association drives mitochondrial fission by the Parkinson disease-associated protein alpha-synuclein, The Journal of Biological Chemistry, (2011), 286:20710-20726.
Niemann et al., Ganglioside-induced differentiation associated protein 1 is a regulator of the mitochondrial network: New implications for Charcot-Marie-Tooth disease, The Journal of Cell Biology, (2005), 170: 1067-1078.
Nunnari et al., Mitochondrial transmission during mating in *Saccharomyces cerevisiae* is determined by mitochondrial fusion and fission and the intramitochondrial segregation of mitochondrial DNA, Molecular Biology of the Cell, (1997), 8:1233-1242.
Olichon et al., Loss of OPA1 Perturbates the Mitochondrial Inner Membrane Structure and Integrity, Leading to Cytochrome c Release and Apoptosis, The Journal of Biological Chemistry, (2003), 278:7743-7746.
Olichon et al., OPA1 alternate splicing uncouples an evolutionary conserved function in mitochondrial fusion from a vertebrate restricted function in apoptosis, Cell Death and Differentiation, (2007), 14:682-692.
Ong et al., Mitochondrial-Shaping Proteins in Cardiac Health and Disease-the long and the Short of it, Cardiovascular Drugs Therapy, (2017), 31: 87-107.
Ott et al., Detailed Analysis of the Human Mitochondrial Contact Site Complex Indicate a Hierarchy of Subunits, PLoS One, (2015), 10:e0120213, 15 pages.
Parker et al., Complex I Deficiency in Parkinson's Disease Frontal cortex, Brain Res, (2008), 1189:215-218.
Piquereau et al., Down-regulation of OPA1 alters mouse mitochondrial morphology, PTP function, and cardiac adaptation to pressure overload, Cardiovascular Research, (2012), 94: 408-417.
Piquereau et al., Mitochondrial dynamics in the adult cardiomyocytes: which roles for a highly specialized cell?, Frontiers in Physiology, (2013), 4:12 pages.
Priault et al., Impairing the bioenergetic status and the biogenesis of mitochondria triggers mitophagy in yeast, Cell Death and Fifferentiation, (2005), 12:1613-1621.
Quiros et al., New roles for OMA1 metalloprotease, Adipocyte, (2013), 2:7-11.

(56) References Cited

OTHER PUBLICATIONS

Rainboldt et al., Reciprocal Degradation of YME1L and OMA1 Adapts Mitochondrial Proteolytic Activity during Stress, Cell Reports, (2016), 14: 2041-2049.
Rappold et al., Drp1 inhibition attenuates neurotoxicity and dopamine release defictis in vivo, Nature Communications, (2014), 5:13 pages.
Reddy et al., Gene expression profiles of transcripts in amyloid precursor protein transgenic mice: up-regulation of mitochondrial metabolish and apoptotic genes is an early cellular change in Alzheimer's disease, Human Molecular Genetic, (2004), 13:1225-1240.
Reddy et al., Mitochondria-Division Inhibitor 1 Protects Against Amyloid-β induced Mitochondrial Fragmentation and Synaptic Damage in Alzheimer's Disease, Journal of Alzheimers Disease, (2017), 58:147-162.
Richter et al., Quality control of mitochondrial protein synthesis is required for membrane integrity and cell fitness, Journal of Cell Biology, (2015), 211:373-389.
Sadun et al., Mitochondrial optic neuropathies, The Journal of Neurology, Neurosurgery & Psychiatry, (2002), 72:423-425.
Schmidt et al., Amyloid precursor protein and amyloid b-peptide bind to ATP synthase and regulate its activity at the surface of neural cells, Molecular Psychiatry, (2008), 13: 953-969.
Shields et al., Dynamin-related protein 1 is required for normal mitochondrial bioenergetic and synaptic function in CA1 hippocampal neurons, Cell Death and Disease, (2015), 6:e1725, 11 pages.
Song et al., OPA1 processing controls mitochondrial fusion and is regulated by mRNA splicing, membrane potential, and Yme1L, The Journal of Cell Biology, (2007), 178:749-755.
Stafa et al., Functional Interaction of Parkinson's disease-associated LRRK2 with members of the dynamin GTPase superfamily, Human Molecular Genetics, (2014), 23:2055-2077.
Takihara et al., In vivo imaging of axonal transport of mitochondria in the diseased and aged mammalian CNS, Proceedings of the National Academy of Sciences. (2015), 112: 10515-10520.
Tan et al., Sustained O-GlcNAcylation reprograms mitochondrial function to regulate energy metabolism, Journal of Biology & Chemistry, (2007), 292: 14940-14962.
Tatsuta et al., m-AAA protease-driven membrane dislocation allows intramembrane cleavage by rhomboid in mitochondria, The EMBO Journal, (2007), 26: 325-335.
Taube et al., Epigenetic silencing of microRNA-203 is required for EMT and cancer stem cell properties, Scientific Reports, (2013), 10 pages.
Thomas et al., Ribavirin potentiates interferon action by augmenting interferon-stimulated gene induction in hepatitis C virus cell culture models, Hepatology, (2011), 53:32-41.
Tuccinardi et al., Amber force field implementation, molecular modelling study, synthesis and MMP-1/MMP-2 inhibition profile of (R)- and (S)-N-hydroxy-2-(N-isopropoxybiphenyl-4-ylsulfonamido)-3-methylbutanamides, Bioorganic & Medicinal Chemistry, (2006), 14:4260-4276.
Verstreken et al., Synaptic Mitochondria Are Critical for Mobilization of Reserve Pool Vesicles at *Drosophila* Neuromuscular Junctions, Neuron, (2005), 47:365-378.
Voigt et al., The mitochondrial kinase PINK1: functions beyond mitophagy, Journal of Neurochemistry, (2016), 139: 232-239.
Vyas et al., Mitochondria and Cancer, Cell, (2016), 166:555-566.
Wai et al., The membrane scaffold SLP2 anchors a proteolytic hub in mitochondria containing PARL and the i-AAA protease YME1L, Science, (2016), 17:1844-1856.
Wallace et al., mitochondria and cancer, National Review Cancer, (2012), 12: 685-698.
Wang et al., Amyloid-beta overproducton causes abnormal mitochondrial dynamics via differential modulation of mitochondrial fission/fusion proteins, Proceedings of the National Academy of Sciences, (2008), 105: 19318-19323.
Wang et al., GSK-3 promotes conditional association of CREB and its coactivators with MEIS1 to facilitate HOX-mediated transcription and oncogenesis, Cancer Cell, (2010), 17:297-608.
Wang et al., Parkin Ubiquitinates Drp1 for Proteasome-dependent Degradation, The Journal of Biological Chemistry, (2011), 286:11649-11658.
Wang et al., Apg2 is a novel protein required for the cytoplasm to vacuole targeting, autophagy, and pexophagy pathways, The Journal of Biological Chemistry, (2001), 276:30442-30451.
Warburg et al., On the Origin of Cancer Cells, Science, (1956), 123: 309-314.
Xiao et al., OMA1 mediates OPA1 proteolysis and mitochondrial fragmentation in experimental models of ischemic kidney injury, American Journal of Physiology, Renal Physiology, (2014), 306:1318-1326.
Yang et al., Pink1 regulates mitochondrial dynamics through interaction with the fission/fusion machinery, Proceedings of the National Academy of Sciences, (2008), 105:7070-7075.
Yao et al., Mitochondrial bioenergetic deficit precedes Alzheimer's pathology in female mouse model of Alzheimer's disease, Proceedings of the national Academy of Sciences, (2009), 106:14670-14675.
Zhang et al., BNIP3 Protein Suppresses PINK1 Kinase Proteolytic Cleavage to Promote Mitophagy, The Journal of Biological Chemistry, (2016), 291:21616-21629.
Zhao et al., OPA1 downregulation is involved in sorafenib-induced apoptosis in hepatocellular carcinoma, Lab Invest, (2013), 93: 19 pages.
Zuchner et al., Mutations in the mitochondrial GTPase mitofusin 2 cause Charcot-Marie-Tooth neuropathy type 2A, Nature Genetics, (2004), 36:449-451.
International Search Report and Written Opinion for Application No. PCT/EP2008/005400, dated Jan. 19, 2009.
Zhang et al., Trasncriptional analysis of multiple brain regions in Parkinson's disease supports the involvement of specific protein processing, energy metabolism, and signaling pathways, and suggests novel disease mechanisms, American Journal of Medical Genetics Part B (Neuropsychriatric Genetics), (2005), 137B: 5-16.
Akhtar, et al, Elevated glucose and oligomeric β-amyloid disrupt synapses via a common pathway of aberrant protein S-nitrosylation, Nature Communications, 7:1-11, (2016).
Alavi et al., A splice site mutation in the purine Opa1 gene features pathology of autosomal dominant optic athrophy, (2007), 130:1029-1042.
Alavi et al., Dominant optic atrophy, OPA1, and mitochondrial quality control: understanding mitochondrial networks dynamics, Molecular Neuroegeneration, (2013), 8: 1-12.
Alexander et al., OPA1, encoding a dynamin-related GTPase, is mutated in autosomal dominant optic atrophy linked to chromosome 3q28, Nature Genetics, (2000), 26: 211-215.
Alirol et al., Mitochondria and cancer: is there a morphological connection?, Oncogene, (2006), 25: 4706-4716.
Ameri et al., Nuclear localization of the mitochondrial factor HIGD1A during metabolic stress, PLoS One, (2013), 8: e62758, 11 pages.
Ameri et al., HIGD1A-Mediated dormancy and tumor survival, Molecular & Cellular Oncology, (2015), 2:3 pages.
Ameri et al., HIGD1A regulates oxygen consumption, ROS production and AMPK activity during glucose deprivation to modulate cell survival and tumor growth, Cell Reports, (2016), 20 pages.
An et al., The survival effect of mitochondrial Higd-1a is associated with suppression of cytochrome C release and prevention of caspase activation, Biochimica et Biophysica Acta, Molecular Cell Reaserch, (2011). 1813: 2088-2098.
Arnoult et al., Release of OPA1 during Apoptosis Participates in the Rapid and Complete Release of Cytochrome c and Subsequent Mitochondrial Fragmentation, The Journal of Biological Chemistry, (2005), 280: 3574-35750.
Atorino et al., Loss of m-AAA protease in mitochondria causes complex I deficiencies and increased sensitivity to oxidative stress in hereditary spastic paraplegia, The Journal of Cell Biology, (2003), 163: 777-787.

(56) References Cited

OTHER PUBLICATIONS

Baek et al., Inhibition of Drp1 Ameliorates Synaptic Drepression, Aβ Deosition, and Cognitive Impairment in an Alzheirmer's Disease Model, Journal of Neuroscience, (2017), 37: 5099-5110.
Barrera et al., OPA1 functionally interacts with MIC60 but is dispensable for crista junction formation, FEBS Letter, (2016), 19: 3309-3322.
Bohovych et al., Oma1 Links Mitochondrial Protein Quality Control and TOR Signaling to Modulate Physiological Plasticity and Cellular Stress Responses, Molecular and Cellular Biology, (2016), 36: 2300-2312.
Bond et al., A little sugar goes a long way: The cell biology of O-GlcNAc, The Journal of Cell Biology, (2015), 208: 869-880.
Bose et al., Mitochondrial dysfunction in Parkinson's disease, Journal of Neurochemistry, (2016). 139: 216-231.
Burke et al., OPA1 in Cardiovascular Health and Disease, Current Drug Targets, (2015), 16: 912-920.
Cardoso et al., Mitochondrial dysfunction of Alzheirmer's disease cybrids enhances Abeta toxicity, Journal of Neurochemistry, (2004), 89:1417-1426.
Carelly et al., Optic nerve degeneration and mitochondrial dysfunction: genetic and acquired optic neuropathies, Neurochemistry International, (2002), 40: 573-584.
Carvalho et al., Global mass spectrometry and transcriptomics array based drug profiling provides novel insight into glucosamine induced endoplasmic reticulum stress, Molecular & Cellular Proteomics, (2014), 13:3294-3307.
Casari et al., Spastic paraplegia and OXPHOS impairment caused by mutations in paraplegin, a nuclear-encoded mitochondrial metalloprotese, Cell, (1998), 93: 973-983.
Chen et al., Mitochondrial OPA1, apoptosis, and heart failure, Cardiovascular Research, (2009), 84:91-99.
Chen et al., OPA1 mutation and late-onset cardiomyopathy: mitochondrial dysfunction and mtDNA instability, Journal of the American Heart Association, (2012), 1:e003012, 12 pages.
Chen et al., Disruption of fusion results in mitochondrial heterogeneity and dysfunction, the Journal of Biological Chemistry, (2005), 280:23185-26192.
Choubey et al., Mutant A53T α-Synuclein Induces Neuronal Death by Increasing Mitochondrial Autophagy, The Journal of Biological Chemistry, (2011), 286:10814-10824.
Cipolat et al., Mitochondrial rhomboid PARL regulates cytochrome c release during apoptosis via OAP1-dependent cristae remodeling, Cell, (2006), 126:163-175.
Cipolat et al., OPA1 requires mitofusin 1 to promote mitochondrial fusion, Proceedings of the National Academy of sciences, (2004), 101: 15927-15932.
Cogliati et al., Mitochondrial cristae shape determines respiratory chain supercomplexes assembly and respiratory efficiency, Cell, (2013), 155: 160-171.
Coughlin et al., Mitochondrial Morphology Differences in Mitophagy Deficit in Murine Gaucomatous Optic Nerve, Investigative Opthamology & Visual Science, (2015), 56: 1437-1446.
Delettre et a., Neuclear gene OPA1, encoding a mitochondrial dynamin-related protein, is mutated in dominant optic atrophy, Nature Genetics, (2000), 26:207-210.
Devi et al., Accumulation of amyloid precursor protein in the Mitochondrial Import Channels of Human Alzheimer's Disease Brain Is Associated with Mitochondrial Dysfunction, The Journal of Neuroscience, (2006), 26: 9057-9068.
Diana et al., Mitochondria morphology and DNA content upon sublethal exposure to beta-amyloid (1-42), peptide, Coll Anthropol, (2008), 32: 51-58.
Dolle et al., Defective mitochondrial DNA homeostasis in the substantia nigra in Parkinson disease, Nature Communications, (2016), 7: 13548, 11 pages.
Dorn II et al., Mitochondrial Dynamics in Heart Dynamics in Heart Disease, Biochimica et Biophysica Acta, (2013), 1833: 20 pages.
Duvezin-Caubet et al., Proteolytic processing of OPA1 links mitochondrial dysfunction to alterations in mitochondrial morphology, The Journal of Biological Chemistry, (2006), 281:37972-37979.
Eberlin et al., A comprehensive review of the pharmacodynamics, pharmacokinetics, and clinical effects of the neutral endopeptidase inhibitor racecadotril, Frontiers in Pharmacology, Gastrointestinal Pharmacology, (2012), 3: 16 pages.
Edgar et al., Gene Expression Omnibus: NCBI gene expression and hybridization array data repository, Nucleic Acids Research, (2002), 30: 207-210.
Ehses et al., Regulation of OAP1 processing and mitochondrial fusion by m-AAA protease isoenzymes and OMA1, The Journal of Cell Biology, (2009), 187:1023-1036.
Faccenda et al., Control of Mitochondrial Remodeling by the ATPase Inhibitory Factor 1 Unveils a Pro-survival Relay via OPA1, Cell Reports, (2017), 1869-1883.
Ferreirinha et al., Axonal degeneration in paraplegin-deficient mice is assoicated with abnormal motochondria and impairment of axonal transport, The Journal of Clinical Investigation, 113: 231-242, (2004).
Frank et al., The role of dynamin-related protein 1, a mediator of mitochondrial fission, in apoptosis, Developmental Cell, (2001), 1: 515-525.
Frezza et al., OPA1 controls apoptotic cristae remodeling independently from mitochondrial fusion, Cell, (2006), 126: 177-189.
Frezza et al., Mitochondria in cancer: Not just innocent bystanders, Seminars in Cancer Biology, (2009), 19: 4-11.
Fuhmann et al., Solving a 50 year mystery of a missing OPA1 mutation: more insights from the first family diagnosed with autosomal dominant optic atrophy, Molecular Neurodegeneration, (2010). 5: 13 pages.
Gleissner et al., CXCL4 induces a unique transcriptome in monocyte-derived macrophages, Journal of Immunology, (2010), 184: 4810-4818.
Glytsou et al., Optic Atrophy 1 us Epistatic to the Core MICOS Component MIC60 in Mitochondrial Cristae Shape Control, Cell Reports, (2016), 17:3024-3034.
Griparic et al., Regulation of the mitochondrial dynamin-like protein Opa1 by proteolytic cleavage, The Journal of Cell Biology, (2007), 178:757-764.
Griparic et al., Loss of the intermembrane space protein Mgm1/OPA1 induces swelling and localized constructions along the lenghts of mitochondria, The Journal of Biological Chemistry, (2004), 279: 18792-18798.
Guardia-Laguarta et al., α-synuclein is localized to mitochondria-associated ER membranes, The Journal of Neuroscience, (2014), 34: 249-259.
Supplementary European Search Report from Appl. No. EP17877363, completed on Jun. 24, 2020.
Zhang et al., Membrane depolarization activates the motochondrial protease OMA1 by stimulating sefl-cleavage, EMBO reorts, (2014), 15:576-585.
Anand et al., The i-AAA protease YME1L and OMA1 cleave OPA1 to balance mitochondrial fusion and fission, The Journal of Cell Biology, (2014), 204:919-929.
Xiao et al., OMA1 mediates OPA1 proteolysis and mitochondrial fragmentation in experimental models of ischemic kidney injury, Am J Physiol Renal Physiol, (2014), 306:318-326.
Communication from Appl. No. 17877363.6, dated Jul. 15, 2021.
Office Action from U.S. Appl. No. 16/022,481, dated Jul. 23, 2019.
Office Action from U.S. Appl. No. 16/022,481, dated Nov. 27, 2019.
Office Action from U.S. Appl. No. 16/022,481, dated Apr. 24, 2020.
Aliev et al., Mitochondrial and vascular lesion as a central target for the development of Alzheimer's disease and Alzheimer disease-like pathology in transgenic mice, Neurological Reaserch, (2003), 25: 665-674.
Banfi et al., Indentification and Characterization of AFG3L2, a Novel Paraplegin-Related Gene, Genomics, (1999), 59:52-58.
Bowie et al., Deciphering the message in protein sequences: tolerance to amino acid substitutions, Science, (1990), 247:1306-1610.
Burte et al., Disturbed mitochondrial dynamics and neurodegenerative disorders, Nature Reviews Neurology, (2015), 11:11-24.

(56) References Cited

OTHER PUBLICATIONS

Butterfield et al., Evidence of oxidative damage in Alzheimer's disease brain: central role for amyloid β-peptide, Trends in Molecular Medicine, (2001), 7:548-554.
Carelli et al., Mitochondrial dysfunction as a cause of optic neuropathies, Progress in Retinal and Eye Research, (2004), 23:53-59.
Caspersen et al., Mitochondrial Aβ: a potential focal point for neuronal metabolic dysfunction in Alzheimer's disease, FASEB J., (2005), 19:2040-2041.
Chrysostomou et al., Oxidative stress and mitochondrial dysfunction in glaucoma, Current Opinion in Pharmacology, (2013), 13: 12-15.
Daoud et al., Resequencing of 29 Candidate Genes in Patients with Familial ad Sporadic Amyotrophic Lateral Sclerosis, Archives of Neurology, (2011), 68:587-593.
Delettre et al., Mutation Spectrum and splicing variants in the OPA1 gene, Human Genetics, (2001), 109: 584-591.
Del Dotto et al., OPA1: How much do we know to approach therapy?, Pharmacoligical Research, (2018), 12 Pages.
Ekert et al., Soluble Beta-Amyloid Leads to Mitochondrial Defects in Amyloid Precursor Protein and Tau Trasngenic Mice, Neuro-Degenerative Diseases, (2008), 5: 157-159.
Ghio et al., Interaction of α-synuclein with biomembranes in Parkinson's disease—role of cardiolipin, Pregress in Lipid Research, (2016), 61: 73-82.
Gibson et al., Abnormalities of mitochondrial enzymes in Alzheimer disease, Journal of Neural Trasnmission, (1998), 105:855-870.
Kong et al., Mitochondrial dynamics regulating chemoresistance in gynecological cancers, Annals of the New York Academy od Sciences, (2015), 1350: 1-16.
Kong et al., Mitochondrial dysfunction and glaucoma, Journal of Glaucoma, (2009), 18:93-100.
Lenaers et al., OPA1 functions in mitochondria and dysfunctions in optic nerve, The international Journal of Biochemistry & Cell Biology, (2009), 41: 1866-1874.
Lee et al., Mitochondrial dysfunction in glaucoma and emerging bioenergetic therapies, Experimental Eye Reserch, (2011), 93: 204-212.
Martin-Garcia et al., Mitochondrial dynamics and cell death in heart failure, Heart Failure Reviews, (2016), 21:123-136.
Maurer et al., A selective defect of cytochrome c oxidase is present in brain of Alzheimer disease patients, Neurobiology of Aging, (2000). 21: 455-462.
McQuibban et al., Mitochondrial membrane remodelling regulated by a conserved rhomboid protease, Nature, (2003), 423:537-541.
Nakada et al., Inter-mitochondrial complementation: Mitochondria-specific system preventing mice from expression of disease phenotypes by mutant mtDNA, Nature Medicine, (2001), 7: 934-940.
Okamoto et al., Mitochondrial morphology and dynamics in yeast and multicellular eukaryotes, Annual Review of Genetics, (2005), 39: 503-536.
Ono et al, Human cells are protected from mitochondrial dysfunction by complementation of DNA products in fused mitochondria, Nature Genetics, (2001), 28: 272-275.
Osborne, Mitochondria: Their role in ganglion cell death and survival in primary open angle glaucoma, Experimental Eye Research, (210), 90: 750-757.
Parker et al., Cytochrome oxidase deficiency in Alzheimer's disease, Neurology, (1990), 40: 1302-1303.
Philibert et al., Transcriptional profiling of subjects from the lowa adoption studies, American Journal of Medical Genetics Part B, Neuropsychiatric Genetics, (2007), 144B: 683-690.
Rossello et al., New N-arylsulfonyl-N-alkoxyaminoacetohydoxamic acids as selective inhibitors of gelatinase A (MMP-2), Bioorganic & Medicinal Chemistry, (2004), 12: 2441-2450.
Salminen et al., Impaired mitochondrial energy metabolism in Alzheimer's disease: Impact on Pathogenesis via disturbed epigenetic regulation of chromatin landscape, Progress in Neurobiology, (2015), 131:1-20.
Santos et al., The Impact of Mitochondrial Fusion and Fission Modulation in Sporadic Parkinson's Disease, Mol Neurobiology, (2014), 52:573-586.
Satoh et al., Differential sublocalization of the dynamin-related protein OPA1 isoforms in mitochondria, Biochemical and Biophysical Research Communications, (2003), 300: 482-493.
Schapira et al., Mitochondrial complex I deficiency in Parkinson's disease, Journal of Neurochemistry, (1990), 54:823-827.
Sesaki et al., Cells lacking Pcp1p/Ugo2p, a rhomboid-like protease required for Mgm1p processing, lose mtDNA and mitochondrial structure in a Dnm1p-dependent manner, but remain competent for mitochondrial fusion, Biochemical and Biophysical Research communications, (2003), 308: 276-283.
Sit el al., Intraocular pressure variations: causes and clinical significance, Can J Ophthalmol, (2014), 49:484-488.
Skulachev et al., Thread-grain transition of mitochondrial reticulum as a step of mitoptosis and apoptosis, Molecular and Cellular Biochemistry, (2004), 256:341-358.
Smith et al., Oxidative damage in Alzheirmer's, Nature, (1996), 382:120-121.
Taylor et al., Toxic proteins in neurodegenerative disease, Science, (2002), 296: 1991-1995.
Wai et al., Imbalanced OPA1 processing and mitochondrial fragmentation cause heart failure in mice, Science, (2015), 350: 1221, (aad116 p. 1-11).
Wells et al., Additivity of mutational effects in proteins, Biochemistry, (1990), 29: 8509-8517.
Yan et al., Blockage of GSK2beta-mediated Drp1 phosphorylation provides neuroprotection in neuronal and mouse models of Alzheimer's disease, Neurobiology of Aging, (2015), 36: 211-227.
Yang et al., Aberrant Alterations of Mitochondrial Factors Drp1 and Opa1 in the Brains of Scrapie Experiment Rodents, Journal of Molecular Neuroscience, (2017), 61: 368-378.
Pan et al., Rat brain DNA trasncript profile of halothane and isoflurane exposure, Pharmacogent Genomics, (2006), 16: 171-172.

* cited by examiner

Fig. 4
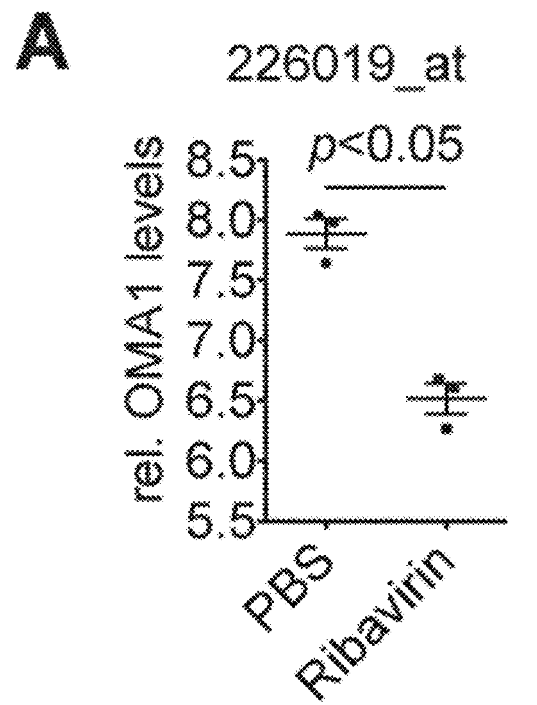
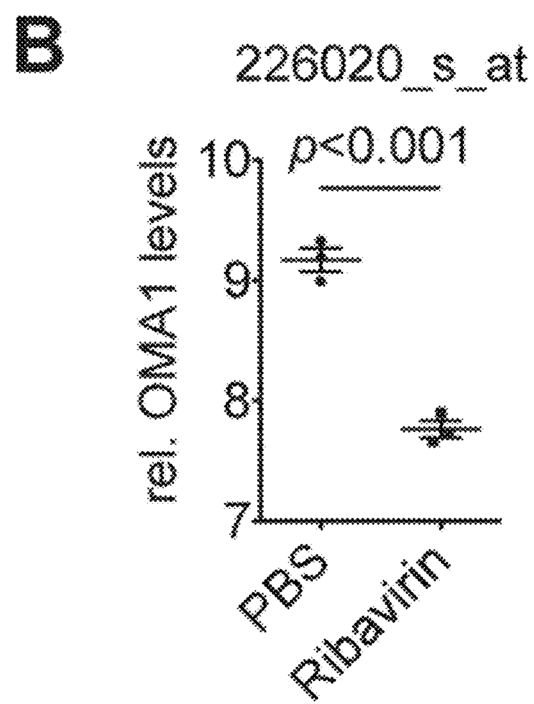

Fig. 8

*Breast Cancer*

| Gene | Gene ID | Min | Max | Median | Group "low" | Group "high" |
|---|---|---|---|---|---|---|
| OPA1 | 4976 | 6 | 1853 | 319 | 6-319 | 320-1853 |
| OMA1 | 115209 | 48 | 3238 | 807 | 48-807 | 808-3238 |
| HIGD1A | 25994 | 20 | 4949 | 284 | 20-284 | 285-4949 |
| BNIP3 | 664 | 121 | 17729 | 1325 | 121-1325 | 1326-17729 |
| YME1L1 | 10730 | 113 | 17733 | 3597 | 113-3597 | 3598-17733 |
| PHB | 5245 | 36 | 18120 | 617 | 36-617 | 618-18120 |
| PHB2 | 11331 | 730 | 25835 | 6605 | 730-6605 | 6606-25835 |
| SAMM50 | 25813 | 18 | 4437 | 825 | 18-825 | 826-4437 |
| IMMT | 10989 | 337 | 9324 | 1714 | 337-1714 | 1715-9324 |

*Lung Cancer*

| Gene | Gene ID | Min | Max | Median | Group "low" | Group "high" |
|---|---|---|---|---|---|---|
| OPA1 | 4976 | 18 | 6742 | 329 | 18-329 | 330-6742 |
| OMA1 | 115209 | 23 | 3181 | 577 | 23-577 | 578-3181 |
| HIGD1A | 25994 | 7 | 3573 | 249 | 7-249 | 250-3573 |
| BNIP3 | 664 | 126 | 16723 | 2193 | 126-2193 | 2194-16723 |
| YME1L1 | 10730 | 348 | 22613 | 3186 | 348-3186 | 3187-22613 |
| PHB | 5245 | 40 | 3328 | 575 | 40-575 | 576-3328 |
| PHB2 | 11331 | 298 | 28456 | 6737 | 298-6737 | 6738-28456 |
| SAMM50 | 25813 | 166 | 3378 | 800 | 166-800 | 801-3378 |
| IMMT | 10989 | 110 | 6432 | 1563 | 110-1563 | 1564-6432 |

Fig. 9

*Gastric Cancer*

| Gene | Gene ID | Min | Max | Median | Group "low" | Group "high" |
|---|---|---|---|---|---|---|
| OPA1 | 4976 | 68 | 1693 | 411 | 68-411 | 412-1693 |
| OMA1 | 115209 | 38 | 2403 | 1096 | 38-1096 | 1097-2403 |
| HIGD1A | 25994 | 78 | 3247 | 580 | 78-580 | 581-3247 |
| BNIP3 | 664 | 15 | 7614 | 319 | 15-319 | 320-7614 |
| YME1L1 | 10730 | 811 | 10704 | 3388 | 811-3388 | 3389-10704 |
| PHB | 5245 | 138 | 2014 | 622 | 138-622 | 623-2014 |
| PHB2 | 11331 | 2187 | 22306 | 5434 | 2187-5434 | 5435-22306 |
| SAMM50 | 25813 | 217 | 2532 | 1181 | 217-1181 | 1182-2532 |
| IMMT | 10989 | 459 | 5445 | 2017 | 459-2017 | 2018-5445 |

*Ovarian Cancer*

| Gene | Gene ID | Min | Max | Median | Group "low" | Group "high" |
|---|---|---|---|---|---|---|
| OPA1 | 4976 | 4 | 1872 | 378 | 4-378 | 379-1872 |
| OMA1 | 115209 | 12 | 2459 | 827 | 12-827 | 828-2459 |
| HIGD1A | 25994 | 2 | 2820 | 344 | 2-344 | 345-2820 |
| BNIP3 | 664 | 4 | 15905 | 2256 | 4-2256 | 2257-15905 |
| YME1L1 | 10730 | 63 | 16279 | 4363 | 63-4363 | 4364-16279 |
| PHB | 5245 | 42 | 2441 | 562 | 42-562 | 563-2441 |
| PHB2 | 11331 | 170 | 35557 | 10261 | 170-10261 | 10262-35557 |
| SAMM50 | 25813 | 20 | 35563 | 922 | 20-922 | 923-35563 |
| IMMT | 10989 | 32 | 6025 | 1798 | 32-1798 | 1799-6025 |

Fig. 20

| Name | Cas number | Name | Cas number |
|---|---|---|---|
| N-acetyl-L-Carnosine | 56353-15-2 | NSC319726 | 71555-25-4 |
| 1-Napthylisothiocyanate | 551-06-4 | ONO 4817 | 223472-31-9 |
| Actinonin | 13434-13-4 | Paclitaxel | 33069-62-4 |
| Afimoxifene | 68392-35-8 | Palbociclib | 827022-32-2 |
| ARP 100 | 704888-90-4 | PD166793 | 199850-67-4 |
| Ascorbic acid | 50-81-7 | PhIP | 105650-23-5 |
| Atazanavir | 198904-31-3 | Prinomastat | 192329-42-3 |
| Batimastat | 130370-60-4 | Racecadrotil | 81110-73-8 |
| Belinostat | 414864-00-9 | Ritonavir | 155213-67-5 |
| BIO | 667463-62-9 | Ro-28-2653 | 261956-22-3 |
| Brodalumab | 1174395-19-7 | SAHA | 149647-78-9 |
| CCCP | 555-60-2 | Saquinavir | 149845-06-7 |
| CGS 27023A | 161314-70-1 | SB-3CT | 292605-14-2 |
| Decitabin | 2353-33-5 | SCH 32615 | 83861-02-3 |
| Dexamethasone | 50-02-2 | SCH 34826 | 105262-04-2 |
| edelfosine | 70641-51-9 | Sodium valproate | 1069-66-5 |
| Elamipretide | 736992-21-5 | Sulforaphane | 4478-93-7 |
| GM6001 | 142880-36-2 | Tamoxifen | 10540-29-1 |
| Indinavir sulfate | 157810-81-6 | TAPI-0 | 143457-40-3 |
| Interleukin 2 | P60568 (Uniprot) | TAPI-1 | 171235-71-5 |
| JQ1 | 1268524-70-4 | TAPI-2 | 187034-31-7 |
| Lisinopril | 76547-98-3 | Tazemetostat | 1403254-99-8 |
| Lopinavir | 192725-17-0 | Thiorphan | 76721-89-6 |
| LY2811376 | 1194044-20-6 | Tipranavir | 174484-41-4 |
| Marimastat | 154039-60-8 | TPEN | 16858-02-9 |
| Metformin | 1115-70-4 | Trichostatin A | 58880-19-6 |
| MG132 | 133407-82-6 | Trovafloxacin | 147059-72-1 |
| MLN4924 | 905579-51-3 | UCF 101 | 313649-08-0 |
| MMP-3 Inhibitor VIII | 208663-26-7 | Valproic acid | 99-66-1 |
| Napthylisothiocyanate | 551-06-4 | Verubecestat | 1286770-55-5 |
| NNGH | 161314-17-6 | | |

SEQUENCE LISTING

```
<160> NUMBER OF SEQ ID NOS: 63

<210> SEQ ID NO 1
<211> LENGTH: 6345
<212> TYPE: DNA
<213> ORGANISM: Homo sapiens

<400> SEQUENCE: 1

gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgtgag gtctgccagt ctttagtgaa acacagctct    300

ggaataaaag gaagtttacc actacaaaaa ctacatctgg tttcacgaag catttatcat    360

tcacatcatc ctaccttaaa gcttcaacga ccccaattaa ggacatcctt tcagcagttc    420

tcttctctga caaaccttcc tttacgtaaa ctgaaattct ctccaattaa atatggctac    480

cagcctcgca ggaatttttg gccagcaaga ttagctacga gactcttaaa acttcgctat    540

ctcatactag gatcggctgt tgggggtggc tacacagcca aaaagacttt tgatcagtgg    600

aaagatatga taccggacct tagtgaatat aaatggattg tgcctgacat tgtgtgggaa    660

attgatgagt atatcgattt tgagaaaatt agaaaagccc ttcctagttc agaagacctt    720

gtaaagttag caccagactt tgacaagatt gttgaaagcc ttagcttatt gaaggacttt    780

tttacctcag gttctccgga agaaacggcg tttagagcaa cagatcgtgg atctgaaagt    840

gacaagcatt ttagaaaggt gtcagacaaa gagaaaattg accaacttca ggaagaactt    900

ctgcacactc agttgaagta tcagagaatc ttggaacgat tagaaaagga gaacaaagaa    960

ttgagaaaat tagtattgca gaaagatgac aaaggcattc atcatagaaa gcttaagaaa   1020

tctttgattg acatgtattc tgaagttctt gatgttctct ctgattatga tgccagttat   1080

aatacgcaag atcatctgcc acgggttgtt gtggttggag atcagagtgc tggaaagact   1140

agtgtgttgg aaatgattgc ccaagctcga atattcccaa gaggatctgg ggagatgatg   1200

acacgttctc cagttaaggt gactctgagt gaaggtcctc accatgtggc cctatttaaa   1260

gatagttctc gggagtttga tcttaccaaa gaagaagatc ttgcagcatt aagacatgaa   1320
```

```
atagaacttc gaatgaggaa aaatgtgaaa gaaggctgta ccgttagccc tgagaccata   1380
tccttaaatg taaaaggccc tggactacag aggatggtgc ttgttgactt accaggtgtg   1440
attaatactg tgacatcagg catggctcct gacacaaagg aaactatttt cagtatcagc   1500
aaagcttaca tgcagaatcc taatgccatc atactgtgta ttcaagatgg atctgtggat   1560
gctgaacgca gtattgttac agacttggtc agtcaaatgg accctcatgg aaggagaacc   1620
atattcgttt tgaccaaagt agacctggca gagaaaaatg tagccagtcc aagcaggatt   1680
cagcagataa ttgaaggaaa gctcttccca atgaaagctt taggttattt tgctgttgta   1740
acaggaaaag ggaacagctc tgaaagcatt gaagctataa gagaatatga agaagagttt   1800
tttcagaatt caaagctcct aaagacaagc atgctaaagg cacaccaagt gactacaaga   1860
aatttaagcc ttgcagtatc agactgcttt tggaaaatgg tacgagagtc tgttgaacaa   1920
caggctgata gtttcaaagc aacacgtttt aaccttgaaa ctgaatggaa gaataactat   1980
cctcgcctgc gggaacttga ccggaatgaa ctatttgaaa aagctaaaaa tgaaatcctt   2040
gatgaagtta tcagtctgag ccaggttaca ccaaaacatt gggaggaaat ccttcaacaa   2100
tctttgtggg aaagagtatc aactcatgtg attgaaaaca tctaccttcc agctgcgcag   2160
accatgaatt caggaacttt taacaccaca gtggatatca agcttaaaca gtggactgat   2220
aaacaacttc ctaataaagc agtagaggtt gcttgggaga ccctacaaga agaattttcc   2280
cgctttatga cagaaccgaa agggaaagag catgatgaca tatttgataa acttaaagag   2340
gctgttaagg aagaaagtat taaacgacac aagtggaatg actttgcgga ggacagcttg   2400
agggttattc aacacaatgc tttggaagac cgatccatat ctgataaaca gcaatgggat   2460
gcagctattt attttatgga agaggctctg caggctcgtc tcaaggatac tgaaaatgca   2520
attgaaaaca tggtgggtcc agactggaaa aagaggtggt tatactggaa gaatcggacc   2580
caagaacagt gtgttcacaa tgaaaccaag aatgaattgg agaagatgtt gaaatgtaat   2640
gaggagcacc cagcttatct tgcaagtgat gaaataacca cagtccggaa gaaccttgaa   2700
tcccgaggag tagaagtaga tccaagcttg attaaggata cttggcatca agtttataga   2760
agacattttt taaaaacagc tctaaaccat tgtaaccttt gtcgaagagg tttttattac   2820
taccaaaggc attttgtaga ttctgagttg gaatgcaatg atgtggtctt gttttggcgt   2880
atacagcgca tgcttgctat caccgcaaat actttaaggc aacaacttac aaatactgaa   2940
gttaggcgat tagagaaaaa tgttaaagag gtattggaag attttgctga agatggtgag   3000
aagaagatta aattgcttac tggtaaacgc gttcaactgg cggaagacct caagaaagtt   3060
agagaaattc aagaaaaact tgatgctttc attgaagctc ttcatcagga gaaataaatt   3120
aaaatcgtac tcataatcag ctctgcatac atctgaagaa caaaaacatc aacgtctttt   3180
gtccagcctc tttttcttct gctgttccac ctttctaaac atacaataaa gtcatgggat   3240
aaaaataatc gatgtatgtt acgggcgctt taaccatcag ctgcctctcg aatggaagaa   3300
cagtggtaat ggattaacat cctattttgt tgtactaaag tgacaaatcg gaataatata   3360
attggtatgg ccattaggtt cagtccttga agataagaaa cttgttctct gtttgttgtc   3420
ttatttgtgg tggcactcgt ttaatggatt aactgaggtt gctcaatgtt cagtttcttt   3480
tccagaaata caatgctagg tgttttgaaa taaaacttat atagcaattg tttaaagtta   3540
tcaattgtat ataaaatcac agtagcctgc taaatcattg tatgtgtctg tagtattcta   3600
ttcccagaaa ctatttgacc atgataattc agtttatatt caccacatga aagaaaaatg   3660
```

```
ggtaacagaa gaacccttaa aacaggttaa tttggattgt aacgttcagt gaaagaaatt   3720
tcaacccttc atagccagcg aagaaatttg ccttggaagc caagtcagta ccagcttacc   3780
tatttgattc agttgctgtt ttctcactct ctatatccat ttgaaattga tttattttag   3840
atgttgtata cttacgttag gctttctgtt aatagtggtt tttctcctgt tgacagagcc   3900
accggattat gacacaggat gaggaagatt aaggataatc aattgactaa tttcatttag   3960
aatattatca aacatttcaa ctaggtatca gaaaaaggct ttctttcata agactatttt   4020
aaatagaaat tatttcaaca attaaagtaa tgttgaccat ccccctctca gctgaataaa   4080
gaaaaattta gttcaattta ttgcaattta attacaatac taccttcaca acattttcat   4140
gtgttttaaa taaatatttt ttaattggct aaaggacatt caagcaaaga aatgctttct   4200
ttacttaaaa tgtctatctc atttgctgcc ttttcactaa gcctttactt tgttaataaa   4260
agtgtccatt gtgtgatgtt tttgatttta cagtttgcta aatcttattt tcttggagtt   4320
gctttttggt aacagcccca ttgctactcc ccattttatt gttttacatc aatgcatgct   4380
tcgttgtgat ccctcaagat gtaacacttg gtatgctcgg ttgaggatat gaaaaaatac   4440
ttccgaaacc aggaattcaa tgtatgtttg ttttatactg tttgataaga aaagtaggtc   4500
cagccttaag cagcacagat gcgctggtag atgcatagtc aggaactttt tttatttctt   4560
ttaggtctag ggacaggagt gaatagaaag ggaggagagc tctattatgt tctatacaca   4620
gattaggaga tgaccttact gggtacaccc ctctaaccag tgcttacagg ttaatgcatg   4680
ttaatgaata tttttgcagt tgtaaagcat aacaattaca actacacatc tatttctaaa   4740
gaataaaaca ggaccatatt tatttacttc tgtcaactat agaaagaaag accttcagct   4800
gtatttccac agatttctcc caaggaaaag gctaatatta gtcactactg ttatcacatc   4860
cctttgtata agttttaaaa agagatggag ggagatcttc atttctttga ggagatcagt   4920
attgtaacgt atgtgaatag atgataacaa ttaatattac taaaagtccc acatgagagt   4980
cctgacgccc tctccatgcc ccacagtaat gtggcttctt tcatgggttt ttttttcttc   5040
tttttagctg atctcatcct aagcatgctt tatttttcct tgaaagctag gtatttatca   5100
actgcagatg ttattgaaag aaaataaaat tcagtctcaa gagtaaaccc tgtgtcttgt   5160
gtctgtagtt caaaagtcag aaatgattct aatttaaaca aaaagatact aaatatacag   5220
aagttaaatt cgaactagcc acagaatcat ttgtttttat gtcagaattt gcaaagagtg   5280
gagtggacaa agctctgtat ggaagactga acaactgtaa atagatgata tccaaactta   5340
atttggctag gacttcaatt ttaaaaatca gtgtacctag gcagtgcaca gcacgaaata   5400
agtggccctt gcagcttccc cgtttaaccc actgtgctat agttgcgggt ggaacagtca   5460
acctttctag tagtttatga tattgccctc tttgtattcc cattttctac agtttttttcc   5520
gcagacttct ttctgcaaat tattcagcct ccaaatgcaa atgaatgata taaaaataag   5580
tagggaacat ggcagagagt ggtgcttccc agcctcacaa tgtgggaatt tgacatagga   5640
tgagagtcag agtataggtt taaaagataa aatctttagt taataatttt gtatttattt   5700
attctagatg tatgtatctg aggaaagaaa tctggtattt ttgctttcca ataaagggga   5760
tcaaagtaat ggtttttctc tcagttctct aagctggtct atgttatagc tctagcagta   5820
tggaaatgtg ctttaaaata tgcttacctt ttgaatgatc atggctatat gttgttgaga   5880
tatttgaaac ttaccttgtt ttcacttgtg cactgtgaat gaactttgta ttattttttt   5940
aaaaccttca cattacgtgt agatattatt gcaacttata ttttgcctga gcttgatcaa   6000
aggtcatttg tgtagatgag taattaaaaa atatttaaat cacattataa ttctattatt   6060
```

ggagagcatc ttttaaattt ttttctgttt taacgaggga aagagaaacc tgtataccta 6120
gggtcattat ttgaccccat agtataacca gattcatggt ctaacaagct ctcagtgtgg 6180
cttttctctg aatgcttgaa tttcacatgc cttgcatttc acagttgtac tccatggtca 6240
accggtgctt tttttcacat cgtggtactt gtcaaaacat tttgttattt tccttggtaa 6300
aatatataaa aaaggttttc taatttcaaa aaaaaaaaaa aaaaa 6345

<210> SEQ ID NO 2
<211> LENGTH: 960
<212> TYPE: PRT
<213> ORGANISM: Homo sapiens

<400> SEQUENCE: 2

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly Ser Pro Glu Glu Thr Ala
            180                 185                 190

Phe Arg Ala Thr Asp Arg Gly Ser Glu Ser Asp Lys His Phe Arg Lys
        195                 200                 205

Val Ser Asp Lys Glu Lys Ile Asp Gln Leu Gln Glu Glu Leu Leu His
    210                 215                 220

Thr Gln Leu Lys Tyr Gln Arg Ile Leu Glu Arg Leu Glu Lys Glu Asn
225                 230                 235                 240

Lys Glu Leu Arg Lys Leu Val Leu Gln Lys Asp Asp Lys Gly Ile His
                245                 250                 255

His Arg Lys Leu Lys Lys Ser Leu Ile Asp Met Tyr Ser Glu Val Leu
            260                 265                 270

Asp Val Leu Ser Asp Tyr Asp Ala Ser Tyr Asn Thr Gln Asp His Leu
        275                 280                 285

Pro Arg Val Val Val Val Gly Asp Gln Ser Ala Gly Lys Thr Ser Val
    290                 295                 300

Leu Glu Met Ile Ala Gln Ala Arg Ile Phe Pro Arg Gly Ser Gly Glu
305                 310                 315                 320
```

```
Met Met Thr Arg Ser Pro Val Lys Val Thr Leu Ser Glu Gly Pro His
                325                 330                 335

His Val Ala Leu Phe Lys Asp Ser Ser Arg Glu Phe Asp Leu Thr Lys
            340                 345                 350

Glu Glu Asp Leu Ala Ala Leu Arg His Glu Ile Glu Leu Arg Met Arg
        355                 360                 365

Lys Asn Val Lys Glu Gly Cys Thr Val Ser Pro Glu Thr Ile Ser Leu
    370                 375                 380

Asn Val Lys Gly Pro Gly Leu Gln Arg Met Val Leu Val Asp Leu Pro
385                 390                 395                 400

Gly Val Ile Asn Thr Val Thr Ser Gly Met Ala Pro Asp Thr Lys Glu
                405                 410                 415

Thr Ile Phe Ser Ile Ser Lys Ala Tyr Met Gln Asn Pro Asn Ala Ile
            420                 425                 430

Ile Leu Cys Ile Gln Asp Gly Ser Val Asp Ala Glu Arg Ser Ile Val
        435                 440                 445

Thr Asp Leu Val Ser Gln Met Asp Pro His Gly Arg Arg Thr Ile Phe
    450                 455                 460

Val Leu Thr Lys Val Asp Leu Ala Glu Lys Asn Val Ala Ser Pro Ser
465                 470                 475                 480

Arg Ile Gln Gln Ile Ile Glu Gly Lys Leu Phe Pro Met Lys Ala Leu
                485                 490                 495

Gly Tyr Phe Ala Val Val Thr Gly Lys Gly Asn Ser Ser Glu Ser Ile
            500                 505                 510

Glu Ala Ile Arg Glu Tyr Glu Glu Glu Phe Phe Gln Asn Ser Lys Leu
        515                 520                 525

Leu Lys Thr Ser Met Leu Lys Ala His Gln Val Thr Thr Arg Asn Leu
    530                 535                 540

Ser Leu Ala Val Ser Asp Cys Phe Trp Lys Met Val Arg Glu Ser Val
545                 550                 555                 560

Glu Gln Gln Ala Asp Ser Phe Lys Ala Thr Arg Phe Asn Leu Glu Thr
                565                 570                 575

Glu Trp Lys Asn Asn Tyr Pro Arg Leu Arg Glu Leu Asp Arg Asn Glu
            580                 585                 590

Leu Phe Glu Lys Ala Lys Asn Glu Ile Leu Asp Glu Val Ile Ser Leu
        595                 600                 605

Ser Gln Val Thr Pro Lys His Trp Glu Glu Ile Leu Gln Gln Ser Leu
    610                 615                 620

Trp Glu Arg Val Ser Thr His Val Ile Glu Asn Ile Tyr Leu Pro Ala
625                 630                 635                 640

Ala Gln Thr Met Asn Ser Gly Thr Phe Asn Thr Thr Val Asp Ile Lys
                645                 650                 655

Leu Lys Gln Trp Thr Asp Lys Gln Leu Pro Asn Lys Ala Val Glu Val
            660                 665                 670

Ala Trp Glu Thr Leu Gln Glu Glu Phe Ser Arg Phe Met Thr Glu Pro
        675                 680                 685

Lys Gly Lys Glu His Asp Asp Ile Phe Asp Lys Leu Lys Glu Ala Val
    690                 695                 700

Lys Glu Glu Ser Ile Lys Arg His Lys Trp Asn Asp Phe Ala Glu Asp
705                 710                 715                 720

Ser Leu Arg Val Ile Gln His Asn Ala Leu Glu Asp Arg Ser Ile Ser
                725                 730                 735

Asp Lys Gln Gln Trp Asp Ala Ala Ile Tyr Phe Met Glu Glu Ala Leu
```

```
            740                 745                 750

Gln Ala Arg Leu Lys Asp Thr Glu Asn Ala Ile Glu Asn Met Val Gly
        755                 760                 765

Pro Asp Trp Lys Lys Arg Trp Leu Tyr Trp Lys Asn Arg Thr Gln Glu
    770                 775                 780

Gln Cys Val His Asn Glu Thr Lys Asn Glu Leu Glu Lys Met Leu Lys
785                 790                 795                 800

Cys Asn Glu Glu His Pro Ala Tyr Leu Ala Ser Asp Glu Ile Thr Thr
                805                 810                 815

Val Arg Lys Asn Leu Glu Ser Arg Gly Val Glu Val Asp Pro Ser Leu
            820                 825                 830

Ile Lys Asp Thr Trp His Gln Val Tyr Arg Arg His Phe Leu Lys Thr
        835                 840                 845

Ala Leu Asn His Cys Asn Leu Cys Arg Arg Gly Phe Tyr Tyr Tyr Gln
    850                 855                 860

Arg His Phe Val Asp Ser Glu Leu Glu Cys Asn Asp Val Val Leu Phe
865                 870                 875                 880

Trp Arg Ile Gln Arg Met Leu Ala Ile Thr Ala Asn Thr Leu Arg Gln
                885                 890                 895

Gln Leu Thr Asn Thr Glu Val Arg Arg Leu Glu Lys Asn Val Lys Glu
            900                 905                 910

Val Leu Glu Asp Phe Ala Glu Asp Gly Glu Lys Lys Ile Lys Leu Leu
        915                 920                 925

Thr Gly Lys Arg Val Gln Leu Ala Glu Asp Leu Lys Lys Val Arg Glu
    930                 935                 940

Ile Gln Glu Lys Leu Asp Ala Phe Ile Glu Ala Leu His Gln Glu Lys
945                 950                 955                 960
```

```
<210> SEQ ID NO 3
<211> LENGTH: 6237
<212> TYPE: DNA
<213> ORGANISM: Homo sapiens

<400> SEQUENCE: 3

gtgctgcccg cctagaaagg gtgaagtggt tgtttccgtg acggactgag tacgggtgcc      60

tgtcaggctc ttgcggaagt ccatgcgcca ttgggagggc ctcggccgcg gctctgtgcc     120

cttgctgctg agggccactt cctgggtcat tcctggaccg ggagccgggc tggggctcac     180

acgggggctc ccgcgtggcc gtctcggcgc ctgcgtgacc tccccgccgg cgggatgtgg     240

cgactacgtc gggccgctgt ggcctgtgag gtctgccagt ctttagtgaa acacagctct     300

ggaataaaag gaagtttacc actacaaaaa ctacatctgg tttcacgaag catttatcat     360

tcacatcatc ctaccttaaa gcttcaacga ccccaattaa ggacatcctt tcagcagttc     420

tcttctctga caaaccttcc tttacgtaaa ctgaaattct ctccaattaa atatggctac     480

cagcctcgca ggaatttttg gccagcaaga ttagctacga gactcttaaa acttcgctat     540

ctcatactag gatcggctgt tgggggtggc tacacagcca aaaagacttt tgatcagtgg     600

aaagatatga taccggacct tagtgaatat aaatggattg tgcctgacat tgtgtgggaa     660

attgatgagt atatcgattt tggttctccg gaagaaacgg cgtttagagc aacagatcgt     720

ggatctgaaa gtgacaagca ttttagaaag gtgtcagaca aagagaaaat tgaccaactt     780

caggaagaac ttctgcacac tcagttgaag tatcagagaa tcttggaacg attagaaaag     840

gagaacaaag aattgagaaa attagtattg cagaaagatg acaaaggcat tcatcataga     900
```

```
aagcttaaga aatctttgat tgacatgtat tctgaagttc ttgatgttct ctctgattat    960
gatgccagtt ataatacgca agatcatctg ccacgggttg ttgtggttgg agatcagagt   1020
gctggaaaga ctagtgtgtt ggaaatgatt gcccaagctc gaatattccc aagaggatct   1080
ggggagatga tgacacgttc tccagttaag gtgactctga gtgaaggtcc tcaccatgtg   1140
gccctattta aagatagttc tcgggagttt gatcttacca aagaagaaga tcttgcagca   1200
ttaagacatg aaatagaact tcgaatgagg aaaaatgtga aagaaggctg taccgttagc   1260
cctgagacca tatccttaaa tgtaaaaggc cctggactac agaggatggt gcttgttgac   1320
ttaccaggtg tgattaatac tgtgacatca ggcatggctc ctgacacaaa ggaaactatt   1380
ttcagtatca gcaaagctta catgcagaat cctaatgcca tcatactgtg tattcaagat   1440
ggatctgtgg atgctgaacg cagtattgtt acagacttgg tcagtcaaat ggaccctcat   1500
ggaaggagaa ccatattcgt tttgaccaaa gtagacctgg cagagaaaaa tgtagccagt   1560
ccaagcagga ttcagcagat aattgaagga aagctcttcc caatgaaagc tttaggttat   1620
tttgctgttg taacaggaaa agggaacagc tctgaaagca ttgaagctat aagagaatat   1680
gaagaagagt tttttcagaa ttcaaagctc ctaaagacaa gcatgctaaa ggcacaccaa   1740
gtgactacaa gaaatttaag ccttgcagta tcagactgct tttggaaaat ggtacgagag   1800
tctgttgaac aacaggctga tagtttcaaa gcaacacgtt ttaaccttga aactgaatgg   1860
aagaataact atcctcgcct gcgggaactt gaccggaatg aactatttga aaaagctaaa   1920
aatgaaatcc ttgatgaagt tatcagtctg agccaggtta caccaaaaca ttgggaggaa   1980
atccttcaac aatctttgtg ggaaagagta tcaactcatg tgattgaaaa catctacctt   2040
ccagctgcgc agaccatgaa ttcaggaact tttaacacca cagtggatat caagcttaaa   2100
cagtggactg ataaacaact tcctaataaa gcagtagagg ttgcttggga gaccctacaa   2160
gaagaatttt cccgctttat gacagaaccg aaagggaaag agcatgatga catatttgat   2220
aaacttaaag aggctgttaa ggaagaaagt attaaacgac acaagtggaa tgactttgcg   2280
gaggacagct tgagggttat tcaacacaat gctttggaag accgatccat atctgataaa   2340
cagcaatggg atgcagctat ttattttatg gaagaggctc tgcaggctcg tctcaaggat   2400
actgaaaatg caattgaaaa catggtgggt ccagactgga aaaagaggtg gttatactgg   2460
aagaatcgga cccaagaaca gtgtgttcac aatgaaacca agaatgaatt ggagaagatg   2520
ttgaaatgta atgaggagca cccagcttat cttgcaagtg atgaaataac cacagtccgg   2580
aagaaccttg aatcccgagg agtagaagta gatccaagct tgattaagga tacttggcat   2640
caagtttata gaagacattt tttaaaaaca gctctaaacc attgtaacct ttgtcgaaga   2700
ggttttttatt actaccaaag gcattttgta gattctgagt tggaatgcaa tgatgtggtc   2760
ttgttttggc gtatacagcg catgcttgct atcaccgcaa atactttaag gcaacaactt   2820
acaaatactg aagttaggcg attagagaaa aatgttaaag aggtattgga agattttgct   2880
gaagatggtg agaagaagat taaattgctt actggtaaac gcgttcaact ggcggaagac   2940
ctcaagaaag ttagagaaat tcaagaaaaa cttgatgctt tcattgaagc tcttcatcag   3000
gagaaataaa ttaaaatcgt actcataatc agctctgcat acatctgaag aacaaaaaca   3060
tcaacgtctt ttgtccagcc tctttttctt ctgctgttcc acctttctaa acatacaata   3120
aagtcatggg ataaaaataa tcgatgtatg ttacgggcgc tttaaccatc agctgcctct   3180
cgaatggaag aacagtggta atggattaac atcctatttt gttgtactaa agtgacaaat   3240
cggaataata taattggtat ggccattagg ttcagtcctt gaagataaga aacttgttct   3300
```

```
ctgtttgttg tcttatttgt ggtggcactc gtttaatgga ttaactgagg ttgctcaatg   3360
ttcagtttct tttccagaaa tacaatgcta ggtgttttga aataaaactt atatagcaat   3420
tgtttaaagt tatcaattgt atataaaatc acagtagcct gctaaatcat tgtatgtgtc   3480
tgtagtattc tattcccaga aactatttga ccatgataat tcagtttata ttcaccacat   3540
gaaagaaaaa tgggtaacag aagaaccctt aaaacaggtt aatttggatt gtaacgttca   3600
gtgaaagaaa tttcaaccct tcatagccag cgaagaaatt tgccttggaa gccaagtcag   3660
taccagctta cctatttgat tcagttgctg ttttctcact ctctatatcc atttgaaatt   3720
gatttatttt agatgttgta tacttacgtt aggctttctg ttaatagtgg tttttctcct   3780
gttgacagag ccaccggatt atgacacagg atgaggaaga ttaaggataa tcaattgact   3840
aatttcattt agaatattat caaacatttc aactaggtat cagaaaaagg ctttctttca   3900
taagactatt ttaaatagaa attatttcaa caattaaagt aatgttgacc atccccctct   3960
cagctgaata aagaaaaatt tagttcaatt tattgcaatt taattacaat actaccttca   4020
caacattttc atgtgtttta aataaatatt ttttaattgg ctaaaggaca ttcaagcaaa   4080
gaaatgcttt ctttacttaa aatgtctatc tcatttgctg ccttttcact aagcctttac   4140
tttgttaata aaagtgtcca ttgtgtgatg tttttgattt tacagtttgc taaatcttat   4200
tttcttggag ttgctttttg gtaacagccc cattgctact ccccatttta ttgttttaca   4260
tcaatgcatg cttcgttgtg atccctcaag atgtaacact tggtatgctc ggttgaggat   4320
atgaaaaaat acttccgaaa ccaggaattc aatgtatgtt tgttttatac tgtttgataa   4380
gaaaagtagg tccagcctta agcagcacag atgcgctggt agatgcatag tcaggaactt   4440
tttttatttc ttttaggtct agggacagga gtgaatagaa agggaggaga gctctattat   4500
gttctataca cagattagga gatgacctta ctgggtacac ccctctaacc agtgcttaca   4560
ggttaatgca tgttaatgaa tatttttgca gttgtaaagc ataacaatta caactacaca   4620
tctatttcta aagaataaaa caggaccata tttatttact tctgtcaact atagaaagaa   4680
agaccttcag ctgtatttcc acagatttct cccaaggaaa aggctaatat tagtcactac   4740
tgttatcaca tccctttgta taagttttaa aaagagatgg agggagatct tcatttcttt   4800
gaggagatca gtattgtaac gtatgtgaat agatgataac aattaatatt actaaaagtc   4860
ccacatgaga gtcctgacgc cctctccatg ccccacagta atgtggcttc tttcatgggt   4920
tttttttcct tctttttagc tgatctcatc ctaagcatgc tttatttttc cttgaaagct   4980
aggtatttat caactgcaga tgttattgaa agaaaataaa attcagtctc aagagtaaac   5040
cctgtgtctt gtgtctgtag ttcaaaagtc agaaatgatt ctaatttaaa caaaaagata   5100
ctaaatatac agaagttaaa ttcgaactag ccacagaatc atttgttttt atgtcagaat   5160
ttgcaaagag tggagtggac aaagctctgt atggaagact gaacaactgt aaatagatga   5220
tatccaaact taatttggct aggacttcaa ttttaaaaat cagtgtacct aggcagtgca   5280
cagcacgaaa taagtggccc ttgcagcttc cccgtttaac ccactgtgct atagttgcgg   5340
gtggaacagt caacctttct agtagtttat gatattgccc tctttgtatt cccattttct   5400
acagtttttt ccgcagactt ctttctgcaa attattcagc ctccaaatgc aaatgaatga   5460
tataaaaata agtagggaac atggcagaga gtggtgcttc ccagcctcac aatgtgggaa   5520
tttgacatag gatgagagtc agagtatagg tttaaaagat aaaatcttta gttaataatt   5580
ttgtatttat ttattctaga tgtatgtatc tgaggaaaga aatctggtat ttttgctttc   5640
```

```
caataaaggg gatcaaagta atggtttttc tctcagttct ctaagctggt ctatgttata   5700

gctctagcag tatggaaatg tgctttaaaa tatgcttacc ttttgaatga tcatggctat   5760

atgttgttga gatatttgaa acttaccttg ttttcacttg tgcactgtga atgaactttg   5820

tattattttt ttaaaacctt cacattacgt gtagatatta ttgcaactta tattttgcct   5880

gagcttgatc aaaggtcatt tgtgtagatg agtaattaaa aatatttaa atcacattat   5940

aattctatta ttggagagca tcttttaaat ttttttctgt tttaacgagg gaaagagaaa   6000

cctgtatacc tagggtcatt atttgacccc atagtataac cagattcatg gtctaacaag   6060

ctctcagtgt ggcttttctc tgaatgcttg aatttcacat gccttgcatt tcacagttgt   6120

actccatggt caaccggtgc ttttttcac atcgtggtac ttgtcaaaac attttgttat   6180

tttccttggt aaaatatata aaaaaggttt tctaatttca aaaaaaaaaa aaaaaaa      6237
```

<210> SEQ ID NO 4
<211> LENGTH: 924
<212> TYPE: PRT
<213> ORGANISM: Homo sapiens

<400> SEQUENCE: 4

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly Ser Pro Glu Glu Thr Ala Phe Arg Ala Thr
145                 150                 155                 160

Asp Arg Gly Ser Glu Ser Asp Lys His Phe Arg Lys Val Ser Asp Lys
                165                 170                 175

Glu Lys Ile Asp Gln Leu Gln Glu Glu Leu Leu His Thr Gln Leu Lys
            180                 185                 190

Tyr Gln Arg Ile Leu Glu Arg Leu Glu Lys Glu Asn Lys Glu Leu Arg
        195                 200                 205

Lys Leu Val Leu Gln Lys Asp Asp Lys Gly Ile His His Arg Lys Leu
    210                 215                 220

Lys Lys Ser Leu Ile Asp Met Tyr Ser Glu Val Leu Asp Val Leu Ser
225                 230                 235                 240

Asp Tyr Asp Ala Ser Tyr Asn Thr Gln Asp His Leu Pro Arg Val Val
                245                 250                 255

Val Val Gly Asp Gln Ser Ala Gly Lys Thr Ser Val Leu Glu Met Ile
            260                 265                 270
```

```
Ala Gln Ala Arg Ile Phe Pro Arg Gly Ser Gly Glu Met Met Thr Arg
        275                 280                 285

Ser Pro Val Lys Val Thr Leu Ser Glu Gly Pro His His Val Ala Leu
    290                 295                 300

Phe Lys Asp Ser Ser Arg Glu Phe Asp Leu Thr Lys Glu Glu Asp Leu
305                 310                 315                 320

Ala Ala Leu Arg His Glu Ile Glu Leu Arg Met Arg Lys Asn Val Lys
                325                 330                 335

Glu Gly Cys Thr Val Ser Pro Glu Thr Ile Ser Leu Asn Val Lys Gly
            340                 345                 350

Pro Gly Leu Gln Arg Met Val Leu Val Asp Leu Pro Gly Val Ile Asn
        355                 360                 365

Thr Val Thr Ser Gly Met Ala Pro Asp Thr Lys Glu Thr Ile Phe Ser
    370                 375                 380

Ile Ser Lys Ala Tyr Met Gln Asn Pro Asn Ala Ile Ile Leu Cys Ile
385                 390                 395                 400

Gln Asp Gly Ser Val Asp Ala Glu Arg Ser Ile Val Thr Asp Leu Val
                405                 410                 415

Ser Gln Met Asp Pro His Gly Arg Arg Thr Ile Phe Val Leu Thr Lys
            420                 425                 430

Val Asp Leu Ala Glu Lys Asn Val Ala Ser Pro Ser Arg Ile Gln Gln
        435                 440                 445

Ile Ile Glu Gly Lys Leu Phe Pro Met Lys Ala Leu Gly Tyr Phe Ala
    450                 455                 460

Val Val Thr Gly Lys Gly Asn Ser Ser Glu Ser Ile Glu Ala Ile Arg
465                 470                 475                 480

Glu Tyr Glu Glu Glu Phe Phe Gln Asn Ser Lys Leu Leu Lys Thr Ser
                485                 490                 495

Met Leu Lys Ala His Gln Val Thr Thr Arg Asn Leu Ser Leu Ala Val
            500                 505                 510

Ser Asp Cys Phe Trp Lys Met Val Arg Glu Ser Val Glu Gln Gln Ala
        515                 520                 525

Asp Ser Phe Lys Ala Thr Arg Phe Asn Leu Glu Thr Glu Trp Lys Asn
    530                 535                 540

Asn Tyr Pro Arg Leu Arg Glu Leu Asp Arg Asn Glu Leu Phe Glu Lys
545                 550                 555                 560

Ala Lys Asn Glu Ile Leu Asp Glu Val Ile Ser Leu Ser Gln Val Thr
                565                 570                 575

Pro Lys His Trp Glu Glu Ile Leu Gln Gln Ser Leu Trp Glu Arg Val
            580                 585                 590

Ser Thr His Val Ile Glu Asn Ile Tyr Leu Pro Ala Ala Gln Thr Met
        595                 600                 605

Asn Ser Gly Thr Phe Asn Thr Thr Val Asp Ile Lys Leu Lys Gln Trp
    610                 615                 620

Thr Asp Lys Gln Leu Pro Asn Lys Ala Val Glu Val Ala Trp Glu Thr
625                 630                 635                 640

Leu Gln Glu Glu Phe Ser Arg Phe Met Thr Glu Pro Lys Gly Lys Glu
                645                 650                 655

His Asp Asp Ile Phe Asp Lys Leu Lys Glu Ala Val Lys Glu Glu Ser
            660                 665                 670

Ile Lys Arg His Lys Trp Asn Asp Phe Ala Glu Asp Ser Leu Arg Val
        675                 680                 685

Ile Gln His Asn Ala Leu Glu Asp Arg Ser Ile Ser Asp Lys Gln Gln
```

```
    690                 695                 700

Trp Asp Ala Ala Ile Tyr Phe Met Glu Glu Ala Leu Gln Ala Arg Leu
705                 710                 715                 720

Lys Asp Thr Glu Asn Ala Ile Glu Asn Met Val Gly Pro Asp Trp Lys
                725                 730                 735

Lys Arg Trp Leu Tyr Trp Lys Asn Arg Thr Gln Glu Gln Cys Val His
            740                 745                 750

Asn Glu Thr Lys Asn Glu Leu Glu Lys Met Leu Lys Cys Asn Glu Glu
        755                 760                 765

His Pro Ala Tyr Leu Ala Ser Asp Glu Ile Thr Thr Val Arg Lys Asn
    770                 775                 780

Leu Glu Ser Arg Gly Val Glu Val Asp Pro Ser Leu Ile Lys Asp Thr
785                 790                 795                 800

Trp His Gln Val Tyr Arg Arg His Phe Leu Lys Thr Ala Leu Asn His
                805                 810                 815

Cys Asn Leu Cys Arg Arg Gly Phe Tyr Tyr Tyr Gln Arg His Phe Val
            820                 825                 830

Asp Ser Glu Leu Glu Cys Asn Asp Val Val Leu Phe Trp Arg Ile Gln
        835                 840                 845

Arg Met Leu Ala Ile Thr Ala Asn Thr Leu Arg Gln Gln Leu Thr Asn
    850                 855                 860

Thr Glu Val Arg Arg Leu Glu Lys Asn Val Lys Glu Val Leu Glu Asp
865                 870                 875                 880

Phe Ala Glu Asp Gly Glu Lys Lys Ile Lys Leu Leu Thr Gly Lys Arg
                885                 890                 895

Val Gln Leu Ala Glu Asp Leu Lys Lys Val Arg Glu Ile Gln Glu Lys
            900                 905                 910

Leu Asp Ala Phe Ile Glu Ala Leu His Gln Glu Lys
        915                 920

<210> SEQ ID NO 5
<211> LENGTH: 6291
<212> TYPE: DNA
<213> ORGANISM: Homo sapiens

<400> SEQUENCE: 5

gtgctgcccg cctagaaagg gtgaagtggt tgtttccgtg acggactgag tacgggtgcc      60

tgtcaggctc ttgcggaagt ccatgcgcca ttgggagggc ctcggccgcg gctctgtgcc     120

cttgctgctg agggccactt cctgggtcat tcctggaccg ggagccgggc tggggctcac     180

acgggggctc ccgcgtggcc gtctcggcgc ctgcgtgacc tccccgccgg cgggatgtgg     240

cgactacgtc gggccgctgt ggcctgtgag gtctgccagt ctttagtgaa acacagctct     300

ggaataaaag gaagtttacc actacaaaaa ctacatctgg tttcacgaag catttatcat     360

tcacatcatc ctaccttaaa gcttcaacga ccccaattaa ggacatcctt tcagcagttc     420

tcttctctga caaaccttcc tttacgtaaa ctgaaattct ctccaattaa atatggctac     480

cagcctcgca ggaatttttg gccagcaaga ttagctacga gactcttaaa acttcgctat     540

ctcatactag gatcggctgt tgggggtggc tacacagcca aaaagacttt tgatcagtgg     600

aaagatatga taccggacct tagtgaatat aaatggattg tgcctgacat tgtgtgggaa     660

attgatgagt atatcgattt tggtcacaaa ttggttagtg aagtcatagg agcttctgac     720

ctacttctct tgttaggttc tccggaagaa acggcgttta gagcaacaga tcgtggatct     780

gaaagtgaca agcattttag aaaggtgtca gacaaagaga aaattgacca acttcaggaa     840
```

```
gaacttctgc acactcagtt gaagtatcag agaatcttgg aacgattaga aaaggagaac    900
aaagaattga gaaaattagt attgcagaaa gatgacaaag gcattcatca tagaaagctt    960
aagaaatctt tgattgacat gtattctgaa gttcttgatg ttctctctga ttatgatgcc   1020
agttataata cgcaagatca tctgccacgg gttgttgtgg ttggagatca gagtgctgga   1080
aagactagtg tgttggaaat gattgcccaa gctcgaatat tcccaagagg atctggggag   1140
atgatgacac gttctccagt taaggtgact ctgagtgaag gtcctcacca tgtggcccta   1200
tttaaagata gttctcggga gtttgatctt accaaagaag aagatcttgc agcattaaga   1260
catgaaatag aacttcgaat gaggaaaaat gtgaaagaag gctgtaccgt tagccctgag   1320
accatatcct taaatgtaaa aggccctgga ctacagagga tggtgcttgt tgacttacca   1380
ggtgtgatta atactgtgac atcaggcatg gctcctgaca caaaggaaac tattttcagt   1440
atcagcaaag cttacatgca gaatcctaat gccatcatac tgtgtattca agatggatct   1500
gtggatgctg aacgcagtat tgttacagac ttggtcagtc aaatggaccc tcatggaagg   1560
agaaccatat tcgttttgac caaagtagac ctggcagaga aaaatgtagc cagtccaagc   1620
aggattcagc agataattga aggaaagctc ttcccaatga aagctttagg ttattttgct   1680
gttgtaacag gaaaagggaa cagctctgaa agcattgaag ctataagaga atatgaagaa   1740
gagtttttc agaattcaaa gctcctaaag acaagcatgc taaaggcaca ccaagtgact   1800
acaagaaatt taagccttgc agtatcagac tgcttttgga aaatggtacg agagtctgtt   1860
gaacaacagg ctgatagttt caaagcaaca cgttttaacc ttgaaactga atggaagaat   1920
aactatcctc gcctgcggga acttgaccgg aatgaactat ttgaaaaagc taaaaatgaa   1980
atccttgatg aagttatcag tctgagccag gttacaccaa aacattggga ggaaatcctt   2040
caacaatctt tgtgggaaag agtatcaact catgtgattg aaaacatcta ccttccagct   2100
gcgcagacca tgaattcagg aacttttaac accacagtgg atatcaagct taaacagtgg   2160
actgataaac aacttcctaa taaagcagta gaggttgctt gggagaccct acaagaagaa   2220
ttttcccgct ttatgacaga accgaaaggg aaagagcatg atgacatatt tgataaactt   2280
aaagaggctg ttaaggaaga aagtattaaa cgacacaagt ggaatgactt tgcggaggac   2340
agcttgaggg ttattcaaca caatgctttg gaagaccgat ccatatctga taaacagcaa   2400
tgggatgcag ctatttattt tatggaagag gctctgcagg ctcgtctcaa ggatactgaa   2460
aatgcaattg aaaacatggt gggtccagac tggaaaaaga ggtggttata ctggaagaat   2520
cggacccaag aacagtgtgt tcacaatgaa accaagaatg aattggagaa gatgttgaaa   2580
tgtaatgagg agcacccagc ttatcttgca agtgatgaaa taaccacagt ccggaagaac   2640
cttgaatccc gaggagtaga agtagatcca agcttgatta aggatacttg gcatcaagtt   2700
tatagaagac attttttaaa aacagctcta aaccattgta acctttgtcg aagaggtttt   2760
tattactacc aaaggcattt tgtagattct gagttggaat gcaatgatgt ggtcttgttt   2820
tggcgtatac agcgcatgct tgctatcacc gcaaatactt taaggcaaca acttacaaat   2880
actgaagtta ggcgattaga gaaaaatgtt aaagaggtat tggaagattt tgctgaagat   2940
ggtgagaaga agattaaatt gcttactggt aaacgcgttc aactggcgga agacctcaag   3000
aaagttagag aaattcaaga aaaacttgat gctttcattg aagctcttca tcaggagaaa   3060
taaattaaaa tcgtactcat aatcagctct gcatacatct gaagaacaaa aacatcaacg   3120
tcttttgtcc agcctctttt tcttctgctg ttccaccttt ctaaacatac aataaagtca   3180
```

```
tgggataaaa ataatcgatg tatgttacgg gcgctttaac catcagctgc ctctcgaatg   3240

gaagaacagt ggtaatggat taacatccta ttttgttgta ctaaagtgac aaatcggaat   3300

aatataattg gtatggccat taggttcagt ccttgaagat aagaaacttg ttctctgttt   3360

gttgtcttat ttgtggtggc actcgtttaa tggattaact gaggttgctc aatgttcagt   3420

ttcttttcca gaaatacaat gctaggtgtt ttgaaataaa acttatatag caattgttta   3480

aagttatcaa ttgtatataa aatcacagta gcctgctaaa tcattgtatg tgtctgtagt   3540

attctattcc cagaaactat ttgaccatga taattcagtt tatattcacc acatgaaaga   3600

aaaatgggta acagaagaac ccttaaaaca ggttaatttg gattgtaacg ttcagtgaaa   3660

gaaatttcaa cccttcatag ccagcgaaga aatttgcctt ggaagccaag tcagtaccag   3720

cttacctatt tgattcagtt gctgttttct cactctctat atccatttga aattgattta   3780

ttttagatgt tgtatactta cgttaggctt tctgttaata gtggtttttc tcctgttgac   3840

agagccaccg gattatgaca caggatgagg aagattaagg ataatcaatt gactaatttc   3900

atttagaata ttatcaaaca tttcaactag gtatcagaaa aaggctttct ttcataagac   3960

tattttaaat agaaattatt tcaacaatta aagtaatgtt gaccatcccc ctctcagctg   4020

aataaagaaa aatttagttc aatttattgc aatttaatta caatactacc ttcacaacat   4080

tttcatgtgt tttaaataaa tattttttaa ttggctaaag gacattcaag caaagaaatg   4140

ctttctttac ttaaaatgtc tatctcattt gctgcctttt cactaagcct ttactttgtt   4200

aataaaagtg tccattgtgt gatgtttttg attttacagt ttgctaaatc ttattttctt   4260

ggagttgctt tttggtaaca gccccattgc tactccccat tttattgttt tacatcaatg   4320

catgcttcgt tgtgatccct caagatgtaa cacttggtat gctcggttga ggatatgaaa   4380

aaatacttcc gaaaccagga attcaatgta tgtttgtttt atactgtttg ataagaaaag   4440

taggtccagc cttaagcagc acagatgcgc tggtagatgc atagtcagga actttttta   4500

tttcttttag gtctagggac aggagtgaat agaaagggag gagagctcta ttatgttcta   4560

tacacagatt aggagatgac cttactgggt acacccctct aaccagtgct tacaggttaa   4620

tgcatgttaa tgaatatttt tgcagttgta aagcataaca attacaacta cacatctatt   4680

tctaaagaat aaaacaggac catatttatt tacttctgtc aactatagaa agaaagacct   4740

tcagctgtat ttccacagat ttctcccaag gaaaaggcta atattagtca ctactgttat   4800

cacatccctt tgtataagtt ttaaaaagag atggagggag atcttcattt ctttgaggag   4860

atcagtattg taacgtatgt gaatagatga taacaattaa tattactaaa agtcccacat   4920

gagagtcctg acgccctctc catgccccac agtaatgtgg cttctttcat gggtttttt   4980

ttcttctttt tagctgatct catcctaagc atgctttatt tttccttgaa agctaggtat   5040

ttatcaactg cagatgttat tgaaagaaaa taaaattcag tctcaagagt aaaccctgtg   5100

tcttgtgtct gtagttcaaa agtcagaaat gattctaatt taaacaaaaa gatactaaat   5160

atacagaagt taaattcgaa ctagccacag aatcatttgt ttttatgtca gaatttgcaa   5220

agagtggagt ggacaaagct ctgtatggaa gactgaacaa ctgtaaatag atgatatcca   5280

aacttaattt ggctaggact tcaattttaa aaatcagtgt acctaggcag tgcacagcac   5340

gaaataagtg gcccttgcag cttccccgtt taacccactg tgctatagtt gcgggtggaa   5400

cagtcaacct ttctagtagt ttatgatatt gccctctttg tattcccatt ttctacagtt   5460

ttttccgcag acttctttct gcaaattatt cagcctccaa atgcaaatga atgatataaa   5520

aataagtagg gaacatggca gagagtggtg cttcccagcc tcacaatgtg ggaatttgac   5580
```

```
ataggatgag agtcagagta taggtttaaa agataaaatc tttagttaat aattttgtat   5640

ttatttattc tagatgtatg tatctgagga aagaaatctg gtatttttgc tttccaataa   5700

aggggatcaa agtaatggtt tttctctcag ttctctaagc tggtctatgt tatagctcta   5760

gcagtatgga aatgtgcttt aaaatatgct taccttttga atgatcatgg ctatatgttg   5820

ttgagatatt tgaaacttac cttgttttca cttgtgcact gtgaatgaac tttgtattat   5880

tttttaaaa ccttcacatt acgtgtagat attattgcaa cttatatttt gcctgagctt   5940

gatcaaaggt catttgtgta gatgagtaat taaaaaatat ttaaatcaca ttataattct   6000

attattggag agcatctttt aaattttttt ctgttttaac gagggaaaga gaaacctgta   6060

tacctagggt cattatttga ccccatagta taaccagatt catggtctaa caagctctca   6120

gtgtggcttt tctctgaatg cttgaatttc acatgccttg catttcacag ttgtactcca   6180

tggtcaaccg gtgctttttt tcacatcgtg gtacttgtca aaacattttg ttattttcct   6240

tggtaaaata tataaaaaag gttttctaat ttcaaaaaaa aaaaaaaaaa a            6291
```

<210> SEQ ID NO 6
<211> LENGTH: 942
<212> TYPE: PRT
<213> ORGANISM: Homo sapiens

<400> SEQUENCE: 6

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly His Lys Leu Val Ser Glu Val Ile Gly Ala
145                 150                 155                 160

Ser Asp Leu Leu Leu Leu Leu Gly Ser Pro Glu Glu Thr Ala Phe Arg
                165                 170                 175

Ala Thr Asp Arg Gly Ser Glu Ser Asp Lys His Phe Arg Lys Val Ser
            180                 185                 190

Asp Lys Glu Lys Ile Asp Gln Leu Gln Glu Glu Leu Leu His Thr Gln
        195                 200                 205

Leu Lys Tyr Gln Arg Ile Leu Glu Arg Leu Glu Lys Glu Asn Lys Glu
    210                 215                 220

Leu Arg Lys Leu Val Leu Gln Lys Asp Asp Lys Gly Ile His His Arg
225                 230                 235                 240

Lys Leu Lys Lys Ser Leu Ile Asp Met Tyr Ser Glu Val Leu Asp Val
```

```
                245                 250                 255

Leu Ser Asp Tyr Asp Ala Ser Tyr Asn Thr Gln Asp His Leu Pro Arg
            260                 265                 270

Val Val Val Val Gly Asp Gln Ser Ala Gly Lys Thr Ser Val Leu Glu
        275                 280                 285

Met Ile Ala Gln Ala Arg Ile Phe Pro Arg Gly Ser Gly Glu Met Met
    290                 295                 300

Thr Arg Ser Pro Val Lys Val Thr Leu Ser Glu Gly Pro His His Val
305                 310                 315                 320

Ala Leu Phe Lys Asp Ser Ser Arg Glu Phe Asp Leu Thr Lys Glu Glu
                325                 330                 335

Asp Leu Ala Ala Leu Arg His Glu Ile Glu Leu Arg Met Arg Lys Asn
            340                 345                 350

Val Lys Glu Gly Cys Thr Val Ser Pro Glu Thr Ile Ser Leu Asn Val
        355                 360                 365

Lys Gly Pro Gly Leu Gln Arg Met Val Leu Val Asp Leu Pro Gly Val
    370                 375                 380

Ile Asn Thr Val Thr Ser Gly Met Ala Pro Asp Thr Lys Glu Thr Ile
385                 390                 395                 400

Phe Ser Ile Ser Lys Ala Tyr Met Gln Asn Pro Asn Ala Ile Ile Leu
                405                 410                 415

Cys Ile Gln Asp Gly Ser Val Asp Ala Glu Arg Ser Ile Val Thr Asp
            420                 425                 430

Leu Val Ser Gln Met Asp Pro His Gly Arg Arg Thr Ile Phe Val Leu
        435                 440                 445

Thr Lys Val Asp Leu Ala Glu Lys Asn Val Ala Ser Pro Ser Arg Ile
    450                 455                 460

Gln Gln Ile Ile Glu Gly Lys Leu Phe Pro Met Lys Ala Leu Gly Tyr
465                 470                 475                 480

Phe Ala Val Val Thr Gly Lys Gly Asn Ser Ser Glu Ser Ile Glu Ala
                485                 490                 495

Ile Arg Glu Tyr Glu Glu Glu Phe Phe Gln Asn Ser Lys Leu Leu Lys
            500                 505                 510

Thr Ser Met Leu Lys Ala His Gln Val Thr Thr Arg Asn Leu Ser Leu
        515                 520                 525

Ala Val Ser Asp Cys Phe Trp Lys Met Val Arg Glu Ser Val Glu Gln
    530                 535                 540

Gln Ala Asp Ser Phe Lys Ala Thr Arg Phe Asn Leu Glu Thr Glu Trp
545                 550                 555                 560

Lys Asn Asn Tyr Pro Arg Leu Arg Glu Leu Asp Arg Asn Glu Leu Phe
                565                 570                 575

Glu Lys Ala Lys Asn Glu Ile Leu Asp Glu Val Ile Ser Leu Ser Gln
            580                 585                 590

Val Thr Pro Lys His Trp Glu Glu Ile Leu Gln Gln Ser Leu Trp Glu
        595                 600                 605

Arg Val Ser Thr His Val Ile Glu Asn Ile Tyr Leu Pro Ala Ala Gln
    610                 615                 620

Thr Met Asn Ser Gly Thr Phe Asn Thr Thr Val Asp Ile Lys Leu Lys
625                 630                 635                 640

Gln Trp Thr Asp Lys Gln Leu Pro Asn Lys Ala Val Glu Val Ala Trp
                645                 650                 655

Glu Thr Leu Gln Glu Glu Phe Ser Arg Phe Met Thr Glu Pro Lys Gly
            660                 665                 670
```

```
Lys Glu His Asp Asp Ile Phe Asp Lys Leu Lys Glu Ala Val Lys Glu
        675                 680                 685

Glu Ser Ile Lys Arg His Lys Trp Asn Asp Phe Ala Glu Asp Ser Leu
    690                 695                 700

Arg Val Ile Gln His Asn Ala Leu Glu Asp Arg Ser Ile Ser Asp Lys
705                 710                 715                 720

Gln Gln Trp Asp Ala Ala Ile Tyr Phe Met Glu Glu Ala Leu Gln Ala
                725                 730                 735

Arg Leu Lys Asp Thr Glu Asn Ala Ile Glu Asn Met Val Gly Pro Asp
            740                 745                 750

Trp Lys Lys Arg Trp Leu Tyr Trp Lys Asn Arg Thr Gln Glu Gln Cys
        755                 760                 765

Val His Asn Glu Thr Lys Asn Glu Leu Glu Lys Met Leu Lys Cys Asn
    770                 775                 780

Glu Glu His Pro Ala Tyr Leu Ala Ser Asp Glu Ile Thr Thr Val Arg
785                 790                 795                 800

Lys Asn Leu Glu Ser Arg Gly Val Glu Val Asp Pro Ser Leu Ile Lys
                805                 810                 815

Asp Thr Trp His Gln Val Tyr Arg Arg His Phe Leu Lys Thr Ala Leu
            820                 825                 830

Asn His Cys Asn Leu Cys Arg Arg Gly Phe Tyr Tyr Tyr Gln Arg His
        835                 840                 845

Phe Val Asp Ser Glu Leu Glu Cys Asn Asp Val Val Leu Phe Trp Arg
    850                 855                 860

Ile Gln Arg Met Leu Ala Ile Thr Ala Asn Thr Leu Arg Gln Gln Leu
865                 870                 875                 880

Thr Asn Thr Glu Val Arg Arg Leu Glu Lys Asn Val Lys Glu Val Leu
                885                 890                 895

Glu Asp Phe Ala Glu Asp Gly Glu Lys Lys Ile Lys Leu Leu Thr Gly
            900                 905                 910

Lys Arg Val Gln Leu Ala Glu Asp Leu Lys Lys Val Arg Glu Ile Gln
        915                 920                 925

Glu Lys Leu Asp Ala Phe Ile Glu Ala Leu His Gln Glu Lys
    930                 935                 940
```

<210> SEQ ID NO 7
<211> LENGTH: 6348
<212> TYPE: DNA
<213> ORGANISM: Homo sapiens

<400> SEQUENCE: 7

```
gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgtgag gtctgccagt ctttagtgaa acacagctct    300

ggaataaaag gaagtttacc actacaaaaa ctacatctgg tttcacgaag catttatcat    360

tcacatcatc ctaccttaaa gcttcaacga ccccaattaa ggacatcctt tcagcagttc    420

tcttctctga caaaccttcc tttacgtaaa ctgaaattct ctccaattaa atatggctac    480

cagcctcgca ggaatttttg gccagcaaga ttagctacga gactcttaaa acttcgctat    540

ctcatactag gatcggctgt tgggggtggc tacacagcca aaaagacttt tgatcagtgg    600
```

```
aaagatatga taccggacct tagtgaatat aaatggattg tgcctgacat tgtgtgggaa    660
attgatgagt atatcgattt tggttctccg gaagaaacgg cgtttagagc aacagatcgt    720
ggatctgaaa gtgacaagca ttttagaaag ggtctgcttg gtgagctcat tctcttacaa    780
caacaaattc aagagcatga agaggaagcg cgcagagccg ctggccaata tagcacgagc    840
tatgcccaac agaagcgcaa ggtgtcagac aaagagaaaa ttgaccaact tcaggaagaa    900
cttctgcaca ctcagttgaa gtatcagaga atcttggaac gattagaaaa ggagaacaaa    960
gaattgagaa aattagtatt gcagaaagat gacaaaggca ttcatcatag aaagcttaag   1020
aaatctttga ttgacatgta ttctgaagtt cttgatgttc tctctgatta tgatgccagt   1080
tataatacgc aagatcatct gccacgggtt gttgtggttg gagatcagag tgctggaaag   1140
actagtgtgt tggaaatgat tgcccaagct cgaatattcc caagaggatc tggggagatg   1200
atgacacgtt ctccagttaa ggtgactctg agtgaaggtc ctcaccatgt ggccctattt   1260
aaagatagtt ctcgggagtt tgatcttacc aaagaagaag atcttgcagc attaagacat   1320
gaaatagaac ttcgaatgag gaaaaatgtg aaagaaggct gtaccgttag ccctgagacc   1380
atatccttaa atgtaaaagg ccctggacta cagaggatgg tgcttgttga cttaccaggt   1440
gtgattaata ctgtgacatc aggcatggct cctgacacaa aggaaactat tttcagtatc   1500
agcaaagctt acatgcagaa tcctaatgcc atcatactgt gtattcaaga tggatctgtg   1560
gatgctgaac gcagtattgt tacagacttg gtcagtcaaa tggaccctca tggaaggaga   1620
accatattcg ttttgaccaa agtagacctg gcagagaaaa atgtagccag tccaagcagg   1680
attcagcaga taattgaagg aaagctcttc ccaatgaaag ctttaggtta ttttgctgtt   1740
gtaacaggaa aagggaacag ctctgaaagc attgaagcta taagagaata tgaagaagag   1800
ttttttcaga attcaaagct cctaaagaca agcatgctaa aggcacacca agtgactaca   1860
agaaatttaa gccttgcagt atcagactgc ttttggaaaa tggtacgaga gtctgttgaa   1920
caacaggctg atagtttcaa agcaacacgt tttaaccttg aaactgaatg gaagaataac   1980
tatcctcgcc tgcgggaact tgaccggaat gaactatttg aaaaagctaa aaatgaaatc   2040
cttgatgaag ttatcagtct gagccaggtt acaccaaaac attgggagga aatccttcaa   2100
caatctttgt gggaaagagt atcaactcat gtgattgaaa acatctacct tccagctgcg   2160
cagaccatga attcaggaac ttttaacacc acagtggata tcaagcttaa acagtggact   2220
gataaacaac ttcctaataa agcagtagag gttgcttggg agaccctaca agaagaattt   2280
tcccgcttta tgacagaacc gaaagggaaa gagcatgatg acatatttga taaacttaaa   2340
gaggctgtta aggaagaaag tattaaacga cacaagtgga atgactttgc ggaggacagc   2400
ttgagggtta ttcaacacaa tgctttggaa gaccgatcca tatctgataa acagcaatgg   2460
gatgcagcta tttattttat ggaagaggct ctgcaggctc gtctcaagga tactgaaaat   2520
gcaattgaaa acatggtggg tccagactgg aaaaagaggt ggttatactg gaagaatcgg   2580
acccaagaac agtgtgttca caatgaaacc aagaatgaat tggagaagat gttgaaatgt   2640
aatgaggagc acccagctta tcttgcaagt gatgaaataa ccacagtccg gaagaacctt   2700
gaatcccgag gagtagaagt agatccaagc ttgattaagg atacttggca tcaagtttat   2760
agaagacatt ttttaaaaac agctctaaac cattgtaacc tttgtcgaag aggtttttat   2820
tactaccaaa ggcattttgt agattctgag ttggaatgca atgatgtggt cttgttttgg   2880
cgtatacagc gcatgcttgc tatcaccgca aatactttaa ggcaacaact tacaaatact   2940
```

-continued

```
gaagttaggc gattagagaa aaatgttaaa gaggtattgg aagattttgc tgaagatggt   3000
gagaagaaga ttaaattgct tactggtaaa cgcgttcaac tggcggaaga cctcaagaaa   3060
gttagagaaa ttcaagaaaa acttgatgct ttcattgaag ctcttcatca ggagaaataa   3120
attaaaatcg tactcataat cagctctgca tacatctgaa gaacaaaaac atcaacgtct   3180
tttgtccagc ctctttttct tctgctgttc cacctttcta aacatacaat aaagtcatgg   3240
gataaaaata atcgatgtat gttacgggcg ctttaaccat cagctgcctc tcgaatggaa   3300
gaacagtggt aatggattaa catcctattt tgttgtacta aagtgacaaa tcggaataat   3360
ataattggta tggccattag gttcagtcct tgaagataag aaacttgttc tctgtttgtt   3420
gtcttatttg tggtggcact cgtttaatgg attaactgag gttgctcaat gttcagtttc   3480
ttttccagaa atacaatgct aggtgttttg aaataaaact tatatagcaa ttgtttaaag   3540
ttatcaattg tatataaaat cacagtagcc tgctaaatca ttgtatgtgt ctgtagtatt   3600
ctattcccag aaactatttg accatgataa ttcagtttat attcaccaca tgaaagaaaa   3660
atgggtaaca gaagaaccct taaaacaggt taatttggat tgtaacgttc agtgaaagaa   3720
atttcaaccc ttcatagcca gcgaagaaat ttgccttgga agccaagtca gtaccagctt   3780
acctatttga ttcagttgct gttttctcac tctctatatc catttgaaat tgatttattt   3840
tagatgttgt atacttacgt taggctttct gttaatagtg gtttttctcc tgttgacaga   3900
gccaccggat tatgacacag gatgaggaag attaaggata atcaattgac taatttcatt   3960
tagaatatta tcaaacattt caactaggta tcagaaaaag gctttctttc ataagactat   4020
tttaaataga aattatttca acaattaaag taatgttgac catccccctc tcagctgaat   4080
aaagaaaaat ttagttcaat ttattgcaat ttaattacaa tactaccttc acaacatttt   4140
catgtgtttt aaataaatat tttttaattg gctaaaggac attcaagcaa agaaatgctt   4200
tctttactta aaatgtctat ctcatttgct gccttttcac taagccttta ctttgttaat   4260
aaaagtgtcc attgtgtgat gtttttgatt ttacagtttg ctaaatctta ttttcttgga   4320
gttgcttttt ggtaacagcc ccattgctac tccccatttt attgttttac atcaatgcat   4380
gcttcgttgt gatccctcaa gatgtaacac ttggtatgct cggttgagga tatgaaaaaa   4440
tacttccgaa accaggaatt caatgtatgt ttgttttata ctgtttgata agaaaagtag   4500
gtccagcctt aagcagcaca gatgcgctgg tagatgcata gtcaggaact ttttttattt   4560
cttttaggtc tagggacagg agtgaataga aagggaggag agctctatta tgttctatac   4620
acagattagg agatgacctt actgggtaca cccctctaac cagtgcttac aggttaatgc   4680
atgttaatga atatttttgc agttgtaaag cataacaatt acaactacac atctatttct   4740
aaagaataaa acaggaccat atttatttac ttctgtcaac tatagaaaga aagaccttca   4800
gctgtatttc cacagatttc tcccaaggaa aaggctaata ttagtcacta ctgttatcac   4860
atccctttgt ataagtttta aaaagagatg gagggagatc ttcatttctt tgaggagatc   4920
agtattgtaa cgtatgtgaa tagatgataa caattaatat tactaaaagt cccacatgag   4980
agtcctgacg ccctctccat gccccacagt aatgtggctt ctttcatggg tttttttttc   5040
ttctttttag ctgatctcat cctaagcatg ctttattttt ccttgaaagc taggtattta   5100
tcaactgcag atgttattga aagaaaataa aattcagtct caagagtaaa ccctgtgtct   5160
tgtgtctgta gttcaaaagt cagaaatgat tctaatttaa acaaaaagat actaaatata   5220
cagaagttaa attcgaacta gccacagaat catttgtttt tatgtcagaa tttgcaaaga   5280
gtggagtgga caaagctctg tatggaagac tgaacaactg taaatagatg atatccaaac   5340
```

```
ttaatttggc taggacttca attttaaaaa tcagtgtacc taggcagtgc acagcacgaa   5400

ataagtggcc cttgcagctt ccccgtttaa cccactgtgc tatagttgcg ggtggaacag   5460

tcaacctttc tagtagttta tgatattgcc ctctttgtat tcccattttc tacagttttt   5520

tccgcagact tctttctgca aattattcag cctccaaatg caaatgaatg atataaaaat   5580

aagtagggaa catggcagag agtggtgctt cccagcctca caatgtggga atttgacata   5640

ggatgagagt cagagtatag gtttaaaaga taaaatcttt agttaataat tttgtattta   5700

tttattctag atgtatgtat ctgaggaaag aaatctggta tttttgcttt ccaataaagg   5760

ggatcaaagt aatggttttt ctctcagttc tctaagctgg tctatgttat agctctagca   5820

gtatggaaat gtgctttaaa atatgcttac cttttgaatg atcatggcta tatgttgttg   5880

agatatttga aacttacctt gttttcactt gtgcactgtg aatgaacttt gtattatttt   5940

tttaaaacct tcacattacg tgtagatatt attgcaactt atattttgcc tgagcttgat   6000

caaaggtcat ttgtgtagat gagtaattaa aaaatattta aatcacatta taattctatt   6060

attggagagc atcttttaaa ttttttctg ttttaacgag ggaaagagaa acctgtatac   6120

ctagggtcat tatttgaccc catagtataa ccagattcat ggtctaacaa gctctcagtg   6180

tggcttttct ctgaatgctt gaatttcaca tgccttgcat ttcacagttg tactccatgg   6240

tcaaccggtg ctttttttca catcgtggta cttgtcaaaa cattttgtta ttttccttgg   6300

taaaatatat aaaaaaggtt ttctaatttc aaaaaaaaaa aaaaaaaa               6348
```

<210> SEQ ID NO 8
<211> LENGTH: 961
<212> TYPE: PRT
<213> ORGANISM: Homo sapiens

<400> SEQUENCE: 8

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly Ser Pro Glu Glu Thr Ala Phe Arg Ala Thr
145                 150                 155                 160

Asp Arg Gly Ser Glu Ser Asp Lys His Phe Arg Lys Gly Leu Leu Gly
                165                 170                 175

Glu Leu Ile Leu Leu Gln Gln Gln Ile Gln Glu His Glu Glu Glu Ala
            180                 185                 190
```

```
Arg Arg Ala Ala Gly Gln Tyr Ser Thr Ser Tyr Ala Gln Gln Lys Arg
        195                 200                 205

Lys Val Ser Asp Lys Glu Lys Ile Asp Gln Leu Gln Glu Glu Leu Leu
    210                 215                 220

His Thr Gln Leu Lys Tyr Gln Arg Ile Leu Glu Arg Leu Glu Lys Glu
225                 230                 235                 240

Asn Lys Glu Leu Arg Lys Leu Val Leu Gln Lys Asp Asp Lys Gly Ile
                245                 250                 255

His His Arg Lys Leu Lys Lys Ser Leu Ile Asp Met Tyr Ser Glu Val
            260                 265                 270

Leu Asp Val Leu Ser Asp Tyr Asp Ala Ser Tyr Asn Thr Gln Asp His
        275                 280                 285

Leu Pro Arg Val Val Val Val Gly Asp Gln Ser Ala Gly Lys Thr Ser
    290                 295                 300

Val Leu Glu Met Ile Ala Gln Ala Arg Ile Phe Pro Arg Gly Ser Gly
305                 310                 315                 320

Glu Met Met Thr Arg Ser Pro Val Lys Val Thr Leu Ser Glu Gly Pro
                325                 330                 335

His His Val Ala Leu Phe Lys Asp Ser Ser Arg Glu Phe Asp Leu Thr
            340                 345                 350

Lys Glu Glu Asp Leu Ala Ala Leu Arg His Glu Ile Glu Leu Arg Met
        355                 360                 365

Arg Lys Asn Val Lys Glu Gly Cys Thr Val Ser Pro Glu Thr Ile Ser
    370                 375                 380

Leu Asn Val Lys Gly Pro Gly Leu Gln Arg Met Val Leu Val Asp Leu
385                 390                 395                 400

Pro Gly Val Ile Asn Thr Val Thr Ser Gly Met Ala Pro Asp Thr Lys
                405                 410                 415

Glu Thr Ile Phe Ser Ile Ser Lys Ala Tyr Met Gln Asn Pro Asn Ala
            420                 425                 430

Ile Ile Leu Cys Ile Gln Asp Gly Ser Val Asp Ala Glu Arg Ser Ile
        435                 440                 445

Val Thr Asp Leu Val Ser Gln Met Asp Pro His Gly Arg Arg Thr Ile
    450                 455                 460

Phe Val Leu Thr Lys Val Asp Leu Ala Glu Lys Asn Val Ala Ser Pro
465                 470                 475                 480

Ser Arg Ile Gln Gln Ile Ile Glu Gly Lys Leu Phe Pro Met Lys Ala
                485                 490                 495

Leu Gly Tyr Phe Ala Val Val Thr Gly Lys Gly Asn Ser Ser Glu Ser
            500                 505                 510

Ile Glu Ala Ile Arg Glu Tyr Glu Glu Glu Phe Phe Gln Asn Ser Lys
        515                 520                 525

Leu Leu Lys Thr Ser Met Leu Lys Ala His Gln Val Thr Thr Arg Asn
    530                 535                 540

Leu Ser Leu Ala Val Ser Asp Cys Phe Trp Lys Met Val Arg Glu Ser
545                 550                 555                 560

Val Glu Gln Gln Ala Asp Ser Phe Lys Ala Thr Arg Phe Asn Leu Glu
                565                 570                 575

Thr Glu Trp Lys Asn Asn Tyr Pro Arg Leu Arg Glu Leu Asp Arg Asn
            580                 585                 590

Glu Leu Phe Glu Lys Ala Lys Asn Glu Ile Leu Asp Glu Val Ile Ser
        595                 600                 605

Leu Ser Gln Val Thr Pro Lys His Trp Glu Glu Ile Leu Gln Gln Ser
```

```
    610                 615                 620

Leu Trp Glu Arg Val Ser Thr His Val Ile Glu Asn Ile Tyr Leu Pro
625                 630                 635                 640

Ala Ala Gln Thr Met Asn Ser Gly Thr Phe Asn Thr Thr Val Asp Ile
                645                 650                 655

Lys Leu Lys Gln Trp Thr Asp Lys Gln Leu Pro Asn Lys Ala Val Glu
            660                 665                 670

Val Ala Trp Glu Thr Leu Gln Glu Glu Phe Ser Arg Phe Met Thr Glu
        675                 680                 685

Pro Lys Gly Lys Glu His Asp Asp Ile Phe Asp Lys Leu Lys Glu Ala
    690                 695                 700

Val Lys Glu Glu Ser Ile Lys Arg His Lys Trp Asn Asp Phe Ala Glu
705                 710                 715                 720

Asp Ser Leu Arg Val Ile Gln His Asn Ala Leu Glu Asp Arg Ser Ile
                725                 730                 735

Ser Asp Lys Gln Gln Trp Asp Ala Ala Ile Tyr Phe Met Glu Glu Ala
            740                 745                 750

Leu Gln Ala Arg Leu Lys Asp Thr Glu Asn Ala Ile Glu Asn Met Val
        755                 760                 765

Gly Pro Asp Trp Lys Lys Arg Trp Leu Tyr Trp Lys Asn Arg Thr Gln
    770                 775                 780

Glu Gln Cys Val His Asn Glu Thr Lys Asn Glu Leu Glu Lys Met Leu
785                 790                 795                 800

Lys Cys Asn Glu Glu His Pro Ala Tyr Leu Ala Ser Asp Glu Ile Thr
                805                 810                 815

Thr Val Arg Lys Asn Leu Glu Ser Arg Gly Val Glu Val Asp Pro Ser
            820                 825                 830

Leu Ile Lys Asp Thr Trp His Gln Val Tyr Arg Arg His Phe Leu Lys
        835                 840                 845

Thr Ala Leu Asn His Cys Asn Leu Cys Arg Arg Gly Phe Tyr Tyr Tyr
    850                 855                 860

Gln Arg His Phe Val Asp Ser Glu Leu Glu Cys Asn Asp Val Val Leu
865                 870                 875                 880

Phe Trp Arg Ile Gln Arg Met Leu Ala Ile Thr Ala Asn Thr Leu Arg
                885                 890                 895

Gln Gln Leu Thr Asn Thr Glu Val Arg Arg Leu Glu Lys Asn Val Lys
            900                 905                 910

Glu Val Leu Glu Asp Phe Ala Glu Asp Gly Glu Lys Lys Ile Lys Leu
        915                 920                 925

Leu Thr Gly Lys Arg Val Gln Leu Ala Glu Asp Leu Lys Lys Val Arg
    930                 935                 940

Glu Ile Gln Glu Lys Leu Asp Ala Phe Ile Glu Ala Leu His Gln Glu
945                 950                 955                 960

Lys


<210> SEQ ID NO 9
<211> LENGTH: 6399
<212> TYPE: DNA
<213> ORGANISM: Homo sapiens

<400> SEQUENCE: 9

gtgctgcccg cctagaaagg gtgaagtggt tgtttccgtg acggactgag tacgggtgcc      60

tgtcaggctc ttgcggaagt ccatgcgcca ttgggagggc ctcggccgcg gctctgtgcc     120
```

-continued

```
cttgctgctg agggccactt cctgggtcat tcctggaccg ggagccgggc tggggctcac    180
acgggggctc ccgcgtggcc gtctcggcgc ctgcgtgacc tccccgccgg cgggatgtgg    240
cgactacgtc gggccgctgt ggcctgtgag gtctgccagt ctttagtgaa acacagctct    300
ggaataaaag gaagtttacc actacaaaaa ctacatctgg tttcacgaag catttatcat    360
tcacatcatc ctaccttaaa gcttcaacga ccccaattaa ggacatcctt tcagcagttc    420
tcttctctga caaaccttcc tttacgtaaa ctgaaattct ctccaattaa atatggctac    480
cagcctcgca ggaatttttg gccagcaaga ttagctacga gactcttaaa acttcgctat    540
ctcatactag gatcggctgt tgggggtggc tacacagcca aaaagacttt tgatcagtgg    600
aaagatatga taccggacct tagtgaatat aaatggattg tgcctgacat tgtgtgggaa    660
attgatgagt atatcgattt tgagaaaatt agaaaagccc ttcctagttc agaagacctt    720
gtaaagttag caccagactt tgacaagatt gttgaaagcc ttagcttatt gaaggacttt    780
tttacctcag gtcacaaatt ggttagtgaa gtcataggag cttctgacct acttctcttg    840
ttaggttctc cggaagaaac ggcgtttaga gcaacagatc gtggatctga aagtgacaag    900
cattttagaa aggtgtcaga caaagagaaa attgaccaac ttcaggaaga acttctgcac    960
actcagttga agtatcagag aatcttggaa cgattagaaa aggagaacaa agaattgaga   1020
aaattagtat tgcagaaaga tgacaaaggc attcatcata gaaagcttaa gaaatctttg   1080
attgacatgt attctgaagt tcttgatgtt ctctctgatt atgatgccag ttataatacg   1140
caagatcatc tgccacgggt tgttgtggtt ggagatcaga gtgctggaaa gactagtgtg   1200
ttggaaatga ttgcccaagc tcgaatattc ccaagaggat ctggggagat gatgacacgt   1260
tctccagtta aggtgactct gagtgaaggt cctcaccatg tggccctatt taaagatagt   1320
tctcgggagt ttgatcttac caaagaagaa gatcttgcag cattaagaca tgaaatagaa   1380
cttcgaatga ggaaaaatgt gaaagaaggc tgtaccgtta gccctgagac catatcctta   1440
aatgtaaaag gccctggact acagaggatg gtgcttgttg acttaccagg tgtgattaat   1500
actgtgacat caggcatggc tcctgacaca aaggaaacta ttttcagtat cagcaaagct   1560
tacatgcaga atcctaatgc catcatactg tgtattcaag atggatctgt ggatgctgaa   1620
cgcagtattg ttacagactt ggtcagtcaa atggaccctc atggaaggag aaccatattc   1680
gttttgacca aagtagacct ggcagagaaa aatgtagcca gtccaagcag gattcagcag   1740
ataattgaag gaaagctctt cccaatgaaa gctttaggtt attttgctgt tgtaacagga   1800
aaagggaaca gctctgaaag cattgaagct ataagagaat atgaagaaga gtttttttcag   1860
aattcaaagc tcctaaagac aagcatgcta aaggcacacc aagtgactac aagaaattta   1920
agccttgcag tatcagactg cttttggaaa atggtacgag agtctgttga acaacaggct   1980
gatagtttca aagcaacacg ttttaacctt gaaactgaat ggaagaataa ctatcctcgc   2040
ctgcgggaac ttgaccggaa tgaactattt gaaaaagcta aaaatgaaat ccttgatgaa   2100
gttatcagtc tgagccaggt tacaccaaaa cattgggagg aaatccttca acaatctttg   2160
tgggaaagag tatcaactca tgtgattgaa aacatctacc ttccagctgc gcagaccatg   2220
aattcaggaa cttttaacac cacagtggat atcaagctta aacagtggac tgataaacaa   2280
cttcctaata aagcagtaga ggttgcttgg gagaccctac aagaagaatt ttcccgcttt   2340
atgacagaac cgaaagggaa agagcatgat gacatatttg ataaacttaa agaggctgtt   2400
aaggaagaaa gtattaaacg acacaagtgg aatgactttg cggaggacag cttgagggtt   2460
attcaacaca atgctttgga agaccgatcc atatctgata aacagcaatg ggatgcagct   2520
```

```
atttatttta tggaagaggc tctgcaggct cgtctcaagg atactgaaaa tgcaattgaa   2580
aacatggtgg gtccagactg gaaaaagagg tggttatact ggaagaatcg gacccaagaa   2640
cagtgtgttc acaatgaaac caagaatgaa ttggagaaga tgttgaaatg taatgaggag   2700
cacccagctt atcttgcaag tgatgaaata accacagtcc ggaagaacct tgaatcccga   2760
ggagtagaag tagatccaag cttgattaag gatacttggc atcaagttta tagaagacat   2820
tttttaaaaa cagctctaaa ccattgtaac ctttgtcgaa gaggttttta ttactaccaa   2880
aggcattttg tagattctga gttggaatgc aatgatgtgg tcttgttttg gcgtatacag   2940
cgcatgcttg ctatcaccgc aaatacttta aggcaacaac ttacaaatac tgaagttagg   3000
cgattagaga aaaatgttaa agaggtattg gaagattttg ctgaagatgg tgagaagaag   3060
attaaattgc ttactggtaa acgcgttcaa ctggcggaag acctcaagaa agttagagaa   3120
attcaagaaa aacttgatgc tttcattgaa gctcttcatc aggagaaata aattaaaatc   3180
gtactcataa tcagctctgc atacatctga agaacaaaaa catcaacgtc ttttgtccag   3240
cctctttttc ttctgctgtt ccacctttct aaacatacaa taaagtcatg ggataaaaat   3300
aatcgatgta tgttacgggc gctttaacca tcagctgcct ctcgaatgga agaacagtgg   3360
taatggatta acatcctatt ttgttgtact aaagtgacaa atcggaataa tataattggt   3420
atggccatta ggttcagtcc ttgaagataa gaaacttgtt ctctgtttgt tgtcttattt   3480
gtggtggcac tcgtttaatg gattaactga ggttgctcaa tgttcagttt cttttccaga   3540
aatacaatgc taggtgtttt gaaataaaac ttatatagca attgtttaaa gttatcaatt   3600
gtatataaaa tcacagtagc ctgctaaatc attgtatgtg tctgtagtat tctattccca   3660
gaaactattt gaccatgata attcagttta tattcaccac atgaaagaaa aatgggtaac   3720
agaagaaccc ttaaaacagg ttaatttgga ttgtaacgtt cagtgaaaga aatttcaacc   3780
cttcatagcc agcgaagaaa tttgccttgg aagccaagtc agtaccagct tacctatttg   3840
attcagttgc tgttttctca ctctctatat ccatttgaaa ttgatttatt ttagatgttg   3900
tatacttacg ttaggctttc tgttaatagt ggtttttctc ctgttgacag agccaccgga   3960
ttatgacaca ggatgaggaa gattaaggat aatcaattga ctaatttcat ttagaatatt   4020
atcaaacatt tcaactaggt atcagaaaaa ggctttcttt cataagacta ttttaaatag   4080
aaattatttc aacaattaaa gtaatgttga ccatcccccct ctcagctgaa taaagaaaaa   4140
tttagttcaa tttattgcaa tttaattaca atactacctt cacaacattt tcatgtgttt   4200
taaataaata ttttttaatt ggctaaagga cattcaagca aagaaatgct ttctttactt   4260
aaaatgtcta tctcatttgc tgccttttca ctaagccttt actttgttaa taaaagtgtc   4320
cattgtgtga tgtttttgat tttacagttt gctaaatctt attttcttgg agttgctttt   4380
tggtaacagc cccattgcta ctccccattt tattgtttta catcaatgca tgcttcgttg   4440
tgatccctca agatgtaaca cttggtatgc tcggttgagg atatgaaaaa atacttccga   4500
aaccaggaat tcaatgtatg tttgttttat actgtttgat aagaaaagta ggtccagcct   4560
taagcagcac agatgcgctg gtagatgcat agtcaggaac ttttttttatt tcttttaggt   4620
ctagggacag gagtgaatag aaagggagga gagctctatt atgttctata cacagattag   4680
gagatgacct tactgggtac acccctctaa ccagtgctta caggttaatg catgttaatg   4740
aatatttttg cagttgtaaa gcataacaat tacaactaca catctatttc taaagaataa   4800
aacaggacca tatttattta cttctgtcaa ctatagaaag aaagaccttc agctgtattt   4860
```

```
ccacagattt ctcccaagga aaaggctaat attagtcact actgttatca catccctttg   4920

tataagtttt aaaaagagat ggagggagat cttcatttct ttgaggagat cagtattgta   4980

acgtatgtga atagatgata acaattaata ttactaaaag tcccacatga gagtcctgac   5040

gccctctcca tgccccacag taatgtggct tctttcatgg gttttttttt cttcttttta   5100

gctgatctca tcctaagcat gctttatttt tccttgaaag ctaggtattt atcaactgca   5160

gatgttattg aaagaaaata aaattcagtc tcaagagtaa accctgtgtc ttgtgtctgt   5220

agttcaaaag tcagaaatga ttctaattta aacaaaaaga tactaaatat acagaagtta   5280

aattcgaact agccacagaa tcatttgttt ttatgtcaga atttgcaaag agtggagtgg   5340

acaaagctct gtatggaaga ctgaacaact gtaaatagat gatatccaaa cttaatttgg   5400

ctaggacttc aattttaaaa atcagtgtac ctaggcagtg cacagcacga aataagtggc   5460

ccttgcagct tccccgttta acccactgtg ctatagttgc gggtggaaca gtcaaccttt   5520

ctagtagttt atgatattgc cctctttgta ttcccatttt ctacagtttt ttccgcagac   5580

ttctttctgc aaattattca gcctccaaat gcaaatgaat gatataaaaa taagtaggga   5640

acatggcaga gagtggtgct tcccagcctc acaatgtggg aatttgacat aggatgagag   5700

tcagagtata ggtttaaaag ataaaatctt tagttaataa ttttgtattt atttattcta   5760

gatgtatgta tctgaggaaa gaaatctggt atttttgctt tccaataaag gggatcaaag   5820

taatggtttt tctctcagtt ctctaagctg gtctatgtta tagctctagc agtatggaaa   5880

tgtgctttaa aatatgctta ccttttgaat gatcatggct atatgttgtt gagatatttg   5940

aaacttacct tgttttcact tgtgcactgt gaatgaactt tgtattattt ttttaaaacc   6000

ttcacattac gtgtagatat tattgcaact tatattttgc ctgagcttga tcaaaggtca   6060

tttgtgtaga tgagtaatta aaaaatattt aaatcacatt ataattctat tattggagag   6120

catcttttaa atttttttct gttttaacga gggaaagaga aacctgtata cctagggtca   6180

ttatttgacc ccatagtata accagattca tggtctaaca agctctcagt gtggcttttc   6240

tctgaatgct tgaatttcac atgccttgca tttcacagtt gtactccatg gtcaaccggt   6300

gctttttttc acatcgtggt acttgtcaaa acattttgtt attttccttg gtaaaatata   6360

taaaaaaggt tttctaattt caaaaaaaaa aaaaaaaaa                         6399
```

```
<210> SEQ ID NO 10
<211> LENGTH: 978
<212> TYPE: PRT
<213> ORGANISM: Homo sapiens

<400> SEQUENCE: 10

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
```

-continued

```
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly His Lys Leu Val Ser Glu
            180                 185                 190

Val Ile Gly Ala Ser Asp Leu Leu Leu Leu Leu Gly Ser Pro Glu Glu
        195                 200                 205

Thr Ala Phe Arg Ala Thr Asp Arg Gly Ser Glu Ser Asp Lys His Phe
    210                 215                 220

Arg Lys Val Ser Asp Lys Glu Lys Ile Asp Gln Leu Gln Glu Glu Leu
225                 230                 235                 240

Leu His Thr Gln Leu Lys Tyr Gln Arg Ile Leu Glu Arg Leu Glu Lys
                245                 250                 255

Glu Asn Lys Glu Leu Arg Lys Leu Val Leu Gln Lys Asp Asp Lys Gly
            260                 265                 270

Ile His His Arg Lys Leu Lys Lys Ser Leu Ile Asp Met Tyr Ser Glu
        275                 280                 285

Val Leu Asp Val Leu Ser Asp Tyr Asp Ala Ser Tyr Asn Thr Gln Asp
    290                 295                 300

His Leu Pro Arg Val Val Val Val Gly Asp Gln Ser Ala Gly Lys Thr
305                 310                 315                 320

Ser Val Leu Glu Met Ile Ala Gln Ala Arg Ile Phe Pro Arg Gly Ser
                325                 330                 335

Gly Glu Met Met Thr Arg Ser Pro Val Lys Val Thr Leu Ser Glu Gly
            340                 345                 350

Pro His His Val Ala Leu Phe Lys Asp Ser Ser Arg Glu Phe Asp Leu
        355                 360                 365

Thr Lys Glu Glu Asp Leu Ala Ala Leu Arg His Glu Ile Glu Leu Arg
    370                 375                 380

Met Arg Lys Asn Val Lys Glu Gly Cys Thr Val Ser Pro Glu Thr Ile
385                 390                 395                 400

Ser Leu Asn Val Lys Gly Pro Gly Leu Gln Arg Met Val Leu Val Asp
                405                 410                 415

Leu Pro Gly Val Ile Asn Thr Val Thr Ser Gly Met Ala Pro Asp Thr
            420                 425                 430

Lys Glu Thr Ile Phe Ser Ile Ser Lys Ala Tyr Met Gln Asn Pro Asn
        435                 440                 445

Ala Ile Ile Leu Cys Ile Gln Asp Gly Ser Val Asp Ala Glu Arg Ser
    450                 455                 460

Ile Val Thr Asp Leu Val Ser Gln Met Asp Pro His Gly Arg Arg Thr
465                 470                 475                 480

Ile Phe Val Leu Thr Lys Val Asp Leu Ala Glu Lys Asn Val Ala Ser
                485                 490                 495

Pro Ser Arg Ile Gln Gln Ile Ile Glu Gly Lys Leu Phe Pro Met Lys
            500                 505                 510

Ala Leu Gly Tyr Phe Ala Val Val Thr Gly Lys Gly Asn Ser Ser Glu
        515                 520                 525
```

```
Ser Ile Glu Ala Ile Arg Glu Tyr Glu Glu Glu Phe Phe Gln Asn Ser
    530                 535                 540

Lys Leu Leu Lys Thr Ser Met Leu Lys Ala His Gln Val Thr Thr Arg
545                 550                 555                 560

Asn Leu Ser Leu Ala Val Ser Asp Cys Phe Trp Lys Met Val Arg Glu
                565                 570                 575

Ser Val Glu Gln Gln Ala Asp Ser Phe Lys Ala Thr Arg Phe Asn Leu
            580                 585                 590

Glu Thr Glu Trp Lys Asn Asn Tyr Pro Arg Leu Arg Glu Leu Asp Arg
        595                 600                 605

Asn Glu Leu Phe Glu Lys Ala Lys Asn Glu Ile Leu Asp Glu Val Ile
    610                 615                 620

Ser Leu Ser Gln Val Thr Pro Lys His Trp Glu Glu Ile Leu Gln Gln
625                 630                 635                 640

Ser Leu Trp Glu Arg Val Ser Thr His Val Ile Glu Asn Ile Tyr Leu
                645                 650                 655

Pro Ala Ala Gln Thr Met Asn Ser Gly Thr Phe Asn Thr Thr Val Asp
            660                 665                 670

Ile Lys Leu Lys Gln Trp Thr Asp Lys Gln Leu Pro Asn Lys Ala Val
        675                 680                 685

Glu Val Ala Trp Glu Thr Leu Gln Glu Glu Phe Ser Arg Phe Met Thr
    690                 695                 700

Glu Pro Lys Gly Lys Glu His Asp Asp Ile Phe Asp Lys Leu Lys Glu
705                 710                 715                 720

Ala Val Lys Glu Glu Ser Ile Lys Arg His Lys Trp Asn Asp Phe Ala
                725                 730                 735

Glu Asp Ser Leu Arg Val Ile Gln His Asn Ala Leu Glu Asp Arg Ser
            740                 745                 750

Ile Ser Asp Lys Gln Gln Trp Asp Ala Ala Ile Tyr Phe Met Glu Glu
        755                 760                 765

Ala Leu Gln Ala Arg Leu Lys Asp Thr Glu Asn Ala Ile Glu Asn Met
    770                 775                 780

Val Gly Pro Asp Trp Lys Lys Arg Trp Leu Tyr Trp Lys Asn Arg Thr
785                 790                 795                 800

Gln Glu Gln Cys Val His Asn Glu Thr Lys Asn Glu Leu Glu Lys Met
                805                 810                 815

Leu Lys Cys Asn Glu Glu His Pro Ala Tyr Leu Ala Ser Asp Glu Ile
            820                 825                 830

Thr Thr Val Arg Lys Asn Leu Glu Ser Arg Gly Val Glu Val Asp Pro
        835                 840                 845

Ser Leu Ile Lys Asp Thr Trp His Gln Val Tyr Arg Arg His Phe Leu
    850                 855                 860

Lys Thr Ala Leu Asn His Cys Asn Leu Cys Arg Arg Gly Phe Tyr Tyr
865                 870                 875                 880

Tyr Gln Arg His Phe Val Asp Ser Glu Leu Glu Cys Asn Asp Val Val
                885                 890                 895

Leu Phe Trp Arg Ile Gln Arg Met Leu Ala Ile Thr Ala Asn Thr Leu
            900                 905                 910

Arg Gln Gln Leu Thr Asn Thr Glu Val Arg Arg Leu Glu Lys Asn Val
        915                 920                 925

Lys Glu Val Leu Glu Asp Phe Ala Glu Asp Gly Glu Lys Lys Ile Lys
    930                 935                 940
```

```
Leu Leu Thr Gly Lys Arg Val Gln Leu Ala Glu Asp Leu Lys Lys Val
945                 950                 955                 960

Arg Glu Ile Gln Glu Lys Leu Asp Ala Phe Ile Glu Ala Leu His Gln
                965                 970                 975

Glu Lys


<210> SEQ ID NO 11
<211> LENGTH: 6402
<212> TYPE: DNA
<213> ORGANISM: Homo sapiens

<400> SEQUENCE: 11

gtgctgcccg cctagaaagg gtgaagtggt tgtttccgtg acggactgag tacgggtgcc      60

tgtcaggctc ttgcggaagt ccatgcgcca ttgggagggc ctcggccgcg gctctgtgcc     120

cttgctgctg agggccactt cctgggtcat tcctggaccg ggagccgggc tggggctcac     180

acgggggctc ccgcgtggcc gtctcggcgc ctgcgtgacc tccccgccgg cgggatgtgg     240

cgactacgtc gggccgctgt ggcctgtgag gtctgccagt ctttagtgaa acacagctct     300

ggaataaaag gaagtttacc actacaaaaa ctacatctgg tttcacgaag catttatcat     360

tcacatcatc ctaccttaaa gcttcaacga ccccaattaa ggacatcctt tcagcagttc     420

tcttctctga caaaccttcc tttacgtaaa ctgaaattct ctccaattaa atatggctac     480

cagcctcgca ggaatttttg gccagcaaga ttagctacga gactcttaaa acttcgctat     540

ctcatactag gatcggctgt tgggggtggc tacacagcca aaaagacttt tgatcagtgg     600

aaagatatga taccggacct tagtgaatat aaatggattg tgcctgacat tgtgtgggaa     660

attgatgagt atatcgattt tggtcacaaa ttggttagtg aagtcatagg agcttctgac     720

ctacttctct tgttaggttc tccggaagaa acggcgttta gagcaacaga tcgtggatct     780

gaaagtgaca agcattttag aaagggtctg cttggtgagc tcattctctt acaacaacaa     840

attcaagagc atgaagagga agcgcgcaga gccgctggcc aatatagcac gagctatgcc     900

caacagaagc gcaaggtgtc agacaaagag aaaattgacc aacttcagga agaacttctg     960

cacactcagt tgaagtatca gagaatcttg gaacgattag aaaaggagaa caaagaattg    1020

agaaaattag tattgcagaa agatgacaaa ggcattcatc atagaaagct taagaaatct    1080

ttgattgaca tgtattctga agttcttgat gttctctctg attatgatgc cagttataat    1140

acgcaagatc atctgccacg ggttgttgtg gttggagatc agagtgctgg aaagactagt    1200

gtgttggaaa tgattgccca agctcgaata ttcccaagag gatctgggga gatgatgaca    1260

cgttctccag ttaaggtgac tctgagtgaa ggtcctcacc atgtggccct atttaaagat    1320

agttctcggg agtttgatct taccaaagaa gaagatcttg cagcattaag acatgaaata    1380

gaacttcgaa tgaggaaaaa tgtgaaagaa ggctgtaccg ttagccctga gaccatatcc    1440

ttaaatgtaa aaggccctgg actacagagg atggtgcttg ttgacttacc aggtgtgatt    1500

aatactgtga catcaggcat ggctcctgac acaaaggaaa ctattttcag tatcagcaaa    1560

gcttacatgc agaatcctaa tgccatcata ctgtgtattc aagatggatc tgtggatgct    1620

gaacgcagta ttgttacaga cttggtcagt caaatggacc ctcatggaag gagaaccata    1680

ttcgttttga ccaaagtaga cctggcagag aaaaatgtag ccagtccaag caggattcag    1740

cagataattg aaggaaagct cttcccaatg aaagctttag gttattttgc tgttgtaaca    1800

ggaaaaggga acagctctga aagcattgaa gctataagag aatatgaaga agagtttttt    1860

cagaattcaa agctcctaaa gacaagcatg ctaaaggcac accaagtgac tacaagaaat    1920
```

```
ttaagccttg cagtatcaga ctgcttttgg aaaatggtac gagagtctgt tgaacaacag   1980
gctgatagtt tcaaagcaac acgttttaac cttgaaactg aatggaagaa taactatcct   2040
cgcctgcggg aacttgaccg gaatgaacta tttgaaaaag ctaaaaatga aatccttgat   2100
gaagttatca gtctgagcca ggttacacca aaacattggg aggaaatcct tcaacaatct   2160
ttgtgggaaa gagtatcaac tcatgtgatt gaaaacatct accttccagc tgcgcagacc   2220
atgaattcag gaacttttaa caccacagtg gatatcaagc ttaaacagtg gactgataaa   2280
caacttccta ataaagcagt agaggttgct tgggagaccc tacaagaaga attttcccgc   2340
tttatgacag aaccgaaagg gaaagagcat gatgacatat ttgataaact taaagaggct   2400
gttaaggaag aaagtattaa acgacacaag tggaatgact ttgcggagga cagcttgagg   2460
gttattcaac acaatgcttt ggaagaccga tccatatctg ataaacagca atgggatgca   2520
gctatttatt ttatggaaga ggctctgcag gctcgtctca aggatactga aaatgcaatt   2580
gaaaacatgg tgggtccaga ctggaaaaag aggtggttat actggaagaa tcggacccaa   2640
gaacagtgtg ttcacaatga aaccaagaat gaattggaga agatgttgaa atgtaatgag   2700
gagcacccag cttatcttgc aagtgatgaa ataaccacag tccggaagaa ccttgaatcc   2760
cgaggagtag aagtagatcc aagcttgatt aaggatactt ggcatcaagt ttatagaaga   2820
catttttttaa aaacagctct aaaccattgt aacctttgtc gaagaggttt ttattactac   2880
caaaggcatt ttgtagattc tgagttggaa tgcaatgatg tggtcttgtt ttggcgtata   2940
cagcgcatgc ttgctatcac cgcaaatact ttaaggcaac aacttacaaa tactgaagtt   3000
aggcgattag agaaaaatgt taaagaggta ttggaagatt ttgctgaaga tggtgagaag   3060
aagattaaat tgcttactgg taaacgcgtt caactggcgg aagacctcaa gaaagttaga   3120
gaaattcaag aaaaacttga tgctttcatt gaagctcttc atcaggagaa ataaattaaa   3180
atcgtactca taatcagctc tgcatacatc tgaagaacaa aaacatcaac gtcttttgtc   3240
cagcctcttt ttcttctgct gttccacctt tctaaacata caataaagtc atgggataaa   3300
aataatcgat gtatgttacg ggcgctttaa ccatcagctg cctctcgaat ggaagaacag   3360
tggtaatgga ttaacatcct attttgttgt actaaagtga caaatcggaa taatataatt   3420
ggtatggcca ttaggttcag tccttgaaga taagaaactt gttctctgtt tgttgtctta   3480
tttgtggtgg cactcgttta atggattaac tgaggttgct caatgttcag tttcttttcc   3540
agaaatacaa tgctaggtgt tttgaaataa aacttatata gcaattgttt aaagttatca   3600
attgtatata aaatcacagt agcctgctaa atcattgtat gtgtctgtag tattctattc   3660
ccagaaacta tttgaccatg ataattcagt ttatattcac cacatgaaag aaaaatgggt   3720
aacagaagaa cccttaaaac aggttaattt ggattgtaac gttcagtgaa agaaatttca   3780
acccttcata gccagcgaag aaatttgcct tggaagccaa gtcagtacca gcttacctat   3840
ttgattcagt tgctgttttc tcactctcta tatccatttg aaattgattt attttagatg   3900
ttgtatactt acgttaggct ttctgttaat agtggttttt ctcctgttga cagagccacc   3960
ggattatgac acaggatgag gaagattaag gataatcaat tgactaattt catttagaat   4020
attatcaaac atttcaacta ggtatcagaa aaaggctttc tttcataaga ctattttaaa   4080
tagaaattat ttcaacaatt aaagtaatgt tgaccatccc cctctcagct gaataaagaa   4140
aaatttagtt caatttattg caatttaatt acaatactac cttcacaaca ttttcatgtg   4200
ttttaaataa atatttttta attggctaaa ggacattcaa gcaaagaaat gctttcttta   4260
```

```
cttaaaatgt ctatctcatt tgctgccttt tcactaagcc tttactttgt taataaaagt   4320

gtccattgtg tgatgttttt gattttacag tttgctaaat cttattttct tggagttgct   4380

ttttggtaac agccccattg ctactcccca ttttattgtt ttacatcaat gcatgcttcg   4440

ttgtgatccc tcaagatgta acacttggta tgctcggttg aggatatgaa aaaatacttc   4500

cgaaaccagg aattcaatgt atgtttgttt tatactgttt gataagaaaa gtaggtccag   4560

ccttaagcag cacagatgcg ctggtagatg catagtcagg aacttttttt atttctttta   4620

ggtctaggga caggagtgaa tagaaaggga ggagagctct attatgttct atacacagat   4680

taggagatga ccttactggg tacacccctc taaccagtgc ttacaggtta atgcatgtta   4740

atgaatattt ttgcagttgt aaagcataac aattacaact acacatctat ttctaaagaa   4800

taaaacagga ccatatttat ttacttctgt caactataga aagaaagacc ttcagctgta   4860

tttccacaga tttctcccaa ggaaaaggct aatattagtc actactgtta tcacatccct   4920

ttgtataagt tttaaaaaga gatggaggga gatcttcatt tctttgagga gatcagtatt   4980

gtaacgtatg tgaatagatg ataacaatta atattactaa aagtcccaca tgagagtcct   5040

gacgccctct ccatgcccca cagtaatgtg gcttctttca tgggtttttt tttcttcttt   5100

ttagctgatc tcatcctaag catgctttat ttttccttga aagctaggta tttatcaact   5160

gcagatgtta ttgaaagaaa ataaaattca gtctcaagag taaaccctgt gtcttgtgtc   5220

tgtagttcaa aagtcagaaa tgattctaat ttaaacaaaa agatactaaa tatacagaag   5280

ttaaattcga actagccaca gaatcatttg tttttatgtc agaatttgca aagagtggag   5340

tggacaaagc tctgtatgga agactgaaca actgtaaata gatgatatcc aaacttaatt   5400

tggctaggac ttcaatttta aaaatcagtg tacctaggca gtgcacagca cgaaataagt   5460

ggcccttgca gcttccccgt ttaacccact gtgctatagt tgcgggtgga acagtcaacc   5520

tttctagtag tttatgatat tgccctcttt gtattcccat tttctacagt tttttccgca   5580

gacttctttc tgcaaattat tcagcctcca aatgcaaatg aatgatataa aaataagtag   5640

ggaacatggc agagagtggt gcttcccagc ctcacaatgt gggaatttga cataggatga   5700

gagtcagagt ataggtttaa aagataaaat ctttagttaa taattttgta tttatttatt   5760

ctagatgtat gtatctgagg aaagaaatct ggtatttttg ctttccaata aaggggatca   5820

aagtaatggt ttttctctca gttctctaag ctggtctatg ttatagctct agcagtatgg   5880

aaatgtgctt taaaatatgc ttaccttttg aatgatcatg gctatatgtt gttgagatat   5940

ttgaaactta ccttgttttc acttgtgcac tgtgaatgaa ctttgtatta ttttttttaaa   6000

accttcacat tacgtgtaga tattattgca acttatattt tgcctgagct tgatcaaagg   6060

tcatttgtgt agatgagtaa ttaaaaaata tttaaatcac attataattc tattattgga   6120

gagcatcttt taaatttttt tctgttttaa cgagggaaag agaaacctgt atacctaggg   6180

tcattatttg accccatagt ataaccagat tcatggtcta acaagctctc agtgtggctt   6240

ttctctgaat gcttgaattt cacatgcctt gcatttcaca gttgtactcc atggtcaacc   6300

ggtgcttttt ttcacatcgt ggtacttgtc aaaacatttt gttattttcc ttggtaaaat   6360

atataaaaaa ggttttctaa tttcaaaaaa aaaaaaaaaa aa                      6402
```

<210> SEQ ID NO 12
<211> LENGTH: 979
<212> TYPE: PRT
<213> ORGANISM: Homo sapiens

<400> SEQUENCE: 12

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly His Lys Leu Val Ser Glu Val Ile Gly Ala
145                 150                 155                 160

Ser Asp Leu Leu Leu Leu Leu Gly Ser Pro Glu Glu Thr Ala Phe Arg
                165                 170                 175

Ala Thr Asp Arg Gly Ser Glu Ser Asp Lys His Phe Arg Lys Gly Leu
            180                 185                 190

Leu Gly Glu Leu Ile Leu Leu Gln Gln Gln Ile Gln Glu His Glu Glu
        195                 200                 205

Glu Ala Arg Arg Ala Ala Gly Gln Tyr Ser Thr Ser Tyr Ala Gln Gln
    210                 215                 220

Lys Arg Lys Val Ser Asp Lys Glu Lys Ile Asp Gln Leu Gln Glu Glu
225                 230                 235                 240

Leu Leu His Thr Gln Leu Lys Tyr Gln Arg Ile Leu Glu Arg Leu Glu
                245                 250                 255

Lys Glu Asn Lys Glu Leu Arg Lys Leu Val Leu Gln Lys Asp Asp Lys
            260                 265                 270

Gly Ile His His Arg Lys Leu Lys Lys Ser Leu Ile Asp Met Tyr Ser
        275                 280                 285

Glu Val Leu Asp Val Leu Ser Asp Tyr Asp Ala Ser Tyr Asn Thr Gln
    290                 295                 300

Asp His Leu Pro Arg Val Val Val Val Gly Asp Gln Ser Ala Gly Lys
305                 310                 315                 320

Thr Ser Val Leu Glu Met Ile Ala Gln Ala Arg Ile Phe Pro Arg Gly
                325                 330                 335

Ser Gly Glu Met Met Thr Arg Ser Pro Val Lys Val Thr Leu Ser Glu
            340                 345                 350

Gly Pro His His Val Ala Leu Phe Lys Asp Ser Ser Arg Glu Phe Asp
        355                 360                 365

Leu Thr Lys Glu Glu Asp Leu Ala Ala Leu Arg His Glu Ile Glu Leu
    370                 375                 380

Arg Met Arg Lys Asn Val Lys Glu Gly Cys Thr Val Ser Pro Glu Thr
385                 390                 395                 400

Ile Ser Leu Asn Val Lys Gly Pro Gly Leu Gln Arg Met Val Leu Val
                405                 410                 415
```

-continued

```
Asp Leu Pro Gly Val Ile Asn Thr Val Thr Ser Gly Met Ala Pro Asp
            420                 425                 430

Thr Lys Glu Thr Ile Phe Ser Ile Ser Lys Ala Tyr Met Gln Asn Pro
        435                 440                 445

Asn Ala Ile Ile Leu Cys Ile Gln Asp Gly Ser Val Asp Ala Glu Arg
    450                 455                 460

Ser Ile Val Thr Asp Leu Val Ser Gln Met Asp Pro His Gly Arg Arg
465                 470                 475                 480

Thr Ile Phe Val Leu Thr Lys Val Asp Leu Ala Glu Lys Asn Val Ala
                485                 490                 495

Ser Pro Ser Arg Ile Gln Gln Ile Ile Glu Gly Lys Leu Phe Pro Met
            500                 505                 510

Lys Ala Leu Gly Tyr Phe Ala Val Val Thr Gly Lys Gly Asn Ser Ser
        515                 520                 525

Glu Ser Ile Glu Ala Ile Arg Glu Tyr Glu Glu Glu Phe Phe Gln Asn
    530                 535                 540

Ser Lys Leu Leu Lys Thr Ser Met Leu Lys Ala His Gln Val Thr Thr
545                 550                 555                 560

Arg Asn Leu Ser Leu Ala Val Ser Asp Cys Phe Trp Lys Met Val Arg
                565                 570                 575

Glu Ser Val Glu Gln Gln Ala Asp Ser Phe Lys Ala Thr Arg Phe Asn
            580                 585                 590

Leu Glu Thr Glu Trp Lys Asn Asn Tyr Pro Arg Leu Arg Glu Leu Asp
        595                 600                 605

Arg Asn Glu Leu Phe Glu Lys Ala Lys Asn Glu Ile Leu Asp Glu Val
    610                 615                 620

Ile Ser Leu Ser Gln Val Thr Pro Lys His Trp Glu Glu Ile Leu Gln
625                 630                 635                 640

Gln Ser Leu Trp Glu Arg Val Ser Thr His Val Ile Glu Asn Ile Tyr
                645                 650                 655

Leu Pro Ala Ala Gln Thr Met Asn Ser Gly Thr Phe Asn Thr Thr Val
            660                 665                 670

Asp Ile Lys Leu Lys Gln Trp Thr Asp Lys Gln Leu Pro Asn Lys Ala
        675                 680                 685

Val Glu Val Ala Trp Glu Thr Leu Gln Glu Glu Phe Ser Arg Phe Met
    690                 695                 700

Thr Glu Pro Lys Gly Lys Glu His Asp Asp Ile Phe Asp Lys Leu Lys
705                 710                 715                 720

Glu Ala Val Lys Glu Glu Ser Ile Lys Arg His Lys Trp Asn Asp Phe
                725                 730                 735

Ala Glu Asp Ser Leu Arg Val Ile Gln His Asn Ala Leu Glu Asp Arg
            740                 745                 750

Ser Ile Ser Asp Lys Gln Gln Trp Asp Ala Ala Ile Tyr Phe Met Glu
        755                 760                 765

Glu Ala Leu Gln Ala Arg Leu Lys Asp Thr Glu Asn Ala Ile Glu Asn
    770                 775                 780

Met Val Gly Pro Asp Trp Lys Lys Arg Trp Leu Tyr Trp Lys Asn Arg
785                 790                 795                 800

Thr Gln Glu Gln Cys Val His Asn Glu Thr Lys Asn Glu Leu Glu Lys
                805                 810                 815

Met Leu Lys Cys Asn Glu Glu His Pro Ala Tyr Leu Ala Ser Asp Glu
            820                 825                 830

Ile Thr Thr Val Arg Lys Asn Leu Glu Ser Arg Gly Val Glu Val Asp
```

```
        835                 840                 845

Pro Ser Leu Ile Lys Asp Thr Trp His Gln Val Tyr Arg Arg His Phe
    850                 855                 860

Leu Lys Thr Ala Leu Asn His Cys Asn Leu Cys Arg Arg Gly Phe Tyr
865                 870                 875                 880

Tyr Tyr Gln Arg His Phe Val Asp Ser Glu Leu Glu Cys Asn Asp Val
                885                 890                 895

Val Leu Phe Trp Arg Ile Gln Arg Met Leu Ala Ile Thr Ala Asn Thr
            900                 905                 910

Leu Arg Gln Gln Leu Thr Asn Thr Glu Val Arg Arg Leu Glu Lys Asn
        915                 920                 925

Val Lys Glu Val Leu Glu Asp Phe Ala Glu Asp Gly Glu Lys Lys Ile
    930                 935                 940

Lys Leu Leu Thr Gly Lys Arg Val Gln Leu Ala Glu Asp Leu Lys Lys
945                 950                 955                 960

Val Arg Glu Ile Gln Glu Lys Leu Asp Ala Phe Ile Glu Ala Leu His
                965                 970                 975

Gln Glu Lys


<210> SEQ ID NO 13
<211> LENGTH: 6456
<212> TYPE: DNA
<213> ORGANISM: Homo sapiens

<400> SEQUENCE: 13

gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgtgag gtctgccagt ctttagtgaa acacagctct    300

ggaataaaag gaagtttacc actacaaaaa ctacatctgg tttcacgaag catttatcat    360

tcacatcatc ctaccttaaa gcttcaacga ccccaattaa ggacatcctt tcagcagttc    420

tcttctctga caaaccttcc tttacgtaaa ctgaaattct ctccaattaa atatggctac    480

cagcctcgca ggaatttttg gccagcaaga ttagctacga gactcttaaa acttcgctat    540

ctcatactag gatcggctgt tgggggtggc tacacagcca aaaagacttt tgatcagtgg    600

aaagatatga taccggacct tagtgaatat aaatggattg tgcctgacat tgtgtgggaa    660

attgatgagt atatcgattt tgagaaaatt agaaaagccc ttcctagttc agaagacctt    720

gtaaagttag caccagactt tgacaagatt gttgaaagcc ttagcttatt gaaggacttt    780

tttacctcag gttctccgga agaaacggcg tttagagcaa cagatcgtgg atctgaaagt    840

gacaagcatt ttagaaaggg tctgcttggt gagctcattc tcttacaaca acaaattcaa    900

gagcatgaag aggaagcgcg cagagccgct ggccaatata gcacgagcta tgcccaacag    960

aagcgcaagg tgtcagacaa agagaaaatt gaccaacttc aggaagaact tctgcacact   1020

cagttgaagt atcagagaat cttggaacga ttagaaaagg agaacaaaga attgagaaaa   1080

ttagtattgc agaaagatga caaaggcatt catcatagaa agcttaagaa atctttgatt   1140

gacatgtatt ctgaagttct tgatgttctc tctgattatg atgccagtta taatacgcaa   1200

gatcatctgc cacgggttgt tgtggttgga gatcagagtg ctggaaagac tagtgtgttg   1260

gaaatgattg cccaagctcg aatattccca agaggatctg ggagatgat gacacgttct   1320
```

```
ccagttaagg tgactctgag tgaaggtcct caccatgtgg ccctatttaa agatagttct   1380
cgggagtttg atcttaccaa agaagaagat cttgcagcat taagacatga aatagaactt   1440
cgaatgagga aaaatgtgaa agaaggctgt accgttagcc ctgagaccat atccttaaat   1500
gtaaaaggcc ctggactaca gaggatggtg cttgttgact taccaggtgt gattaatact   1560
gtgacatcag gcatggctcc tgacacaaag gaaactattt tcagtatcag caaagcttac   1620
atgcagaatc ctaatgccat catactgtgt attcaagatg gatctgtgga tgctgaacgc   1680
agtattgtta cagacttggt cagtcaaatg gaccctcatg gaaggagaac catattcgtt   1740
ttgaccaaag tagacctggc agagaaaaat gtagccagtc caagcaggat tcagcagata   1800
attgaaggaa agctcttccc aatgaaagct ttaggttatt ttgctgttgt aacaggaaaa   1860
gggaacagct ctgaaagcat tgaagctata agagaatatg aagaagagtt ttttcagaat   1920
tcaaagctcc taaagacaag catgctaaag gcacaccaag tgactacaag aaatttaagc   1980
cttgcagtat cagactgctt ttggaaaatg gtacgagagt ctgttgaaca acaggctgat   2040
agtttcaaag caacacgttt taaccttgaa actgaatgga agaataacta tcctcgcctg   2100
cgggaacttg accggaatga actatttgaa aaagctaaaa atgaaatcct tgatgaagtt   2160
atcagtctga gccaggttac accaaaacat tgggaggaaa tccttcaaca atctttgtgg   2220
gaaagagtat caactcatgt gattgaaaac atctaccttc cagctgcgca gaccatgaat   2280
tcaggaactt ttaacaccac agtggatatc aagcttaaac agtggactga taaacaactt   2340
cctaataaag cagtagaggt tgcttgggag accctacaag aagaattttc ccgctttatg   2400
acagaaccga aagggaaaga gcatgatgac atatttgata aacttaaaga ggctgttaag   2460
gaagaaagta ttaaacgaca caagtggaat gactttgcgg aggacagctt gagggttatt   2520
caacacaatg ctttggaaga ccgatccata tctgataaac agcaatggga tgcagctatt   2580
tattttatgg aagaggctct gcaggctcgt ctcaaggata ctgaaaatgc aattgaaaac   2640
atggtgggtc cagactggaa aaagaggtgg ttatactgga agaatcggac ccaagaacag   2700
tgtgttcaca atgaaaccaa gaatgaattg gagaagatgt tgaaatgtaa tgaggagcac   2760
ccagcttatc ttgcaagtga tgaaataacc acagtccgga agaaccttga atcccgagga   2820
gtagaagtag atccaagctt gattaaggat acttggcatc aagtttatag aagacatttt   2880
ttaaaaaacag ctctaaacca ttgtaacctt tgtcgaagag gtttttatta ctaccaaagg   2940
cattttgtag attctgagtt ggaatgcaat gatgtggtct tgttttggcg tatacagcgc   3000
atgcttgcta tcaccgcaaa tactttaagg caacaactta caaatactga agttaggcga   3060
ttagagaaaa atgttaaaga ggtattggaa gattttgctg aagatggtga gaagaagatt   3120
aaattgctta ctggtaaacg cgttcaactg gcggaagacc tcaagaaagt tagagaaatt   3180
caagaaaaac ttgatgcttt cattgaagct cttcatcagg agaaataaat taaaatcgta   3240
ctcataatca gctctgcata catctgaaga acaaaaacat caacgtcttt tgtccagcct   3300
ctttttcttc tgctgttcca cctttctaaa catacaataa agtcatggga taaaaataat   3360
cgatgtatgt tacgggcgct ttaaccatca gctgcctctc gaatggaaga acagtggtaa   3420
tggattaaca tcctattttg ttgtactaaa gtgacaaatc ggaataatat aattggtatg   3480
gccattaggt tcagtccttg aagataagaa acttgttctc tgtttgttgt cttatttgtg   3540
gtggcactcg tttaatggat taactgaggt tgctcaatgt tcagtttctt ttccagaaat   3600
acaatgctag gtgttttgaa ataaaactta tatagcaatt gtttaaagtt atcaattgta   3660
```

```
tataaaatca cagtagcctg ctaaatcatt gtatgtgtct gtagtattct attcccagaa   3720
actatttgac catgataatt cagtttatat tcaccacatg aaagaaaaat gggtaacaga   3780
agaaccctta aaacaggtta atttggattg taacgttcag tgaaagaaat ttcaaccctt   3840
catagccagc gaagaaattt gccttggaag ccaagtcagt accagcttac ctatttgatt   3900
cagttgctgt tttctcactc tctatatcca tttgaaattg atttatttta gatgttgtat   3960
acttacgtta ggctttctgt taatagtggt ttttctcctg ttgacagagc caccggatta   4020
tgacacagga tgaggaagat taaggataat caattgacta atttcattta gaatattatc   4080
aaacatttca actaggtatc agaaaaaggc tttctttcat aagactattt taaatagaaa   4140
ttatttcaac aattaaagta atgttgacca tccccctctc agctgaataa agaaaaattt   4200
agttcaattt attgcaattt aattacaata ctaccttcac aacattttca tgtgttttaa   4260
ataaatattt tttaattggc taaaggacat tcaagcaaag aaatgctttc tttacttaaa   4320
atgtctatct catttgctgc cttttcacta agcctttact ttgttaataa aagtgtccat   4380
tgtgtgatgt ttttgatttt acagtttgct aaatcttatt ttcttggagt tgctttttgg   4440
taacagcccc attgctactc cccattttat tgttttacat caatgcatgc ttcgttgtga   4500
tccctcaaga tgtaacactt ggtatgctcg gttgaggata tgaaaaaata cttccgaaac   4560
caggaattca atgtatgttt gttttatact gtttgataag aaaagtaggt ccagccttaa   4620
gcagcacaga tgcgctggta gatgcatagt caggaacttt ttttatttct tttaggtcta   4680
gggacaggag tgaatagaaa gggaggagag ctctattatg ttctatacac agattaggag   4740
atgaccttac tgggtacacc cctctaacca gtgcttacag gttaatgcat gttaatgaat   4800
atttttgcag ttgtaaagca taacaattac aactacacat ctatttctaa agaataaaac   4860
aggaccatat ttatttactt ctgtcaacta tagaaagaaa gaccttcagc tgtatttcca   4920
cagatttctc ccaaggaaaa ggctaatatt agtcactact gttatcacat ccctttgtat   4980
aagttttaaa aagagatgga gggagatctt catttctttg aggagatcag tattgtaacg   5040
tatgtgaata gatgataaca attaatatta ctaaaagtcc cacatgagag tcctgacgcc   5100
ctctccatgc cccacagtaa tgtggcttct ttcatgggtt tttttttctt ctttttagct   5160
gatctcatcc taagcatgct ttatttttcc ttgaaagcta ggtatttatc aactgcagat   5220
gttattgaaa gaaaataaaa ttcagtctca agagtaaacc ctgtgtcttg tgtctgtagt   5280
tcaaaagtca gaaatgattc taatttaaac aaaaagatac taaatataca gaagttaaat   5340
tcgaactagc cacagaatca tttgttttta tgtcagaatt tgcaaagagt ggagtggaca   5400
aagctctgta tggaagactg aacaactgta aatagatgat atccaaactt aatttggcta   5460
ggacttcaat tttaaaaatc agtgtaccta ggcagtgcac agcacgaaat aagtggccct   5520
tgcagcttcc ccgtttaacc cactgtgcta tagttgcggg tggaacagtc aacctttcta   5580
gtagtttatg atattgccct ctttgtattc ccattttcta cagtttttttc cgcagacttc   5640
tttctgcaaa ttattcagcc tccaaatgca aatgaatgat ataaaaataa gtagggaaca   5700
tggcagagag tggtgcttcc cagcctcaca atgtgggaat ttgacatagg atgagagtca   5760
gagtataggt ttaaaagata aaatctttag ttaataattt tgtatttatt tattctagat   5820
gtatgtatct gaggaaagaa atctggtatt tttgctttcc aataaagggg atcaaagtaa   5880
tggtttttct ctcagttctc taagctggtc tatgttatag ctctagcagt atggaaatgt   5940
gctttaaaat atgcttacct tttgaatgat catggctata tgttgttgag atatttgaaa   6000
cttaccttgt tttcacttgt gcactgtgaa tgaactttgt attatttttt taaaaccttc   6060
```

```
acattacgtg tagatattat tgcaacttat attttgcctg agcttgatca aaggtcattt   6120

gtgtagatga gtaattaaaa aatatttaaa tcacattata attctattat tggagagcat   6180

cttttaaatt tttttctgtt ttaacgaggg aaagagaaac ctgtatacct agggtcatta   6240

tttgacccca tagtataacc agattcatgg tctaacaagc tctcagtgtg gcttttctct   6300

gaatgcttga atttcacatg ccttgcattt cacagttgta ctccatggtc aaccggtgct   6360

ttttttcaca tcgtggtact tgtcaaaaca ttttgttatt ttccttggta aaatatataa   6420

aaaaggtttt ctaatttcaa aaaaaaaaaa aaaaaa                             6456


<210> SEQ ID NO 14
<211> LENGTH: 997
<212> TYPE: PRT
<213> ORGANISM: Homo sapiens

<400> SEQUENCE: 14

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly Ser Pro Glu Glu Thr Ala
            180                 185                 190

Phe Arg Ala Thr Asp Arg Gly Ser Glu Ser Asp Lys His Phe Arg Lys
        195                 200                 205

Gly Leu Leu Gly Glu Leu Ile Leu Leu Gln Gln Gln Ile Gln Glu His
    210                 215                 220

Glu Glu Glu Ala Arg Arg Ala Ala Gly Gln Tyr Ser Thr Ser Tyr Ala
225                 230                 235                 240

Gln Gln Lys Arg Lys Val Ser Asp Lys Glu Lys Ile Asp Gln Leu Gln
                245                 250                 255

Glu Glu Leu Leu His Thr Gln Leu Lys Tyr Gln Arg Ile Leu Glu Arg
            260                 265                 270

Leu Glu Lys Glu Asn Lys Glu Leu Arg Lys Leu Val Leu Gln Lys Asp
        275                 280                 285

Asp Lys Gly Ile His His Arg Lys Leu Lys Lys Ser Leu Ile Asp Met
    290                 295                 300
```

```
Tyr Ser Glu Val Leu Asp Val Leu Ser Asp Tyr Asp Ala Ser Tyr Asn
305                 310                 315                 320

Thr Gln Asp His Leu Pro Arg Val Val Val Val Gly Asp Gln Ser Ala
                325                 330                 335

Gly Lys Thr Ser Val Leu Glu Met Ile Ala Gln Ala Arg Ile Phe Pro
            340                 345                 350

Arg Gly Ser Gly Glu Met Met Thr Arg Ser Pro Val Lys Val Thr Leu
        355                 360                 365

Ser Glu Gly Pro His His Val Ala Leu Phe Lys Asp Ser Ser Arg Glu
    370                 375                 380

Phe Asp Leu Thr Lys Glu Glu Asp Leu Ala Ala Leu Arg His Glu Ile
385                 390                 395                 400

Glu Leu Arg Met Arg Lys Asn Val Lys Glu Gly Cys Thr Val Ser Pro
                405                 410                 415

Glu Thr Ile Ser Leu Asn Val Lys Gly Pro Gly Leu Gln Arg Met Val
            420                 425                 430

Leu Val Asp Leu Pro Gly Val Ile Asn Thr Val Thr Ser Gly Met Ala
        435                 440                 445

Pro Asp Thr Lys Glu Thr Ile Phe Ser Ile Ser Lys Ala Tyr Met Gln
    450                 455                 460

Asn Pro Asn Ala Ile Ile Leu Cys Ile Gln Asp Gly Ser Val Asp Ala
465                 470                 475                 480

Glu Arg Ser Ile Val Thr Asp Leu Val Ser Gln Met Asp Pro His Gly
                485                 490                 495

Arg Arg Thr Ile Phe Val Leu Thr Lys Val Asp Leu Ala Glu Lys Asn
            500                 505                 510

Val Ala Ser Pro Ser Arg Ile Gln Gln Ile Ile Glu Gly Lys Leu Phe
        515                 520                 525

Pro Met Lys Ala Leu Gly Tyr Phe Ala Val Val Thr Gly Lys Gly Asn
    530                 535                 540

Ser Ser Glu Ser Ile Glu Ala Ile Arg Glu Tyr Glu Glu Glu Phe Phe
545                 550                 555                 560

Gln Asn Ser Lys Leu Leu Lys Thr Ser Met Leu Lys Ala His Gln Val
                565                 570                 575

Thr Thr Arg Asn Leu Ser Leu Ala Val Ser Asp Cys Phe Trp Lys Met
            580                 585                 590

Val Arg Glu Ser Val Glu Gln Gln Ala Asp Ser Phe Lys Ala Thr Arg
        595                 600                 605

Phe Asn Leu Glu Thr Glu Trp Lys Asn Asn Tyr Pro Arg Leu Arg Glu
    610                 615                 620

Leu Asp Arg Asn Glu Leu Phe Glu Lys Ala Lys Asn Glu Ile Leu Asp
625                 630                 635                 640

Glu Val Ile Ser Leu Ser Gln Val Thr Pro Lys His Trp Glu Glu Ile
                645                 650                 655

Leu Gln Gln Ser Leu Trp Glu Arg Val Ser Thr His Val Ile Glu Asn
            660                 665                 670

Ile Tyr Leu Pro Ala Ala Gln Thr Met Asn Ser Gly Thr Phe Asn Thr
        675                 680                 685

Thr Val Asp Ile Lys Leu Lys Gln Trp Thr Asp Lys Gln Leu Pro Asn
    690                 695                 700

Lys Ala Val Glu Val Ala Trp Glu Thr Leu Gln Glu Glu Phe Ser Arg
705                 710                 715                 720
```

```
Phe Met Thr Glu Pro Lys Gly Lys Glu His Asp Asp Ile Phe Asp Lys
                725                 730                 735

Leu Lys Glu Ala Val Lys Glu Glu Ser Ile Lys Arg His Lys Trp Asn
            740                 745                 750

Asp Phe Ala Glu Asp Ser Leu Arg Val Ile Gln His Asn Ala Leu Glu
        755                 760                 765

Asp Arg Ser Ile Ser Asp Lys Gln Gln Trp Asp Ala Ala Ile Tyr Phe
    770                 775                 780

Met Glu Glu Ala Leu Gln Ala Arg Leu Lys Asp Thr Glu Asn Ala Ile
785                 790                 795                 800

Glu Asn Met Val Gly Pro Asp Trp Lys Lys Arg Trp Leu Tyr Trp Lys
                805                 810                 815

Asn Arg Thr Gln Glu Gln Cys Val His Asn Glu Thr Lys Asn Glu Leu
            820                 825                 830

Glu Lys Met Leu Lys Cys Asn Glu Glu His Pro Ala Tyr Leu Ala Ser
        835                 840                 845

Asp Glu Ile Thr Thr Val Arg Lys Asn Leu Glu Ser Arg Gly Val Glu
    850                 855                 860

Val Asp Pro Ser Leu Ile Lys Asp Thr Trp His Gln Val Tyr Arg Arg
865                 870                 875                 880

His Phe Leu Lys Thr Ala Leu Asn His Cys Asn Leu Cys Arg Arg Gly
                885                 890                 895

Phe Tyr Tyr Tyr Gln Arg His Phe Val Asp Ser Glu Leu Glu Cys Asn
            900                 905                 910

Asp Val Val Leu Phe Trp Arg Ile Gln Arg Met Leu Ala Ile Thr Ala
        915                 920                 925

Asn Thr Leu Arg Gln Gln Leu Thr Asn Thr Glu Val Arg Arg Leu Glu
    930                 935                 940

Lys Asn Val Lys Glu Val Leu Glu Asp Phe Ala Glu Asp Gly Glu Lys
945                 950                 955                 960

Lys Ile Lys Leu Leu Thr Gly Lys Arg Val Gln Leu Ala Glu Asp Leu
                965                 970                 975

Lys Lys Val Arg Glu Ile Gln Glu Lys Leu Asp Ala Phe Ile Glu Ala
            980                 985                 990

Leu His Gln Glu Lys
        995
```

<210> SEQ ID NO 15
<211> LENGTH: 6510
<212> TYPE: DNA
<213> ORGANISM: Homo sapiens

<400> SEQUENCE: 15

```
gtgctgcccg cctagaaagg gtgaagtggt tgtttccgtg acggactgag tacgggtgcc      60

tgtcaggctc ttgcggaagt ccatgcgcca ttgggagggc ctcggccgcg gctctgtgcc     120

cttgctgctg agggccactt cctgggtcat tcctggaccg ggagccgggc tggggctcac     180

acgggggctc ccgcgtggcc gtctcggcgc ctgcgtgacc tccccgccgg cgggatgtgg     240

cgactacgtc gggccgctgt ggcctgtgag gtctgccagt ctttagtgaa acacagctct     300

ggaataaaag gaagtttacc actacaaaaa ctacatctgg tttcacgaag catttatcat     360

tcacatcatc ctaccttaaa gcttcaacga ccccaattaa ggacatcctt tcagcagttc     420

tcttctctga caaaccttcc tttacgtaaa ctgaaattct ctccaattaa atatggctac     480

cagcctcgca ggaatttttg gccagcaaga ttagctacga gactcttaaa acttcgctat     540
```

```
ctcatactag gatcggctgt tgggggtggc tacacagcca aaaagacttt tgatcagtgg    600
aaagatatga taccggacct tagtgaatat aaatggattg tgcctgacat tgtgtgggaa    660
attgatgagt atatcgattt tgagaaaatt agaaaagccc ttcctagttc agaagacctt    720
gtaaagttag caccagactt tgacaagatt gttgaaagcc ttagcttatt gaaggacttt    780
tttacctcag gtcacaaatt ggttagtgaa gtcataggag cttctgacct acttctcttg    840
ttaggttctc cggaagaaac ggcgtttaga gcaacagatc gtggatctga aagtgacaag    900
cattttagaa agggtctgct tggtgagctc attctcttac aacaacaaat tcaagagcat    960
gaagaggaag cgcgcagagc cgctggccaa tatagcacga gctatgccca acagaagcgc   1020
aaggtgtcag acaaagagaa aattgaccaa cttcaggaag aacttctgca cactcagttg   1080
aagtatcaga gaatcttgga acgattagaa aaggagaaca aagaattgag aaaattagta   1140
ttgcagaaag atgacaaagg cattcatcat agaaagctta agaaatcttt gattgacatg   1200
tattctgaag ttcttgatgt tctctctgat tatgatgcca gttataatac gcaagatcat   1260
ctgccacggg ttgttgtggt tggagatcag agtgctggaa agactagtgt gttggaaatg   1320
attgcccaag ctcgaatatt cccaagagga tctggggaga tgatgacacg ttctccagtt   1380
aaggtgactc tgagtgaagg tcctcaccat gtggccctat ttaaagatag ttctcgggag   1440
tttgatctta ccaaagaaga agatcttgca gcattaagac atgaaataga acttcgaatg   1500
aggaaaaatg tgaaagaagg ctgtaccgtt agccctgaga ccatatcctt aaatgtaaaa   1560
ggccctggac tacagaggat ggtgcttgtt gacttaccag gtgtgattaa tactgtgaca   1620
tcaggcatgg ctcctgacac aaaggaaact attttcagta tcagcaaagc ttacatgcag   1680
aatcctaatg ccatcatact gtgtattcaa gatggatctg tggatgctga acgcagtatt   1740
gttacagact tggtcagtca aatggaccct catggaagga gaaccatatt cgttttgacc   1800
aaagtagacc tggcagagaa aaatgtagcc agtccaagca ggattcagca gataattgaa   1860
ggaaagctct tcccaatgaa agctttaggt tattttgctg ttgtaacagg aaaagggaac   1920
agctctgaaa gcattgaagc tataagagaa tatgaagaag agtttttca gaattcaaag    1980
ctcctaaaga caagcatgct aaaggcacac caagtgacta caagaaattt aagccttgca   2040
gtatcagact gcttttggaa aatggtacga gagtctgttg aacaacaggc tgatagtttc   2100
aaagcaacac gttttaacct tgaaactgaa tggaagaata actatcctcg cctgcgggaa   2160
cttgaccgga atgaactatt tgaaaaagct aaaaatgaaa tccttgatga agttatcagt   2220
ctgagccagg ttacaccaaa acattgggag gaaatccttc aacaatcttt gtgggaaaga   2280
gtatcaactc atgtgattga aaacatctac cttccagctg cgcagaccat gaattcagga   2340
acttttaaca ccacagtgga tatcaagctt aaacagtgga ctgataaaca acttcctaat   2400
aaagcagtag aggttgcttg ggagacccta caagaagaat tttcccgctt tatgacagaa   2460
ccgaaaggga aagagcatga tgacatattt gataaactta aagaggctgt taaggaagaa   2520
agtattaaac gacacaagtg gaatgacttt gcggaggaca gcttgagggt tattcaacac   2580
aatgctttgg aagaccgatc catatctgat aaacagcaat gggatgcagc tatttatttt   2640
atggaagagg ctctgcaggc tcgtctcaag gatactgaaa atgcaattga aaacatggtg   2700
ggtccagact ggaaaaagag gtggttatac tggaagaatc ggacccaaga acagtgtgtt   2760
cacaatgaaa ccaagaatga attggagaag atgttgaaat gtaatgagga gcacccagct   2820
tatcttgcaa gtgatgaaat aaccacagtc cggaagaacc ttgaatcccg aggagtagaa   2880
```

-continued

```
gtagatccaa gcttgattaa ggatacttgg catcaagttt atagaagaca ttttttaaaa   2940
acagctctaa accattgtaa cctttgtcga agaggttttt attactacca aaggcatttt   3000
gtagattctg agttggaatg caatgatgtg gtcttgtttt ggcgtataca gcgcatgctt   3060
gctatcaccg caaatacttt aaggcaacaa cttacaaata ctgaagttag gcgattagag   3120
aaaaatgtta aagaggtatt ggaagatttt gctgaagatg gtgagaagaa gattaaattg   3180
cttactggta aacgcgttca actggcggaa gacctcaaga aagttagaga aattcaagaa   3240
aaacttgatg ctttcattga agctcttcat caggagaaat aaattaaaat cgtactcata   3300
atcagctctg catacatctg aagaacaaaa acatcaacgt cttttgtcca gcctcttttt   3360
cttctgctgt tccacctttc taaacataca ataaagtcat gggataaaaa taatcgatgt   3420
atgttacggg cgctttaacc atcagctgcc tctcgaatgg aagaacagtg gtaatggatt   3480
aacatcctat tttgttgtac taaagtgaca aatcggaata atataattgg tatggccatt   3540
aggttcagtc cttgaagata agaaacttgt tctctgtttg ttgtcttatt tgtggtggca   3600
ctcgtttaat ggattaactg aggttgctca atgttcagtt tcttttccag aaatacaatg   3660
ctaggtgttt tgaaataaaa cttatatagc aattgtttaa agttatcaat tgtatataaa   3720
atcacagtag cctgctaaat cattgtatgt gtctgtagta ttctattccc agaaactatt   3780
tgaccatgat aattcagttt atattcacca catgaaagaa aaatgggtaa cagaagaacc   3840
cttaaaacag gttaatttgg attgtaacgt tcagtgaaag aaatttcaac ccttcatagc   3900
cagcgaagaa atttgccttg gaagccaagt cagtaccagc ttacctattt gattcagttg   3960
ctgttttctc actctctata tccatttgaa attgatttat tttagatgtt gtatacttac   4020
gttaggcttt ctgttaatag tggtttttct cctgttgaca gagccaccgg attatgacac   4080
aggatgagga agattaagga taatcaattg actaatttca tttagaatat tatcaaacat   4140
ttcaactagg tatcagaaaa aggctttctt tcataagact attttaaata gaaattattt   4200
caacaattaa agtaatgttg accatccccc tctcagctga ataaagaaaa atttagttca   4260
atttattgca atttaattac aatactacct tcacaacatt ttcatgtgtt ttaaataaat   4320
atttttttaat tggctaaagg acattcaagc aaagaaatgc tttctttact taaaatgtct   4380
atctcatttg ctgccttttc actaagcctt tactttgtta ataaaagtgt ccattgtgtg   4440
atgtttttga ttttacagtt tgctaaatct tattttcttg gagttgcttt ttggtaacag   4500
ccccattgct actccccatt ttattgtttt acatcaatgc atgcttcgtt gtgatccctc   4560
aagatgtaac acttggtatg ctcggttgag gatatgaaaa aatacttccg aaaccaggaa   4620
ttcaatgtat gtttgtttta tactgtttga taagaaaagt aggtccagcc ttaagcagca   4680
cagatgcgct ggtagatgca tagtcaggaa cttttttttat ttcttttagg tctagggaca   4740
ggagtgaata gaaagggagg agagctctat tatgttctat acacagatta ggagatgacc   4800
ttactgggta cacccctcta accagtgctt acaggttaat gcatgttaat gaatattttt   4860
gcagttgtaa agcataacaa ttacaactac acatctattt ctaaagaata aaacaggacc   4920
atatttattt acttctgtca actatagaaa gaaagacctt cagctgtatt tccacagatt   4980
tctcccaagg aaaaggctaa tattagtcac tactgttatc acatcccttt gtataagttt   5040
taaaaagaga tggagggaga tcttcatttc tttgaggaga tcagtattgt aacgtatgtg   5100
aatagatgat aacaattaat attactaaaa gtcccacatg agagtcctga cgccctctcc   5160
atgccccaca gtaatgtggc ttctttcatg ggtttttttt tcttcttttt agctgatctc   5220
atcctaagca tgctttattt ttccttgaaa gctaggtatt tatcaactgc agatgttatt   5280
```

```
gaaagaaaat aaaattcagt ctcaagagta aaccctgtgt cttgtgtctg tagttcaaaa   5340

gtcagaaatg attctaattt aaacaaaaag atactaaata tacagaagtt aaattcgaac   5400

tagccacaga atcatttgtt tttatgtcag aatttgcaaa gagtggagtg gacaaagctc   5460

tgtatggaag actgaacaac tgtaaataga tgatatccaa acttaatttg gctaggactt   5520

caattttaaa aatcagtgta cctaggcagt gcacagcacg aaataagtgg cccttgcagc   5580

ttccccgttt aacccactgt gctatagttg cgggtggaac agtcaacctt tctagtagtt   5640

tatgatattg ccctctttgt attcccattt tctacagttt tttccgcaga cttctttctg   5700

caaattattc agcctccaaa tgcaaatgaa tgatataaaa ataagtaggg aacatggcag   5760

agagtggtgc ttcccagcct cacaatgtgg gaatttgaca taggatgaga gtcagagtat   5820

aggtttaaaa gataaaatct ttagttaata attttgtatt tatttattct agatgtatgt   5880

atctgaggaa agaaatctgg tatttttgct ttccaataaa ggggatcaaa gtaatggttt   5940

ttctctcagt tctctaagct ggtctatgtt atagctctag cagtatggaa atgtgcttta   6000

aaatatgctt accttttgaa tgatcatggc tatatgttgt tgagatattt gaaacttacc   6060

ttgttttcac ttgtgcactg tgaatgaact ttgtattatt tttttaaaac cttcacatta   6120

cgtgtagata ttattgcaac ttatattttg cctgagcttg atcaaaggtc atttgtgtag   6180

atgagtaatt aaaaaatatt taaatcacat tataattcta ttattggaga gcatctttta   6240

aatttttttc tgttttaacg agggaaagag aaacctgtat acctagggtc attatttgac   6300

cccatagtat aaccagattc atggtctaac aagctctcag tgtggctttt ctctgaatgc   6360

ttgaatttca catgccttgc atttcacagt tgtactccat ggtcaaccgg tgcttttttt   6420

cacatcgtgg tacttgtcaa aacattttgt tattttcctt ggtaaaatat ataaaaaagg   6480

ttttctaatt tcaaaaaaaa aaaaaaaaaa                                    6510


<210> SEQ ID NO 16
<211> LENGTH: 1015
<212> TYPE: PRT
<213> ORGANISM: Homo sapiens

<400> SEQUENCE: 16

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
```

```
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly His Lys Leu Val Ser Glu
            180                 185                 190

Val Ile Gly Ala Ser Asp Leu Leu Leu Leu Leu Gly Ser Pro Glu Glu
        195                 200                 205

Thr Ala Phe Arg Ala Thr Asp Arg Gly Ser Glu Ser Asp Lys His Phe
    210                 215                 220

Arg Lys Gly Leu Leu Gly Glu Leu Ile Leu Leu Gln Gln Gln Ile Gln
225                 230                 235                 240

Glu His Glu Glu Glu Ala Arg Arg Ala Ala Gly Gln Tyr Ser Thr Ser
                245                 250                 255

Tyr Ala Gln Gln Lys Arg Lys Val Ser Asp Lys Glu Lys Ile Asp Gln
            260                 265                 270

Leu Gln Glu Glu Leu Leu His Thr Gln Leu Lys Tyr Gln Arg Ile Leu
        275                 280                 285

Glu Arg Leu Glu Lys Glu Asn Lys Glu Leu Arg Lys Leu Val Leu Gln
    290                 295                 300

Lys Asp Asp Lys Gly Ile His His Arg Lys Leu Lys Lys Ser Leu Ile
305                 310                 315                 320

Asp Met Tyr Ser Glu Val Leu Asp Val Leu Ser Asp Tyr Asp Ala Ser
                325                 330                 335

Tyr Asn Thr Gln Asp His Leu Pro Arg Val Val Val Val Gly Asp Gln
            340                 345                 350

Ser Ala Gly Lys Thr Ser Val Leu Glu Met Ile Ala Gln Ala Arg Ile
        355                 360                 365

Phe Pro Arg Gly Ser Gly Glu Met Met Thr Arg Ser Pro Val Lys Val
    370                 375                 380

Thr Leu Ser Glu Gly Pro His His Val Ala Leu Phe Lys Asp Ser Ser
385                 390                 395                 400

Arg Glu Phe Asp Leu Thr Lys Glu Glu Asp Leu Ala Ala Leu Arg His
                405                 410                 415

Glu Ile Glu Leu Arg Met Arg Lys Asn Val Lys Glu Gly Cys Thr Val
            420                 425                 430

Ser Pro Glu Thr Ile Ser Leu Asn Val Lys Gly Pro Gly Leu Gln Arg
        435                 440                 445

Met Val Leu Val Asp Leu Pro Gly Val Ile Asn Thr Val Thr Ser Gly
    450                 455                 460

Met Ala Pro Asp Thr Lys Glu Thr Ile Phe Ser Ile Ser Lys Ala Tyr
465                 470                 475                 480

Met Gln Asn Pro Asn Ala Ile Ile Leu Cys Ile Gln Asp Gly Ser Val
                485                 490                 495

Asp Ala Glu Arg Ser Ile Val Thr Asp Leu Val Ser Gln Met Asp Pro
            500                 505                 510

His Gly Arg Arg Thr Ile Phe Val Leu Thr Lys Val Asp Leu Ala Glu
        515                 520                 525

Lys Asn Val Ala Ser Pro Ser Arg Ile Gln Gln Ile Ile Glu Gly Lys
    530                 535                 540

Leu Phe Pro Met Lys Ala Leu Gly Tyr Phe Ala Val Val Thr Gly Lys
545                 550                 555                 560

Gly Asn Ser Ser Glu Ser Ile Glu Ala Ile Arg Glu Tyr Glu Glu Glu
                565                 570                 575
```

```
Phe Phe Gln Asn Ser Lys Leu Leu Lys Thr Ser Met Leu Lys Ala His
            580                 585                 590

Gln Val Thr Thr Arg Asn Leu Ser Leu Ala Val Ser Asp Cys Phe Trp
        595                 600                 605

Lys Met Val Arg Glu Ser Val Glu Gln Gln Ala Asp Ser Phe Lys Ala
    610                 615                 620

Thr Arg Phe Asn Leu Glu Thr Glu Trp Lys Asn Asn Tyr Pro Arg Leu
625                 630                 635                 640

Arg Glu Leu Asp Arg Asn Glu Leu Phe Glu Lys Ala Lys Asn Glu Ile
                645                 650                 655

Leu Asp Glu Val Ile Ser Leu Ser Gln Val Thr Pro Lys His Trp Glu
            660                 665                 670

Glu Ile Leu Gln Gln Ser Leu Trp Glu Arg Val Ser Thr His Val Ile
        675                 680                 685

Glu Asn Ile Tyr Leu Pro Ala Ala Gln Thr Met Asn Ser Gly Thr Phe
    690                 695                 700

Asn Thr Thr Val Asp Ile Lys Leu Lys Gln Trp Thr Asp Lys Gln Leu
705                 710                 715                 720

Pro Asn Lys Ala Val Glu Val Ala Trp Glu Thr Leu Gln Glu Glu Phe
                725                 730                 735

Ser Arg Phe Met Thr Glu Pro Lys Gly Lys Glu His Asp Asp Ile Phe
            740                 745                 750

Asp Lys Leu Lys Glu Ala Val Lys Glu Glu Ser Ile Lys Arg His Lys
        755                 760                 765

Trp Asn Asp Phe Ala Glu Asp Ser Leu Arg Val Ile Gln His Asn Ala
    770                 775                 780

Leu Glu Asp Arg Ser Ile Ser Asp Lys Gln Gln Trp Asp Ala Ala Ile
785                 790                 795                 800

Tyr Phe Met Glu Glu Ala Leu Gln Ala Arg Leu Lys Asp Thr Glu Asn
                805                 810                 815

Ala Ile Glu Asn Met Val Gly Pro Asp Trp Lys Lys Arg Trp Leu Tyr
            820                 825                 830

Trp Lys Asn Arg Thr Gln Glu Gln Cys Val His Asn Glu Thr Lys Asn
        835                 840                 845

Glu Leu Glu Lys Met Leu Lys Cys Asn Glu Glu His Pro Ala Tyr Leu
    850                 855                 860

Ala Ser Asp Glu Ile Thr Thr Val Arg Lys Asn Leu Glu Ser Arg Gly
865                 870                 875                 880

Val Glu Val Asp Pro Ser Leu Ile Lys Asp Thr Trp His Gln Val Tyr
                885                 890                 895

Arg Arg His Phe Leu Lys Thr Ala Leu Asn His Cys Asn Leu Cys Arg
            900                 905                 910

Arg Gly Phe Tyr Tyr Tyr Gln Arg His Phe Val Asp Ser Glu Leu Glu
        915                 920                 925

Cys Asn Asp Val Val Leu Phe Trp Arg Ile Gln Arg Met Leu Ala Ile
    930                 935                 940

Thr Ala Asn Thr Leu Arg Gln Gln Leu Thr Asn Thr Glu Val Arg Arg
945                 950                 955                 960

Leu Glu Lys Asn Val Lys Glu Val Leu Glu Asp Phe Ala Glu Asp Gly
                965                 970                 975

Glu Lys Lys Ile Lys Leu Leu Thr Gly Lys Arg Val Gln Leu Ala Glu
            980                 985                 990
```

```
Asp Leu Lys Lys Val Arg Glu Ile  Gln Glu Lys Leu Asp  Ala Phe Ile
        995                 1000                1005

Glu Ala  Leu His Gln Glu Lys
    1010                1015


<210> SEQ ID NO 17
<211> LENGTH: 1953
<212> TYPE: DNA
<213> ORGANISM: Homo sapiens

<400> SEQUENCE: 17

gcgaagggcg ccccggccgg tatggcgggc aggaagtgcg ggtgcgcgcc tgcgcatagg     60

tcgggtctgc ggtgtcaccg ctttcgcttc tgcttgagta atcaagtgaa aaaatgagct    120

tcatctgtgg attgcagtct gctgctagaa accatgtttt cttccgattt aattcactgt    180

ctaactggag aaaatgtaac acattagcat ccacctcacg ggctgtcat caagtacaag     240

ttaaccatat agtaaataag tatcagggac tgggagtaaa tcagtgtgac aggtggagtt    300

ttctgcctgg aaactttcat ttttatagta cttttaacaa caaaagaaca ggaggcctct    360

caagtaccaa aagtaaggaa atttggagga ttaccagcaa atgtactgta tggaatgatg    420

ctttttcaag acagctgcta ataaaagaag ttacagcagt ccctagtctg tcagtattgc    480

atcctctaag ccctgcttcc ataagagcta ttaggaattt ccatacttct ccacggtttc    540

aagctgctcc ggttcctctc ttgttgatga ttcttaaacc agtacagaag ttatttgcaa    600

tcattgtagg caggggcata aggaaatggt ggcaggcact tcctcctaac aagaaggaag    660

tagttaaaga aaatataagg aagaataaat ggaagctatt ccttggtttg agtagttttg    720

gattgctctt tgtggtgttt tattttactc acctggaagt aagtccaatc acaggaagga    780

gcaagctact attattgggg aaagaacagt tcagactttt atcggaactg gaatatgaag    840

catggatgga agaatttaaa aatgatatgc taactgagaa agatgcccga tacctggctg    900

ttaaagaagt gctttgtcat ctaattgaat gcaataaaga tgttccaggg atctctcaga    960

tcaattgggt tattcatgtg gttgattccc caattattaa tgccttcgtg cttccaaatg   1020

gacaaatgtt tgttttcact ggatttttaa atagtgtaac cgatattcat caactttctt   1080

tccttctggg ccatgaaata gcacatgcag tacttgggca tgctgcagaa aaggctggca   1140

tggttcattt gttggatttc ctaggtatga ttttcctcac aatgatttgg gccatttgtc   1200

ctcgagatag cttggcactt ttgtgccagt ggatacagtc taaattgcag gagtatatgt   1260

ttaatagacc atacagcaga aaattggagg ccgaagctga caaaattgga ctactgcttg   1320

ctgcaaaggc ttgtgcagac ataagagcca gttcagtgtt ttggcagcaa atggagttcg   1380

ttgatagcct gcatggccaa cccaagatgc cagaatggtt atctacacac ccttctcatg   1440

gcaatcgagt tgagtacttg gatagactta tacctcaggc tctcaaaatt agagagatgt   1500

gtaattgtcc accactgtct aatccagacc ctcgattact attcaaactc agcacgaagc   1560

attttcttga agaatcagag aaagaagacc taaatatcac gaagaaacag aaaatggata   1620

ctcttcctat tcaaaaacag gagcaaatac cattaacata catagttgag aaaagaacgg   1680

gcagttgaat taaaatttat gagacacaag atatatgaag aatgttgcag tccttatcat   1740

tttatgttac tttttaaaaa atgatgtttg aagtgaaaaa aaaaaggata ttcagggtca   1800

aatcatgtac attacagata ttatctaaat tcttctagaa tttatttttc atgaaatatt   1860

gatgtatttt aatctatgtt aaaatatctt caatgaggaa aatgtcacag aataaattta   1920

tattacacat tttaaaaaaa aaaaaaaaaa aaa                                1953
```

<210> SEQ ID NO 18
<211> LENGTH: 524
<212> TYPE: PRT
<213> ORGANISM: Homo sapiens

<400> SEQUENCE: 18

```
Met Ser Phe Ile Cys Gly Leu Gln Ser Ala Ala Arg Asn His Val Phe
1               5                   10                  15

Phe Arg Phe Asn Ser Leu Ser Asn Trp Arg Lys Cys Asn Thr Leu Ala
            20                  25                  30

Ser Thr Ser Arg Gly Cys His Gln Val Gln Val Asn His Ile Val Asn
        35                  40                  45

Lys Tyr Gln Gly Leu Gly Val Asn Gln Cys Asp Arg Trp Ser Phe Leu
    50                  55                  60

Pro Gly Asn Phe His Phe Tyr Ser Thr Phe Asn Asn Lys Arg Thr Gly
65                  70                  75                  80

Gly Leu Ser Ser Thr Lys Ser Lys Glu Ile Trp Arg Ile Thr Ser Lys
                85                  90                  95

Cys Thr Val Trp Asn Asp Ala Phe Ser Arg Gln Leu Leu Ile Lys Glu
            100                 105                 110

Val Thr Ala Val Pro Ser Leu Ser Val Leu His Pro Leu Ser Pro Ala
        115                 120                 125

Ser Ile Arg Ala Ile Arg Asn Phe His Thr Ser Pro Arg Phe Gln Ala
    130                 135                 140

Ala Pro Val Pro Leu Leu Leu Met Ile Leu Lys Pro Val Gln Lys Leu
145                 150                 155                 160

Phe Ala Ile Ile Val Gly Arg Gly Ile Arg Lys Trp Trp Gln Ala Leu
                165                 170                 175

Pro Pro Asn Lys Lys Glu Val Val Lys Glu Asn Ile Arg Lys Asn Lys
            180                 185                 190

Trp Lys Leu Phe Leu Gly Leu Ser Ser Phe Gly Leu Leu Phe Val Val
        195                 200                 205

Phe Tyr Phe Thr His Leu Glu Val Ser Pro Ile Thr Gly Arg Ser Lys
    210                 215                 220

Leu Leu Leu Leu Gly Lys Glu Gln Phe Arg Leu Leu Ser Glu Leu Glu
225                 230                 235                 240

Tyr Glu Ala Trp Met Glu Glu Phe Lys Asn Asp Met Leu Thr Glu Lys
                245                 250                 255

Asp Ala Arg Tyr Leu Ala Val Lys Glu Val Leu Cys His Leu Ile Glu
            260                 265                 270

Cys Asn Lys Asp Val Pro Gly Ile Ser Gln Ile Asn Trp Val Ile His
        275                 280                 285

Val Val Asp Ser Pro Ile Ile Asn Ala Phe Val Leu Pro Asn Gly Gln
    290                 295                 300

Met Phe Val Phe Thr Gly Phe Leu Asn Ser Val Thr Asp Ile His Gln
305                 310                 315                 320

Leu Ser Phe Leu Leu Gly His Glu Ile Ala His Ala Val Leu Gly His
                325                 330                 335

Ala Ala Glu Lys Ala Gly Met Val His Leu Leu Asp Phe Leu Gly Met
            340                 345                 350

Ile Phe Leu Thr Met Ile Trp Ala Ile Cys Pro Arg Asp Ser Leu Ala
        355                 360                 365

Leu Leu Cys Gln Trp Ile Gln Ser Lys Leu Gln Glu Tyr Met Phe Asn
```

```
    370                 375                 380

Arg Pro Tyr Ser Arg Lys Leu Glu Ala Glu Ala Asp Lys Ile Gly Leu
385                 390                 395                 400

Leu Leu Ala Ala Lys Ala Cys Ala Asp Ile Arg Ala Ser Ser Val Phe
                405                 410                 415

Trp Gln Gln Met Glu Phe Val Asp Ser Leu His Gly Gln Pro Lys Met
            420                 425                 430

Pro Glu Trp Leu Ser Thr His Pro Ser His Gly Asn Arg Val Glu Tyr
        435                 440                 445

Leu Asp Arg Leu Ile Pro Gln Ala Leu Lys Ile Arg Glu Met Cys Asn
    450                 455                 460

Cys Pro Pro Leu Ser Asn Pro Asp Pro Arg Leu Leu Phe Lys Leu Ser
465                 470                 475                 480

Thr Lys His Phe Leu Glu Glu Ser Glu Lys Glu Asp Leu Asn Ile Thr
                485                 490                 495

Lys Lys Gln Lys Met Asp Thr Leu Pro Ile Gln Lys Gln Glu Gln Ile
            500                 505                 510

Pro Leu Thr Tyr Ile Val Glu Lys Arg Thr Gly Ser
        515                 520


<210> SEQ ID NO 19
<211> LENGTH: 2952
<212> TYPE: DNA
<213> ORGANISM: Homo sapiens

<400> SEQUENCE: 19

gctctaggta agcgaaacaa gccgggggac tgcgagccag ggactcgggc cgcggggcgg      60

gaagaagtgg ggcagcgctt ggccaggccg aaaggacttt gggggtgggg gctgggagtc     120

cgtgtctcga atgagggagg agaggtggag ttgccggggc tcaggcccgg cctcgagcat     180

gggcggatga gaggagtcgg gagccgaggc ctagggtcct tcgggtgagg ggagacggag     240

ccagcgagga gatggagcag aagcttgtgg aggagattct tcaagcaatc actatgtcaa     300

cagacacagg tgtttccctt ccttcatatg aggaagatca gggatcaaaa ctcattcgaa     360

aagctaaaga ggcaccattc gtacccgttg gaatagcggg ttttgcagca attgttgcat     420

atggattata taaactgaag agcaggggaa atactaaaat gtccattcat ctgatccaca     480

tgcgtgtggc agcccaaggc tttgttgtag gagcaatgac tgttggtatg ggctattcca     540

tgtatcggga attctgggca aaacctaagc cttagaagaa gagatgctgt cttggtcttg     600

ttggaggagc ttgctttagt tagatgtctt attattaaag ttacctatta ttgttggaaa     660

taaactaatt tgtatgggtt tagatggtaa catggcattt tgaatattgg cttcctttct     720

tgcaggcttg atttgcttgg tgaccgaatt actagtgact agtttactaa ctaggtcatt     780

caaggaagtc aagttaactt aaacatgtca cctaaatgca cttgatggtg ttgaaatgtc     840

caccttctta aatttttaag atgaacttag ttctaaagaa gataacaggc caatcctgaa     900

ggtactccct gtttgctgca gaatgtcaga tattttggat gttgcataag agtcctattt     960

gccccagtta attcaacttt tgtctgcctg ttttgtggac tggctggctc tgttagaact    1020

ctgtccaaaa agtgcatgga atataacttg taaagcttcc cacaattgac aatatatatg    1080

catgtgttta aaccaaatcc agaaagctta aacaatagag ctgcataata gtatttatta    1140

aagaatcaca actgtaaaca tgagaataat ttaaggattc tagtttagtt ttttgtaatt    1200

gcaaattata tttttgctgc tgatatatta gaataatttt taaatgtcat cttgaaatag    1260
```

```
aaatatgtat tttaagcact cacgcaaagg taaatgaaca cgttttaaat gtgtgtgttg   1320

ctaatttttt ccataagaat tgtaaacatt gaactgaaca aattacctat aatggatttg   1380

gttaatgact tatgagcaag ctggtttggc cagacagtat acccaaactt ttatataata   1440

tacagaaggc tatcacactt gtgaaattct cttgtctaat ctgaatttgc attccatggt   1500

gttaacatgg tatatgtatt gttattaaag taagtgaccc atgtcaaatg tcttttattt   1560

atttcatgag gaaaagcttt ctgtagagga acaaatttga gaacaagttt caggaaattg   1620

tctttttgt tgttgttctc taatcatgtt ctcctttctg tttcaacgat tttaaaaata   1680

ttttacttta tggtatgttt tatttttttt ccttttgtgg gtaatttttg ttctattgat   1740

tatccatata aatttttttt tttttttttt gagacggagt tattctctgt catcttggct   1800

ggcgtgcagt ggcacgatct tggctcactg caacttccat cccccaggtt caagtgattc   1860

tcttgcctca gcctcctgag tagctgtgat tacaggcatg caccaacatg cctggctaat   1920

ttttgtatat ttagtagaga cgaggtttca ccatgttggc caggctgatc ttgaattcct   1980

gacctcaggt tatccacctg cctcggcctc ccaaagtgct aggattacag gcgtgagcca   2040

ccacgcccag ctgattatcc atataattat aacactcttc tatttatttt cagtcaccaa   2100

taattccttt tgagcaatat ttaagcctag catatttctt ccttccctcc tcctctacta   2160

accagttctg gtcgatatat tattggattt tactcttata ctgtttgttt gtttgtttgt   2220

ttgtttattt tgagacagag tcttgctctg ttgctgaggc tggagtacag tggtgtgatc   2280

tgagctcacg gcaccctcca cctcctagct tcgtgcgatt ctgatgcttc aaccttccga   2340

gtagctggga ttacaggcat gcgccaccat gtcgggctaa tttttgtgtt tttagtaaag   2400

gcgaggtttc accatgttgg atgatcttga actcctggct tcaagagatc tatctgcctc   2460

agcctcccaa agtgctggga ttacaagcat aatccaccac acctgaccta cttttgtatg   2520

ttaaatgtga ttatacttct ctttgacttg tcagcttagc tttagctgat acactctggt   2580

gcccaactat tattgtatca gtgaacttcc actttctttt ccttttctct caatttttgt   2640

tgtatcattc ctaccttgtg aggacatata atatttacat tctgttgtca tcctcacatt   2700

tcttagttcc acagtttaaa tgtatttgaa actcaaaaca ttcccattaa tctcttggtc   2760

agctgaaatt aatgatttaa tagtttcctt aaaaaagact catggaacaa tttccctaaa   2820

tttttgccat gtcaaatatg tttatctgta gcctttacac agtaaaaaca atttggctag   2880

ataatacaat tctcagttca tatttttctt tggaatatta aagtattgct atagagaaaa   2940

aaaaaaaaaa aa                                                       2952
```

<210> SEQ ID NO 20
<211> LENGTH: 107
<212> TYPE: PRT
<213> ORGANISM: Homo sapiens

<400> SEQUENCE: 20

```
Met Glu Gln Lys Leu Val Glu Glu Ile Leu Gln Ala Ile Thr Met Ser
1               5                   10                  15

Thr Asp Thr Gly Val Ser Leu Pro Ser Tyr Glu Glu Asp Gln Gly Ser
            20                  25                  30

Lys Leu Ile Arg Lys Ala Lys Glu Ala Pro Phe Val Pro Val Gly Ile
        35                  40                  45

Ala Gly Phe Ala Ala Ile Val Ala Tyr Gly Leu Tyr Lys Leu Lys Ser
    50                  55                  60

Arg Gly Asn Thr Lys Met Ser Ile His Leu Ile His Met Arg Val Ala
```

```
65                  70                  75                  80

Ala Gln Gly Phe Val Val Gly Ala Met Thr Val Gly Met Gly Tyr Ser
                85                  90                  95

Met Tyr Arg Glu Phe Trp Ala Lys Pro Lys Pro
            100                 105


<210> SEQ ID NO 21
<211> LENGTH: 2805
<212> TYPE: DNA
<213> ORGANISM: Homo sapiens

<400> SEQUENCE: 21

gattggctgg gacggctgtg ggtggggaga agccgggagg actgggtgcg cctgcaggga     60

tcggaagccg gttggggtgt gagaggtttt ctcgctctag aacctcatag aaattctttc    120

tcagggagat tcttcaagca atcactatgt caacagacac aggtgtttcc cttccttcat    180

atgaggaaga tcagggatca aaactcattc gaaaagctaa agaggcacca ttcgtacccg    240

ttggaatagc gggttttgca gcaattgttg catatggatt atataaactg aagagcaggg    300

gaaatactaa aatgtccatt catctgatcc acatgcgtgt ggcagcccaa ggctttgttg    360

taggagcaat gactgttggt atgggctatt ccatgtatcg ggaattctgg gcaaaaccta    420

agccttagaa gaagagatgc tgtcttggtc ttgttggagg agcttgcttt agttagatgt    480

cttattatta aagttaccta ttattgttgg aaataaacta atttgtatgg gtttagatgg    540

taacatggca ttttgaatat tggcttcctt tcttgcaggc ttgatttgct tggtgaccga    600

attactagtg actagtttac taactaggtc attcaaggaa gtcaagttaa cttaaacatg    660

tcacctaaat gcacttgatg gtgttgaaat gtccaccttc ttaaattttt aagatgaact    720

tagttctaaa gaagataaca ggccaatcct gaaggtactc cctgtttgct gcagaatgtc    780

agatattttg gatgttgcat aagagtccta tttgccccag ttaattcaac ttttgtctgc    840

ctgttttgtg gactggctgg ctctgttaga actctgtcca aaaagtgcat ggaatataac    900

ttgtaaagct tcccacaatt gacaatatat atgcatgtgt ttaaaccaaa tccagaaagc    960

ttaaacaata gagctgcata atagtattta ttaaagaatc acaactgtaa acatgagaat   1020

aatttaagga ttctagttta gtttttgta attgcaaatt atatttttgc tgctgatata   1080

ttagaataat ttttaaatgt catcttgaaa tagaaatatg tattttaagc actcacgcaa   1140

aggtaaatga acacgtttta aatgtgtgtg ttgctaattt tttccataag aattgtaaac   1200

attgaactga acaaattacc tataatggat ttggttaatg acttatgagc aagctggttt   1260

ggccagacag tatacccaaa cttttatata atatacagaa ggctatcaca cttgtgaaat   1320

tctcttgtct aatctgaatt tgcattccat ggtgttaaca tggtatatgt attgttatta   1380

aagtaagtga cccatgtcaa atgtctttta tttatttcat gaggaaaagc tttctgtaga   1440

ggaacaaatt tgagaacaag tttcaggaaa ttgtcttttt tgttgttgtt ctctaatcat   1500

gttctccttt ctgtttcaac gattttaaaa atattttact ttatggtatg ttttattttt   1560

tttccttttg tgggtaattt ttgttctatt gattatccat ataaattttt tttttttttt   1620

tttgagacgg agttattctc tgtcatcttg gctggcgtgc agtggcacga tcttggctca   1680

ctgcaacttc catcccccag gttcaagtga ttctcttgcc tcagcctcct gagtagctgt   1740

gattacaggc atgcaccaac atgcctggct aatttttgta tatttagtag agacgaggtt   1800

tcaccatgtt ggccaggctg atcttgaatt cctgacctca ggttatccac ctgcctcggc   1860

ctcccaaagt gctaggatta caggcgtgag ccaccacgcc cagctgatta tccatataat   1920
```

```
tataacactc ttctatttat tttcagtcac caataattcc ttttgagcaa tatttaagcc   1980

tagcatattt cttccttccc tcctcctcta ctaaccagtt ctggtcgata tattattgga   2040

ttttactctt atactgtttg tttgtttgtt tgtttgttta ttttgagaca gagtcttgct   2100

ctgttgctga ggctggagta cagtggtgtg atctgagctc acggcaccct ccacctccta   2160

gcttcgtgcg attctgatgc ttcaaccttc cgagtagctg ggattacagg catgcgccac   2220

catgtcgggc taatttttgt gtttttagta aaggcgaggt ttcaccatgt tggatgatct   2280

tgaactcctg gcttcaagag atctatctgc ctcagcctcc caaagtgctg ggattacaag   2340

cataatccac cacacctgac ctacttttgt atgttaaatg tgattatact tctctttgac   2400

ttgtcagctt agctttagct gatacactct ggtgcccaac tattattgta tcagtgaact   2460

tccactttct tttcctttc tctcaatttt tgttgtatca ttcctacctt gtgaggacat    2520

ataatattta cattctgttg tcatcctcac atttcttagt tccacagttt aaatgtattt   2580

gaaactcaaa acattcccat taatctcttg gtcagctgaa attaatgatt taatagtttc   2640

cttaaaaaag actcatggaa caatttccct aaatttttgc catgtcaaat atgtttatct   2700

gtagccttta cacagtaaaa acaatttggc tagataatac aattctcagt tcatattttt   2760

ctttggaata ttaaagtatt gctatagaga aaaaaaaaaa aaaaa                   2805
```

<210> SEQ ID NO 22
<211> LENGTH: 93
<212> TYPE: PRT
<213> ORGANISM: Homo sapiens

<400> SEQUENCE: 22

```
Met Ser Thr Asp Thr Gly Val Ser Leu Pro Ser Tyr Glu Glu Asp Gln
1               5                   10                  15

Gly Ser Lys Leu Ile Arg Lys Ala Lys Glu Ala Pro Phe Val Pro Val
            20                  25                  30

Gly Ile Ala Gly Phe Ala Ala Ile Val Ala Tyr Gly Leu Tyr Lys Leu
        35                  40                  45

Lys Ser Arg Gly Asn Thr Lys Met Ser Ile His Leu Ile His Met Arg
    50                  55                  60

Val Ala Ala Gln Gly Phe Val Val Gly Ala Met Thr Val Gly Met Gly
65                  70                  75                  80

Tyr Ser Met Tyr Arg Glu Phe Trp Ala Lys Pro Lys Pro
                85                  90
```

<210> SEQ ID NO 23
<211> LENGTH: 1661
<212> TYPE: DNA
<213> ORGANISM: Homo sapiens

<400> SEQUENCE: 23

```
aagtcgcggc caatgggcga cgcggccgca gatccgcccg gccccgccct gccctgtgag     60

ttcctccggc cgggctgcgg ggctccgctc agtccgggag cgcagctggg ccgcggcgct    120

ccgacctccg ctttcccacc gcccgcagct gaagcacatc ccgcagcccg gcgcggactc    180

cgatcgccgc agttgccctc tggcgccatg tcgcagaacg gagcgcccgg gatgcaggag    240

gagagcctgc agggctcctg ggtagaactg cacttcagca ataatgggaa cgggggcagc    300

gttccagcct cggtttctat ttataatgga gacatggaaa aaatactgct ggacgcacag    360

catgagtctg gacggagtag ctccaagagc tctcactgtg acagcccacc tcgctcgcag    420
```

```
acaccacaag ataccaacag agcttctgaa acagataccc atagcattgg agagaaaaac    480

agctcacagt ctgaggaaga tgatattgaa agaaggaaag aagttgaaag catcttgaag    540

aaaaactcag attggatatg ggattggtca agtcggccgg aaaatattcc ccccaaggag    600

ttcctcttta aacacccgaa gcgcacggcc accctcagca tgaggaacac gagcgtcatg    660

aagaaagggg gcatattctc tgcagaattt ctgaaagttt tccttccatc tctgctgctc    720

tctcatttgc tggccatcgg attggggatc tatattggaa ggcgtctgac aacctccacc    780

agcacctttt gatgaagaac tggagtctga cttggttcgt tagtggatta cttctgagct    840

tgcaacatag ctcactgaag agctgttaga tcctggggtg gccacgtcac ttgtgtttat    900

ttgttctgta aatgctgcgt tcctaattta gtaaaataaa agaatagaca ctaaaatcat    960

gttgatctat aattacacct atgggatcaa taagcatgtc agactgatta atgtctactg   1020

tgaaaatttg gtagtaaatt ttcatttgat attagatata aatatctgaa tataaataat   1080

tttaatatac tagtcatgat gtgtgttgta ttttaaaaat tatctgcaac cttaattcag   1140

ctgaagtact ttatatttca aaagaatgaa taacattgat aataaaatcg ctactttaag   1200

gggtttgtcc aaaataaata ttgtggcctt atatatcaca ctattgtaga aagtattatt   1260

taatttaaat ggatgcaggt tgtctactaa agaaagatta tatataacta tgctaattgt   1320

tcataatcaa cagaaaccaa gatagagcta caaactcagc tgtacagttc gtacactaaa   1380

ctcttcttgc ttttgcatta taaggaatta agtctccgat tattaggtga tcaccctgga   1440

tgatcagttt tctgctgaag gcacctactc agtatctttt cctctttatc actctgcatt   1500

ggtgaattta atcctctcct ttgtgttcaa cttttgtgtg cttttaaaat cagctttatt   1560

ctaagcaaat ctgtgtctac tttaaaaaac tggaaatgga aaaaaaaata aatctttgcc   1620

aaatccttca gataaaaaaa aaaaaaaaaa aaaaaaaaaa a                        1661
```

<210> SEQ ID NO 24
<211> LENGTH: 259
<212> TYPE: PRT
<213> ORGANISM: Homo sapiens

<400> SEQUENCE: 24

```
Met Gly Asp Ala Ala Ala Asp Pro Pro Gly Pro Ala Leu Pro Cys Glu
1               5                   10                  15

Phe Leu Arg Pro Gly Cys Gly Ala Pro Leu Ser Pro Gly Ala Gln Leu
            20                  25                  30

Gly Arg Gly Ala Pro Thr Ser Ala Phe Pro Pro Pro Ala Ala Glu Ala
        35                  40                  45

His Pro Ala Ala Arg Arg Gly Leu Arg Ser Pro Gln Leu Pro Ser Gly
    50                  55                  60

Ala Met Ser Gln Asn Gly Ala Pro Gly Met Gln Glu Glu Ser Leu Gln
65                  70                  75                  80

Gly Ser Trp Val Glu Leu His Phe Ser Asn Asn Gly Asn Gly Gly Ser
                85                  90                  95

Val Pro Ala Ser Val Ser Ile Tyr Asn Gly Asp Met Glu Lys Ile Leu
            100                 105                 110

Leu Asp Ala Gln His Glu Ser Gly Arg Ser Ser Ser Lys Ser Ser His
        115                 120                 125

Cys Asp Ser Pro Pro Arg Ser Gln Thr Pro Gln Asp Thr Asn Arg Ala
    130                 135                 140

Ser Glu Thr Asp Thr His Ser Ile Gly Glu Lys Asn Ser Ser Gln Ser
145                 150                 155                 160
```

```
Glu Glu Asp Asp Ile Glu Arg Arg Lys Glu Val Glu Ser Ile Leu Lys
                165                 170                 175

Lys Asn Ser Asp Trp Ile Trp Asp Trp Ser Ser Arg Pro Glu Asn Ile
            180                 185                 190

Pro Pro Lys Glu Phe Leu Phe Lys His Pro Lys Arg Thr Ala Thr Leu
        195                 200                 205

Ser Met Arg Asn Thr Ser Val Met Lys Lys Gly Gly Ile Phe Ser Ala
    210                 215                 220

Glu Phe Leu Lys Val Phe Leu Pro Ser Leu Leu Leu Ser His Leu Leu
225                 230                 235                 240

Ala Ile Gly Leu Gly Ile Tyr Ile Gly Arg Arg Leu Thr Thr Ser Thr
                245                 250                 255

Ser Thr Phe


<210> SEQ ID NO 25
<211> LENGTH: 4403
<212> TYPE: DNA
<213> ORGANISM: Homo sapiens

<400> SEQUENCE: 25

actgttgagt tagcgcctcg ccttccgggg cggattgtct gtcgttgcag tagctgtagg      60

aaggggaggc cattttccgt ttctgggagg agtgaggggc aacgggtcgg agaaaaagga     120

aaaaagaagg gctcagcgcc tccccgccgg gccgtggaca gaggggcaca gtttcggcag     180

gcgggtgagg tcgctgaggg cccgccggag atgttttcct tgtcgagcac ggtgcaaccc     240

caggttacag ttcctctgag tcatctcatc aatgccttcc atacaccaaa aaacacttct     300

gtttctctca gtggagtgtc agtttctcaa aaccagcatc gagatgtagt tcctgagcat     360

gaggctccca gcagtgagtg tatgttcagt gacttcctga cgaagcttaa cattgtttca     420

attggcaaag gaaaaatatt cgaagggtac agatccatgt tcatggagcc agcaaaaagg     480

atgaagaaga gcttggacac aaccgataac tggcacatcc gtccagaacc cttctccctc     540

tcaatccctc cttcacttaa cttaagggac cttggattat ctgaactaaa aattggacag     600

attgatcagc tggtagaaaa tctacttcct ggattttgta aaggcaaaaa catttcttcc     660

cattggcata catcccatgt ctctgcacaa tccttctttg aaaataaata tggtaactta     720

gatatattta gtacattacg ttcctcttgc ttgtatcgac atcattcaag agctcttcaa     780

agcatttgtt cagatcttca gtactggcca gttttcatac agtctcgggg ttttaaaact     840

ttgaaatcaa ggacacgacg tctccagtct acctccgaga gattagctga aacacagaat     900

atagcgccat cattcgtgaa ggggtttctt ttgcgggaca gaggatcaga tgttgagagt     960

ttggacaaac tcatgaaaac caaaaatata cctgaagctc accaagatgc atttaaaact    1020

ggttttgcgg aaggttttct gaaagctcaa gcactcacac aaaaaaccaa tgattcccta    1080

aggcgaaccc gtctgattct cttcgttctg ctgctattcg gcatttatgg acttctaaaa    1140

aacccatttt tatctgtccg cttccggaca acaacagggc ttgattctgc agtagatcct    1200

gtccagatga aaaatgtcac ctttgaacat gttaaagggg tggaggaagc taaacaagaa    1260

ttacaggaag ttgttgaatt cttgaaaaat ccacaaaaat ttactattct tggaggtaaa    1320

cttccaaaag gaattctttt agttggaccc ccagggactg gaaagacact tcttgcccga    1380

gctgtggcgg gagaagctga tgttcctttt tattatgctt ctggatccga atttgatgag    1440

atgtttgtgg gtgtgggagc cagccgtatc agaaatcttt ttagggaagc aaaggcgaat    1500
```

```
gctccttgtg ttatatttat tgatgaatta gattctgttg gtgggaagag aattgaatct   1560
ccaatgcatc catattcaag gcagaccata aatcaacttc ttgctgaaat ggatggtttt   1620
aaacccaatg aaggagttat cataatagga gccacaaact tcccagaggc attagataat   1680
gccttaatac gtcctggtcg ttttgacatg caagttacag ttccaaggcc agatgtaaaa   1740
ggtcgaacag aaattttgaa atggtatctc aataaaataa agtttgatca atccgttgat   1800
ccagaaatta tagctcgagg tactgttggc ttttccggag cagagttgga gaatcttgtg   1860
aaccaggctg cattaaaagc agctgttgat ggaaaagaaa tggttaccat gaaggagctg   1920
gagttttcca aagacaaaat tctaatgggg cctgaaagaa gaagtgtgga aattgataac   1980
aaaaacaaaa ccatcacagc atatcatgaa tctggtcatg ccattattgc atattacaca   2040
aaagatgcaa tgcctatcaa caaagctaca atcatgccac gggggccaac acttggacat   2100
gtgtccctgt tacctgagaa tgacagatgg aatgaaacta gagcccagct gcttgcacaa   2160
atggatgtta gtatgggagg aagagtggca gaggagctta tatttggaac cgaccatatt   2220
acaacaggtg cttccagtga ttttgataat gccactaaaa tagcaaagcg gatggttacc   2280
aaatttggaa tgagtgaaaa gcttggagtt atgacctaca gtgatacagg gaaactaagt   2340
ccagaaaccc aatctgccat cgaacaagaa ataagaatcc ttctaaggga ctcatatgaa   2400
cgagcaaaac atatcttgaa aactcatgca aaggagcata agaatctcgc agaagcttta   2460
ttgacctatg agactttgga tgccaaagag attcaaattg ttcttgaggg gaaaaagttg   2520
gaagtgagat gataactctc ttgatatgga tgcttgctgg ttttattgca agaatacaag   2580
tagcattgca gtagtctact tttacaacgc tttcccctca ttcttgatgt ggtgtaattg   2640
aagggtgtga aatgctttgt caatcatttg tcacatttat ccagtttggg ttattctcat   2700
tatgacacct attgcaaatt agcatcccat ggcaaatata ttttgaaaaa ataaagaact   2760
atcaggattg aaaacagctc ttttgaggaa tgtcaattag ttattaagtt gaaagtaatt   2820
aatgatttta tgtttggtta ctctactaga tttgataaaa attgtgcctt tagccttcta   2880
tatacatcag tggaaactta agatgcagta attatgttcc agattgacca tgaataaaat   2940
attttttaat ctaaatgtag agaagttggg attaaaagca gtctcggaaa cacagagcca   3000
ggaatatagc cttttggcat ggtgccatgg ctcacatctg taatcccagc acttttggag   3060
gctgaggcgg gtggattgct tgaggccagg agttcgagac cagcctggcc aacgtggtga   3120
aacgctgtct ctactaaaat acaaaaaaat agggctgggc gcggttgctc acgcctgtaa   3180
tcccagcact tttcagaggc caaggcgggc aaatcacctg aggtcaagag tttgagacca   3240
gcctggccaa catggtgaaa ccccatctct actaaacatg caaaaattac ctgggcatgg   3300
tggcaggtgc ttataatccc agctactctg gggccaagg caggagaatt gcttgagcct    3360
gggagatgga ggttgcagtg agctgagatc atgccactgc actccagcct gggcaacaga   3420
gcaagactct gcctcaaaaa aaaattaaaa taaatttaaa tacaaaaaaa aatagccagg   3480
tgtggggtgc atgcctggaa tcccagctac ttgagaggct gaggcacgag aattgcttga   3540
acccaggagg tggaggttgc agtgagccaa gatcacagga gccactgcac tccagcctgg   3600
gtgacagagt gagactctgt ctcaaaaaaa aattaaataa attattataa cctttcagaa   3660
atgctgtgtg cattttcatg ttcttttttt tagcattact gtcactctcc ctaatgaaat   3720
gtacttcaga gaagcagtat tttgttaaat aaatacataa cctcattctg aataatgtcc   3780
ctcattttga ctataactgt gcttggtttc aaaagcaaaa ttaaacaaaa atctcagtcc   3840
cctccgaagt gaactttgtg ttaccctgcg tcagaaatgc caagttgtgt ttacttttca   3900
```

```
ttcagatttt gtgaatatga acatgctgtt ataggatcta cagatgaata tttaactcaa   3960

tagaaaaatt attttagaac acattgtatt ggtattacaa ccagattata ttcttgacgt   4020

tgacttcatt aaaattatct acaatttcct aataatttaa gctgtatatg gtcttcattg   4080

aaaaaagata gatattgtta caggaagctt gttacattat attcttgacc ttttggttga   4140

taatcttaaa tcttaatgta atttcaaact ggcagaaatg ttgccagcat aatacatgga   4200

tgtctcatat accctgcatc cagatttacc agttgttatc attctgcccg tttttattg   4260

ccccaaacct gttctgtctc cctctctgta tgtacataca tacacgtata aaatattgat   4320

aaagtcttat ctgtcttaaa ttttttttaca tatttgttga ggtataattt acatatgata   4380

aaattcattt taaatgtaaa aaa                                            4403
```

```
<210> SEQ ID NO 26
<211> LENGTH: 773
<212> TYPE: PRT
<213> ORGANISM: Homo sapiens

<400> SEQUENCE: 26

Met Phe Ser Leu Ser Ser Thr Val Gln Pro Gln Val Thr Val Pro Leu
1               5                   10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
        35                  40                  45

Glu His Glu Ala Pro Ser Ser Glu Cys Met Phe Ser Asp Phe Leu Thr
    50                  55                  60

Lys Leu Asn Ile Val Ser Ile Gly Lys Gly Lys Ile Phe Glu Gly Tyr
65                  70                  75                  80

Arg Ser Met Phe Met Glu Pro Ala Lys Arg Met Lys Lys Ser Leu Asp
                85                  90                  95

Thr Thr Asp Asn Trp His Ile Arg Pro Glu Pro Phe Ser Leu Ser Ile
            100                 105                 110

Pro Pro Ser Leu Asn Leu Arg Asp Leu Gly Leu Ser Glu Leu Lys Ile
        115                 120                 125

Gly Gln Ile Asp Gln Leu Val Glu Asn Leu Leu Pro Gly Phe Cys Lys
    130                 135                 140

Gly Lys Asn Ile Ser Ser His Trp His Thr Ser His Val Ser Ala Gln
145                 150                 155                 160

Ser Phe Phe Glu Asn Lys Tyr Gly Asn Leu Asp Ile Phe Ser Thr Leu
                165                 170                 175

Arg Ser Ser Cys Leu Tyr Arg His His Ser Arg Ala Leu Gln Ser Ile
            180                 185                 190

Cys Ser Asp Leu Gln Tyr Trp Pro Val Phe Ile Gln Ser Arg Gly Phe
        195                 200                 205

Lys Thr Leu Lys Ser Arg Thr Arg Arg Leu Gln Ser Thr Ser Glu Arg
    210                 215                 220

Leu Ala Glu Thr Gln Asn Ile Ala Pro Ser Phe Val Lys Gly Phe Leu
225                 230                 235                 240

Leu Arg Asp Arg Gly Ser Asp Val Glu Ser Leu Asp Lys Leu Met Lys
                245                 250                 255

Thr Lys Asn Ile Pro Glu Ala His Gln Asp Ala Phe Lys Thr Gly Phe
            260                 265                 270

Ala Glu Gly Phe Leu Lys Ala Gln Ala Leu Thr Gln Lys Thr Asn Asp
```

```
        275                 280                 285

Ser Leu Arg Arg Thr Arg Leu Ile Leu Phe Val Leu Leu Leu Phe Gly
    290                 295                 300

Ile Tyr Gly Leu Leu Lys Asn Pro Phe Leu Ser Val Arg Phe Arg Thr
305                 310                 315                 320

Thr Thr Gly Leu Asp Ser Ala Val Asp Pro Val Gln Met Lys Asn Val
                325                 330                 335

Thr Phe Glu His Val Lys Gly Val Glu Glu Ala Lys Gln Glu Leu Gln
            340                 345                 350

Glu Val Val Glu Phe Leu Lys Asn Pro Gln Lys Phe Thr Ile Leu Gly
        355                 360                 365

Gly Lys Leu Pro Lys Gly Ile Leu Leu Val Gly Pro Pro Gly Thr Gly
    370                 375                 380

Lys Thr Leu Leu Ala Arg Ala Val Ala Gly Glu Ala Asp Val Pro Phe
385                 390                 395                 400

Tyr Tyr Ala Ser Gly Ser Glu Phe Asp Glu Met Phe Val Gly Val Gly
                405                 410                 415

Ala Ser Arg Ile Arg Asn Leu Phe Arg Glu Ala Lys Ala Asn Ala Pro
            420                 425                 430

Cys Val Ile Phe Ile Asp Glu Leu Asp Ser Val Gly Gly Lys Arg Ile
        435                 440                 445

Glu Ser Pro Met His Pro Tyr Ser Arg Gln Thr Ile Asn Gln Leu Leu
    450                 455                 460

Ala Glu Met Asp Gly Phe Lys Pro Asn Glu Gly Val Ile Ile Ile Gly
465                 470                 475                 480

Ala Thr Asn Phe Pro Glu Ala Leu Asp Asn Ala Leu Ile Arg Pro Gly
                485                 490                 495

Arg Phe Asp Met Gln Val Thr Val Pro Arg Pro Asp Val Lys Gly Arg
            500                 505                 510

Thr Glu Ile Leu Lys Trp Tyr Leu Asn Lys Ile Lys Phe Asp Gln Ser
        515                 520                 525

Val Asp Pro Glu Ile Ile Ala Arg Gly Thr Val Gly Phe Ser Gly Ala
    530                 535                 540

Glu Leu Glu Asn Leu Val Asn Gln Ala Ala Leu Lys Ala Ala Val Asp
545                 550                 555                 560

Gly Lys Glu Met Val Thr Met Lys Glu Leu Glu Phe Ser Lys Asp Lys
                565                 570                 575

Ile Leu Met Gly Pro Glu Arg Arg Ser Val Glu Ile Asp Asn Lys Asn
            580                 585                 590

Lys Thr Ile Thr Ala Tyr His Glu Ser Gly His Ala Ile Ile Ala Tyr
        595                 600                 605

Tyr Thr Lys Asp Ala Met Pro Ile Asn Lys Ala Thr Ile Met Pro Arg
    610                 615                 620

Gly Pro Thr Leu Gly His Val Ser Leu Leu Pro Glu Asn Asp Arg Trp
625                 630                 635                 640

Asn Glu Thr Arg Ala Gln Leu Leu Ala Gln Met Asp Val Ser Met Gly
                645                 650                 655

Gly Arg Val Ala Glu Glu Leu Ile Phe Gly Thr Asp His Ile Thr Thr
            660                 665                 670

Gly Ala Ser Ser Asp Phe Asp Asn Ala Thr Lys Ile Ala Lys Arg Met
        675                 680                 685

Val Thr Lys Phe Gly Met Ser Glu Lys Leu Gly Val Met Thr Tyr Ser
    690                 695                 700
```

```
Asp Thr Gly Lys Leu Ser Pro Glu Thr Gln Ser Ala Ile Glu Gln Glu
705                 710                 715                 720

Ile Arg Ile Leu Leu Arg Asp Ser Tyr Glu Arg Ala Lys His Ile Leu
                725                 730                 735

Lys Thr His Ala Lys Glu His Lys Asn Leu Ala Glu Ala Leu Leu Thr
            740                 745                 750

Tyr Glu Thr Leu Asp Ala Lys Glu Ile Gln Ile Val Leu Glu Gly Lys
        755                 760                 765

Lys Leu Glu Val Arg
    770


<210> SEQ ID NO 27
<211> LENGTH: 4232
<212> TYPE: DNA
<213> ORGANISM: Homo sapiens

<400> SEQUENCE: 27

actgttgagt tagcgcctcg ccttccgggg cggattgtct gtcgttgcag tagctgtagg     60

aaggggaggc cattttccgt ttctgggagg agtgaggggc aacgggtcgg agaaaaagga    120

aaaaagaagg gctcagcgcc tccccgccgg gccgtggaca gaggggcaca gtttcggcag    180

gcgggtgagg tcgctgaggg cccgccggag atgttttcct tgtcgagcac ggtgcaaccc    240

caggttacag ttcctctgag tcatctcatc aatgccttcc atacaccaaa aaacacttct    300

gtttctctca gtggagtgtc agtttctcaa aaccagcatc gagatgtagt tcctgagcat    360

gaggctccca gcagtgagcc ttcacttaac ttaagggacc ttggattatc tgaactaaaa    420

attggacaga ttgatcagct ggtagaaaat ctacttcctg gattttgtaa aggcaaaaac    480

atttcttccc attggcatac atcccatgtc tctgcacaat ccttctttga aaataaatat    540

ggtaacttag atatatttag tacattacgt tcctcttgct tgtatcgaca tcattcaaga    600

gctcttcaaa gcatttgttc agatcttcag tactggccag ttttcataca gtctcggggt    660

tttaaaactt tgaaatcaag gacacgacgt ctccagtcta cctccgagag attagctgaa    720

acacagaata tagcgccatc attcgtgaag ggtttctttt tgcgggacag aggatcagat    780

gttgagagtt tggacaaact catgaaaacc aaaaatatac ctgaagctca ccaagatgca    840

tttaaaactg gttttgcgga aggttttctg aaagctcaag cactcacaca aaaaaccaat    900

gattccctaa ggcgaacccg tctgattctc ttcgttctgc tgctattcgg catttatgga    960

cttctaaaaa acccattttt atctgtccgc ttccggacaa caacagggct tgattctgca   1020

gtagatcctg tccagatgaa aaatgtcacc tttgaacatg ttaaaggggt ggaggaagct   1080

aaacaagaat tacaggaagt tgttgaattc ttgaaaaatc cacaaaaatt tactattctt   1140

ggaggtaaac ttccaaaagg aattctttta gttggacccc cagggactgg aaagacactt   1200

cttgcccgag ctgtggcggg agaagctgat gttccttttt attatgcttc tggatccgaa   1260

tttgatgaga tgtttgtggg tgtgggagcc agccgtatca gaaatctttt tagggaagca   1320

aaggcgaatg ctccttgtgt tatatttatt gatgaattag attctgttgg tgggaagaga   1380

attgaatctc caatgcatcc atattcaagg cagaccataa atcaacttct tgctgaaatg   1440

gatggtttta aacccaatga aggagttatc ataataggag ccacaaactt cccagaggca   1500

ttagataatg ccttaatacg tcctggtcgt tttgacatgc aagttacagt tccaaggcca   1560

gatgtaaaag gtcgaacaga aattttgaaa tggtatctca ataaaataaa gtttgatcaa   1620

tccgttgatc cagaaattat agctcgaggt actgttggct tttccggagc agagttggag   1680
```

```
aatcttgtga accaggctgc attaaaagca gctgttgatg gaaaagaaat ggttaccatg   1740
aaggagctgg agttttccaa agacaaaatt ctaatggggc ctgaaagaag aagtgtggaa   1800
attgataaca aaaacaaaac catcacagca tatcatgaat ctggtcatgc cattattgca   1860
tattacacaa aagatgcaat gcctatcaac aaagctacaa tcatgccacg gggggccaaca  1920
cttggacatg tgtccctgtt acctgagaat gacagatgga atgaaactag agcccagctg   1980
cttgcacaaa tggatgttag tatgggagga agagtggcag aggagcttat atttggaacc   2040
gaccatatta caacaggtgc ttccagtgat tttgataatg ccactaaaat agcaaagcgg   2100
atggttacca aatttggaat gagtgaaaag cttggagtta tgacctacag tgatacaggg   2160
aaactaagtc cagaaaccca atctgccatc gaacaagaaa taagaatcct tctaagggac   2220
tcatatgaac gagcaaaaca tatcttgaaa actcatgcaa aggagcataa gaatctcgca   2280
gaagctttat tgacctatga gactttggat gccaaagaga ttcaaattgt tcttgagggg   2340
aaaaagttgg aagtgagatg ataactctct tgatatggat gcttgctggt tttattgcaa   2400
gaatacaagt agcattgcag tagtctactt ttacaacgct ttcccctcat tcttgatgtg   2460
gtgtaattga agggtgtgaa atgctttgtc aatcatttgt cacatttatc cagtttgggt   2520
tattctcatt atgacaccta ttgcaaatta gcatcccatg gcaaatatat tttgaaaaaa   2580
taaagaacta tcaggattga aaacagctct tttgaggaat gtcaattagt tattaagttg   2640
aaagtaatta atgattttat gtttggttac tctactagat ttgataaaaa ttgtgccttt   2700
agccttctat atacatcagt ggaaacttaa gatgcagtaa ttatgttcca gattgaccat   2760
gaataaaata ttttttaatc taaatgtaga gaagttggga ttaaaagcag tctcggaaac   2820
acagagccag gaatatagcc ttttggcatg gtgccatggc tcacatctgt aatcccagca   2880
cttttggagg ctgaggcggg tggattgctt gaggccagga gttcgagacc agcctggcca   2940
acgtggtgaa acgctgtctc tactaaaata caaaaaaata gggctgggcg cggttgctca   3000
cgcctgtaat cccagcactt ttcagaggcc aaggcgggca aatcacctga ggtcaagagt   3060
ttgagaccag cctggccaac atggtgaaac cccatctcta ctaaacatgc aaaaattacc   3120
tgggcatggt ggcaggtgct tataatccca gctactctgg gggccaaggc aggagaattg   3180
cttgagcctg ggagatggag gttgcagtga gctgagatca tgccactgca ctccagcctg   3240
ggcaacagag caagactctg cctcaaaaaa aaattaaaat aaatttaaat acaaaaaaaa   3300
atagccaggt gtggggtgca tgcctggaat cccagctact tgagaggctg aggcacgaga   3360
attgcttgaa cccaggaggt ggaggttgca gtgagccaag atcacaggag ccactgcact   3420
ccagcctggg tgacagagtg agactctgtc tcaaaaaaaa attaaataaa ttattataac   3480
ctttcagaaa tgctgtgtgc attttcatgt tcttttttt agcattactg tcactctccc    3540
taatgaaatg tacttcagag aagcagtatt ttgttaaata aatacataac ctcattctga   3600
ataatgtccc tcattttgac tataactgtg cttggtttca aaagcaaaat taaacaaaaa   3660
tctcagtccc ctccgaagtg aactttgtgt taccctgcgt cagaaatgcc aagttgtgtt   3720
tacttttcat tcagattttg tgaatatgaa catgctgtta taggatctac agatgaatat   3780
ttaactcaat agaaaaatta ttttagaaca cattgtattg gtattacaac cagattatat   3840
tcttgacgtt gacttcatta aaattatcta caatttccta ataatttaag ctgtatatgg   3900
tcttcattga aaaaagatag atattgttac aggaagcttg ttacattata ttcttgacct   3960
tttggttgat aatcttaaat cttaatgtaa tttcaaactg gcagaaatgt tgccagcata   4020
```

```
atacatggat gtctcatata ccctgcatcc agatttacca gttgttatca ttctgcccgt   4080

tttttattgc cccaaacctg ttctgtctcc ctctctgtat gtacatacat acacgtataa   4140

aatattgata aagtcttatc tgtcttaaat ttttttacat atttgttgag gtataattta   4200

catatgataa aattcatttt aaatgtaaaa aa                                 4232


<210> SEQ ID NO 28
<211> LENGTH: 716
<212> TYPE: PRT
<213> ORGANISM: Homo sapiens

<400> SEQUENCE: 28

Met Phe Ser Leu Ser Ser Thr Val Gln Pro Gln Val Thr Val Pro Leu
1               5                   10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
        35                  40                  45

Glu His Glu Ala Pro Ser Ser Glu Pro Ser Leu Asn Leu Arg Asp Leu
    50                  55                  60

Gly Leu Ser Glu Leu Lys Ile Gly Gln Ile Asp Gln Leu Val Glu Asn
65                  70                  75                  80

Leu Leu Pro Gly Phe Cys Lys Gly Lys Asn Ile Ser Ser His Trp His
                85                  90                  95

Thr Ser His Val Ser Ala Gln Ser Phe Phe Glu Asn Lys Tyr Gly Asn
            100                 105                 110

Leu Asp Ile Phe Ser Thr Leu Arg Ser Ser Cys Leu Tyr Arg His His
        115                 120                 125

Ser Arg Ala Leu Gln Ser Ile Cys Ser Asp Leu Gln Tyr Trp Pro Val
    130                 135                 140

Phe Ile Gln Ser Arg Gly Phe Lys Thr Leu Lys Ser Arg Thr Arg Arg
145                 150                 155                 160

Leu Gln Ser Thr Ser Glu Arg Leu Ala Glu Thr Gln Asn Ile Ala Pro
                165                 170                 175

Ser Phe Val Lys Gly Phe Leu Leu Arg Asp Arg Gly Ser Asp Val Glu
            180                 185                 190

Ser Leu Asp Lys Leu Met Lys Thr Lys Asn Ile Pro Glu Ala His Gln
        195                 200                 205

Asp Ala Phe Lys Thr Gly Phe Ala Glu Gly Phe Leu Lys Ala Gln Ala
    210                 215                 220

Leu Thr Gln Lys Thr Asn Asp Ser Leu Arg Arg Thr Arg Leu Ile Leu
225                 230                 235                 240

Phe Val Leu Leu Leu Phe Gly Ile Tyr Gly Leu Leu Lys Asn Pro Phe
                245                 250                 255

Leu Ser Val Arg Phe Arg Thr Thr Thr Gly Leu Asp Ser Ala Val Asp
            260                 265                 270

Pro Val Gln Met Lys Asn Val Thr Phe Glu His Val Lys Gly Val Glu
        275                 280                 285

Glu Ala Lys Gln Glu Leu Gln Glu Val Val Glu Phe Leu Lys Asn Pro
    290                 295                 300

Gln Lys Phe Thr Ile Leu Gly Gly Lys Leu Pro Lys Gly Ile Leu Leu
305                 310                 315                 320

Val Gly Pro Pro Gly Thr Gly Lys Thr Leu Leu Ala Arg Ala Val Ala
                325                 330                 335
```

```
Gly Glu Ala Asp Val Pro Phe Tyr Tyr Ala Ser Gly Ser Glu Phe Asp
            340                 345                 350

Glu Met Phe Val Gly Val Gly Ala Ser Arg Ile Arg Asn Leu Phe Arg
        355                 360                 365

Glu Ala Lys Ala Asn Ala Pro Cys Val Ile Phe Ile Asp Glu Leu Asp
    370                 375                 380

Ser Val Gly Gly Lys Arg Ile Glu Ser Pro Met His Pro Tyr Ser Arg
385                 390                 395                 400

Gln Thr Ile Asn Gln Leu Leu Ala Glu Met Asp Gly Phe Lys Pro Asn
                405                 410                 415

Glu Gly Val Ile Ile Ile Gly Ala Thr Asn Phe Pro Glu Ala Leu Asp
            420                 425                 430

Asn Ala Leu Ile Arg Pro Gly Arg Phe Asp Met Gln Val Thr Val Pro
        435                 440                 445

Arg Pro Asp Val Lys Gly Arg Thr Glu Ile Leu Lys Trp Tyr Leu Asn
    450                 455                 460

Lys Ile Lys Phe Asp Gln Ser Val Asp Pro Glu Ile Ile Ala Arg Gly
465                 470                 475                 480

Thr Val Gly Phe Ser Gly Ala Glu Leu Glu Asn Leu Val Asn Gln Ala
                485                 490                 495

Ala Leu Lys Ala Ala Val Asp Gly Lys Glu Met Val Thr Met Lys Glu
            500                 505                 510

Leu Glu Phe Ser Lys Asp Lys Ile Leu Met Gly Pro Glu Arg Arg Ser
        515                 520                 525

Val Glu Ile Asp Asn Lys Asn Lys Thr Ile Thr Ala Tyr His Glu Ser
    530                 535                 540

Gly His Ala Ile Ile Ala Tyr Tyr Thr Lys Asp Ala Met Pro Ile Asn
545                 550                 555                 560

Lys Ala Thr Ile Met Pro Arg Gly Pro Thr Leu Gly His Val Ser Leu
                565                 570                 575

Leu Pro Glu Asn Asp Arg Trp Asn Glu Thr Arg Ala Gln Leu Leu Ala
            580                 585                 590

Gln Met Asp Val Ser Met Gly Gly Arg Val Ala Glu Glu Leu Ile Phe
        595                 600                 605

Gly Thr Asp His Ile Thr Thr Gly Ala Ser Ser Asp Phe Asp Asn Ala
    610                 615                 620

Thr Lys Ile Ala Lys Arg Met Val Thr Lys Phe Gly Met Ser Glu Lys
625                 630                 635                 640

Leu Gly Val Met Thr Tyr Ser Asp Thr Gly Lys Leu Ser Pro Glu Thr
                645                 650                 655

Gln Ser Ala Ile Glu Gln Glu Ile Arg Ile Leu Leu Arg Asp Ser Tyr
            660                 665                 670

Glu Arg Ala Lys His Ile Leu Lys Thr His Ala Lys Glu His Lys Asn
        675                 680                 685

Leu Ala Glu Ala Leu Leu Thr Tyr Glu Thr Leu Asp Ala Lys Glu Ile
    690                 695                 700

Gln Ile Val Leu Glu Gly Lys Lys Leu Glu Val Arg
705                 710                 715
```

<210> SEQ ID NO 29
<211> LENGTH: 4133
<212> TYPE: DNA
<213> ORGANISM: Homo sapiens

<400> SEQUENCE: 29

```
actgttgagt tagcgcctcg ccttccgggg cggattgtct gtcgttgcag tagctgtagg      60
aaggggaggc cattttccgt ttctgggagg agtgaggggc aacgggtcgg agaaaaagga     120
aaaaagaagg gctcagcgcc tccccgccgg gccgtggaca gaggggcaca gtttcggcag     180
gcgggtgagg tcgctgaggg cccgccggag atgttttcct tgtcgagcac ggtgcaaccc     240
caggttacag ttcctctgag tcatctcatc aatgccttcc atacaccaaa aaacacttct     300
gtttctctca gtggagtgtc agtttctcaa aaccagcatc gagatgtagt tcctgagcat     360
gaggctccca gcagtgagcc ttcacttaac ttaagggacc ttggattatc tgaactaaaa     420
attggacaga ttgatcagct ggtagaaaat ctacttcctg gattttgtaa aggcaaaaac     480
atttcttccc attggcatac atcccatgtc tctgcacaat ccttctttga aaataaatat     540
gttttcatac agtctcgggg ttttaaaact ttgaaatcaa ggacacgacg tctccagtct     600
acctccgaga gattagctga aacacagaat atagcgccat cattcgtgaa ggggtttctt     660
ttgcgggaca gaggatcaga tgttgagagt ttggacaaac tcatgaaaac caaaaatata     720
cctgaagctc accaagatgc atttaaaact ggttttgcgg aaggttttct gaaagctcaa     780
gcactcacac aaaaaaccaa tgattcccta aggcgaaccc gtctgattct cttcgttctg     840
ctgctattcg gcatttatgg acttctaaaa aacccatttt tatctgtccg cttccggaca     900
acaacagggc ttgattctgc agtagatcct gtccagatga aaaatgtcac ctttgaacat     960
gttaaagggg tggaggaagc taaacaagaa ttacaggaag ttgttgaatt cttgaaaaat    1020
ccacaaaaat ttactattct tggaggtaaa cttccaaaag gaattctttt agttggaccc    1080
ccagggactg gaaagacact tcttgcccga gctgtggcgg gagaagctga tgttcctttt    1140
tattatgctt ctggatccga atttgatgag atgtttgtgg gtgtgggagc cagccgtatc    1200
agaaatcttt ttagggaagc aaaggcgaat gctccttgtg ttatatttat tgatgaatta    1260
gattctgttg gtgggaagag aattgaatct ccaatgcatc catattcaag gcagaccata    1320
aatcaacttc ttgctgaaat ggatggtttt aaacccaatg aaggagttat cataatagga    1380
gccacaaact tcccagaggc attagataat gccttaatac gtcctggtcg ttttgacatg    1440
caagttacag ttccaaggcc agatgtaaaa ggtcgaacag aaattttgaa atggtatctc    1500
aataaaataa agtttgatca atccgttgat ccagaaatta tagctcgagg tactgttggc    1560
ttttccggag cagagttgga gaatcttgtg aaccaggctg cattaaaagc agctgttgat    1620
ggaaaagaaa tggttaccat gaaggagctg gagttttcca aagacaaaat tctaatgggg    1680
cctgaaagaa gaagtgtgga aattgataac aaaaacaaaa ccatcacagc atatcatgaa    1740
tctggtcatg ccattattgc atattacaca aaagatgcaa tgcctatcaa caaagctaca    1800
atcatgccac gggggccaac acttggacat gtgtccctgt tacctgagaa tgacagatgg    1860
aatgaaacta gagcccagct gcttgcacaa atggatgtta gtatgggagg aagagtggca    1920
gaggagctta tatttggaac cgaccatatt acaacaggtg cttccagtga ttttgataat    1980
gccactaaaa tagcaaagcg gatggttacc aaatttggaa tgagtgaaaa gcttggagtt    2040
atgacctaca gtgatacagg gaaactaagt ccagaaaccc aatctgccat cgaacaagaa    2100
ataagaatcc ttctaaggga ctcatatgaa cgagcaaaac atatcttgaa aactcatgca    2160
aaggagcata agaatctcgc agaagcttta ttgacctatg agactttgga tgccaaagag    2220
attcaaattg ttcttgaggg gaaaaagttg gaagtgagat gataactctc ttgatatgga    2280
tgcttgctgg ttttattgca agaatacaag tagcattgca gtagtctact tttacaacgc    2340
```

```
tttcccctca ttcttgatgt ggtgtaattg aagggtgtga aatgctttgt caatcatttg   2400
tcacatttat ccagtttggg ttattctcat tatgacacct attgcaaatt agcatcccat   2460
ggcaaatata ttttgaaaaa ataaagaact atcaggattg aaaacagctc ttttgaggaa   2520
tgtcaattag ttattaagtt gaaagtaatt aatgatttta tgtttggtta ctctactaga   2580
tttgataaaa attgtgcctt tagccttcta tatacatcag tggaaactta agatgcagta   2640
attatgttcc agattgacca tgaataaaat atttttaat ctaaatgtag agaagttggg    2700
attaaaagca gtctcggaaa cacagagcca ggaatatagc cttttggcat ggtgccatgg   2760
ctcacatctg taatcccagc acttttggag gctgaggcgg gtggattgct tgaggccagg   2820
agttcgagac cagcctggcc aacgtggtga aacgctgtct ctactaaaat acaaaaaaat   2880
agggctgggc gcggttgctc acgcctgtaa tcccagcact tttcagaggc caaggcgggc   2940
aaatcacctg aggtcaagag tttgagacca gcctggccaa catggtgaaa ccccatctct   3000
actaaacatg caaaaattac ctgggcatgg tggcaggtgc ttataatccc agctactctg   3060
ggggccaagg caggagaatt gcttgagcct gggagatgga ggttgcagtg agctgagatc   3120
atgccactgc actccagcct gggcaacaga gcaagactct gcctcaaaaa aaaattaaaa   3180
taaatttaaa tacaaaaaaa aatagccagg tgtggggtgc atgcctggaa tcccagctac   3240
ttgagaggct gaggcacgag aattgcttga acccaggagg tggaggttgc agtgagccaa   3300
gatcacagga gccactgcac tccagcctgg gtgacagagt gagactctgt ctcaaaaaaa   3360
aattaaataa attattataa cctttcagaa atgctgtgtg cattttcatg ttcttttttt   3420
tagcattact gtcactctcc ctaatgaaat gtacttcaga gaagcagtat tttgttaaat   3480
aaatacataa cctcattctg aataatgtcc ctcattttga ctataactgt gcttggtttc   3540
aaaagcaaaa ttaaacaaaa atctcagtcc cctccgaagt gaactttgtg ttaccctgcg   3600
tcagaaatgc caagttgtgt ttacttttca ttcagatttt gtgaatatga acatgctgtt   3660
ataggatcta cagatgaata tttaactcaa tagaaaaatt attttagaac acattgtatt   3720
ggtattacaa ccagattata ttcttgacgt tgacttcatt aaaattatct acaatttcct   3780
aataatttaa gctgtatatg gtcttcattg aaaaaagata gatattgtta caggaagctt   3840
gttacattat attcttgacc ttttggttga taatcttaaa tcttaatgta atttcaaact   3900
ggcagaaatg ttgccagcat aatacatgga tgtctcatat accctgcatc cagatttacc   3960
agttgttatc attctgcccg ttttttattg ccccaaacct gttctgtctc cctctctgta   4020
tgtacataca tacacgtata aaatattgat aaagtcttat ctgtcttaaa ttttttttaca   4080
tatttgttga ggtataattt acatatgata aaattcattt taaatgtaaa aaa          4133
```

<210> SEQ ID NO 30
<211> LENGTH: 683
<212> TYPE: PRT
<213> ORGANISM: Homo sapiens

<400> SEQUENCE: 30

```
Met Phe Ser Leu Ser Ser Thr Val Gln Pro Gln Val Thr Val Pro Leu
1               5                   10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
        35                  40                  45

Glu His Glu Ala Pro Ser Ser Glu Pro Ser Leu Asn Leu Arg Asp Leu
    50                  55                  60
```

```
Gly Leu Ser Glu Leu Lys Ile Gly Gln Ile Asp Gln Leu Val Glu Asn
65                  70                  75                  80

Leu Leu Pro Gly Phe Cys Lys Gly Lys Asn Ile Ser Ser His Trp His
                85                  90                  95

Thr Ser His Val Ser Ala Gln Ser Phe Phe Glu Asn Lys Tyr Val Phe
            100                 105                 110

Ile Gln Ser Arg Gly Phe Lys Thr Leu Lys Ser Arg Thr Arg Arg Leu
        115                 120                 125

Gln Ser Thr Ser Glu Arg Leu Ala Glu Thr Gln Asn Ile Ala Pro Ser
    130                 135                 140

Phe Val Lys Gly Phe Leu Leu Arg Asp Arg Gly Ser Asp Val Glu Ser
145                 150                 155                 160

Leu Asp Lys Leu Met Lys Thr Lys Asn Ile Pro Glu Ala His Gln Asp
                165                 170                 175

Ala Phe Lys Thr Gly Phe Ala Glu Gly Phe Leu Lys Ala Gln Ala Leu
            180                 185                 190

Thr Gln Lys Thr Asn Asp Ser Leu Arg Arg Thr Arg Leu Ile Leu Phe
        195                 200                 205

Val Leu Leu Leu Phe Gly Ile Tyr Gly Leu Leu Lys Asn Pro Phe Leu
    210                 215                 220

Ser Val Arg Phe Arg Thr Thr Thr Gly Leu Asp Ser Ala Val Asp Pro
225                 230                 235                 240

Val Gln Met Lys Asn Val Thr Phe Glu His Val Lys Gly Val Glu Glu
                245                 250                 255

Ala Lys Gln Glu Leu Gln Glu Val Val Glu Phe Leu Lys Asn Pro Gln
            260                 265                 270

Lys Phe Thr Ile Leu Gly Gly Lys Leu Pro Lys Gly Ile Leu Leu Val
        275                 280                 285

Gly Pro Pro Gly Thr Gly Lys Thr Leu Leu Ala Arg Ala Val Ala Gly
    290                 295                 300

Glu Ala Asp Val Pro Phe Tyr Tyr Ala Ser Gly Ser Glu Phe Asp Glu
305                 310                 315                 320

Met Phe Val Gly Val Gly Ala Ser Arg Ile Arg Asn Leu Phe Arg Glu
                325                 330                 335

Ala Lys Ala Asn Ala Pro Cys Val Ile Phe Ile Asp Glu Leu Asp Ser
            340                 345                 350

Val Gly Gly Lys Arg Ile Glu Ser Pro Met His Pro Tyr Ser Arg Gln
        355                 360                 365

Thr Ile Asn Gln Leu Leu Ala Glu Met Asp Gly Phe Lys Pro Asn Glu
    370                 375                 380

Gly Val Ile Ile Ile Gly Ala Thr Asn Phe Pro Glu Ala Leu Asp Asn
385                 390                 395                 400

Ala Leu Ile Arg Pro Gly Arg Phe Asp Met Gln Val Thr Val Pro Arg
                405                 410                 415

Pro Asp Val Lys Gly Arg Thr Glu Ile Leu Lys Trp Tyr Leu Asn Lys
            420                 425                 430

Ile Lys Phe Asp Gln Ser Val Asp Pro Glu Ile Ile Ala Arg Gly Thr
        435                 440                 445

Val Gly Phe Ser Gly Ala Glu Leu Glu Asn Leu Val Asn Gln Ala Ala
    450                 455                 460

Leu Lys Ala Ala Val Asp Gly Lys Glu Met Val Thr Met Lys Glu Leu
465                 470                 475                 480
```

```
Glu Phe Ser Lys Asp Lys Ile Leu Met Gly Pro Glu Arg Arg Ser Val
                485                 490                 495

Glu Ile Asp Asn Lys Asn Lys Thr Ile Thr Ala Tyr His Glu Ser Gly
            500                 505                 510

His Ala Ile Ile Ala Tyr Tyr Thr Lys Asp Ala Met Pro Ile Asn Lys
        515                 520                 525

Ala Thr Ile Met Pro Arg Gly Pro Thr Leu Gly His Val Ser Leu Leu
    530                 535                 540

Pro Glu Asn Asp Arg Trp Asn Glu Thr Arg Ala Gln Leu Leu Ala Gln
545                 550                 555                 560

Met Asp Val Ser Met Gly Gly Arg Val Ala Glu Glu Leu Ile Phe Gly
                565                 570                 575

Thr Asp His Ile Thr Thr Gly Ala Ser Ser Asp Phe Asp Asn Ala Thr
            580                 585                 590

Lys Ile Ala Lys Arg Met Val Thr Lys Phe Gly Met Ser Glu Lys Leu
        595                 600                 605

Gly Val Met Thr Tyr Ser Asp Thr Gly Lys Leu Ser Pro Glu Thr Gln
    610                 615                 620

Ser Ala Ile Glu Gln Glu Ile Arg Ile Leu Leu Arg Asp Ser Tyr Glu
625                 630                 635                 640

Arg Ala Lys His Ile Leu Lys Thr His Ala Lys Glu His Lys Asn Leu
                645                 650                 655

Ala Glu Ala Leu Leu Thr Tyr Glu Thr Leu Asp Ala Lys Glu Ile Gln
            660                 665                 670

Ile Val Leu Glu Gly Lys Lys Leu Glu Val Arg
        675                 680
```

<210> SEQ ID NO 31
<211> LENGTH: 1919
<212> TYPE: DNA
<213> ORGANISM: Homo sapiens

<400> SEQUENCE: 31

```
atgtggaggt cagagtggaa gcaggtgaga atggaggggg cggcaaaggc tcgtttctgg      60

gcatctctgc agtcctcctc tgctccatga tgtgcacttt gggcgaggag agtgcgtgcg     120

tgtgagaggg tccagcagaa ggaaacatgg ctgccaaagt gtttgagtcc attggcaagt     180

ttggcctggc cttagctgtt gcaggaggcg tggtgaactc tgccttatat aatgtggatg     240

ctgggcacag agctgtcatc tttgaccgat tccgtggagt gcaggacatt gtggtagggg     300

aagggactca ttttctcatc ccgtgggtac agaaaccaat tatctttgac tgccgttctc     360

gaccacgtaa tgtgccagtc atcactggta gcaaagattt acagaatgtc aacatcacac     420

tgcgcatcct cttccggcct gtcgccagcc agcttcctcg catcttcacc agcatcggag     480

aggactatga tgagcgtgtg ctgccgtcca tcacaactga gatcctcaag tcagtggtgg     540

ctcgctttga tgctggagaa ctaatcaccc agagagagct ggtctccagg caggtgagcg     600

acgaccttac agagcgagcc gccacctttg ggctcatcct ggatgacgtg tccttgacac     660

atctgacctt cgggaaggag ttcacagaag cggtggaagc caaacaggtg gctcagcagg     720

aagcagagag ggccagattt gtggtggaaa aggctgagca acagaaaaag gcggccatca     780

tctctgctga gggcgactcc aaggcagctg agctgattgc caactcactg gccactgcag     840

gggatggcct gatcgagctg cgcaagctgg aagctgcaga ggacatcgcg taccagctct     900

cacgctctcg gaacatcacc tacctgccag cggggcagtc cgtgctcctc cagctgcccc     960
```

```
agtgagggcc caccctgcct gcacctccgc gggctgactg ggccacagcc ccgatgattc   1020

ttaacacagc cttccttctg ctcccacccc agaaatcact gtgaaatttc atgattggct   1080

taaagtgaag gaaataaagg taaaatcact tcagatctct aattagtcta tcaaatgaaa   1140

ctctttcatt cttctcacat ccatctactt ttttatccac ctccctacca aaaattgcca   1200

agtgcctatg caaaccagct ttaggtccca attcggggcc tgctggagtt ccggcctggg   1260

caccagcatt tggcagcacg caggcggggc agtatgtgat ggactgggga gcacaggtgt   1320

ctgcctagat ccacgtgtgg cctccgtcct gtcactgatg gaaggtttgc ggatgagggc   1380

atgtgcggct gaactgagaa ggcaggcctc cgtcttccca gcggttcctg tgcagatgct   1440

gctgaagaga ggtgccgggg aggggcagag aggaagtggt ctgtctgtta ccataagtct   1500

gattctcttt aactgtgtga ccagcggaaa caggtgtgtg tgaactgggc acagattgaa   1560

gaatctgccc ctgttgaggt gggtgggcct gactgttgcc ccccagggtc ctaaaacttg   1620

gatggacttg tatagtgaga gaggaggcct ggaccgagat gtgagtcctg ttgaagactt   1680

cctctctacc ccccaccttg gtccctctca gatacccagt ggaattccaa cttgaaggat   1740

tgcatcctgc tggggctgaa catgcctgcc aaagacgtgt ccgacctacg ttcctggccc   1800

cctcgttcag agactgccct tctcacgggc tctatgcctg cactgggaag gaaacaaatg   1860

tgtataaact gctgtcaata aatgacaccc agaccttccg gctcagccaa aaaaaaaaa    1919
```

```
<210> SEQ ID NO 32
<211> LENGTH: 272
<212> TYPE: PRT
<213> ORGANISM: Homo sapiens

<400> SEQUENCE: 32

Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Gln Arg Glu
    130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205
```

```
Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
            260                 265                 270


<210> SEQ ID NO 33
<211> LENGTH: 1520
<212> TYPE: DNA
<213> ORGANISM: Homo sapiens

<400> SEQUENCE: 33

gggcggggca gaggagctca tgcgcagtat gtgtggttgg ggaattcatg tggaggtcag     60

agtggaagca ggtgtgagag ggtccagcag aaggaaacat ggctgccaaa gtgtttgagt    120

ccattggcaa gtttggcctg gccttagctg ttgcaggagg cgtggtgaac tctgccttat    180

ataatgtgga tgctgggcac agagctgtca tctttgaccg attccgtgga gtgcaggaca    240

ttgtggtagg ggaagggact cattttctca tcccgtgggt acagaaacca attatctttg    300

actgccgttc tcgaccacgt aatgtgccag tcatcactgg tagcaaagat ttacagaatg    360

tcaacatcac actgcgcatc ctcttccggc ctgtcgccag ccagcttcct cgcatcttca    420

ccagcatcgg agaggactat gatgagcgtg tgctgccgtc catcacaact gagatcctca    480

agtcagtggt ggctcgcttt gatgctggag aactaatcac ctacctgcca gcggggcagt    540

ccgtgctcct ccagctgccc cagtgagggc ccaccctgcc tgcacctccg cgggctgact    600

gggccacagc cccgatgatt cttaacacag ccttccttct gctcccaccc cagaaatcac    660

tgtgaaattt catgattggc ttaaagtgaa ggaaataaag gtaaaatcac ttcagatctc    720

taattagtct atcaaatgaa actctttcat tcttctcaca tccatctact tttttatcca    780

cctccctacc aaaaattgcc aagtgcctat gcaaaccagc tttaggtccc aattcggggc    840

ctgctggagt tccggcctgg gcaccagcat ttggcagcac gcaggcgggg cagtatgtga    900

tggactgggg agcacaggtg tctgcctaga tccacgtgtg gcctccgtcc tgtcactgat    960

ggaaggtttg cggatgaggg catgtgcggc tgaactgaga aggcaggcct ccgtcttccc   1020

agcggttcct gtgcagatgc tgctgaagag aggtgccggg gaggggcaga gaggaagtgg   1080

tctgtctgtt accataagtc tgattctctt taactgtgtg accagcggaa acaggtgtgt   1140

gtgaactggg cacagattga agaatctgcc cctgttgagg tgggtgggcc tgactgttgc   1200

cccccagggt cctaaaactt ggatggactt gtatagtgag agaggaggcc tggaccgaga   1260

tgtgagtcct gttgaagact tcctctctac cccccacctt ggtccctctc agatacccag   1320

tggaattcca acttgaagga ttgcatcctg ctggggctga acatgcctgc caaagacgtg   1380

tccgacctac gttcctggcc ccctcgttca gagactgccc ttctcacggg ctctatgcct   1440

gcactgggaa ggaaacaaat gtgtataaac tgctgtcaat aaatgacacc cagaccttcc   1500

ggctcagcca aaaaaaaaaa                                               1520


<210> SEQ ID NO 34
<211> LENGTH: 155
<212> TYPE: PRT
<213> ORGANISM: Homo sapiens

<400> SEQUENCE: 34
```

```
Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Tyr Leu Pro
    130                 135                 140

Ala Gly Gln Ser Val Leu Leu Gln Leu Pro Gln
145                 150                 155
```

<210> SEQ ID NO 35
<211> LENGTH: 1457
<212> TYPE: DNA
<213> ORGANISM: Homo sapiens

<400> SEQUENCE: 35

```
tccgtatgcg cgattcctgt gcgcgaagtt cgggtccgta gtgggctaag gggagggtt      60

tcaaagggag cgcacttccg ctgccctttc tttcgccagc cttacgggcc cgaaccctcg    120

tgtgaagggt gcagtaccta agccggagcg gggtagaggc gggccggcac cccttctga     180

cctccagtgc cgccggcctc aagatcagac atggcccaga acttgaagga cttggcggga    240

cggctgcccg ccgggccccg gggcatgggc acggccctga agctgttgct gggggccggc    300

gccgtggcct acggtgtgcg cgaatctgtg ttcaccgtgg aaggcgggca cagagccatc    360

ttcttcaatc ggatcggtgg agtgcagcag gacactatcc tggccgaggg ccttcacttc    420

aggatccctt ggttccagta ccccattatc tatgacattc gggccagacc tcgaaaaatc    480

tcctccccta caggctccaa agacctacag atggtgaata tctccctgcg agtgttgtct    540

cgacccaatg ctcaggagct tcctagcatg taccagcgcc tagggctgga ctacgaggaa    600

cgagtgttgc cgtccattgt caacgaggtg ctcaagagtg tggtggccaa gttcaatgcc    660

tcacagctga tcacccagcg ggcccaggta tccctgttga tccgccggga gctgacagag    720

agggccaagg acttcagcct catcctggat gatgtggcca tcacagagct gagctttagc    780

cgagagtaca cagctgctgt agaagccaaa caagtggccc agcaggaggc ccagcgggcc    840

caattcttgg tagaaaaagc aaagcaggaa cagcggcaga aaattgtgca ggccgagggt    900

gaggccgagg ctgccaagat gcttggagaa gcactgagca agaaccctgg ctacatcaaa    960

cttcgcaaga ttcgagcagc ccagaatatc tccaagacga tcgccacatc acagaatcgt   1020

atctatctca cagctgacaa ccttgtgctg aacctacagg atgaaagttt caccagggga   1080

agtgacagcc tcatcaaggg taagaaatga gcctagtcac caagaactcc acccccagag   1140

gaagtggatc tgcttctcca gtttttgagg agccagccag ggtccagca cagccctacc    1200
```

```
ccgccccagt atcatgcgat ggtcccccac accggttccc tgaacccctc ttggattaag   1260

gaagactgaa gactagcccc ttttctgggg aattactttc ctcctccctg tgttaactgg   1320

ggctgttggg gacagtgcgt gatttctcag tgatttccta cagtgttgtt ccctccctca   1380

aggctgggag gagataaaca ccaacccagg aattctcaat aaatttttat tacttaacct   1440

gaaaaaaaaa aaaaaaa                                                  1457
```

<210> SEQ ID NO 36
<211> LENGTH: 299
<212> TYPE: PRT
<213> ORGANISM: Homo sapiens

<400> SEQUENCE: 36

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
    210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295
```

<210> SEQ ID NO 37
<211> LENGTH: 1343
<212> TYPE: DNA

<213> ORGANISM: Homo sapiens

<400> SEQUENCE: 37

```
tccgtatgcg cgattcctgt gcgcgaagtt cgggtccgta gtgggctaag gggagggtt     60
tcaaagggag cgcacttccg ctgccctttc tttcgccagc cttacgggcc cgaaccctcg   120
tgtgaagggt gcagtaccta agccggagcg gggtagaggc gggccggcac cccttctga    180
cctccagtgc cgccggcctc aagatcagac atggcccaga acttgaagga cttggcggga   240
cggctgcccg ccgggccccg gggcatgggc acggccctga agctgttgct gggggccggc   300
gccgtggcct acggtgtgcg cgaatctgtg ttcaccgtgg aaggcgggca cagagccatc   360
ttcttcaatc ggatcggtgg agtgcagcag gacactatcc tggccgaggg ccttcacttc   420
aggatccctt ggttccagta ccccattatc tatgacattc gggccagacc tcgaaaaatc   480
tcctccccta caggctccaa agacctacag atggtgaata tctccctgcg agtgttgtct   540
cgacccaatg ctcaggagct tcctagcatg taccagcgcc tagggctgga ctacgaggaa   600
cgagtgttgc cgtccattgt caacgaggtg ctcaagagtg tggtggccaa gttcaatgcc   660
tcacagctga tcacccagcg ggcccaggta tccctgttga tccgccggga gctgacagag   720
agggccaagg acttcagcct catcctggat gatgtggcca tcacagagct gagctttagc   780
cgagagtaca cagctgctgt agaagccaaa caagtggcac tgagcaagaa ccctggctac   840
atcaaacttc gcaagattcg agcagcccag aatatctcca agacgatcgc cacatcacag   900
aatcgtatct atctcacagc tgacaacctt gtgctgaacc tacaggatga aagtttcacc   960
aggggaagtg acagcctcat caagggtaag aaatgagcct agtcaccaag aactccaccc  1020
ccagaggaag tggatctgct tctccagttt ttgaggagcc agccaggggt ccagcacagc  1080
cctaccccgc cccagtatca tgcgatggtc ccccacaccg gttccctgaa cccctcttgg  1140
attaaggaag actgaagact agcccctttt ctggggaatt actttcctcc tccctgtgtt  1200
aactggggct gttggggaca gtgcgtgatt tctcagtgat ttcctacagt gttgttccct  1260
ccctcaaggc tgggaggaga taaacaccaa cccaggaatt ctcaataaat ttttattact  1320
taacctgaaa aaaaaaaaaa aaa                                           1343
```

<210> SEQ ID NO 38
<211> LENGTH: 261
<212> TYPE: PRT
<213> ORGANISM: Homo sapiens

<400> SEQUENCE: 38

```
Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110
```

```
Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Leu Ser Lys Asn Pro
        195                 200                 205

Gly Tyr Ile Lys Leu Arg Lys Ile Arg Ala Ala Gln Asn Ile Ser Lys
    210                 215                 220

Thr Ile Ala Thr Ser Gln Asn Arg Ile Tyr Leu Thr Ala Asp Asn Leu
225                 230                 235                 240

Val Leu Asn Leu Gln Asp Glu Ser Phe Thr Arg Gly Ser Asp Ser Leu
                245                 250                 255

Ile Lys Gly Lys Lys
            260


<210> SEQ ID NO 39
<211> LENGTH: 1773
<212> TYPE: DNA
<213> ORGANISM: Homo sapiens

<400> SEQUENCE: 39

aatgagcgaa ggcatcgcga gccagggggc gcggagaagg cggggaatca tggccgcccc     60

cagtgttccg cgtccggggg tttgtgggag ttgccttgac ctgcagctcc gccaccgcgg    120

acccgccttc tgccctcagc agcagacgct ctgtcccgcc cgggcagctc tgcgaggcag    180

cggctggaga gggaaccatg ggactgtgc acgcccggag tttggagcct cttccatcaa    240

gtggacctga ttttggagga ttaggagaag aagctgaatt tgttgaagtt gagcctgaag    300

ctaaacagga aattcttgaa aacaaagatg tggttgttca acatgttcat tttgatggac    360

ttggaaggac taaagatgat atcatcattt gtgaaattgg agatgttttc aaggccaaaa    420

acctaattga ggtaatgcgg aaatctcatg aagcccgtga aaaattgctc cgtcttggaa    480

tttttagaca agtggatgtt ttgattgaca catgtcaagg tgatgacgca cttccaaatg    540

ggttagacgt tacctttgaa gtaactgaat tgaggagatt aacgggcagt tataacacca    600

tggttggaaa caatgaaggc agtatggtac ttggcctcaa gcttcctaat cttcttggtc    660

gtgcagaaaa ggtgaccttt cagttttcct atggaacaaa agaaacttcg tatggcctgt    720

ccttcttcaa accacggccc ggaaacttcg aaagaaattt ctctgtaaac ttatataaag    780

ttactggaca gttcccttgg agctcactgc gggagacgga cagaggaatg tcagctgagt    840

acagttttcc catatggaag accagccaca ctgtcaagtg ggaaggcgta tggcgagaac    900

tgggctgcct ctcaaggacg gcgtcatttg ctgttcgaaa agaaagcgga cattcactga    960

aatcatctct ttcgcacgcc atggtcatcg attctcggaa ttcttccatc ttaccaagga   1020

gaggtgcttt gctgaaagtt aaccaggaac tggcaggcta cactggcggg gatgtgagct   1080

tcatcaaaga agattttgaa cttcagttga acaagcaact catatttgat tcagtttttt   1140

cagcgtcttt ctggggcgga atgttggtac ccattggtga taagccgtca agcattgctg   1200

ataggtttta ccttggggga cccacaagca tccgcggatt cagcatgcac agcatcgggc   1260
```

```
cacagagcga aggagactac ctaggtggag aagcgtactg ggccggcggc ctgcacctct   1320

acaccccatt acctttccgg ccaggccagg gtggctttgg agaacttttc cgaacacact   1380

tctttctcaa cgcaggaaac ctctgcaacc tcaactatgg ggagggcccc aaagctcata   1440

ttcgtaagct ggctgagtgc atccgctggt cgtacggggc cgggattgtc ctcaggcttg   1500

gcaacatcgc tcggttggaa cttaattact gcgtccccat gggagtacag acaggcgaca   1560

ggatatgtga tggcgtccag tttggagctg ggataaggtt cctgtagccg acacccctac   1620

aggagaagct ctgggactgg ggcagcagca aggcgcccat gccacacacc gtctctcgag   1680

gaaacgcggt tcagcgattc tttgactgcg gaccctgtgg gaaaccccgt caataaatgt   1740

taaagacaca ctccgaaaaa aaaaaaaaaa aaa                                 1773
```

<210> SEQ ID NO 40
<211> LENGTH: 469
<212> TYPE: PRT
<213> ORGANISM: Homo sapiens

<400> SEQUENCE: 40

```
Met Gly Thr Val His Ala Arg Ser Leu Glu Pro Leu Pro Ser Ser Gly
1               5                   10                  15

Pro Asp Phe Gly Gly Leu Gly Glu Glu Ala Glu Phe Val Glu Val Glu
            20                  25                  30

Pro Glu Ala Lys Gln Glu Ile Leu Glu Asn Lys Asp Val Val Val Gln
        35                  40                  45

His Val His Phe Asp Gly Leu Gly Arg Thr Lys Asp Asp Ile Ile Ile
    50                  55                  60

Cys Glu Ile Gly Asp Val Phe Lys Ala Lys Asn Leu Ile Glu Val Met
65                  70                  75                  80

Arg Lys Ser His Glu Ala Arg Glu Lys Leu Leu Arg Leu Gly Ile Phe
                85                  90                  95

Arg Gln Val Asp Val Leu Ile Asp Thr Cys Gln Gly Asp Asp Ala Leu
            100                 105                 110

Pro Asn Gly Leu Asp Val Thr Phe Glu Val Thr Glu Leu Arg Arg Leu
        115                 120                 125

Thr Gly Ser Tyr Asn Thr Met Val Gly Asn Asn Glu Gly Ser Met Val
    130                 135                 140

Leu Gly Leu Lys Leu Pro Asn Leu Leu Gly Arg Ala Glu Lys Val Thr
145                 150                 155                 160

Phe Gln Phe Ser Tyr Gly Thr Lys Glu Thr Ser Tyr Gly Leu Ser Phe
                165                 170                 175

Phe Lys Pro Arg Pro Gly Asn Phe Glu Arg Asn Phe Ser Val Asn Leu
            180                 185                 190

Tyr Lys Val Thr Gly Gln Phe Pro Trp Ser Ser Leu Arg Glu Thr Asp
        195                 200                 205

Arg Gly Met Ser Ala Glu Tyr Ser Phe Pro Ile Trp Lys Thr Ser His
    210                 215                 220

Thr Val Lys Trp Glu Gly Val Trp Arg Glu Leu Gly Cys Leu Ser Arg
225                 230                 235                 240

Thr Ala Ser Phe Ala Val Arg Lys Glu Ser Gly His Ser Leu Lys Ser
                245                 250                 255

Ser Leu Ser His Ala Met Val Ile Asp Ser Arg Asn Ser Ser Ile Leu
            260                 265                 270

Pro Arg Arg Gly Ala Leu Leu Lys Val Asn Gln Glu Leu Ala Gly Tyr
```

```
        275                 280                 285

Thr Gly Gly Asp Val Ser Phe Ile Lys Glu Asp Phe Glu Leu Gln Leu
    290                 295                 300

Asn Lys Gln Leu Ile Phe Asp Ser Val Phe Ser Ala Ser Phe Trp Gly
305                 310                 315                 320

Gly Met Leu Val Pro Ile Gly Asp Lys Pro Ser Ser Ile Ala Asp Arg
                325                 330                 335

Phe Tyr Leu Gly Gly Pro Thr Ser Ile Arg Gly Phe Ser Met His Ser
            340                 345                 350

Ile Gly Pro Gln Ser Glu Gly Asp Tyr Leu Gly Gly Glu Ala Tyr Trp
        355                 360                 365

Ala Gly Gly Leu His Leu Tyr Thr Pro Leu Pro Phe Arg Pro Gly Gln
    370                 375                 380

Gly Gly Phe Gly Glu Leu Phe Arg Thr His Phe Phe Leu Asn Ala Gly
385                 390                 395                 400

Asn Leu Cys Asn Leu Asn Tyr Gly Glu Gly Pro Lys Ala His Ile Arg
                405                 410                 415

Lys Leu Ala Glu Cys Ile Arg Trp Ser Tyr Gly Ala Gly Ile Val Leu
            420                 425                 430

Arg Leu Gly Asn Ile Ala Arg Leu Glu Leu Asn Tyr Cys Val Pro Met
        435                 440                 445

Gly Val Gln Thr Gly Asp Arg Ile Cys Asp Gly Val Gln Phe Gly Ala
    450                 455                 460

Gly Ile Arg Phe Leu
465


<210> SEQ ID NO 41
<211> LENGTH: 3018
<212> TYPE: DNA
<213> ORGANISM: Homo sapiens

<400> SEQUENCE: 41

aattctcttt aagagtcaca gctgtccatt ttccacgtgc ggctgaagaa tggatttcag      60

agcgctctcc ctccggcagt gttcacctag taaccccttc cggataagga cctgcagccc     120

gggcgcgacc cggaaaggga atccgccctt ttcgcctcct tcgcgccaat cgcctggagt     180

tggcgtttcc gcagccggga cacagcccac cctctaagag ccgcggagtc ggggacggta     240

gaaggggccg cgcgtgcgca gtggcgtccg ctgtgcttcc ggtgcgccgg gcgcggacgc     300

gggcacgcac acacgcaagc acgcctccac ttaactcgcg ccgccgcggc agctcgagtc     360

caccagcagc gccgtccgct tgaccgagat gctgcgggcc tgtcagttat cgggtgtgac     420

cgccgccgcc cagagttgtc tctgtgggaa gtttgtcctc cgtccattgc gaccatgccg     480

cagatactct acttcaggca gctctgggtt gactactggc aaaattgctg gagctggcct     540

tttgtttgtt ggtggaggta ttggtggcac tatcctatat gccaaatggg attcccattt     600

ccgggaaagt gtagagaaaa ccatacctta ctcagacaaa ctcttcgaga tggttcttgg     660

tcctgcagct tataatgttc cattgccaaa gaaatcgatt cagtcgggtc cactaaaaat     720

ctctagtgta tcagaagtaa tgaaagaatc taaacagcct gcctcacaac tccaaaaaca     780

aaagggagat actccagctt cagcaacagc acctacagaa gcggctcaaa ttatttctgc     840

agcaggtgat accctgtcgg tcccagcccc tgcagttcag cctgaggaat ctttaaaaac     900

tgatcaccct gaaattggtg aaggaaaacc cacacctgca ctttcagaag aagcatcctc     960

atcttctata agggagcgac cacctgaaga agttgcagct cgccttgcac aacaggaaaa    1020
```

```
acaagaacaa gttaaaattg agtctctagc caagagctta gaagatgctc tgaggcaaac   1080
tgcaagtgtc actctgcagg ctattgcagc tcagaatgct gcggtccagg ctgtcaatgc   1140
acactccaac atattgaaag ccgccatgga caattctgag attgcaggcg agaagaaatc   1200
tgctcagtgg cgcacagtgg agggtgcatt gaaggaacgc agaaaggcag tagatgaagc   1260
tgccgatgcc cttctcaaag ccaaagaaga gttagagaag atgaaaagtg tgattgaaaa   1320
tgcaaagaaa aaagaggttg ctggggccaa gcctcatata actgctgcag agggtaaact   1380
tcacaacatg atagttgatc tggataatgt ggtcaaaaag gtccaagcag ctcagtctga   1440
ggctaaggtt gtatctcagt atcatgagct ggtggtccaa gctcgggatg actttaaacg   1500
agagctggac agtattactc cagaagtcct tcctgggtgg aaaggaatga gtgtttcaga   1560
cttagctgac aagctctcta ctgatgatct gaactccctc attgctcatg cacatcgtcg   1620
tattgatcag ctgaacagag agctggcaga acagaaggcc accgaaaagc agcacatcac   1680
gttagccttg gagaaacaaa agctggaaga aaagcgggca tttgactctg cagtagcaaa   1740
agcattagaa catcacagaa gtgaaataca ggctgaacag gacagaaaga tagaagaagt   1800
cagagatgcc atggaaaatg aaatgagaac ccagcttcgc cgacaggcag ctgcccacac   1860
tgatcacttg cgagatgtcc ttagggtaca agaacaggaa ttgaagtctg aatttgagca   1920
gaacctgtct gagaaactct ctgaacaaga attacaattt cgtcgtctca gtcaagagca   1980
agttgacaac tttactctgg atataaatac tgcctatgcc agactcagag gaatcgaaca   2040
ggctgttcag agccatgcag ttgctgaaga ggaagccaga aaagcccacc aactctggct   2100
ttcagtggag gcattaaagt acagcatgaa gacctcatct gcagaaacac ctactatccc   2160
gctgggtagt gcagttgagg ccatcaaagc caactgttct gataatgaat tcacccaagc   2220
tttaaccgca gctatccctc cagagtccct gacccgtggg gtgtacagtg aagagaccct   2280
tagagcccgt ttctatgctg ttcaaaaact ggcccgaagg gtagcaatga ttgatgaaac   2340
cagaaatagc ttgtaccagt acttcctctc ctacctacag tccctgctcc tattccccacc   2400
tcagcaactg aagccgcccc cagagctctg ccctgaggat ataaacacat ttaaattact   2460
gtcatatgct tcctattgca ttgagcatgg tgatctggag ctagcagcaa agtttgtcaa   2520
tcagctgaag gggggaatcca gacgagtggc acaggactgg ctgaaggaag cccgaatgac   2580
cctagaaacg aaacagatag tggaaatcct gacagcatat gccagcgccg taggaatagg   2640
aaccactcag gtgcagccag agtgaggttt aggaagattt tcataaagtc atatttcatg   2700
tcaaaggaaa tcagcagtga tagatgaagg gttcgcagcg agagtcccgg acttgtctag   2760
aaatgagcag gtttacaagt actgttctaa atgttaacac ctgttgcatt tatattcttt   2820
ccatttgcta tcatgtcagt gaacgccagg agtgctttct ttgcaacttg tgtaacattt   2880
tctgtttttt caggttttac tgatgaggct tgtgaggcca atcaaaataa tgtttgtgat   2940
ctctactact gttgattttg ccctcggagc aaactgaata aagcaacaag atgaaaactg   3000
aaaaaaaaaa aaaaaaaa                                                 3018
```

<210> SEQ ID NO 42
<211> LENGTH: 758
<212> TYPE: PRT
<213> ORGANISM: Homo sapiens

<400> SEQUENCE: 42

```
Met Leu Arg Ala Cys Gln Leu Ser Gly Val Thr Ala Ala Ala Gln Ser
1               5                   10                  15
```

```
Cys Leu Cys Gly Lys Phe Val Leu Arg Pro Leu Arg Pro Cys Arg Arg
            20                  25                  30

Tyr Ser Thr Ser Gly Ser Ser Gly Leu Thr Thr Gly Lys Ile Ala Gly
        35                  40                  45

Ala Gly Leu Leu Phe Val Gly Gly Gly Ile Gly Gly Thr Ile Leu Tyr
    50                  55                  60

Ala Lys Trp Asp Ser His Phe Arg Glu Ser Val Glu Lys Thr Ile Pro
65                  70                  75                  80

Tyr Ser Asp Lys Leu Phe Glu Met Val Leu Gly Pro Ala Ala Tyr Asn
                85                  90                  95

Val Pro Leu Pro Lys Lys Ser Ile Gln Ser Gly Pro Leu Lys Ile Ser
            100                 105                 110

Ser Val Ser Glu Val Met Lys Glu Ser Lys Gln Pro Ala Ser Gln Leu
        115                 120                 125

Gln Lys Gln Lys Gly Asp Thr Pro Ala Ser Ala Thr Ala Pro Thr Glu
    130                 135                 140

Ala Ala Gln Ile Ile Ser Ala Ala Gly Asp Thr Leu Ser Val Pro Ala
145                 150                 155                 160

Pro Ala Val Gln Pro Glu Glu Ser Leu Lys Thr Asp His Pro Glu Ile
                165                 170                 175

Gly Glu Gly Lys Pro Thr Pro Ala Leu Ser Glu Glu Ala Ser Ser Ser
            180                 185                 190

Ser Ile Arg Glu Arg Pro Pro Glu Glu Val Ala Ala Arg Leu Ala Gln
        195                 200                 205

Gln Glu Lys Gln Glu Gln Val Lys Ile Glu Ser Leu Ala Lys Ser Leu
    210                 215                 220

Glu Asp Ala Leu Arg Gln Thr Ala Ser Val Thr Leu Gln Ala Ile Ala
225                 230                 235                 240

Ala Gln Asn Ala Ala Val Gln Ala Val Asn Ala His Ser Asn Ile Leu
                245                 250                 255

Lys Ala Ala Met Asp Asn Ser Glu Ile Ala Gly Glu Lys Lys Ser Ala
            260                 265                 270

Gln Trp Arg Thr Val Glu Gly Ala Leu Lys Glu Arg Arg Lys Ala Val
        275                 280                 285

Asp Glu Ala Ala Asp Ala Leu Leu Lys Ala Lys Glu Glu Leu Glu Lys
    290                 295                 300

Met Lys Ser Val Ile Glu Asn Ala Lys Lys Lys Glu Val Ala Gly Ala
305                 310                 315                 320

Lys Pro His Ile Thr Ala Ala Glu Gly Lys Leu His Asn Met Ile Val
                325                 330                 335

Asp Leu Asp Asn Val Val Lys Lys Val Gln Ala Ala Gln Ser Glu Ala
            340                 345                 350

Lys Val Val Ser Gln Tyr His Glu Leu Val Val Gln Ala Arg Asp Asp
        355                 360                 365

Phe Lys Arg Glu Leu Asp Ser Ile Thr Pro Glu Val Leu Pro Gly Trp
    370                 375                 380

Lys Gly Met Ser Val Ser Asp Leu Ala Asp Lys Leu Ser Thr Asp Asp
385                 390                 395                 400

Leu Asn Ser Leu Ile Ala His Ala His Arg Arg Ile Asp Gln Leu Asn
                405                 410                 415

Arg Glu Leu Ala Glu Gln Lys Ala Thr Glu Lys Gln His Ile Thr Leu
            420                 425                 430
```

```
Ala Leu Glu Lys Gln Lys Leu Glu Glu Lys Arg Ala Phe Asp Ser Ala
        435                 440                 445

Val Ala Lys Ala Leu Glu His His Arg Ser Glu Ile Gln Ala Glu Gln
    450                 455                 460

Asp Arg Lys Ile Glu Glu Val Arg Asp Ala Met Glu Asn Glu Met Arg
465                 470                 475                 480

Thr Gln Leu Arg Arg Gln Ala Ala Ala His Thr Asp His Leu Arg Asp
                485                 490                 495

Val Leu Arg Val Gln Glu Gln Glu Leu Lys Ser Glu Phe Glu Gln Asn
            500                 505                 510

Leu Ser Glu Lys Leu Ser Glu Gln Glu Leu Gln Phe Arg Arg Leu Ser
        515                 520                 525

Gln Glu Gln Val Asp Asn Phe Thr Leu Asp Ile Asn Thr Ala Tyr Ala
    530                 535                 540

Arg Leu Arg Gly Ile Glu Gln Ala Val Gln Ser His Ala Val Ala Glu
545                 550                 555                 560

Glu Glu Ala Arg Lys Ala His Gln Leu Trp Leu Ser Val Glu Ala Leu
                565                 570                 575

Lys Tyr Ser Met Lys Thr Ser Ser Ala Glu Thr Pro Thr Ile Pro Leu
            580                 585                 590

Gly Ser Ala Val Glu Ala Ile Lys Ala Asn Cys Ser Asp Asn Glu Phe
        595                 600                 605

Thr Gln Ala Leu Thr Ala Ala Ile Pro Pro Glu Ser Leu Thr Arg Gly
    610                 615                 620

Val Tyr Ser Glu Glu Thr Leu Arg Ala Arg Phe Tyr Ala Val Gln Lys
625                 630                 635                 640

Leu Ala Arg Arg Val Ala Met Ile Asp Glu Thr Arg Asn Ser Leu Tyr
                645                 650                 655

Gln Tyr Phe Leu Ser Tyr Leu Gln Ser Leu Leu Leu Phe Pro Pro Gln
            660                 665                 670

Gln Leu Lys Pro Pro Pro Glu Leu Cys Pro Glu Asp Ile Asn Thr Phe
        675                 680                 685

Lys Leu Leu Ser Tyr Ala Ser Tyr Cys Ile Glu His Gly Asp Leu Glu
    690                 695                 700

Leu Ala Ala Lys Phe Val Asn Gln Leu Lys Gly Glu Ser Arg Arg Val
705                 710                 715                 720

Ala Gln Asp Trp Leu Lys Glu Ala Arg Met Thr Leu Glu Thr Lys Gln
                725                 730                 735

Ile Val Glu Ile Leu Thr Ala Tyr Ala Ser Ala Val Gly Ile Gly Thr
            740                 745                 750

Thr Gln Val Gln Pro Glu
        755
```

<210> SEQ ID NO 43
<211> LENGTH: 3015
<212> TYPE: DNA
<213> ORGANISM: Homo sapiens

<400> SEQUENCE: 43

```
aattctcttt aagagtcaca gctgtccatt ttccacgtgc ggctgaagaa tggatttcag      60

agcgctctcc ctccggcagt gttcacctag taaccccttc cggataagga cctgcagccc     120

gggcgcgacc cggaaaggga atccgccctt ttcgcctcct tcgcgccaat cgcctggagt     180

tggcgtttcc gcagccggga cacagcccac cctctaagag ccgcggagtc ggggacggta     240
```

```
gaaggggccg cgcgtgcgca gtggcgtccg ctgtgcttcc ggtgcgccgg gcgcggacgc    300
gggcacgcac acacgcaagc acgcctccac ttaactcgcg ccgccgcggc agctcgagtc    360
caccagcagc gccgtccgct tgaccgagat gctgcgggcc tgtcagttat cgggtgtgac    420
cgccgccgcc cagagttgtc tctgtgggaa gtttgtcctc cgtccattgc gaccatgccg    480
cagatactct acttcaggca gctctgggtt gactactggc aaaattgctg gagctggcct    540
tttgtttgtt ggtggaggta ttggtggcac tatcctatat gccaaatggg attcccattt    600
ccgggaaagt gtagagaaaa ccatacctta ctcagacaaa ctcttcgaga tggttcttgg    660
tcctgcagct tataatgttc cattgccaaa gaaatcgatt cagtcgggtc cactaaaaat    720
ctctagtgta tcagaagtaa tgaaagaatc taaacagcct gcctcacaac tccaaaaaca    780
aaagggagat actccagctt cagcaacagc acctacagaa gcggctcaaa ttatttctgc    840
agcaggtgat accctgtcgg tcccagcccc tgcagttcag cctgaggaat ctttaaaaac    900
tgatcaccct gaaattggtg aaggaaaacc cacacctgca ctttcagaag catcctcatc    960
ttctataagg gagcgaccac ctgaagaagt tgcagctcgc cttgcacaac aggaaaaaca   1020
agaacaagtt aaaattgagt ctctagccaa gagcttagaa gatgctctga ggcaaactgc   1080
aagtgtcact ctgcaggcta ttgcagctca gaatgctgcg gtccaggctg tcaatgcaca   1140
ctccaacata ttgaaagccg ccatggacaa ttctgagatt gcaggcgaga agaaatctgc   1200
tcagtggcgc acagtggagg gtgcattgaa ggaacgcaga aaggcagtag atgaagctgc   1260
cgatgccctt ctcaaagcca aagaagagtt agagaagatg aaaagtgtga ttgaaaatgc   1320
aaagaaaaaa gaggttgctg gggccaagcc tcatataact gctgcagagg gtaaacttca   1380
caacatgata gttgatctgg ataatgtggt caaaaaggtc caagcagctc agtctgaggc   1440
taaggttgta tctcagtatc atgagctggt ggtccaagct cgggatgact ttaaacgaga   1500
gctggacagt attactccag aagtccttcc tgggtggaaa ggaatgagtg tttcagactt   1560
agctgacaag ctctctactg atgatctgaa ctccctcatt gctcatgcac atcgtcgtat   1620
tgatcagctg aacagagagc tggcagaaca gaaggccacc gaaaagcagc acatcacgtt   1680
agccttggag aaacaaaagc tggaagaaaa gcgggcattt gactctgcag tagcaaaagc   1740
attagaacat cacagaagtg aaatacaggc tgaacaggac agaaagatag aagaagtcag   1800
agatgccatg gaaaatgaaa tgagaaccca gcttcgccga caggcagctg cccacactga   1860
tcacttgcga gatgtcctta gggtacaaga acaggaattg aagtctgaat ttgagcagaa   1920
cctgtctgag aaactctctg aacaagaatt acaatttcgt cgtctcagtc aagagcaagt   1980
tgacaacttt actctggata taaatactgc ctatgccaga ctcagaggaa tcgaacaggc   2040
tgttcagagc catgcagttg ctgaagagga agccagaaaa gcccaccaac tctggctttc   2100
agtggaggca ttaaagtaca gcatgaagac ctcatctgca gaaacaccta ctatcccgct   2160
gggtagtgca gttgaggcca tcaaagccaa ctgttctgat aatgaattca cccaagcttt   2220
aaccgcagct atccctccag agtccctgac ccgtggggtg tacagtgaag agacccttag   2280
agcccgtttc tatgctgttc aaaaactggc ccgaagggta gcaatgattg atgaaaccag   2340
aaatagcttg taccagtact tcctctccta cctacagtcc ctgctcctat tcccacctca   2400
gcaactgaag ccgcccccag agctctgccc tgaggatata aacacattta aattactgtc   2460
atatgcttcc tattgcattg agcatggtga tctggagcta gcagcaaagt ttgtcaatca   2520
gctgaagggg gaatccagac gagtggcaca ggactggctg aaggaagccc gaatgaccct   2580
agaaacgaaa cagatagtgg aaatcctgac agcatatgcc agcgccgtag gaataggaac   2640
```

```
cactcaggtg cagccagagt gaggtttagg aagattttca taaagtcata tttcatgtca   2700

aaggaaatca gcagtgatag atgaagggtt cgcagcgaga gtcccggact tgtctagaaa   2760

tgagcaggtt tacaagtact gttctaaatg ttaacacctg ttgcatttat attctttcca   2820

tttgctatca tgtcagtgaa cgccaggagt gctttctttg caacttgtgt aacattttct   2880

gtttttttcag gttttactga tgaggcttgt gaggccaatc aaaataatgt ttgtgatctc   2940

tactactgtt gattttgccc tcggagcaaa ctgaataaag caacaagatg aaaactgaaa   3000

aaaaaaaaaa aaaaa                                                     3015
```

<210> SEQ ID NO 44
<211> LENGTH: 757
<212> TYPE: PRT
<213> ORGANISM: Homo sapiens

<400> SEQUENCE: 44

```
Met Leu Arg Ala Cys Gln Leu Ser Gly Val Thr Ala Ala Ala Gln Ser
1               5                   10                  15

Cys Leu Cys Gly Lys Phe Val Leu Arg Pro Leu Arg Pro Cys Arg Arg
            20                  25                  30

Tyr Ser Thr Ser Gly Ser Ser Gly Leu Thr Thr Gly Lys Ile Ala Gly
        35                  40                  45

Ala Gly Leu Leu Phe Val Gly Gly Gly Ile Gly Gly Thr Ile Leu Tyr
    50                  55                  60

Ala Lys Trp Asp Ser His Phe Arg Glu Ser Val Glu Lys Thr Ile Pro
65                  70                  75                  80

Tyr Ser Asp Lys Leu Phe Glu Met Val Leu Gly Pro Ala Ala Tyr Asn
                85                  90                  95

Val Pro Leu Pro Lys Lys Ser Ile Gln Ser Gly Pro Leu Lys Ile Ser
            100                 105                 110

Ser Val Ser Glu Val Met Lys Glu Ser Lys Gln Pro Ala Ser Gln Leu
        115                 120                 125

Gln Lys Gln Lys Gly Asp Thr Pro Ala Ser Ala Thr Ala Pro Thr Glu
    130                 135                 140

Ala Ala Gln Ile Ile Ser Ala Ala Gly Asp Thr Leu Ser Val Pro Ala
145                 150                 155                 160

Pro Ala Val Gln Pro Glu Glu Ser Leu Lys Thr Asp His Pro Glu Ile
                165                 170                 175

Gly Glu Gly Lys Pro Thr Pro Ala Leu Ser Glu Ala Ser Ser Ser Ser
            180                 185                 190

Ile Arg Glu Arg Pro Pro Glu Glu Val Ala Ala Arg Leu Ala Gln Gln
        195                 200                 205

Glu Lys Gln Glu Gln Val Lys Ile Glu Ser Leu Ala Lys Ser Leu Glu
    210                 215                 220

Asp Ala Leu Arg Gln Thr Ala Ser Val Thr Leu Gln Ala Ile Ala Ala
225                 230                 235                 240

Gln Asn Ala Ala Val Gln Ala Val Asn Ala His Ser Asn Ile Leu Lys
                245                 250                 255

Ala Ala Met Asp Asn Ser Glu Ile Ala Gly Glu Lys Lys Ser Ala Gln
            260                 265                 270

Trp Arg Thr Val Glu Gly Ala Leu Lys Glu Arg Arg Lys Ala Val Asp
        275                 280                 285

Glu Ala Ala Asp Ala Leu Leu Lys Ala Lys Glu Glu Leu Glu Lys Met
    290                 295                 300
```

```
Lys Ser Val Ile Glu Asn Ala Lys Lys Lys Glu Val Ala Gly Ala Lys
305                 310                 315                 320

Pro His Ile Thr Ala Ala Glu Gly Lys Leu His Asn Met Ile Val Asp
                325                 330                 335

Leu Asp Asn Val Val Lys Lys Val Gln Ala Ala Gln Ser Glu Ala Lys
            340                 345                 350

Val Val Ser Gln Tyr His Glu Leu Val Val Gln Ala Arg Asp Asp Phe
        355                 360                 365

Lys Arg Glu Leu Asp Ser Ile Thr Pro Glu Val Leu Pro Gly Trp Lys
    370                 375                 380

Gly Met Ser Val Ser Asp Leu Ala Asp Lys Leu Ser Thr Asp Asp Leu
385                 390                 395                 400

Asn Ser Leu Ile Ala His Ala His Arg Arg Ile Asp Gln Leu Asn Arg
                405                 410                 415

Glu Leu Ala Glu Gln Lys Ala Thr Glu Lys Gln His Ile Thr Leu Ala
            420                 425                 430

Leu Glu Lys Gln Lys Leu Glu Glu Lys Arg Ala Phe Asp Ser Ala Val
        435                 440                 445

Ala Lys Ala Leu Glu His His Arg Ser Glu Ile Gln Ala Glu Gln Asp
    450                 455                 460

Arg Lys Ile Glu Glu Val Arg Asp Ala Met Glu Asn Glu Met Arg Thr
465                 470                 475                 480

Gln Leu Arg Arg Gln Ala Ala Ala His Thr Asp His Leu Arg Asp Val
                485                 490                 495

Leu Arg Val Gln Glu Gln Glu Leu Lys Ser Glu Phe Glu Gln Asn Leu
            500                 505                 510

Ser Glu Lys Leu Ser Glu Gln Glu Leu Gln Phe Arg Arg Leu Ser Gln
        515                 520                 525

Glu Gln Val Asp Asn Phe Thr Leu Asp Ile Asn Thr Ala Tyr Ala Arg
    530                 535                 540

Leu Arg Gly Ile Glu Gln Ala Val Gln Ser His Ala Val Ala Glu Glu
545                 550                 555                 560

Glu Ala Arg Lys Ala His Gln Leu Trp Leu Ser Val Glu Ala Leu Lys
                565                 570                 575

Tyr Ser Met Lys Thr Ser Ser Ala Glu Thr Pro Thr Ile Pro Leu Gly
            580                 585                 590

Ser Ala Val Glu Ala Ile Lys Ala Asn Cys Ser Asp Asn Glu Phe Thr
        595                 600                 605

Gln Ala Leu Thr Ala Ala Ile Pro Pro Glu Ser Leu Thr Arg Gly Val
    610                 615                 620

Tyr Ser Glu Glu Thr Leu Arg Ala Arg Phe Tyr Ala Val Gln Lys Leu
625                 630                 635                 640

Ala Arg Arg Val Ala Met Ile Asp Glu Thr Arg Asn Ser Leu Tyr Gln
                645                 650                 655

Tyr Phe Leu Ser Tyr Leu Gln Ser Leu Leu Leu Phe Pro Pro Gln Gln
            660                 665                 670

Leu Lys Pro Pro Pro Glu Leu Cys Pro Glu Asp Ile Asn Thr Phe Lys
        675                 680                 685

Leu Leu Ser Tyr Ala Ser Tyr Cys Ile Glu His Gly Asp Leu Glu Leu
    690                 695                 700

Ala Ala Lys Phe Val Asn Gln Leu Lys Gly Glu Ser Arg Arg Val Ala
705                 710                 715                 720
```

```
Gln Asp Trp Leu Lys Glu Ala Arg Met Thr Leu Glu Thr Lys Gln Ile
                725                 730                 735

Val Glu Ile Leu Thr Ala Tyr Ala Ser Ala Val Gly Ile Gly Thr Thr
            740                 745                 750

Gln Val Gln Pro Glu
        755


<210> SEQ ID NO 45
<211> LENGTH: 2985
<212> TYPE: DNA
<213> ORGANISM: Homo sapiens

<400> SEQUENCE: 45

aattctcttt aagagtcaca gctgtccatt ttccacgtgc ggctgaagaa tggatttcag     60

agcgctctcc ctccggcagt gttcacctag taaccccttc cggataagga cctgcagccc    120

gggcgcgacc cggaaaggga atccgccctt ttcgcctcct tcgcgccaat cgcctggagt    180

tggcgtttcc gcagccggga cacagcccac cctctaagag ccgcggagtc ggggacggta    240

gaaggggccg cgcgtgcgca gtggcgtccg ctgtgcttcc ggtgcgccgg gcgcggacgc    300

gggcacgcac acacgcaagc acgcctccac ttaactcgcg ccgccgcggc agctcgagtc    360

caccagcagc gccgtccgct tgaccgagat gctgcgggcc tgtcagttat cgggtgtgac    420

cgccgccgcc cagagttgtc tctgtgggaa gtttgtcctc cgtccattgc gaccatgccg    480

cagatactct acttcaggca gctctgggtt gactactggc aaaattgctg gagctggcct    540

tttgtttgtt ggtggaggta ttggtggcac tatcctatat gccaaatggg attcccattt    600

ccgggaaagt gtagagaaaa ccatacctta ctcagacaaa ctcttcgaga tggttcttgg    660

tcctgcagct tataatgttc cattgccaaa gaaatcgatt cagtcgggtc cactaaaaat    720

ctctagtgta tcagaagtaa tgaaagaatc taaacagcct gcctcacaac tccaaaaaca    780

aaagggagat actccagctt cagcaacagc aggtgatacc ctgtcggtcc cagcccctgc    840

agttcagcct gaggaatctt taaaaactga tcaccctgaa attggtgaag gaaaacccac    900

acctgcactt tcagaagaag catcctcatc ttctataagg gagcgaccac ctgaagaagt    960

tgcagctcgc cttgcacaac aggaaaaaca agaacaagtt aaaattgagt ctctagccaa   1020

gagcttagaa gatgctctga ggcaaactgc aagtgtcact ctgcaggcta ttgcagctca   1080

gaatgctgcg gtccaggctg tcaatgcaca ctccaacata ttgaaagccg ccatggacaa   1140

ttctgagatt gcaggcgaga agaaatctgc tcagtggcgc acagtggagg gtgcattgaa   1200

ggaacgcaga aaggcagtag atgaagctgc cgatgccctt ctcaaagcca aagaagagtt   1260

agagaagatg aaaagtgtga ttgaaaatgc aaagaaaaaa gaggttgctg gggccaagcc   1320

tcatataact gctgcagagg gtaaacttca caacatgata gttgatctgg ataatgtggt   1380

caaaaaggtc caagcagctc agtctgaggc taaggttgta tctcagtatc atgagctggt   1440

ggtccaagct cgggatgact ttaaacgaga gctggacagt attactccag aagtccttcc   1500

tgggtggaaa ggaatgagtg tttcagactt agctgacaag ctctctactg atgatctgaa   1560

ctccctcatt gctcatgcac atcgtcgtat tgatcagctg aacagagagc tggcagaaca   1620

gaaggccacc gaaaagcagc acatcacgtt agccttggag aaacaaaagc tggaagaaaa   1680

gcgggcattt gactctgcag tagcaaaagc attagaacat cacagaagtg aaatacaggc   1740

tgaacaggac agaaagatag aagaagtcag agatgccatg gaaaatgaaa tgagaaccca   1800

gcttcgccga caggcagctg cccacactga tcacttgcga gatgtcctta gggtacaaga   1860
```

```
acaggaattg aagtctgaat ttgagcagaa cctgtctgag aaactctctg aacaagaatt   1920

acaatttcgt cgtctcagtc aagagcaagt tgacaacttt actctggata taaatactgc   1980

ctatgccaga ctcagaggaa tcgaacaggc tgttcagagc catgcagttg ctgaagagga   2040

agccagaaaa gcccaccaac tctggctttc agtggaggca ttaaagtaca gcatgaagac   2100

ctcatctgca gaaacaccta ctatcccgct gggtagtgca gttgaggcca tcaaagccaa   2160

ctgttctgat aatgaattca cccaagcttt aaccgcagct atccctccag agtccctgac   2220

ccgtggggtg tacagtgaag agacccttag agcccgtttc tatgctgttc aaaaactggc   2280

ccgaagggta gcaatgattg atgaaaccag aaatagcttg taccagtact tcctctccta   2340

cctacagtcc ctgctcctat tcccacctca gcaactgaag ccgcccccag agctctgccc   2400

tgaggatata aacacattta aattactgtc atatgcttcc tattgcattg agcatggtga   2460

tctggagcta gcagcaaagt ttgtcaatca gctgaagggg gaatccagac gagtggcaca   2520

ggactggctg aaggaagccc gaatgaccct agaaacgaaa cagatagtgg aaatcctgac   2580

agcatatgcc agcgccgtag gaataggaac cactcaggtg cagccagagt gaggtttagg   2640

aagattttca taaagtcata tttcatgtca aaggaaatca gcagtgatag atgaagggtt   2700

cgcagcgaga gtcccggact tgtctagaaa tgagcaggtt tacaagtact gttctaaatg   2760

ttaacacctg ttgcatttat attctttcca tttgctatca tgtcagtgaa cgccaggagt   2820

gctttctttg caacttgtgt aacattttct gtttttcag gttttactga tgaggcttgt   2880

gaggccaatc aaaataatgt ttgtgatctc tactactgtt gattttgccc tcggagcaaa   2940

ctgaataaag caacaagatg aaaactgaaa aaaaaaaaaa aaaaa                   2985
```

```
<210> SEQ ID NO 46
<211> LENGTH: 747
<212> TYPE: PRT
<213> ORGANISM: Homo sapiens

<400> SEQUENCE: 46

Met Leu Arg Ala Cys Gln Leu Ser Gly Val Thr Ala Ala Ala Gln Ser
1               5                   10                  15

Cys Leu Cys Gly Lys Phe Val Leu Arg Pro Leu Arg Pro Cys Arg Arg
            20                  25                  30

Tyr Ser Thr Ser Gly Ser Ser Gly Leu Thr Thr Gly Lys Ile Ala Gly
        35                  40                  45

Ala Gly Leu Leu Phe Val Gly Gly Gly Ile Gly Gly Thr Ile Leu Tyr
    50                  55                  60

Ala Lys Trp Asp Ser His Phe Arg Glu Ser Val Glu Lys Thr Ile Pro
65                  70                  75                  80

Tyr Ser Asp Lys Leu Phe Glu Met Val Leu Gly Pro Ala Ala Tyr Asn
                85                  90                  95

Val Pro Leu Pro Lys Lys Ser Ile Gln Ser Gly Pro Leu Lys Ile Ser
            100                 105                 110

Ser Val Ser Glu Val Met Lys Glu Ser Lys Gln Pro Ala Ser Gln Leu
        115                 120                 125

Gln Lys Gln Lys Gly Asp Thr Pro Ala Ser Ala Thr Ala Gly Asp Thr
    130                 135                 140

Leu Ser Val Pro Ala Pro Ala Val Gln Pro Glu Glu Ser Leu Lys Thr
145                 150                 155                 160

Asp His Pro Glu Ile Gly Glu Gly Lys Pro Thr Pro Ala Leu Ser Glu
                165                 170                 175
```

```
Glu Ala Ser Ser Ser Ser Ile Arg Glu Arg Pro Pro Glu Glu Val Ala
            180                 185                 190

Ala Arg Leu Ala Gln Gln Glu Lys Gln Glu Gln Val Lys Ile Glu Ser
        195                 200                 205

Leu Ala Lys Ser Leu Glu Asp Ala Leu Arg Gln Thr Ala Ser Val Thr
    210                 215                 220

Leu Gln Ala Ile Ala Ala Gln Asn Ala Ala Val Gln Ala Val Asn Ala
225                 230                 235                 240

His Ser Asn Ile Leu Lys Ala Ala Met Asp Asn Ser Glu Ile Ala Gly
                245                 250                 255

Glu Lys Lys Ser Ala Gln Trp Arg Thr Val Glu Gly Ala Leu Lys Glu
            260                 265                 270

Arg Arg Lys Ala Val Asp Glu Ala Ala Asp Ala Leu Leu Lys Ala Lys
        275                 280                 285

Glu Glu Leu Glu Lys Met Lys Ser Val Ile Glu Asn Ala Lys Lys Lys
    290                 295                 300

Glu Val Ala Gly Ala Lys Pro His Ile Thr Ala Ala Glu Gly Lys Leu
305                 310                 315                 320

His Asn Met Ile Val Asp Leu Asp Asn Val Val Lys Lys Val Gln Ala
                325                 330                 335

Ala Gln Ser Glu Ala Lys Val Val Ser Gln Tyr His Glu Leu Val Val
            340                 345                 350

Gln Ala Arg Asp Asp Phe Lys Arg Glu Leu Asp Ser Ile Thr Pro Glu
        355                 360                 365

Val Leu Pro Gly Trp Lys Gly Met Ser Val Ser Asp Leu Ala Asp Lys
    370                 375                 380

Leu Ser Thr Asp Asp Leu Asn Ser Leu Ile Ala His Ala His Arg Arg
385                 390                 395                 400

Ile Asp Gln Leu Asn Arg Glu Leu Ala Glu Gln Lys Ala Thr Glu Lys
                405                 410                 415

Gln His Ile Thr Leu Ala Leu Glu Lys Gln Lys Leu Glu Glu Lys Arg
            420                 425                 430

Ala Phe Asp Ser Ala Val Ala Lys Ala Leu Glu His His Arg Ser Glu
        435                 440                 445

Ile Gln Ala Glu Gln Asp Arg Lys Ile Glu Glu Val Arg Asp Ala Met
    450                 455                 460

Glu Asn Glu Met Arg Thr Gln Leu Arg Arg Gln Ala Ala Ala His Thr
465                 470                 475                 480

Asp His Leu Arg Asp Val Leu Arg Val Gln Glu Gln Glu Leu Lys Ser
                485                 490                 495

Glu Phe Glu Gln Asn Leu Ser Glu Lys Leu Ser Glu Gln Glu Leu Gln
            500                 505                 510

Phe Arg Arg Leu Ser Gln Glu Gln Val Asp Asn Phe Thr Leu Asp Ile
        515                 520                 525

Asn Thr Ala Tyr Ala Arg Leu Arg Gly Ile Glu Gln Ala Val Gln Ser
    530                 535                 540

His Ala Val Ala Glu Glu Glu Ala Arg Lys Ala His Gln Leu Trp Leu
545                 550                 555                 560

Ser Val Glu Ala Leu Lys Tyr Ser Met Lys Thr Ser Ser Ala Glu Thr
                565                 570                 575

Pro Thr Ile Pro Leu Gly Ser Ala Val Glu Ala Ile Lys Ala Asn Cys
            580                 585                 590

Ser Asp Asn Glu Phe Thr Gln Ala Leu Thr Ala Ala Ile Pro Pro Glu
```

```
        595                 600                 605

Ser Leu Thr Arg Gly Val Tyr Ser Glu Glu Thr Leu Arg Ala Arg Phe
    610                 615                 620

Tyr Ala Val Gln Lys Leu Ala Arg Arg Val Ala Met Ile Asp Glu Thr
625                 630                 635                 640

Arg Asn Ser Leu Tyr Gln Tyr Phe Leu Ser Tyr Leu Gln Ser Leu Leu
                645                 650                 655

Leu Phe Pro Pro Gln Gln Leu Lys Pro Pro Pro Glu Leu Cys Pro Glu
            660                 665                 670

Asp Ile Asn Thr Phe Lys Leu Leu Ser Tyr Ala Ser Tyr Cys Ile Glu
        675                 680                 685

His Gly Asp Leu Glu Leu Ala Ala Lys Phe Val Asn Gln Leu Lys Gly
    690                 695                 700

Glu Ser Arg Arg Val Ala Gln Asp Trp Leu Lys Glu Ala Arg Met Thr
705                 710                 715                 720

Leu Glu Thr Lys Gln Ile Val Glu Ile Leu Thr Ala Tyr Ala Ser Ala
                725                 730                 735

Val Gly Ile Gly Thr Thr Gln Val Gln Pro Glu
            740                 745


<210> SEQ ID NO 47
<211> LENGTH: 15
<212> TYPE: PRT
<213> ORGANISM: Homo sapiens

<400> SEQUENCE: 47

Tyr Leu Ile Leu Gly Ser Ala Val Gly Gly Gly Tyr Thr Ala Lys
1               5                   10                  15


<210> SEQ ID NO 48
<211> LENGTH: 6
<212> TYPE: PRT
<213> ORGANISM: Homo sapiens

<400> SEQUENCE: 48

Thr Phe Asp Gln Trp Lys
1               5


<210> SEQ ID NO 49
<211> LENGTH: 10
<212> TYPE: PRT
<213> ORGANISM: Homo sapiens

<400> SEQUENCE: 49

Asp Met Ile Pro Asp Leu Ser Glu Tyr Lys
1               5                   10


<210> SEQ ID NO 50
<211> LENGTH: 18
<212> TYPE: PRT
<213> ORGANISM: Homo sapiens

<400> SEQUENCE: 50

Trp Ile Val Pro Asp Ile Val Trp Glu Ile Asp Glu Tyr Ile Asp Phe
1               5                   10                  15

Glu Lys


<210> SEQ ID NO 51
<211> LENGTH: 7
<212> TYPE: PRT
```

<213> ORGANISM: Homo sapiens

<400> SEQUENCE: 51

```
Leu Ala Pro Asp Phe Asp Lys
1               5
```

<210> SEQ ID NO 52
<211> LENGTH: 9
<212> TYPE: PRT
<213> ORGANISM: Homo sapiens

<400> SEQUENCE: 52

```
Ile Val Glu Ser Leu Ser Leu Leu Lys
1               5
```

<210> SEQ ID NO 53
<211> LENGTH: 10
<212> TYPE: PRT
<213> ORGANISM: Homo sapiens

<400> SEQUENCE: 53

```
Ala Leu Pro Asn Ser Glu Asp Leu Val Lys
1               5                   10
```

<210> SEQ ID NO 54
<211> LENGTH: 14
<212> TYPE: PRT
<213> ORGANISM: Homo sapiens

<400> SEQUENCE: 54

```
Asp Phe Phe Thr Ser Gly Ser Pro Glu Glu Thr Ala Phe Arg
1               5                   10
```

<210> SEQ ID NO 55
<211> LENGTH: 13
<212> TYPE: PRT
<213> ORGANISM: Homo sapiens

<400> SEQUENCE: 55

```
Thr Arg Leu Leu Lys Leu Arg Tyr Leu Ile Leu Gly Ser
1               5                   10
```

<210> SEQ ID NO 56
<211> LENGTH: 20
<212> TYPE: PRT
<213> ORGANISM: Homo sapiens

<400> SEQUENCE: 56

```
Phe Trp Pro Ala Arg Leu Ala Thr Arg Leu Leu Lys Leu Arg Tyr Leu
1               5                   10                  15

Ile Leu Gly Ser
            20
```

<210> SEQ ID NO 57
<211> LENGTH: 21
<212> TYPE: PRT
<213> ORGANISM: Homo sapiens

<400> SEQUENCE: 57

```
Gly Leu Leu Gly Glu Leu Ile Leu Leu Gln Gln Gln Ile Gln Glu His
1               5                   10                  15

Glu Glu Glu Ala Arg
            20
```

<210> SEQ ID NO 58
<211> LENGTH: 13
<212> TYPE: PRT
<213> ORGANISM: Homo sapiens

<400> SEQUENCE: 58

```
Ala Ala Gly Gln Tyr Ser Thr Ser Tyr Ala Gln Gln Lys
1               5                   10
```

<210> SEQ ID NO 59
<211> LENGTH: 14
<212> TYPE: PRT
<213> ORGANISM: Homo sapiens

<400> SEQUENCE: 59

```
Ile Asp Gln Leu Gln Glu Glu Leu Leu His Thr Gln Leu Lys
1               5                   10
```

<210> SEQ ID NO 60
<211> LENGTH: 37
<212> TYPE: PRT
<213> ORGANISM: Homo sapiens

<400> SEQUENCE: 60

```
Glu Tyr Lys Trp Ile Val Pro Asp Ile Val Trp Glu Ile Asp Glu Tyr
1               5                   10                  15

Ile Asp Phe Gly His Lys Leu Val Ser Glu Val Ile Gly Ala Ser Asp
            20                  25                  30

Leu Leu Leu Leu Leu
        35
```

<210> SEQ ID NO 61
<211> LENGTH: 42
<212> TYPE: PRT
<213> ORGANISM: Homo sapiens

<400> SEQUENCE: 61

```
Glu Tyr Lys Trp Ile Val Pro Asp Ile Val Trp Glu Ile Asp Glu Tyr
1               5                   10                  15

Ile Asp Phe Gly Ser Pro Glu Glu Thr Ala Phe Arg Ala Thr Asp Arg
            20                  25                  30

Gly Ser Glu Ser Asp Lys His Phe Arg Lys
        35                  40
```

<210> SEQ ID NO 62
<211> LENGTH: 59
<212> TYPE: PRT
<213> ORGANISM: Homo sapiens

<400> SEQUENCE: 62

```
Glu Lys Ile Arg Lys Ala Leu Pro Asn Ser Glu Asp Leu Val Lys Leu
1               5                   10                  15

Ala Pro Asp Phe Asp Lys Ile Val Glu Ser Leu Ser Leu Leu Lys Asp
            20                  25                  30

Phe Phe Thr Ser Gly Ser Pro Glu Glu Thr Ala Phe Arg Ala Thr Asp
        35                  40                  45

Arg Gly Ser Glu Ser Asp Lys His Phe Arg Lys
    50                  55
```

<210> SEQ ID NO 63
<211> LENGTH: 60

-continued

```
<212> TYPE: PRT
<213> ORGANISM: Homo sapiens

<400> SEQUENCE: 63

Gly Ser Pro Glu Glu Thr Ala Phe Arg Ala Thr Asp Arg Gly Ser Glu
1               5                   10                  15

Ser Asp Lys His Phe Arg Lys Val Ser Asp Lys Glu Lys Ile Asp Gln
            20                  25                  30

Leu Gln Glu Glu Leu Leu His Thr Gln Leu Lys Tyr Gln Arg Ile Leu
        35                  40                  45

Glu Arg Leu Glu Lys Glu Asn Lys Glu Leu Arg Lys
    50                  55                  60
```

PYRANONE COMPOUNDS USEFUL TO MODULATE OMA1 PROTEASE

CROSS-REFERENCE TO RELATED APPLICATIONS

This application is a Continuation-in-Part of U.S. application Ser. No. 16/022,481 filed on Jun. 28, 2018, which is a continuation of International Application No. PCT/US2017/064195 filed on Dec. 1, 2017, which claims the benefit under 35 U.S.C. § 119(e) of U.S. Provisional Application No. 62/581,723 filed on Nov. 5, 2017, U.S. Provisional Application No. 62/481,392 filed on Apr. 4, 2017, and U.S. Provisional Application No. 62/429,846 filed on Dec. 4, 2016, each of which is incorporated by reference in its entirety.

This application claims also the benefit under 35 U.S.C. § 119(e) of U.S. Provisional Application No. 63/041,292 filed on Jun. 19, 2020, which is incorporated herein by reference in its entirety as well.

The foregoing applications, and all documents cited therein or during their prosecution ("applications' cited documents") and all documents cited or referenced in the applications' cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

STATEMENT OF FEDERALLY SPONSORED RESEARCH AND DEVELOPMENT

This invention was made with government support under Grant No. 1R43AG063642-01 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 250,071 Byte ASCII (Text) file named "Sequence_Listing_ST25.txt," created on May 5, 2021.

FIELD OF THE INVENTION

The present invention relates to compounds disclosed herein as having OMA1 and/or OPA1 modulatory properties, pharmaceutical compositions comprising these compounds, chemical processes for preparation of these compounds, and their use as pharmacological tools or in the treatment of diseases connected to OMA1 and/or OPA1 in cells, animals and in particular humans. More particularly, the present disclosure provides novel pyranone derivates and methods of use of such compounds.

BACKGROUND

Mitochondria are essential for cells; their proper function is an absolute requirement for cell survival. Mitochondria form large networks of dynamic interconnected tubules that are maintained by balanced fission and fusion events. Morphological alterations of mitochondria and the mitochondrial network have been reported in human disorders. Impairment of mitochondrial fusion or fission is causative of various neurodegenerative diseases such as Charcot-Marie-Tooth disease type 2A and 4A, familial Parkinson's disease, Alzheimer's disease, Autosomal Dominant Optic Atrophy (ADOA) and other optic neuropathies (Alexander et al. 2000; Delettre et al. 2000; Carelli et al. 2002; Sadun 2002; Carelli et al. 2004; Zuchner et al. 2004; Niemann et al. 2005; Kong et al. 2009; Lenaers et al. 2009; Osborne 2010; Lee et al. 2011; Chrysostomou et al. 2013; Maresca et al. 2013; Burte et al. 2015; Salminen et al. 2015; Bose and Beal 2016; Voigt et al. 2016; Zhang et al. 2016). There is strong evidence in particular for a causal relationship between mitochondrial dysfunction and Parkinson's disease (Schapira et al. 1990; Keeney et al. 2006; Parker et al. 2008; Santos et al. 2015; Dolle et al. 2016). On the other hand, dysfunctional mitochondria have been recognized for many years in brains from deceased patients with Alzheimer's disease as well (Parker et al. 1990; Smith et al. 1996; Gibson et al. 1998; Maurer et al. 2000; Butterfield et al. 2001; Devi et al. 2006). Cumulative evidence also exists for mitochondrial fusion/fission being necessary for normal cardiac function (Dorn 2013; Piquereau et al. 2013; Burke et al. 2015; Marin-Garcia and Akhmedov 2016; Ong et al. 2017). Another example for a mitochondrial disorder is cancer. Research over the past century or so has generated a complex and rich body of knowledge revealing cancer to be a disease correlated to mitochondrial dysfunction (Alirol and Martinou 2006; Frezza and Gottlieb 2009; Hanahan and Weinberg 2011; Wallace 2012; Vyas et al. 2016).

OPA1 is a mitochondrial pro-fusion protein with two functions in mitochondrial inner membrane fusion/cristae remodeling and cytochrome C release/cell death (Alavi and Fuhrmann 2013). Proteolytic cleavage of long OPA1 isoforms (OPA1L) produces short OPA1 isoforms (OPA1S). OPA1's dual functions in mitochondrial inner membrane remodeling and cytochrome C release (Olichon et al. 2003; Frezza et al. 2006) are regulated by the ratio of OPA1L-to-OPA1S (Song et al. 2007). OPA1 forms a complex together with IMMT at the inner membrane termed MICOS complex to regulate mitochondrial cristae morphology (Barrera et al. 2016; Glytsou et al. 2016; Hessenberger et al. 2017). This complex is associated with the mitochondrial outer membrane by binding to SAMM50 (Koob et al. 2015; Ott et al. 2015). OPA1 interacts with the apoptotic machinery at the mitochondrial outer membrane through the interaction with BNIP3 (Landes et al. 2010). OPA1L cleavage and OPA1S can promote mitochondrial fragmentation, cytochrome C release and correlates with cell death (Olichon et al. 2003; Duvezin-Caubet et al. 2006; Ishihara et al. 2006; Griparic et al. 2007; Song et al. 2007; Merkwirth et al. 2008; Ehses et al. 2009; Head et al. 2009). Several proteases are directly or indirectly involved in this conversion, such as YME1L1, PARL, HTRA2, and OMA1, which plays the key role during stress-induced OPA1 cleavage (Cipolat et al. 2006; Duvezin-Caubet et al. 2006; Ishihara et al. 2006; Griparic et al. 2007; Song et al. 2007; Ehses et al. 2009; Head et al. 2009).

OMA1 is a zinc metallo-endopeptidase located in the mitochondrial inner membrane (Kaser et al. 2003). Heterozygous mutations in conserved OMA1 residues have been reported in several patients afflicted with familial and sporadic forms of amyotrophic lateral sclerosis (ALS) (Daoud et al. 2011). OMA1 is activated upon cellular stress events, such as increased reactive oxygen species or loss of mitochondrial function (Richter et al. 2015; Bohovych et al. 2016; Rainbolt et al. 2016). In the case of chronic or high stress, there is prolonged OMA1 activation, which in turn triggers the release of cytochrome C, ultimately leading to cell death (Jiang et al. 2014). OMA1 and YME1L1, which proteolytically cleaves OPA1 at the S2 cleavage site, are organized and regulated in the inner mitochondrial membrane by PHB and PHB2 (Wai et al. 2016).

Cells have an innate regulatory feedback loop to counterbalance stress-induced OPA1 cleavage by OMA1 (Alavi and Fuhrmann 2013) (Alavi and Fuhrmann 2013)(Alavi and Fuhrmann 2013)(Alavi and Fuhrmann 2013)(Alavi and Fuhrmann 2013)(Alavi and Fuhrmann 2013). Hypoxic conditions can cause decreased mitochondrial membrane potential, which activates OMA1 (Richter et al. 2015; Bohovych et al. 2016; Rainbolt et al. 2016). HIGD1A is a mitochondrial protein upregulated under hypoxic conditions by HIF1$\alpha$ (Ameri et al. 2015; Ameri and Maltepe 2015). HIGD1A can bind to the S1 cleavage site thereby protecting OPA1 from proteolytic cleavage by OMA1 (An et al. 2011; An et al. 2013), while HIGD1A translocates to the nucleus in cells undergoing apoptosis (Ameri et al. 2013).

SUMMARY

There remains an unmet medical need for therapeutic intervention because at present we still have no method for the treatment, prevention and/or amelioration of a disorder or disease correlated with mitochondrial dysfunction, for a mitochondrial disorder or disease; or for a disorder or disease characterized by OPA1 alterations The present disclosure relates to means and methods for therapeutic intervention of mitochondrial disorders or diseases, in particular to a method for the treatment, prevention and/or amelioration of a disorder or disease correlated with mitochondrial stress or dysfunction, a mitochondrial disorder or disease, or a disorder or disease characterized by OPA1 alterations. Thereby, a pharmaceutically active amount of a compound capable of modulating the activity of OMA1 and/or an oligomeric complex comprising OMA1 is administered to a patient in need of medical intervention. The present invention also relates to a method of screening for a compound capable of modulating the activity of OMA1 and/or an oligomeric complex comprising OMA1. The present invention further relates to a method for determining the susceptibility for, predisposition for, or the presence of such a disorder or disease and whether a person in need will benefit from the therapeutic intervention, i.e. personalized medicine.

We identified compounds disclosed herein which are known in the arts as HIV-1 protease inhibitors. These compounds, as shown in the provided examples, surprisingly and quite unexpectedly activated the OMA1 protease. The disclosed compounds had also a dose-dependent antagonistic effect on OPAL. Low doses resulted in OPA1 cleavage. However, higher doses prevented OPA1 cleavage even under conditions that would otherwise result in OPA1 cleavage.

The OMA1 protease has a number of disease implications and is supported by epidemiological and genetic data from humans and animal disease models. And yet, there are still until now no OMA1 modulators disclosed in the arts although many may have tried without much success to identify such molecules.

The present invention solves this problem by providing OMA1 modulators. Such compounds may be useful for the treatment of cancer and other disorders and diseases for which OMA1 activation and/or OPA1 cleavage is desired. The compounds can be used in medical therapy, alone or in combination, for example to treat cancer, angiogenesis, cardiovascular disease, neurological disease, eye disease, inflammation, autoimmune disease, and for regulating contraception, and other conditions that are connected to OMA1 and/or OPA1.

Clinical and/or pathological examples for a disorder or disease correlated with mitochondrial dysfunction, for a mitochondrial disorder or disease; or for a disorder or disease characterized by OPA1 alterations and hence, intended to be therapeutically intervened in context of this invention, are given in the non-exhaustive table below.

Ageing; in particular pathological and/or pre-mature aging
Age-related Macular Degeneration (AMD)
Alzheimer's disease
Amyotrophic lateral sclerosis (ALS)
Apoptosis
Ataxia
Autism
Autosomal Dominant Optic Atrophy (ADOA)
Barth syndrome, (familial)
Bipolar disorder
Cancer (e.g. renal cell and colorectal carcinoma, early liver, protasta, breast, bladder, primary lung, head and neck tumours, astrocytomas, adenocarcinomas in Barrett's esophagus)
Cardiomyopathy
Charcot-Marie-Tooth disease (e.g., Charcot-Marie-Tooth disease type 2a and type 4a)
Congenital lactic acidosis
Crohn disease
Deafness
Diabetes
Diabetic sensory neuropathy
Encephalomyopathy
Endotoxemia
External ophthalmoplegia (e.g. PEO)
Eye diseases
Friedreich's ataxia
Glaucoma
Heart disease
Hepatopathy (e.g. defects in SCO1)
Hepato-cerebral form of mtDNA depletion syndrome
Hereditary sensory neuropathy
Hereditary spastic paraplegia
Infantile encephalopathy
Infantile myopathy
Infectious diseases
Inflammatory diseases
Ischemia-reperfusion injury/Hypoxic damage/Oxidative damage
Kearns-Sayre syndrome
Lactic acidosis
Leber's hereditary opticus neuropathy (LHON)
Leigh's syndrome
Leukodystrophy
Metabolic disorders (e.g. defective glucose and fatty acid metabolism)
Mitochondrial neurogastrointestinal-encephalomyopathy
Mohr-Tranebjaerg-syndrome
Motor neuron disorders
mtDNA depletion syndrome
Multiple Sclerosis (MS)
Myoclonus epilepsy and ragged-red fibers syndrome (MERRF)

Myopathy
Myopathy encephalopathy lactic acidosis and stroke-like episodes (MELAS)
Myositis
Neurodegenerative disorders
Non-alcoholic fatty liver disease
Obesity
Ocular myopathy
Optic neuropathy
Optic atrophy type 1
Optic atrophy types 2 to 11
Paraganglioma (e.g. defects in complex II/SDH)
Parkinson's disease
Pearson's syndrome
Respiratory chain disorder
Rhabdomyolysis
Schizophrenia
Sideroblastic anemia
Stroke
Tubulopathy (e.g. defects in BCS1L)
Viral and bacterial infections
Wolf-Hirschhorn syndrome
Wolfram syndrome However, the disorders or diseases to be medically intervened in context of this invention are not strictly construed to the clinical and/or pathological situations described above.

The technical problem underlying the present invention is the provision of suitable means and methods for therapeutic intervention against mitochondrial dysfunction and diseases or disorders related thereto. Further, means and methods for determining the susceptibility for, predisposition for, and/or the presence of such a disease or disorder are of need.

The solution to the above technical problem is achieved by providing the embodiments characterized in the claims.

The present invention solves the above identified technical problem since, as documented herein below and in the appended examples, it was found that:

i) a disorder or disease correlated with mitochondrial dysfunction, or a mitochondrial disorder or disease, or a disorder or disease characterized by OPA1 alterations also correlated with changes in the activity of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof.
ii) measurements of the changes of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof informed selection of suitable interventions for patients with such a disorder or disease and in need of medical intervention.
iii) administering a pharmaceutically active amount of a compound capable of adjusting said changes of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof ameliorated, prevented and/or treated said disorder or disease.

In this context, it is evident that measuring the activity and/or the gene expression levels and/or the protein levels of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof can be utilized for determining the susceptibility for, predisposition for or the presence of a disorder or disease correlated with mitochondrial dysfunction or characterized by OPA1 alterations, as well as for selecting the appropriate medical interventions. The term biomarker(s) may be utilized mutatis mutandis to describe the result from such measurements.

It is of note that the present invention is particularly useful in the treatment, prevention and/or amelioration of a disease or disorder described herein before any clinical and/or pathological symptoms are diagnosed or determined or can be diagnosed or determined by the attending physician. Thereby, prior to the herein disclosed medical interventions, particular advantage can and shall also be taken of the means and methods disclosed herein for determining the susceptibility for, predisposition for or the presence of a corresponding disorder or disease.

In an additional main aspect, the present invention relates to a method of screening for a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprising the steps of (a) contacting OPA1 with OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and
(b) evaluating whether OPA1 processing is altered compared to a control, wherein OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur (herein referred to as "control sample").

The herein disclosed method of screening may further comprise the step of determining the extent of OPA1 processing in the test sample and in the control sample and/or the step of comparing the corresponding results from the test sample with those of the control sample. Thereby, if the extent of OPA1 processing in the test sample differs from that of the control sample, the compound to be screened for is considered to be a modulator of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, i.e. a d37 compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in accordance with the present invention.

If the extend of OPA1 processing in the test sample exceeds that of the control sample, the compound screened is considered to be an "agonist" of said oligomeric complex in accordance with the present invention. If the extend of OPA1 processing in the test sample falls short of that of the control sample, the compound screened is considered to be an "antagonist" of said oligomeric complex in accordance with the present invention.

The terms "agonist" and "antagonist" are known in the arts and it is to be understood that both agonists as well as antagonists capable of modulating the activity of OMA1 and/or an oligomeric complex comprising OMA1 and/or HIDG1A and/or OPA1 and/or BNIP3 and/or YME1L1 and/or PHB and/or SAMM50 and/or IMMT and/or PHB2 or (a) variant(s) thereof can provide desirable effects for a patient in need of medical intervention.

A person skilled in the art is, based on the teaching provided herein, readily in a position to select the appropriate medical intervention, i.e. agonist or antagonist, for a patient in need of such intervention based on the evaluation of said biomarker(s). Suitable means and methods for therapeutic intervention and selection of these interventions based on the disclosed biomarker(s) may be referred to as personalized medicine and/or precision medicine.

According to the present invention, methods for the treatment, prevention and/or amelioration of (i) a disorder or disease correlated with mitochondrial dysfunction, or a mitochondrial disorder or disease; or (ii) a disorder or disease characterized by OPA1 alterations, comprise the administration to a patient in need of medical intervention a pharmaceutically active amount of a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

According to the present invention, methods of screening for a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprise the steps of (a) contacting OPA1 with said OMA1 and/or oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

According to the present invention, methods for determining the susceptibility for, predisposition for or the presence of (i) a disorder or disease correlated with mitochondrial dysfunction or a mitochondrial disorder or disease; or (ii) a disorder or disease characterized by OPA1 alterations, comprise the steps of (a) obtaining a sample from the subject and measuring the activity of OMA1 and/or YME1L1 or (a) combination(s) thereof in the sample, and/or measuring the gene expression levels of OMA1, HIGD1A, OPA1, BNIP3, YME1L1, PHB, SAMM50, IMMT and/or PHB2 or (a) combination(s) thereof in the sample, and/or measuring the protein levels of OMA1, HIGD1A, OPA1, BNIP3, YME1L1, PHB, SAMM50, IMMT and/or PHB2 or (a) combination(s) thereof in the sample;

(b) comparing the increase and/or decrease of measured activity and/or gene expression levels and/or protein levels of OMA1 and/or HIGD1A and/or OPA1 and/or BNIP3 and/or YME1L1 and/or PHB and/or SAMM50 and/or IMMT and/or PHB2 or (a) combination(s) thereof in the sample compared to a reference;

(c) integrating the results of these measurements through combination of 3 or more genes selected from the group of OMA1, HIGD1A, OPA1, BNIP3, YME1L1, PHB, SAMM50, IMMT and PHB2.

According to the present invention, compounds are capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof for the treatment, prevention and/or amelioration of:

(i) a disorder or disease correlated with mitochondrial dysfunction or a mitochondrial disorder or disease; or (ii) a disorder or disease characterized by OPA1 alterations, wherein said oligomeric complex is defined as in claim 1, said compound is defined as in claim 1, said disorder or disease is defined as in claim 3 and/or said OPA1 alterations, wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard.

According to the present invention, methods of treating a disease or disorder in a patient comprise administering to a patient in need of such treatment a therapeutically effective amount of a compound according to the present invention.

According to the present invention, pharmaceutical compositions comprise a compound according to the present invention and a pharmaceutically acceptable excipient.

According to the present invention, methods of treating a disease or disorder in a patient comprise administering to a patient in need of such treatment a therapeutically effective amount of the pharmaceutical composition according to the present invention.

According to the present invention, a combination two or more methods according to the present invention result in a medical intervention individualized for one or more patients and that may be referred to as personalized medicine and/or precision medicine.

BRIEF DESCRIPTION OF THE DRAWINGS

The drawings described herein are for illustration purposes only. The drawings are not intended to limit the scope of the present disclosure.

BNIP3 gene expression levels in the temporal cortex (AD: n=13; C: n=16) from post-mortem samples of patients with Alzheimer's disease (AD) and control subjects (C).

Figure 3:
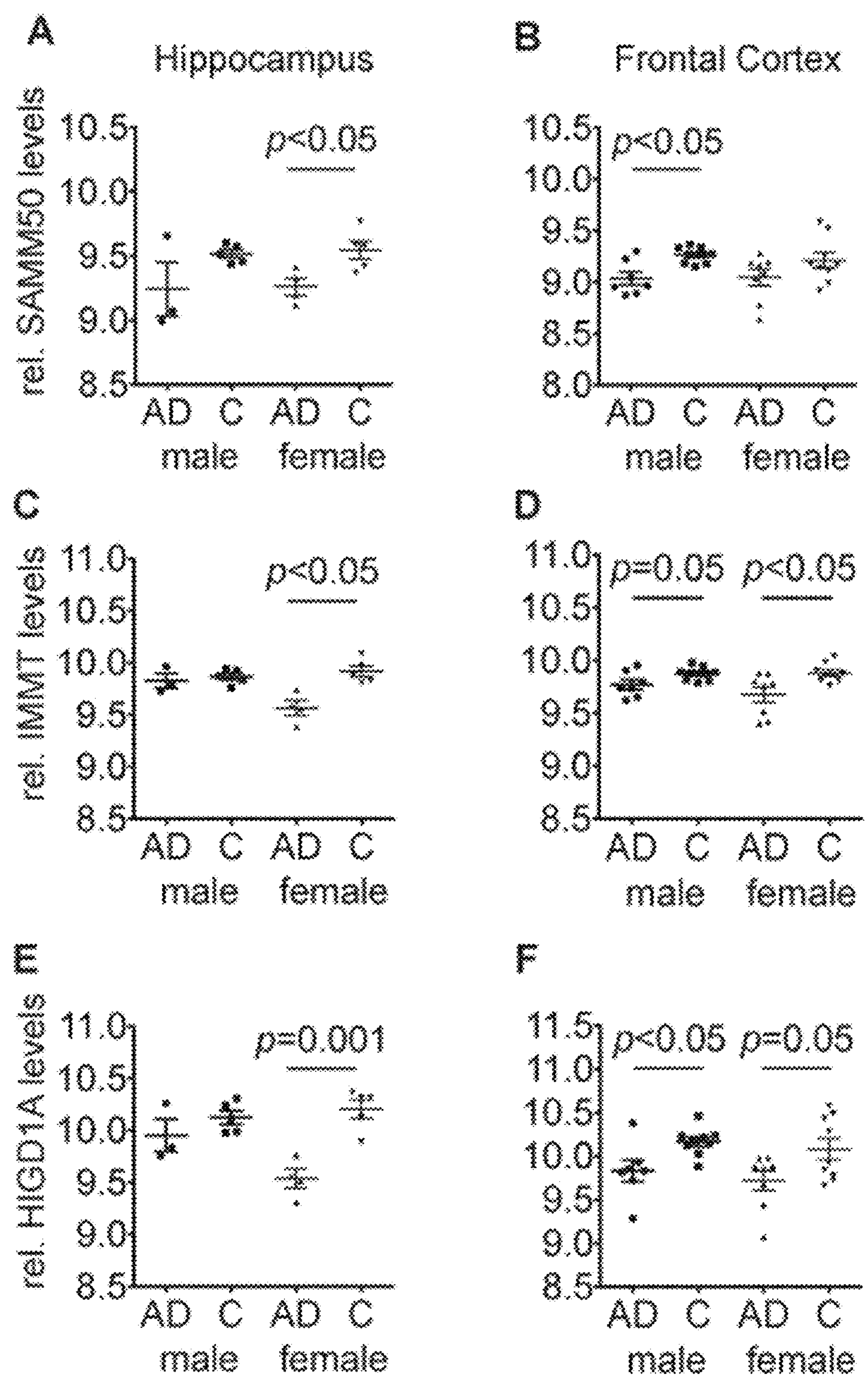

FIG. 3. (A) SAMM50 gene expression levels in the hippocampus (AD: n=8; C: n=9) from post-mortem samples of patients with Alzheimer's disease (AD) and control subjects (C). (B) SAMM50 gene expression levels in the frontal cortex (AD: n=16; C: n=17) from post-mortem samples of patients with Alzheimer's disease (AD) and control subjects (C). (C) IMMT gene expression levels in the hippocampus (AD: n=8; C: n=9) from post-mortem samples of patients with Alzheimer's disease (AD) and control subjects (C). (D) IMMT gene expression levels in the frontal cortex (AD: n=16; C: n=17) from post-mortem samples of patients with Alzheimer's disease (AD) and control subjects (C). (E) HIGD1A gene expression levels in the hippocampus (AD: n=8; C: n=9) from post-mortem samples of patients with Alzheimer's disease (AD) and control subjects (C). (F) HIGD1A gene expression levels in the frontal cortex (AD: n=16; C: n=17) from post-mortem samples of patients with Alzheimer's disease (AD) and control subjects (C).

FIG. 4. (A) shows expression levels of ONA1 in human hepatocytes for Huh7.5.1 cells not exposed and exposed to Ribavirin (CAS #36791-04-5). (B) shows expression levels of ONA1 in human hepatocytes for Huh7.5.1 cells not exposed and exposed to Ribavirin (CAS #36791-04-5).

Figure 5:
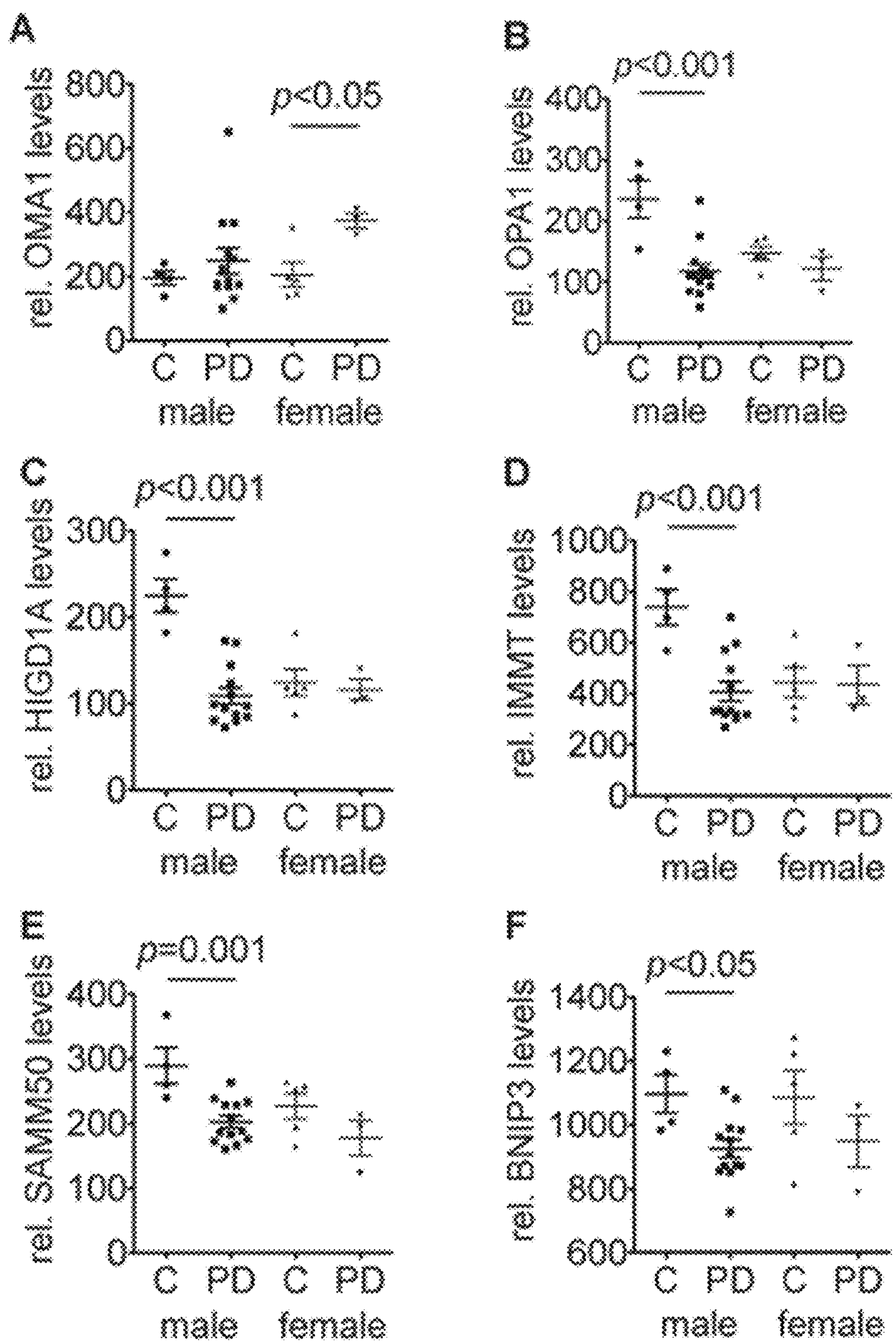

FIG. 5 (A) shows OMA1 gene expression levels in post mortem samples of the substantia nigra from a cohort of healthy subjects (C; n=9) and patients with Parkinson's disease (PD; n=16) collected at Rochester, MN (GEO accession number: GDS2821). (B) shows OPA1 gene expression levels in post mortem samples of the substantia nigra from a cohort of healthy subjects (C; n=9) and patients with Parkinson's disease (PD; n=16) collected at Rochester, MN (GEO accession number: GDS2821). (C) shows HIGD1A gene expression levels in post mortem samples of the substantia nigra from a cohort of healthy subjects (C; n=9) and patients with Parkinson's disease (PD; n=16) collected at Rochester, MN (GEO accession number: GDS2821). (D) shows IMMT gene expression levels in post mortem samples of the substantia nigra from a cohort of healthy subjects (C; n=9) and patients with Parkinson's disease (PD; n=16) collected at Rochester, MN (GEO accession number: GDS2821). (E) shows SAMM50 gene expression levels in post mortem samples of the substantia nigra from a cohort of healthy subjects (C; n=9) and patients with Parkinson's disease (PD; n=16) collected at Rochester, MN (GEO accession number: GDS2821). (F) shows BNIP3 gene expression levels in post mortem samples of the substantia nigra from a cohort of healthy subjects (C; n=9) and patients with Parkinson's disease (PD; n=16) collected at Rochester, MN (GEO accession number: GDS2821).

Figure 6:
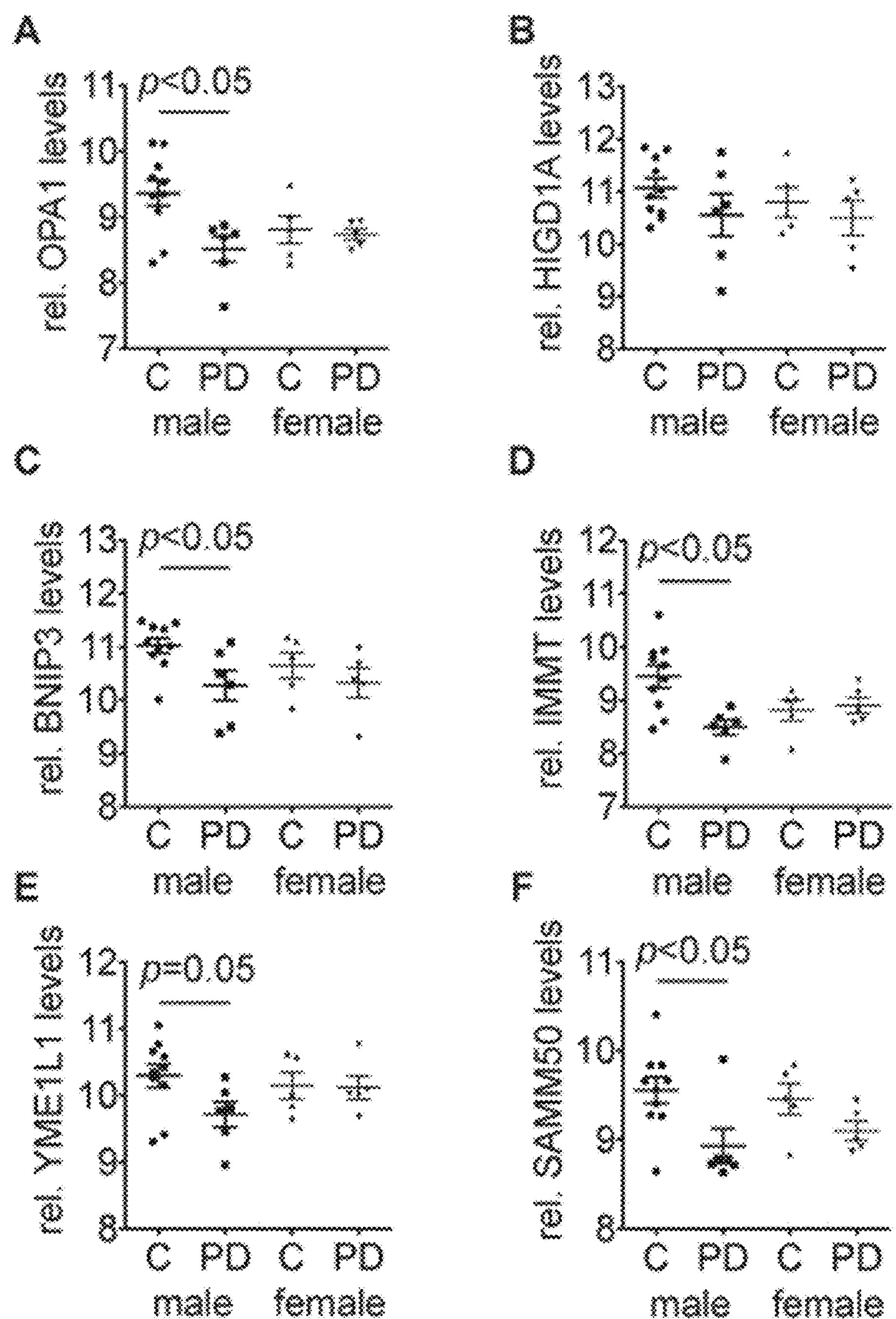

FIG. 6 (A) shows OPA1 gene expression levels in post mortem samples of the substantia nigra from an independent cohort of healthy subjects (C; n=15) and patients with Parkinson's disease (PD; n=11) collected at Syracuse, NY (GEO accession number: GSE20292). (B) shows HIGD1A gene expression levels in post mortem samples of the substantia nigra from an independent cohort of healthy subjects (C; n=15) and patients with Parkinson's disease (PD; n=11) collected at Syracuse, NY (GEO accession number: GSE20292). (C) shows BNIP3 gene expression levels in post mortem samples of the substantia nigra from an independent cohort of healthy subjects (C; n=15) and patients with Parkinson's disease (PD; n=11) collected at Syracuse, NY (GEO accession number: GSE20292). (D) shows IMMT gene expression levels in post mortem samples of the substantia nigra from an independent cohort of healthy subjects (C; n=15) and patients with Parkinson's disease (PD; n=11) collected at Syracuse, NY (GEO accession number: GSE20292). (E) shows YME1L1 gene expression levels in post mortem samples of the substantia nigra from an independent cohort of healthy subjects (C; n=15) and patients with Parkinson's disease (PD; n=11) collected at Syracuse, NY (GEO accession number: GSE20292). (F) shows SAMM50 gene expression levels in post mortem samples of the substantia nigra from an independent cohort of healthy subjects (C; n=15) and patients with Parkinson's disease (PD; n=11) collected at Syracuse, NY (GEO accession number: GSE20292).

Figure 7:
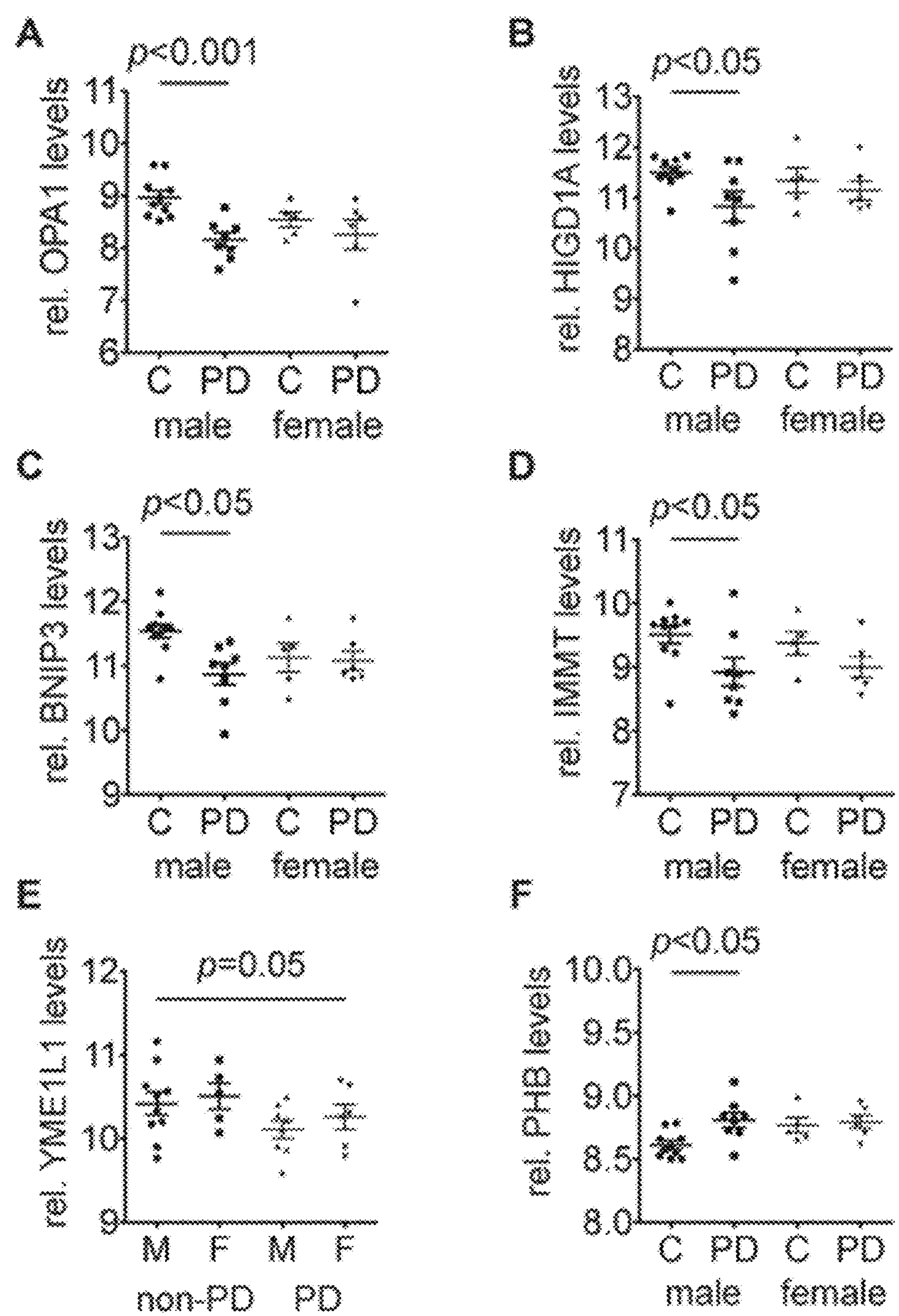

FIG. 7. (A) shows OPA1 gene expression levels in the prefrontal cortex from healthy subjects (C; n=15) and patients with Parkinson's disease (PD; n=11) from Syracuse, NY (GEO accession number: GSE20168). (B) shows HIGD1A gene expression levels in the prefrontal cortex from healthy subjects (C; n=15) and patients with Parkinson's disease (PD; n=11) from Syracuse, NY (GEO accession number: GSE20168). (C) shows BNIP3 gene expression levels in the prefrontal cortex from healthy subjects (C; n=15) and patients with Parkinson's disease (PD; n=11) from Syracuse, NY (GEO accession number: GSE20168). (D) shows IMMT gene expression levels in the prefrontal cortex from healthy subjects (C; n=15) and patients with Parkinson's disease (PD; n=11) from Syracuse, NY (GEO accession number: GSE20168). (E) shows YME1L1 gene expression levels in the prefrontal cortex from healthy subjects (C; n=15) and patients with Parkinson's disease (PD; n=11) from Syracuse, NY (GEO accession number: GSE20168). (F) shows PAB gene expression levels in the prefrontal cortex from healthy subjects (C; n=15) and patients with Parkinson's disease (PD; n=11) from Syracuse, NY (GEO accession number: GSE20168).

FIG. 8 shows data ranges for OPA1, OMA1, HIGD1A, BNIP3, YME1L1, PHB, PHB2, SAMM50 and IMMT gene expression levels in tissue samples from patients with breast cancer (top) and lung cancer (bottom).

FIG. 9 shows data ranges for OPA1, OMA1, HIGD1A, BNIP3, YME1L1, PHB, PHB2, SAMM50 and IMMT gene expression levels in tissue samples from patients with gastric cancer (top) and ovarian cancer (bottom).

Figure 10:
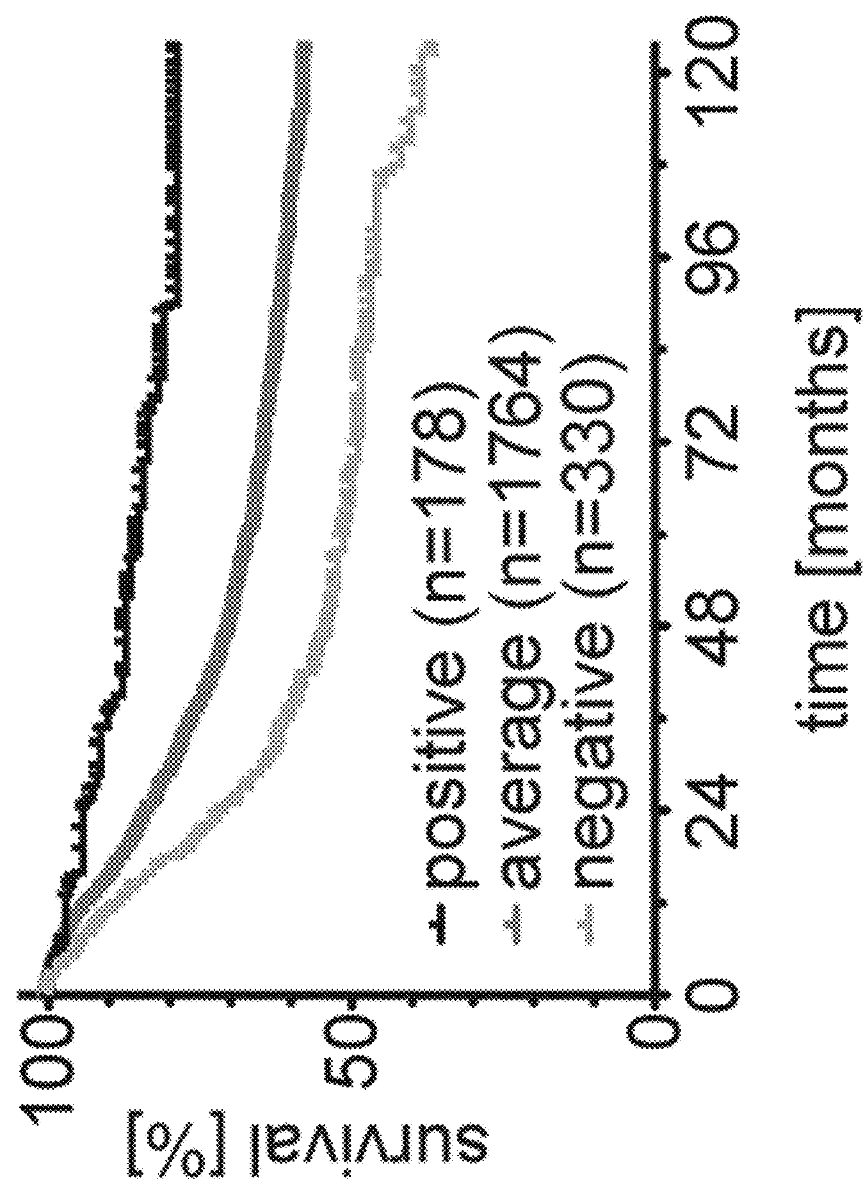

FIG. 10 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 3-gene signature based on OMA1, HIGD1A and BNIP3 expression levels (i.e., OMA1: high, HIGD1A: high, BNIP3: low).

Figure 11:
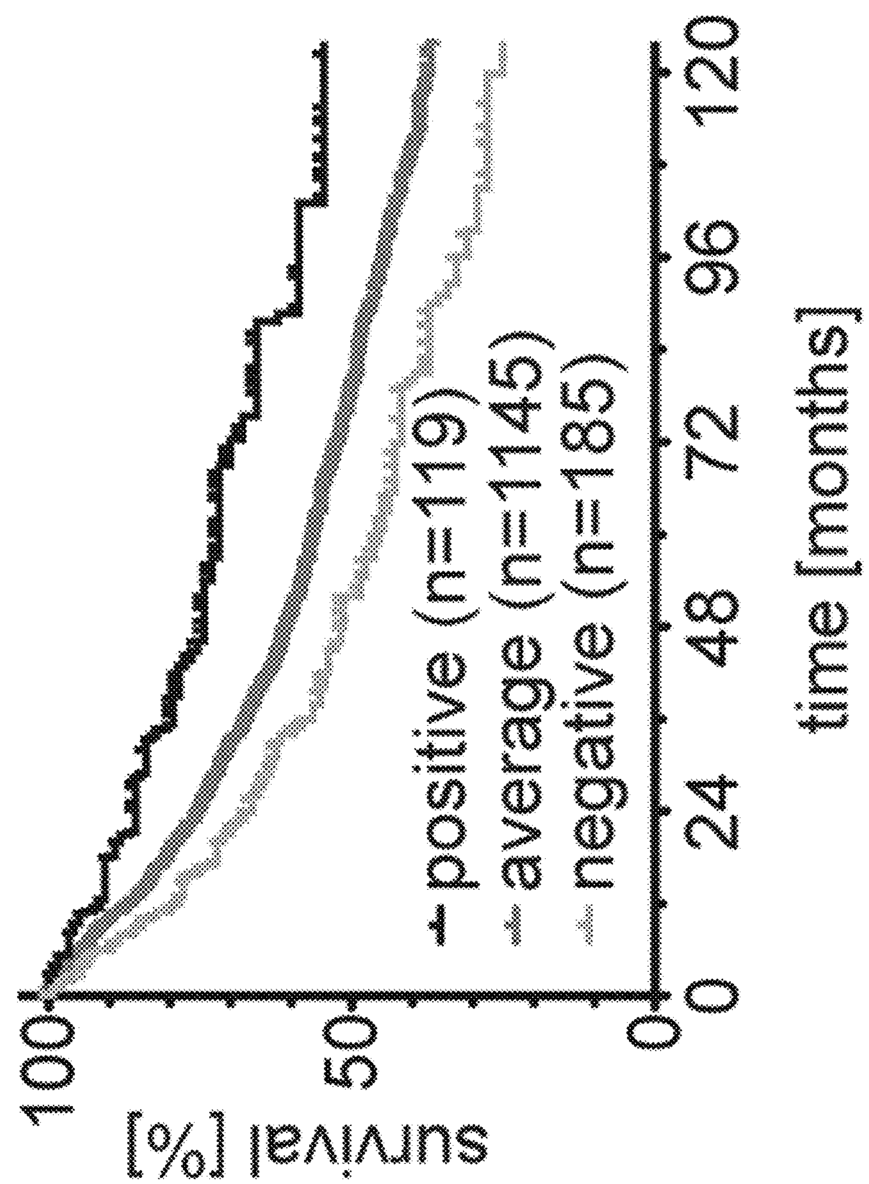

FIG. 11 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by the proprietary 3-gene signature (i.e., OMA1: high, HIGD1A: high, BNIP3: low).

Figure 12:
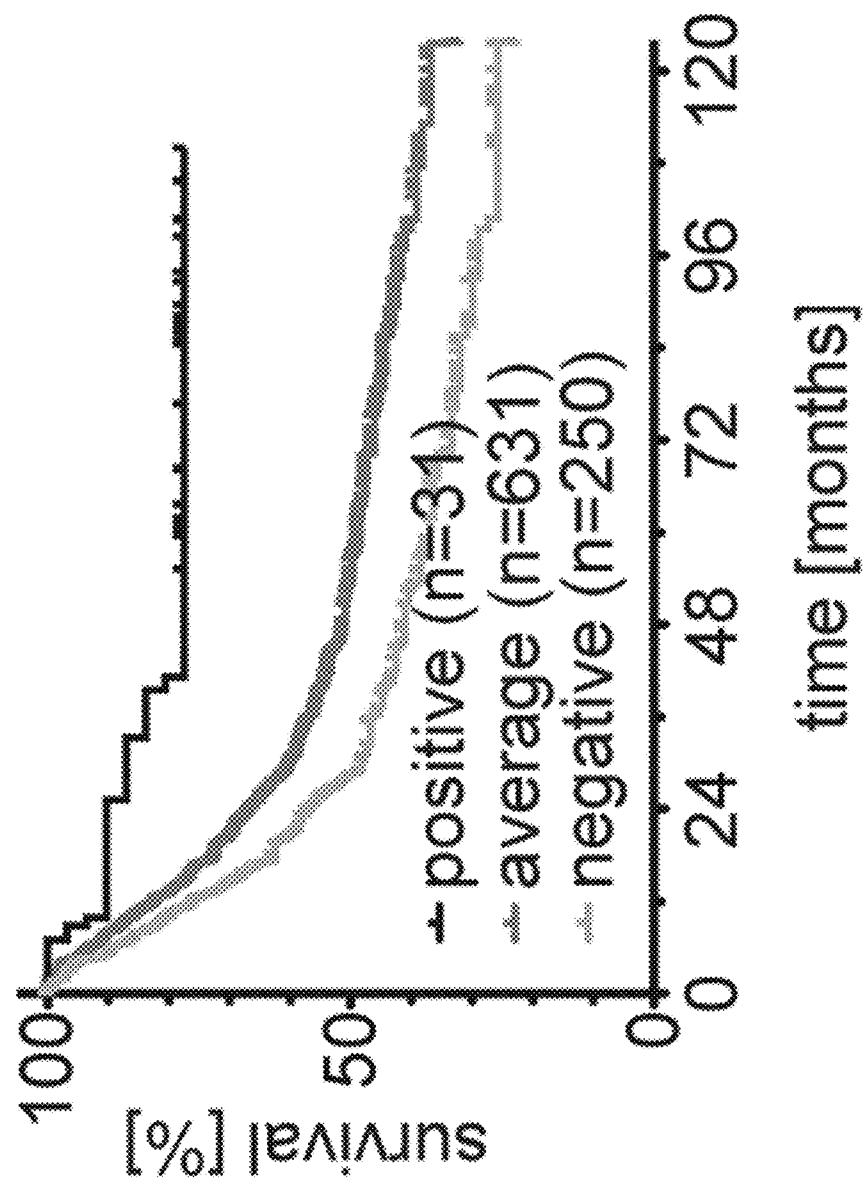

FIG. 12 shows Kaplan-Meier curves showing the overall survival of 631 patients with gastric cancer (average; dark grey, solid line; GEO accession numbers: GSE22377, GSE15459, GSE51105, GSE62254, GSE62254) stratified by the proprietary 3-gene signature (i.e., OMA1: high, HIGD1A: high, BNIP3: low).

Figure 13:
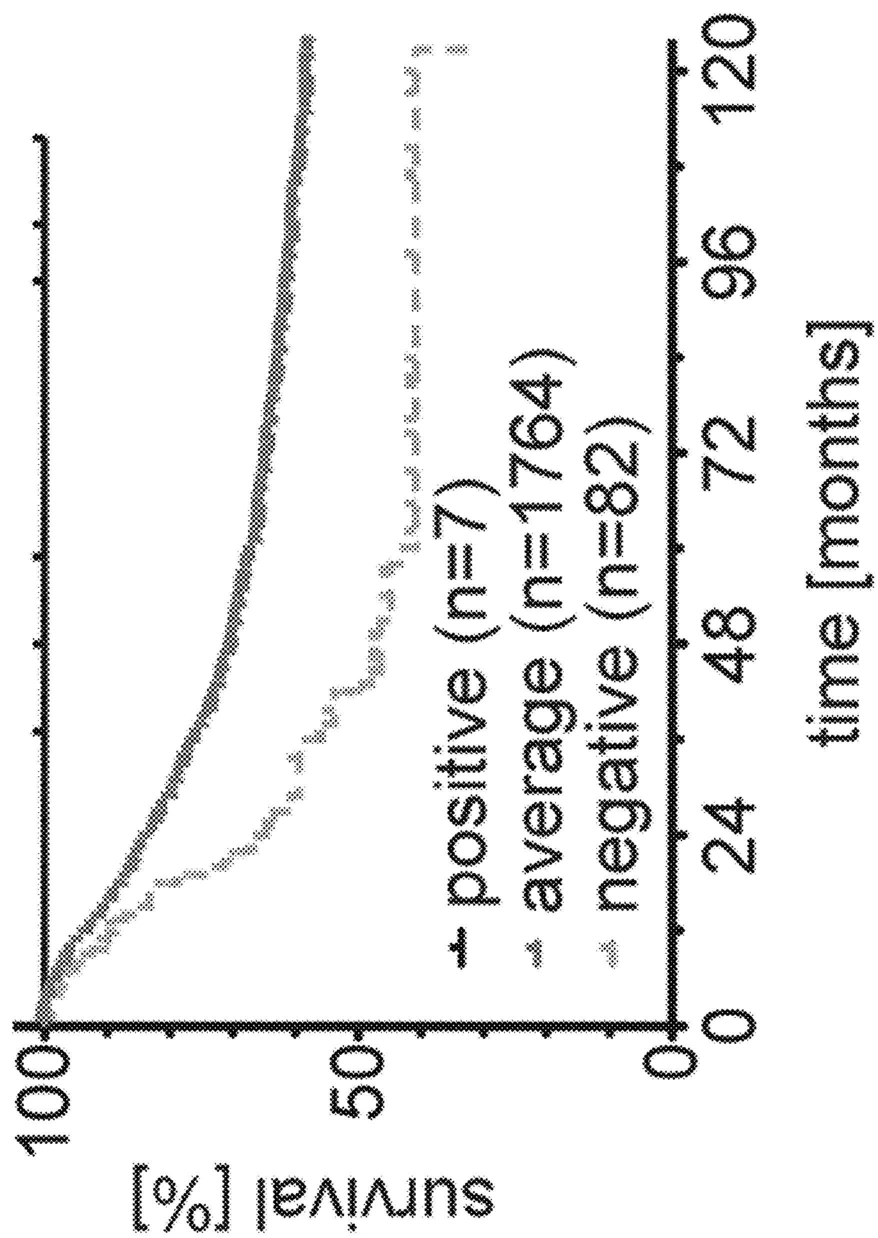

FIG. 13 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 6-gene signature based on OMA1, HIGD1A, OPA1, BNIP3, YME1L1 and IMMT expression levels.

Figure 14:
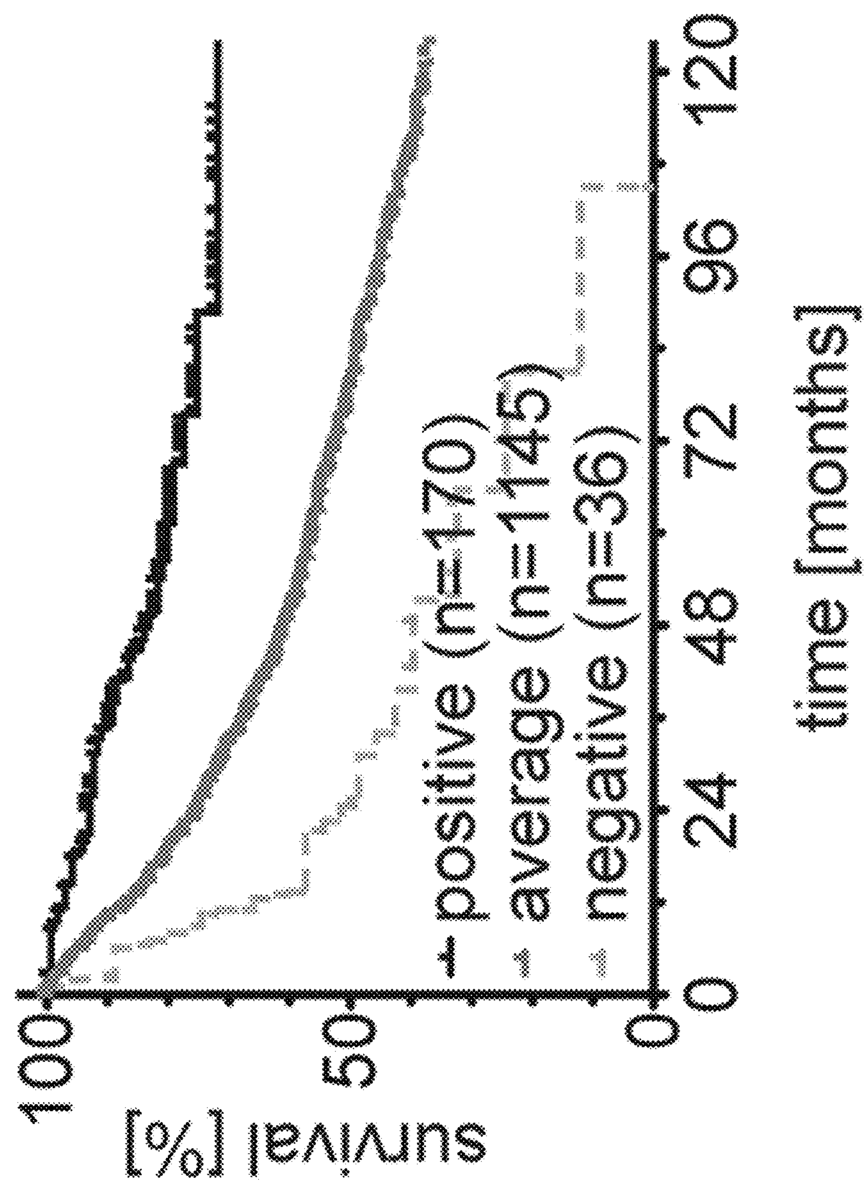

FIG. 14 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by a proprietary 6-gene signature based on OMA1, HIGD1A, YME1L1, PHB, SAMM50 and PHB2 expression levels.

Figure 15:
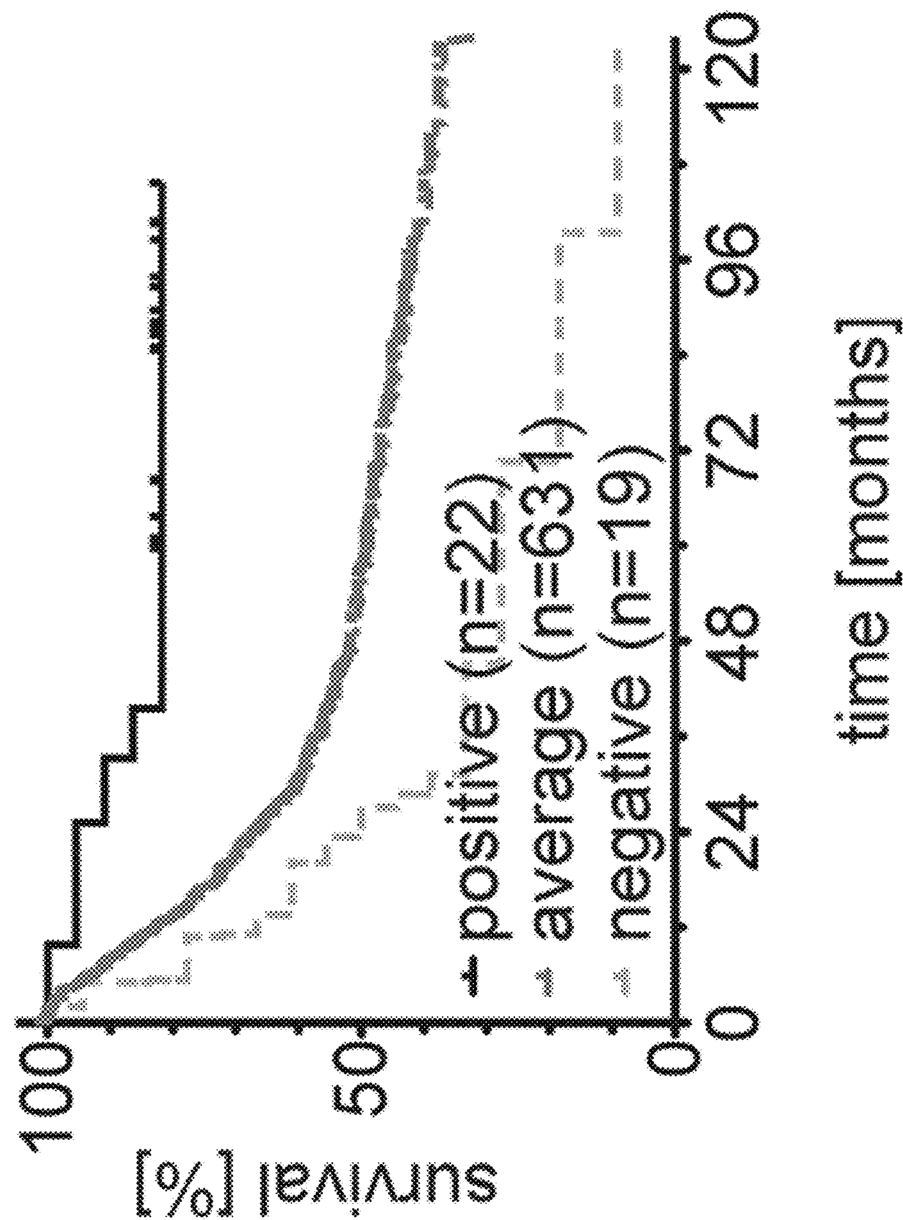

FIG. 15 shows Kaplan-Meier curves showing the overall survival of 631 patients with gastric cancer (average; dark grey, solid line; GEO accession numbers: GSE22377, GSE15459, GSE51105, GSE62254, GSE62254) stratified by a proprietary 7-gene signature based on OMA1, HIGD1A, YME1L1, PHB, SAMM50 and PHB2 expression levels.

Figure 16:
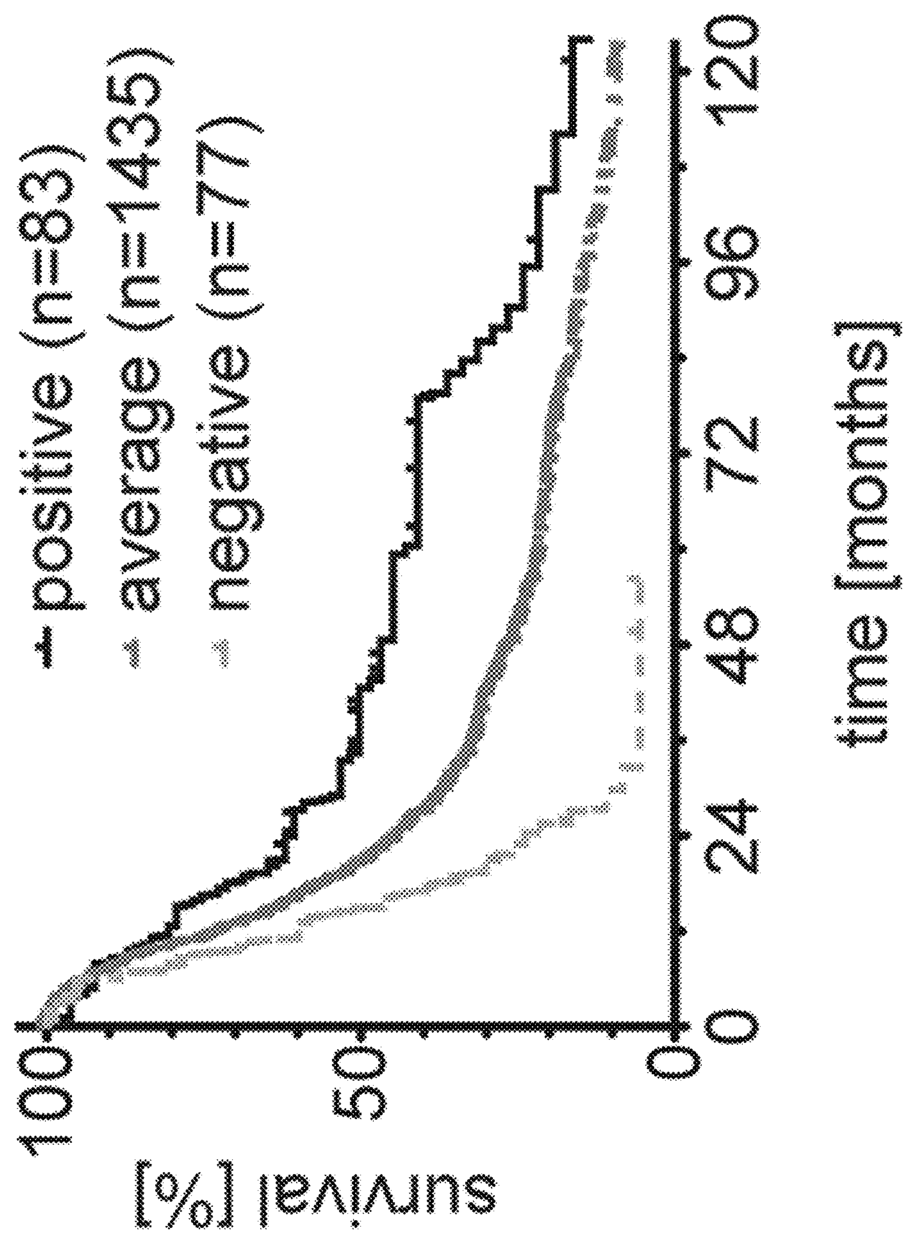

FIG. 16 shows Kaplan-Meier curves showing the overall survival of 1435 patients with ovarian cancer (average; dark grey, solid line; GEO accession numbers: GSE51373, GSE9891, GSE15622, GSE26712, GSE26193, GSE63885, GSE65986, GSE30161, GSE14764, TCGA) stratified by a proprietary 5-gene signature based on OPA1, BNIP3, YME1L1, IMMT, SAMM50 and PHB expression levels.

Figure 17:
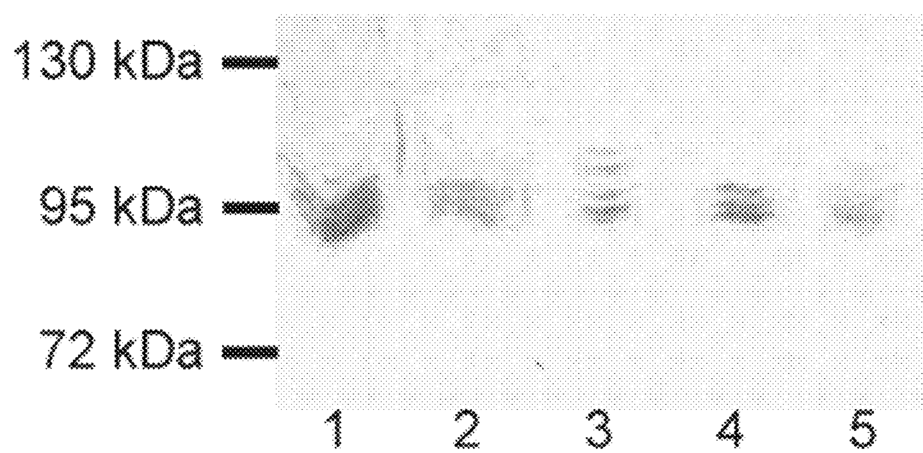

FIG. 17 shows the cleavage of OPA isoforms following exposure of HEK293T cells to thiophan.

Figure 18:
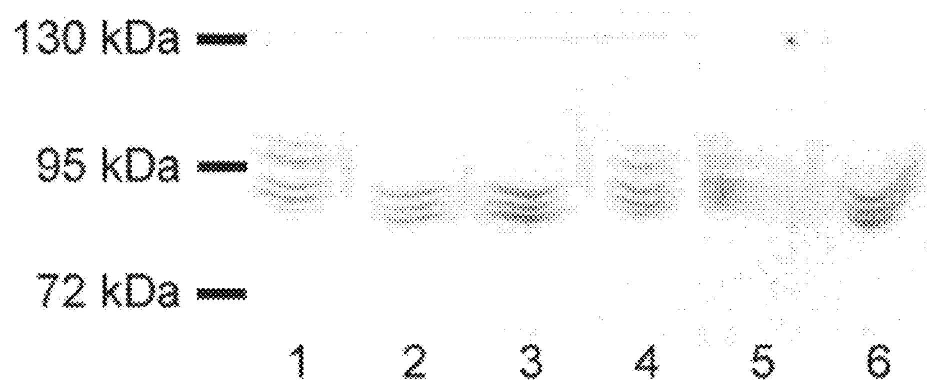

FIG. 18 shows the cleavage of OPA isoforms following exposure of HEK293T cells to phenanthroline.

Figure 19:
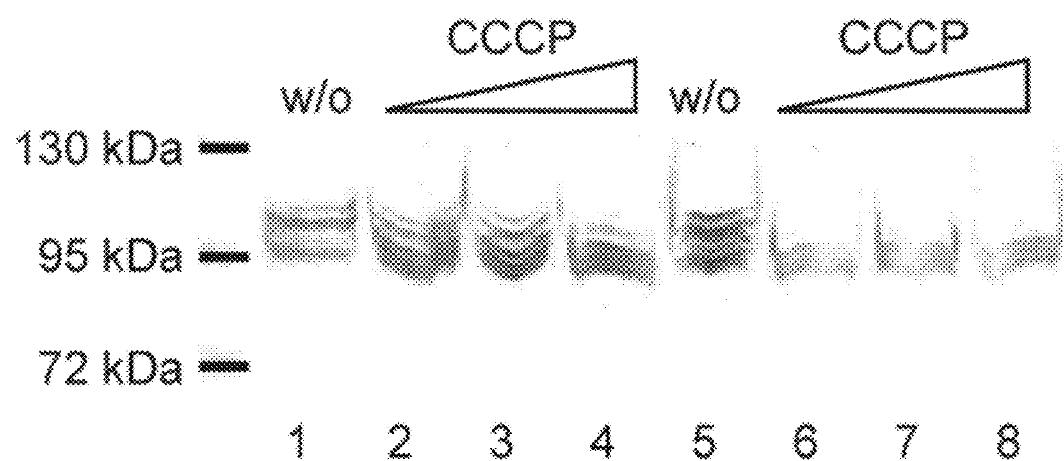

FIG. 19 shows the cleavage of OPA isoforms following exposure of HEK293T cells to SB-3CT.

FIG. 20 shows a list of different drugs and compounds that can modify OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Figure 21:
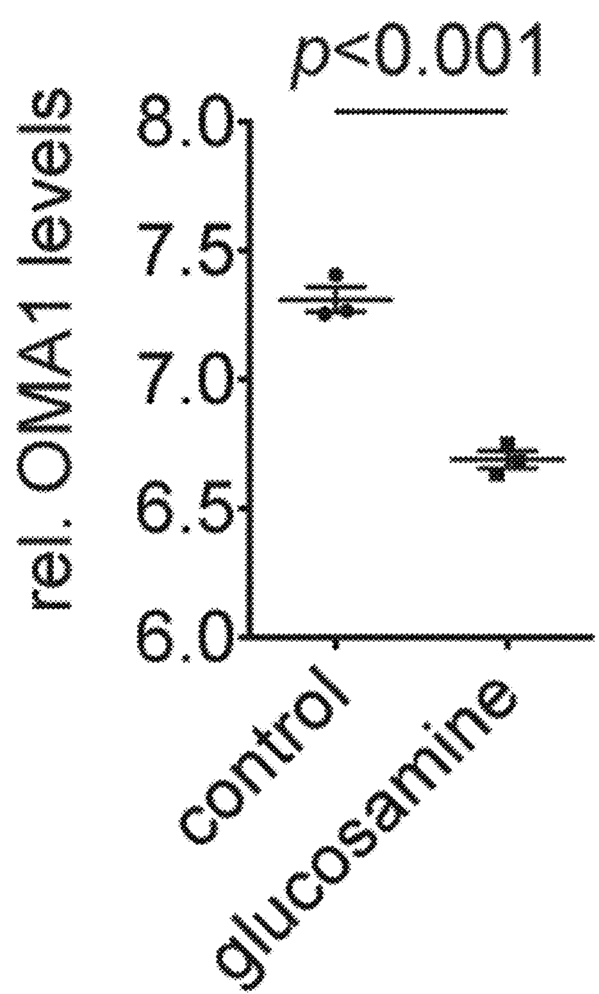

FIG. 21 shows OMA1 gene expression levels of KMH2 cells following exposure to glucosamine.

Figure 22:
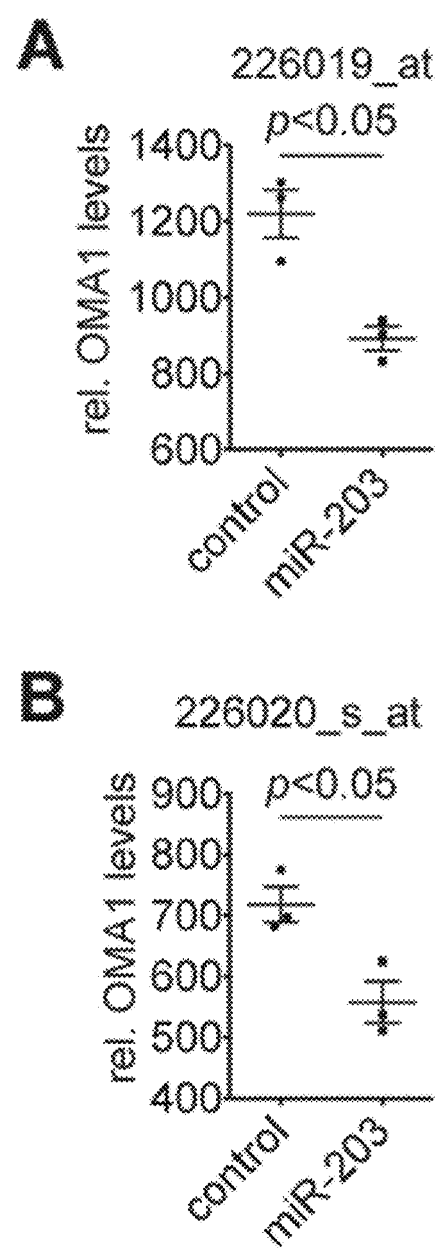

FIG. 22 (A) shows OMA1 gene expression levels of SUM139 cells following exposure to micro-RNA miR-203 (NCBI Reference Sequence: NR_029620.1). (B) shows OMA1 gene expression levels of SUM139 cells following exposure to micro-RNA miR-203 (NCBI Reference Sequence: NR_029620.1).

Figure 23:
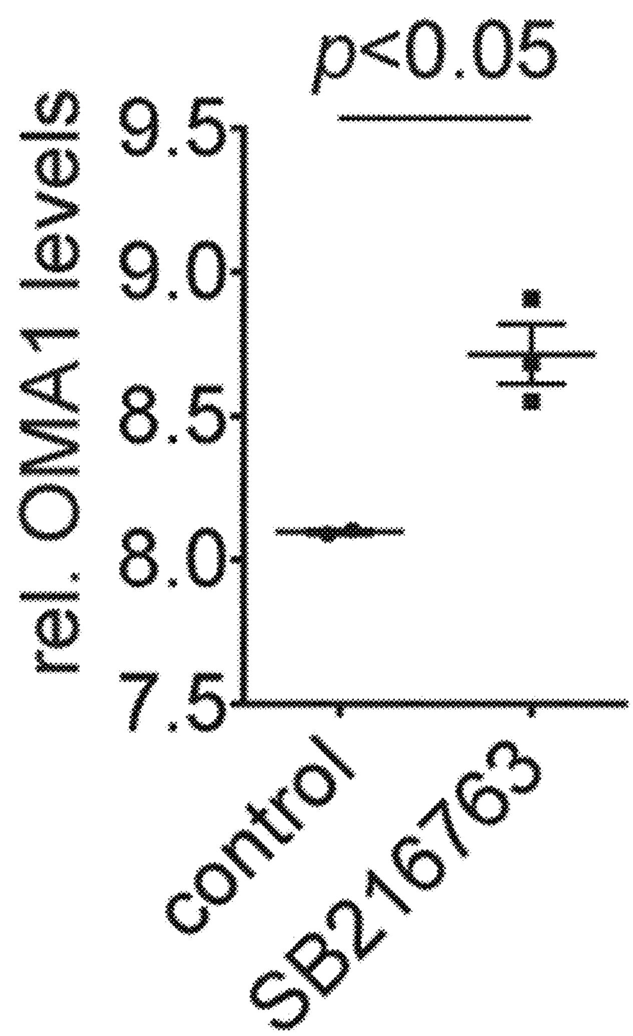

FIG. 23 shows OMA1 gene expression levels of RS4.11 cells following exposure to GSK-3 inhibitor SB216763.

Figure 24:
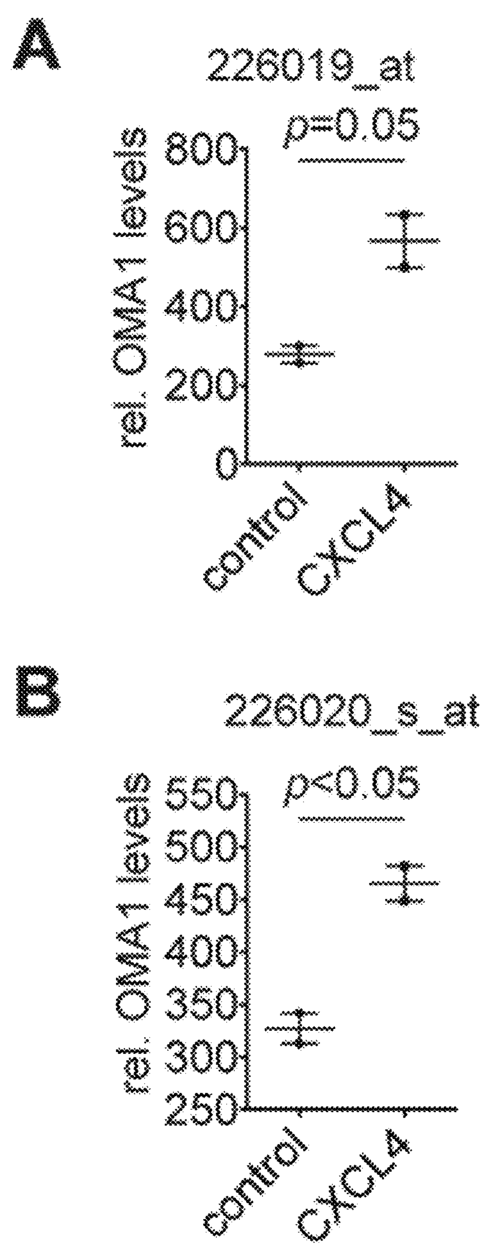

FIG. 24 (A) shows OMA1 gene expression levels in monocyte derived macrophages following exposure to small cytokine CXCL4. (B) shows OMA1 gene expression levels in monocyte derived macrophages following exposure to small cytokine CXCL4.

Figure 25:
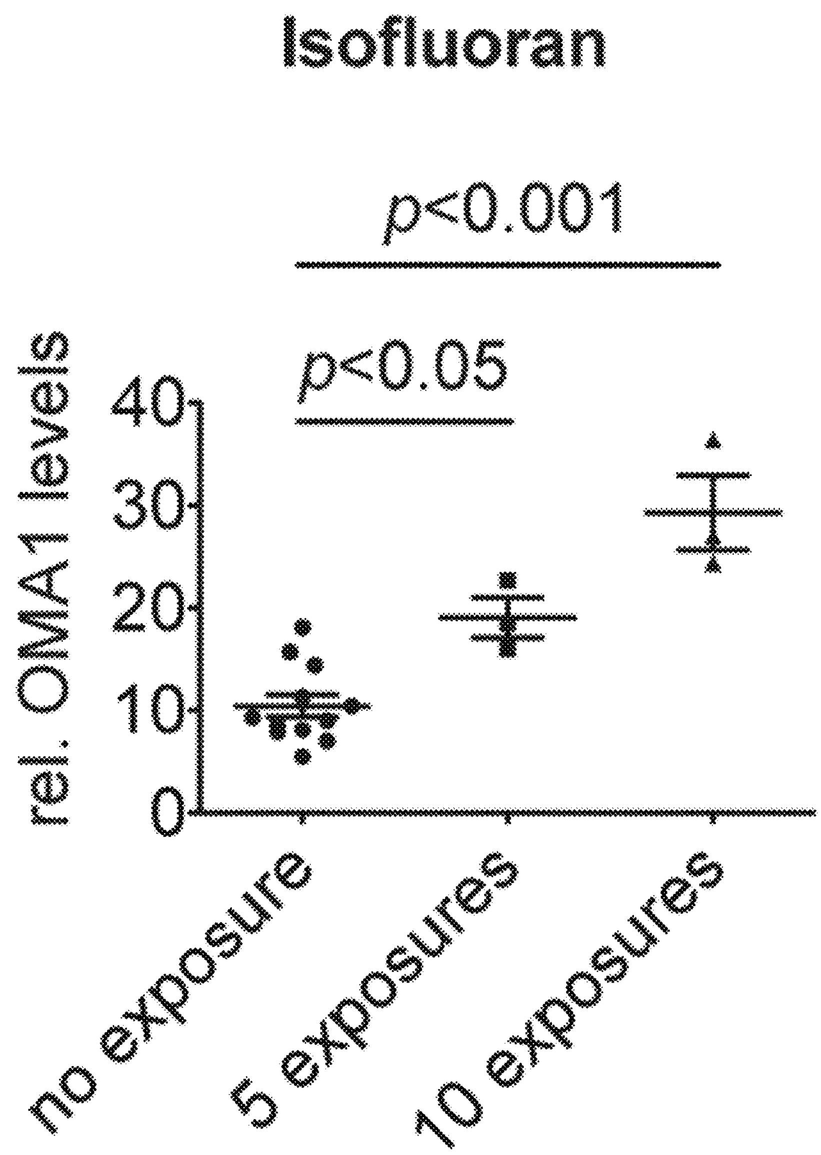

FIG. 25 shows OMA1 gene expression levels in rat brain following exposure to isoflurane.

Figure 26:
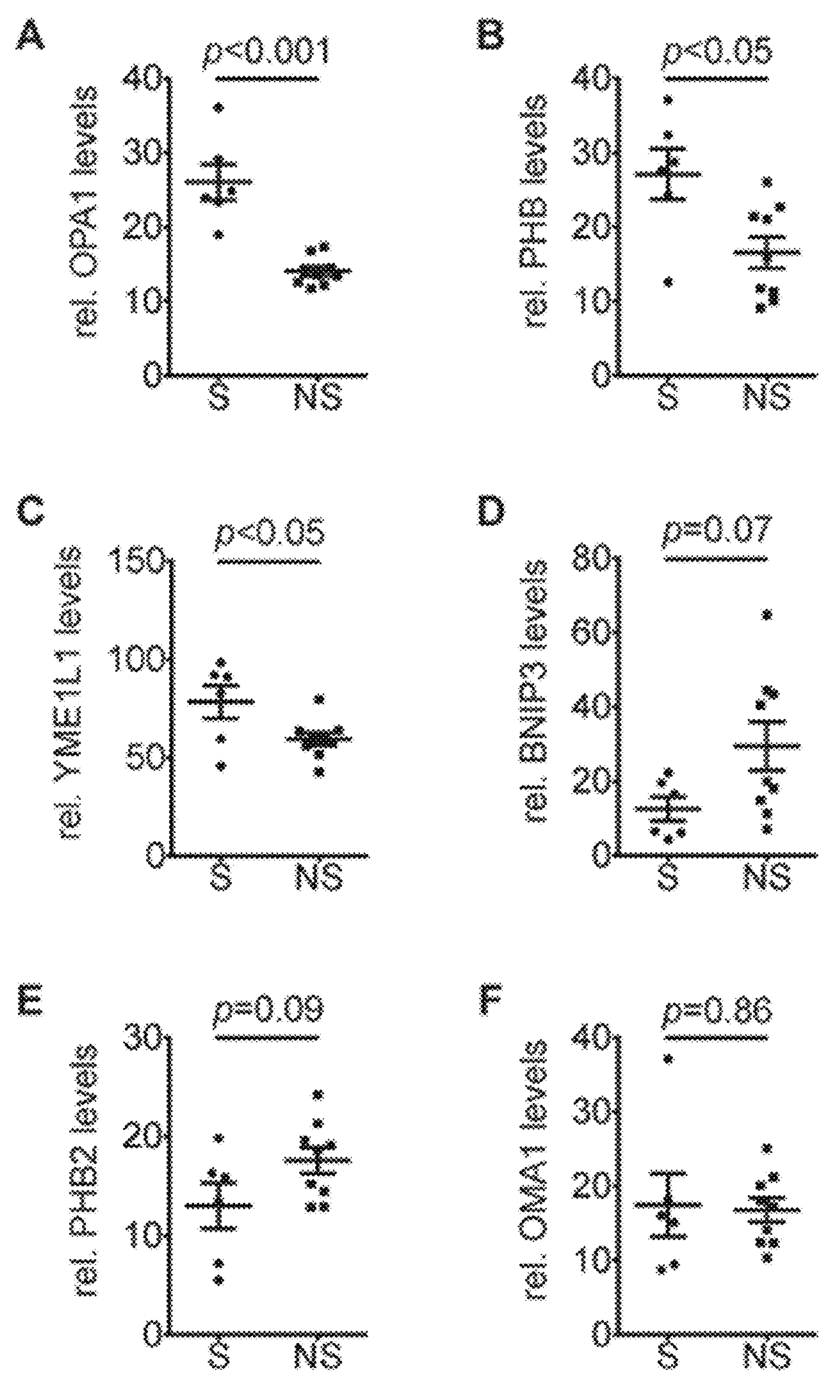

FIG. 26 (A) shows OPA1 gene expression levels in tobacco smokers and non-smokers. (B) shows PHB gene expression levels in tobacco smokers and non-smokers. (C) shows YME1L1 gene expression levels in tobacco smokers and non-smokers. (D) shows BNIP3 gene expression levels in tobacco smokers and non-smokers. (E) shows PHB2 gene expression levels in tobacco smokers and non-smokers. (F) shows OMA1 gene expression levels in tobacco smokers and non-smokers.

Figure 27:
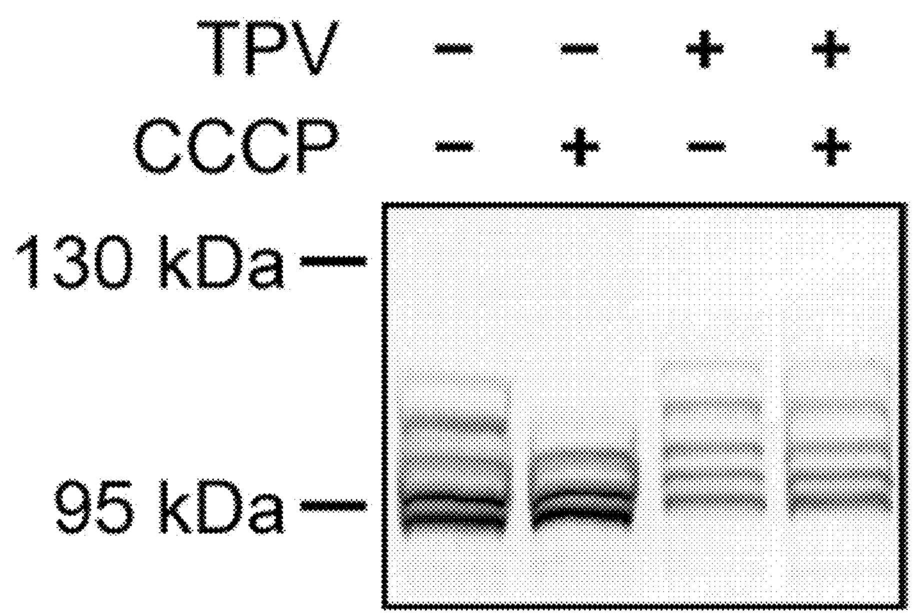

FIG. 27. Tipranavir can prevent CCCP-induced OPA1 cleavage. An OPA1-Western blot shows Hek293T cells incubated with 100 μM tipranavir (TPV) in minimal essential media for 1 hour did not hydrolyze the large isoforms of the OPA1 protein upon exposure to 3 μM CCCP for 30 minutes.

Figure 28:
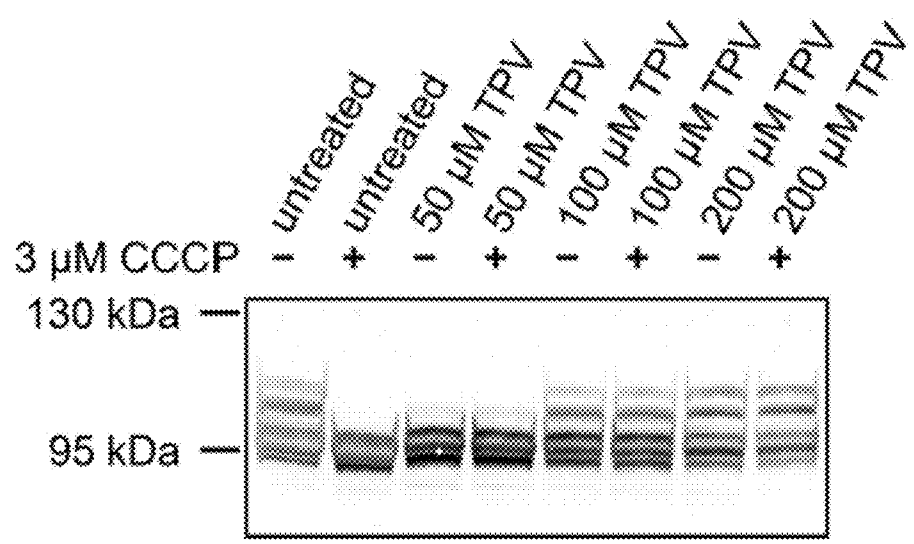

FIG. 28. Tipranavir shows dose-dependent antagonistic effects on OMA1/CCCP-induced OPA1 cleavage. An OPA1-Western blot shows Hek293T cells, which were cultured in minimal essential media for 1 hour with the indicated tipranavir (TPV) concentrations. OMA1 was activated with 3 μM CCCP for 30 minutes.

Figure 29:
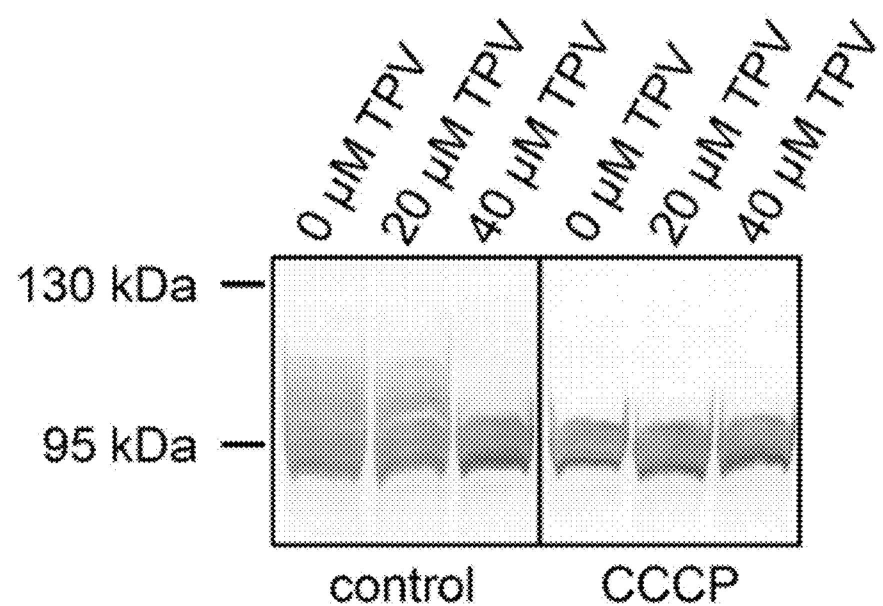

FIG. 29. Tipranavir can activate OMA1 at concentrations above 20 μM. An OPA1-Western blot shows Hek293T cells, which were cultured in minimal essential media for 1 hour with the indicated tipranavir (TPV) concentrations. OMA1 was then activated with 4 μM CCCP for 30 minutes in the indicated samples.

Figure 30:
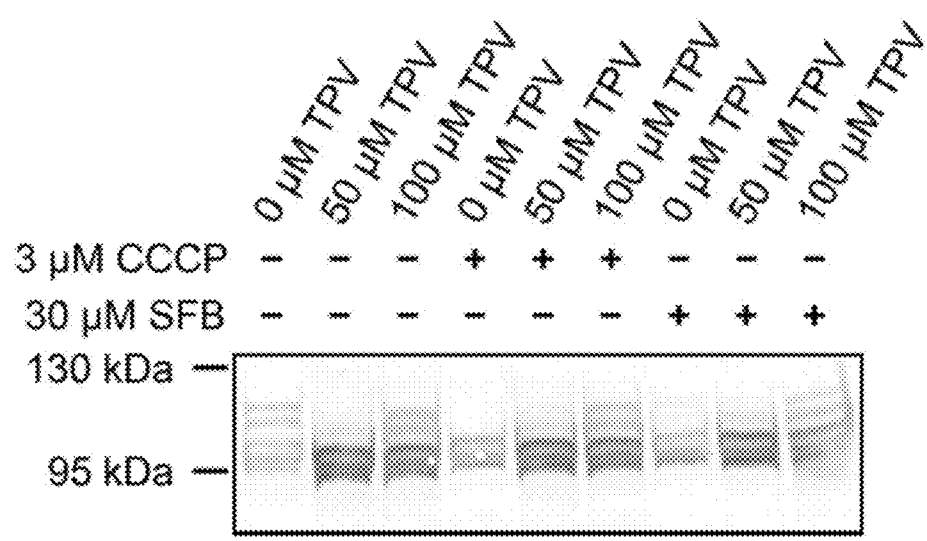

FIG. 30. Tipranavir can prevent CCCP-induced OPA1 cleavage and sorafenib-induced OPA1 cleavage. An OPA1-Western blot shows Hek293T cells incubated with 0 μM, 50 μM or 100 μM tipranavir (TPV) in minimal essential media for 1 hour. OMA1 was then activated with either 3 μM CCCP or 30 μM sorafenib (SFB) for 30 minutes in the indicated samples.

Figure 31:
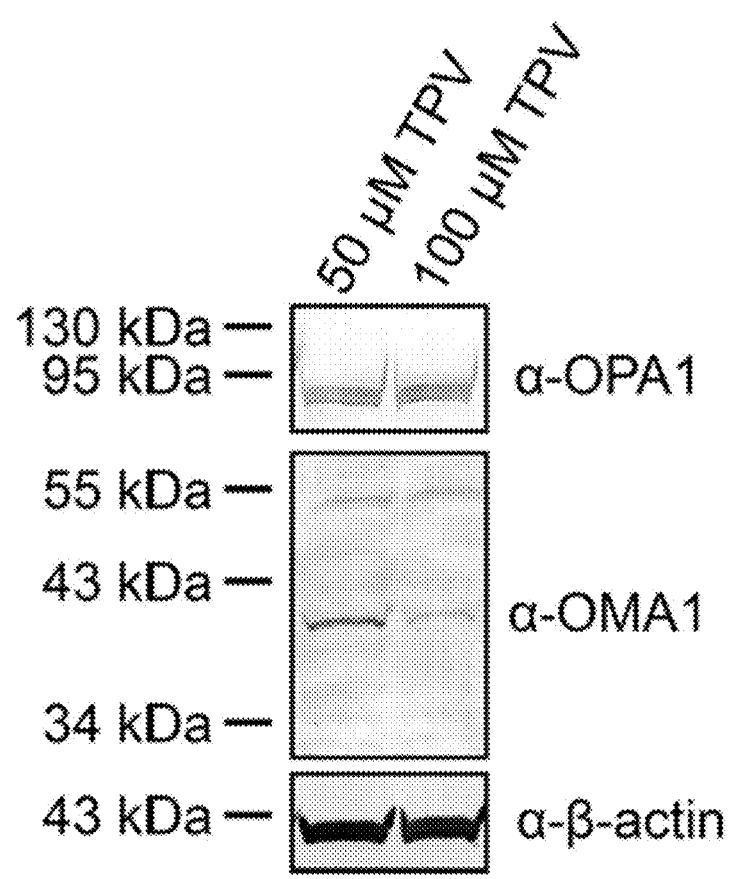

FIG. 31. Tipranavir can reduce OMA1 protein levels. An OMA1-Western blot shows Hek293T cells incubated with 50 μM or 100 μM tipranavir (TPV) in minimal essential media for 1 hour.

DETAILED DESCRIPTION

The terms "personalized medicine" and "precision medicine" are known in the arts and involve, inter alia, the use of molecular markers that characterize a patient's disease to direct the medical care the patient receives.

The terms "agonist" and "antagonist" are known in the arts. If the extend of OPA1 processing in the test sample exceeds that of the control sample, the compound screened is considered to be an "agonist" of said oligomeric complex in accordance with the present invention. If the extend of OPA1 processing in the test sample falls short of that of the control sample, the compound screened is considered to be an "antagonist" of said oligomeric complex in accordance with the present invention.

The term "conditions allowing OPA1 processing to occur" means that OPA1, i.e. one or more of its spliceforms, can be proteolytically cleaved to form one or more of the OPA1 isoforms, whenever an agent/compound capable to cleave OPA1, i.e. capable to trigger OPA1 processing, is present. In other words, said "conditions" are such that said agent/compound capable to cleave OPA1 is active.

In general, the term "oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof" as described and defined in context of this invention (also referred to herein as "oligomeric complex") refers to a certain kind of protease, OMA1 and any interacting protein.

It is of note that at least one subunit comprised in the herein defined oligomeric complex must be proteolytically active regardless whether the remaining subunits are. Otherwise said oligomeric complex would not be proteolytically active. Irrespective whether active or not, all subunits, however, must be assembly competent with respect to said oligomeric complex.

From the above, it is evident that the herein described "oligomeric complex" can be a homo-oligomeric complex or a hetero-oligomeric complex.

The meaning of the terms "OMA1" and "HIGD1A" and "BNIP3" and "OPA1" and "YME1L1" and "PHB" and "SAMM50" and "IMMT" and "PHB2" is well known in the art and is, if not explicitly prescribed differentially, used accordingly in context of the present invention. In context of this invention, these terms are likewise used to refer to the corresponding nucleotide sequences (e.g. the genes) as well as to the corresponding polypeptides (e.g. the polypeptides encoded by said genes). In a specific embodiment of this invention, the oligomeric complex as defined and described herein comprises a polypeptide selected from the group consisting of:

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.
(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
(d) a polypeptide comprising an amino acid sequence being homologous to the polypeptide of any one of (a) to (c);
(e) a polypeptide comprising an amino acid sequence encoded by a nucleic acid molecule being homologous to the nucleic acid molecule as defined in any one of (b) to (c);
(f) a polypeptide comprising an amino acid sequence encoded by a nucleic acid molecule hybridizing (under stringent conditions) to the complement stand of a nucleic acid molecule as defined in any one of (b) to (c); and
(g) fragment of a polypeptide of any one of (a) to (f).

The polypeptides as defined in (d) to (g) and the nucleic acid molecule as defined in (c) to (g) are, for example, "variants" in accordance with the present invention.

"Homologous" or "homology" as used in context of this invention, for example, means at least 50%, at least 60%, at least 70%, at least 80%, at least 85%, at least 90%, at least 95%, at least 98% or at least 99% identical on the level of the amino acid or nucleic acid sequence. Thereby, the higher values of percentage are preferred.

It is of note that the meaning of the terms "nucleic acid molecule", "nucleic acid sequence" or "nucleotide sequence", and the like, as used herein are well known in the art and, for example, comprise DNA (e.g. cDNA or gDNA) and RNA (e.g. mRNA or siRNA).

The term "variant(s)" of the subunits comprised in the "oligomeric complex" is also intended to encompass "(a) fragment(s)" of said subunits (or of the mentioned variants thereof). Thereby, the term "fragment(s)" means amino acid stretches of at least 50, at least 100, at least 150, at least 200, at least 300, at least 500 or at least 700 amino acids of the "subunits" defined herein, or nucleotide stretches of at least 150, at least 300, at least 450, at least 600, at least 900, at least 1500 or at least 2100 nucleotides of the corresponding nucleic acid sequences defined herein.

In context of the present invention the meaning of the mentioned term "variant(s)" also encompasses conservative amino acid exchanges and further known modifications.

The meanings of terms like "OPA1", "OPA1 alterations", "OPA1 processing", "proteolytic cleavage of OPA1", "large/small OPA1 isoforms", and the like, are known in the art (Duvezin-Caubet et al. 2006; Ishihara et al. 2006) and can also be deduced from PCT/EP2007/004466 (claiming priority to U.S. 60/801,484) and PCT/EP2008/005400 (claiming priority to U.S. Ser. No. 12/667,329). Moreover, the corresponding definitions given herein-below, apply here mutatis mutandis.

As mentioned above, a "compound" to be employed, i.e. to be administered, in context of this invention can be any compound "capable of (specifically) modulating the activity, function and/or expression of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof".

In one specific embodiment, such a "compound" is intended to be a compound screened for by the corresponding method of screening of this invention.

Generally, it is intended herein that a "compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof" as employed herein is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

The definitions of the term "activity" given herein-above apply here, mutatis mutandis. In a specific embodiment of this invention an "agonist" or "antagonist" is a molecule compound selected from the group consisting of:

(a) a binding molecule that (specifically) binds to/interacts with OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein or (specifically) binds to/interacts with a nucleic acid molecule encoding ((a) subunit(s) of) OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein;
(b) a nucleic acid molecule capable of specifically introducing an insertion of a heterologous sequence or a mutation into a nucleic acid molecule encoding ((a) subunit(s) of) OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein via in vivo mutagenesis;
(c) a nucleic acid molecule capable of specifically reducing the expression of mRNA encoding ((a) subunit(s) of) OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein by cosuppression; and
(d) a low molecular weight compound or a small molecule, for example being capable of inhibiting the activity of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein.

Non-limiting examples of a binding molecule as employed in context of this invention are is selected form the group consisting of antibodies, affybodies, trinectins, anticalins, aptamers, PNA, DNA or RNA, and the like.

Based on prior art literature, the person skilled in the art is familiar with obtaining specific binding molecules that may be useful in the context of the present invention. These molecules are directed and bind/interact specifically to or specifically label the oligomeric complex as defined herein or nucleotide sequences encoding (a) subunit(s) thereof.

For example, such binding molecules may, inter alia, be selected from the group consisting of:

(a) an antibody that specifically binds to the polypeptide or the nucleic acid molecule as defined herein-above or to ((a) subunit(s) of) OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein;

(b) an antisense nucleotide sequence that specifically hybridizes to the nucleic acid molecule as defined herein-above;

(c) a siRNA that specifically interacts with the nucleic acid molecule as defined herein-above;

(d) an aptamer that specifically binds to the polypeptide or the nucleic acid molecule as defined herein-above or to ((a) subunit(s) of) OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein; and (e) a ribozyme that specifically interacts with the nucleic acid molecule as defined herein-above.

A binding molecule (for example an antibody) to be employed in context of this invention may, for example, (specifically) bind to a particular epitope of the herein defined (subunit(s) of) OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof. Preferably, this particular epitope is essential for the activity of said complex, like, for example, an epitope comprising the active center of said complex. Moreover, such an epitope may, for example, comprise the consensus amino acid sequence of the metal binding site.

In this context, it is to be understood that the person skilled in the art is, based on the teaching provided herein, readily in a position to deduce (further) amino acid stretches/peptides being specific for (a particular subunit of) the oligomeric complex defined herein and therefore, representing an "epitope" as employed herein.

The antibody useful as a binding molecule in context of the present invention (commonly known as therapeutic antibody) can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", CSH Press, Cold Spring Harbor, 1988. These antibodies can be used as particular binding molecules defined herein. Surface plasmon resonance as employed in the BIAcore system can be used to increase the efficiency of phage antibodies which bind to an epitope of the polypeptide/complex employed in this invention. Accordingly, also phage antibodies can be used in context of this invention.

The present invention furthermore includes the use of chimeric, single chain and humanized antibodies, as well as antibody fragments, like, inter alia, Fab fragments. Antibody fragments or derivatives further comprise F(ab')2, Fv or scFv fragments. Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab')2. The term "antibody molecule" also comprises bifunctional antibodies, trifunctional antibodies and antibody constructs, like single chain Fvs (scFv) or antibody-fusion proteins.

Non-limiting examples of a low molecular weight compound or a small molecule to be employed as "agonist" or "antagonists" herein are any protease inhibitors or metal chelators, such as EDTA (CAS #60-00-4), phenanthroline (CAS #66-71-7), Deferiprone (CAS #30652-11-0), Deferasirox (CAS #201530-41-8) capable of inhibiting, preferably specifically inhibiting, the activity of the oligomeric complex described herein.

Particularly, metalloprotease inhibitors (like phenantrolin, DCI, and the like) are intended to be employed as low molecular weight compound or a small molecule in context of the present invention.

A further low molecular weight compound or a small molecule as employed in context of this invention may, for example, be a nucleotide analog, such as, for example, ATPγS, and the like.

As mentioned, in one particular embodiment, the "agonist" or "antagonist" to be employed is a nucleic acid molecule that leads to a reduction or depletion of the activity of the oligomeric complex defined herein via in vivo mutagenesis. Thereby, without being bound by theory, an insertion of a heterologous sequence or a mutation into a nucleotide sequence encoding a subunit of said complex, leads to a reduction of the amount of said subunit and hence, to a reduced expression of the intact complex. Generally, methods of "in vivo mutagenesis" (also known as "chimeroplasty") are known in the art. In such methods, a hybrid RNA/DNA oligonucleotide (chimeroplast) is introduced into cells (WO 95/15972; Kren, Hepatology 25 (21997), 1462-1468; Cole-Stauss, Science 273 (1996), 1386-1389). Without being bound by theory, a part of the DNA component of the RNA/DNA oligonucleotide is thereby homologous to a nucleotide sequence occurring endogenously in the cell and encoding a corresponding protein, but displays a mutation or comprises a heterologous part which lies within the homologous region. Due to base pairing of the regions of the RNA/DNA oligonucleotide which are homologous to the endogenous sequence with these sequences, followed by homologous recombination, the mutation or the heterologous part contained in the DNA component of the oligonucleotide can be introduced into the cell genome. This leads to a reduction of the activity, i.e. expression, of the gene, into which the heterologous part or the mutation has been introduced.

In view of the above, it is clear that the nucleic acid molecule causing in vivo mutagenesis may comprise a heterologous sequence or a sequence carrying a mutation flanked by parts of a nucleotide sequence encoding a subunit of the oligomeric complex defined herein.

In a further particular embodiment of the invention, the "agonist" or "antagonist" to be employed is a nucleic acid molecule that leads to a reduction or depletion of the activity of the oligomeric complex defined herein by a cosuppression effect. "Cosuppression effect" means that the synthesis of a nucleotide sequence, particularly of an RNA, in a living cell reduces the expression of a gene being homologous to said nucleotide sequence. The general principle of cosuppression and corresponding methods are well known to the person skilled in the art and are described, for example, in Pal-Bhadra (Cell 90, 1997), 479-490) and Birchler (Nature Genetics 21 (1999), 148-149). In a particular embodiment, the nucleic acid molecule causing a cosuppression effect comprises a nucleotide sequence encoding a subunit of the oligomeric complex defined herein or a fragment of said nucleotide sequence.

In another specific embodiment of this invention an "agonist" is a molecule selected from the group consisting of:

(a) a polypeptide as defined herein above, for example a subunit of the herein defined oligomeric complex or said oligomeric complex itself, or a nucleotide sequence comprising a nucleic acid molecule as defined herein above, for example a nucleic acid molecule encoding a subunit of the herein defined oligomeric complex;

(b) a low molecular weight compound or a small molecule, for example being capable of enhancing the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined herein; and (c) a binding molecule as defined herein, wherein said binding molecule is agonistic with respect to the activity of the oligomeric complex as defined and described herein (for example an agonistic antibody or agonistic aptamer).

Particularly, a low molecular weight compound or a small molecule as employed in context of this invention may be a compound/molecule having a molecular weight of less than about 2500 g/mol, preferably less than about 1500 g/mol, more preferably less than about 1000 g/mol and most preferably less than about 500 g/mol.

The skilled person is readily in the position to find out whether a certain binding molecule as defined herein is an agonist (for example an agonistic antibody or agonistic aptamer) or an antagonistml (for example an antisense nucleotide sequence, siRNA or ribozyme).

Based on the findings provided herein, it is envisaged in one embodiment of this invention that particular such oligomeric complexes are administered, the subunit composition of which varies dependent on the tissue affected by the disease or disorder to be addressed, i.e. dependent on cell type specific mitochondrial defects. In other words, based on the teaching provided herein, the subunit composition of the oligomeric complex may be adjusted to (a) particular tissue(s) affected by a disorder or disease described herein.

It is envisaged herein that the compound to be administered in accordance with this invention may, optionally, comprise a pharmaceutically acceptable carrier and/or diluent.

Examples of suitable pharmaceutically acceptable carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. The resulting pharmaceutical compositions can be administered to the subject at a suitable dose, i.e. a dose leading to a pharmaceutically active amount of the compound to be employed/used herein at its desired site of effect.

Administration of the compound to be administered in accordance with the present invention may be effected by different ways, e.g., by intravenous, intraperitoneal, subcutaneous, intramuscular, topical, intradermal, intranasal or intrabronchial administration (for example as effected by inhalation) or by direct administration (for example injection) into a particular tissue or organ.

The dosage regimen of the compound to be administered in accordance with this invention will be determined by the attending physician and clinical factors. As it is well known in the medical arts, dosages for any one patient depends upon many factors, including the patient's size, body surface area, age, the particular compound to be administered, sex, time and route of administration, general health, and other drugs being administered concurrently. A person skilled in the art is aware of and is able to test the relevant doses, the compounds to be used in terms of the present invention are to be administered in.

In the context of the invention, it is of note that a preferred subject/patient in the context of the present invention is a mammalian subject/patient, more preferably a primate subject/patient, most preferably a human being, preferably in need of medical intervention, either in form of treatment, prevention and/or amelioration.

In a particular embodiment, the method for medical intervention provided, and hence the corresponding compound to be administered, are envisaged to be employed in context of gene therapy. This is particularly envisaged, when the "compound" as employed herein is or comprises (a) nucleic acid molecule(s) or is encoded by (a) nucleic acid molecule(s). For example, such corresponding nucleic acid molecule(s) may then be employed in form of an insert comprised in a vector, particularly in an expression vector. Such (expression) vector may particularly be a vector suitable for gene therapy approaches (for example a viral (expression) vector).

Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art.

In another particular embodiment, the method for medical intervention provided, and hence the corresponding compound to be administered, are envisaged to be employed in context of gene silencing through RNAi (RNA-interference) by use of short interfering RNA (siRNA) or any other approach suitable to suppress gene expression and/or protein levels by at least 5%, 10%, 20%, 30%, 40%, 50%, 60%, 70% 80%, 90% 95%, or 99%.

The CRISPR/Cas9 systems has emerged as a powerful tool for genomic modification and regulation of gene expression in mammalian cells. In other aspects, the invention is envisioned to also provide compositions and methods for targeted regulation of endogenous genes encoding OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein by use of the CRISPR-Cas reagents. Like the compositions and methods for genome editing, the compositions and methods for genome modulation by transcription regulation utilize the highly targeted DNA binding activity of artificial CRISPR-Cas components, where targeting of a modified Cas9 protein to a promoter region of interest can result in either transcriptional activation or transcriptional repression. The invention also provides for multiplex gene regulation, where more than one gene can be simultaneously targeted for transcriptional modulation (either up regulation or down regulation).

The nucleic acid molecules and vectors may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the above-defined nucleic acid molecules. The introduction and gene therapeutic approach should, preferably, lead to the expression of a functional "compound" in accordance with this invention (for example an antisense or siRNA construct), whereby said expressed "compound" is particularly useful in the treatment, amelioration and/or prevention of the diseases or disorders defined herein.

The term "vector" as used herein particularly refers to plasmids, cosmids, viruses, bacteriophages and other vectors commonly used in genetic engineering. In a preferred embodiment, the vectors of the invention are suitable for the transformation of cells, like fungal cells, cells of microorganisms such as yeast or bacterial cells or animal cells. As mentioned, in a particularly preferred embodiment such vectors are suitable for use in gene therapy.

In one aspect of the invention, the vector to be employed is suitable for stable transformation of an organism, and hence is an expression vector. Generally, expression vectors have been widely described in the literature. As a rule, they may not only contain a selection marker gene and a replication-origin ensuring replication in the host selected, but also a promoter, for example a promoter as defined herein, and in most cases a termination signal for transcription. Between the promoter and the termination signal there is in general at least one restriction site or a polylinker which enables the insertion of a nucleotide sequence desired to be expressed.

Examples of vectors suitable to comprise the nucleic acid molecule(s) as employed in context of the present invention are known in the art.

As mentioned, the meanings of terms like "OPA1 alterations", "OPA1 processing" and "proteolytic cleavage of OPA1" are known in the art and can also be deduced from PCT/EP2007/004466 and PCT/EP2008/005400. These known definitions apply in context of this invention, if not explicitly defined otherwise.

In view of this, "OPA1 alterations" as defined herein is intended to be characterized by a certain amount of at least one large isoform of OPA1, a certain amount of at least one small isoform of OPA1 and/or a certain ratio of at least one large versus at least one small isoform of OPAL. Thereby, the OPA1 isoforms are formed by proteolytic cleavage of OPA1, i.e. of one or more of the OPA1 spliceforms. Usually, in mammalian cells, "OPA1 processing" usually occurs to a relatively moderate extent, referred to herein as "normal OPA1 processing" or simply "OPA1 processing". In difference to this, "altered OPA1 processing" or "OPA1 alterations" as defined herein is intended to be characterized by an altered amount of at least one large and/or at least one small isoform of OPA1 and/or an altered ratio of at least one large versus at least one small isoform of OPA1 (due to an altered proteolytic cleavage of OPA1) as compared to a control/standard. "Control/standard" in this context means a physiological condition, where "normal OPA1 processing" or simply "OPA1 processing" occurs (For example in healthy living cells, like the HEK293T cells cells employed herein).

Figure 1:
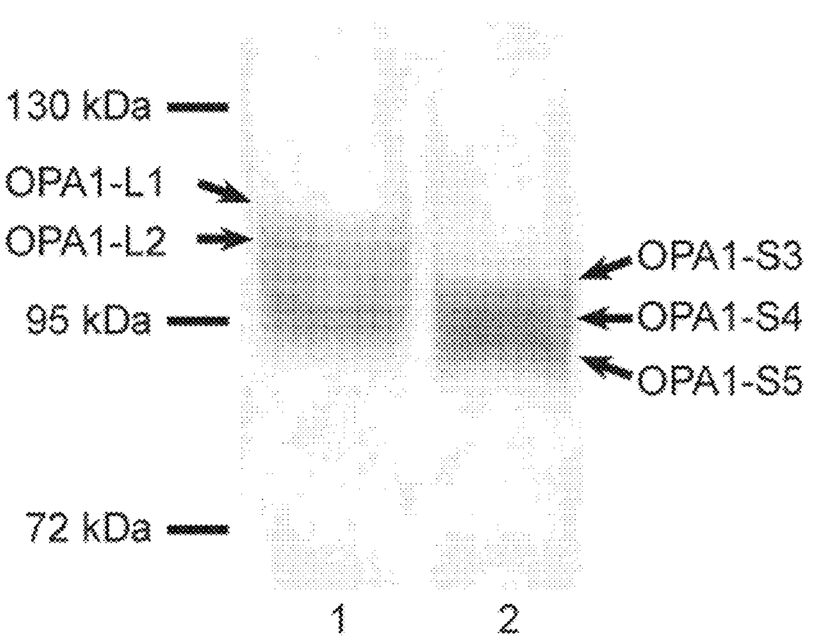
FIG. 1 shows an Illustration of the 5 human OPA1 isoforms resolved by SDS-PAGE/Western-blot.

Large isoform(s) of OPA1 as defined herein have an apparent molecular weight of more than about 95 kD and small isoform(s) as defined herein have an apparent molecular weight of less than about 95 kD, when said molecular weights being determined by SDS-PAGE analysis, as disclosed herein and described in the appended drawings (FIG. 1).

It is evident for the person skilled in the art that also other SDS gels and means (in particular Western-Blot analysis and the like) are useful and envisaged in context of the present invention. It is of note that the herein given value of 91 kD is, accordingly, an illustrative example and the person skilled in the art can also use other means to deduce the identity, amount and/or ratio of the herein described OPA1 isoforms (e.g. the presence or absence of said OPA1-isoforms) in a given sample to be analyzed. For example, said large OPA1 isoforms have an apparent molecular weight of more than about 95 kD or, preferably, of more than about 99 kD and the small OPA1 isoforms have an apparent molecular weight of less than about 95 kD or, preferably, of more than about 99 kD, when said molecular weights being determined by peptide analysis, e.g. mass spectrometry.

In context of the present invention, "OPA" or "OPA1" means the optic atrophy 1 protein/gene, in particular OPA1 of human origin. Yet, in certain embodiments it is also envisaged that OPA1 of other organisms, e.g. of mouse, rat, pig, dog, bovine species or fruit fly, be assessed in context of this invention. The nucleotide and amino acid sequences of human OPA1, particularly of the eight spliceforms of OPA1, are given in the appended sequence listing and examples.

The same applies for "OMA1", "HIGD1A", "YME1L1", "SAMM50", "IMMT", "PHB", "PHB2", and "BNIP3", the nucleotide and amino acid sequences of human OMA1, HIGD1A, YME1L1, SAMM50, IMMT, PHB, PHB2, and BNIP3 are given in the appended sequence listing.

It is of note that the nucleotide and amino acid sequences of OPA1, OMA1, HIGD1A, YME1L1, SAMM50, IMMT, PHB, PHB2, and BNIP3 given herein below are not limiting. Accordingly, the terms "OPA1", "OMA1", "HIGD1A", "YME1L1", "SAMM50", "IMMT", "PHB", "PHB2", and "BNIP3" also encompasses OPA1, OMA1, HIGD1A, YME1L1, SAMM50, IMMT, PHB, PHB2, and BNIP3 proteins/genes having amino acid or nucleotide sequences being derivatives of those given sequences.

In terms of the present invention the term "derivatives" or "derivatives thereof" or "variants" refers to amino acid or nucleotide sequences being homologous to the amino acid or nucleotide sequences shown herein, e.g. those of human OPA1, and/or amino acid or nucleotide sequences as shown herein, e.g. those of human OPA1, but having (a) particular (conservative) amino acid(s) exchanged. For instance, in context of the present invention, "homologous" means that amino acid or nucleotide sequences have identities of at least 50%, 60%, 70%, 80%, 90%, 95%, 98% or 99% to the sequences shown herein, e.g. those of human OPA1, wherein the higher identity values are preferred upon the lower ones.

As shown herein and in the arts, upon drug-induced apoptosis, processing of OPA1 and mitochondrial fragmentation precedes cytochrome c release. When the mitochondrial membrane potential is dissipated, processing of OPA1 and fragmentation of mitochondria can be observed.

Yet, based on the teaching provided in context of this invention, mitochondrial dysfunction (or a corresponding mitochondrial disease or disorder) is not merely correlated with decrease of any one of OPA1 isoforms, but with a decrease of particularly the large isoforms, e.g. OPA1-L1 (as defined herein) and OPA1-L2 (as defined herein), accompanied by an increase of the small isoforms, e.g. OPA1-S3 (as defined herein), OPA1-S4 (as defined herein), and OPA1-S5 (as defined herein).

In context of the present invention, the term "about", with respect to certain given molecular weight values, means+/−3 kD, preferably +/−2 kD, more preferably +/−1 kD, more preferably +1-0.5 kD and most preferably +/−0.1 kD. Moreover, in context of the present invention, it is envisaged that the term "less than about xx kD", for example "less than about 91 kD", "less than about 95 kD" or "less than about 99 kD", also comprises molecular weight values being equal to xx kD, for example equal to 91, 95 kD or 99 kD.

It is evident for the person skilled in the art that certain given molecular weight values may vary, dependent on the preparational/experimental conditions employed, or, for example with respect to mass spectrometry, dependent on the information content resulting from the preparational/experimental method employed or dependent on an employed modification of the proteins/peptides to be analyzed due to a specific preparational/experimental procedure. It is, for example, known in the art that proteins/peptides to be analyzed via mass spectrometry can be modified, i.e. their theoretical molecular weight can be increased (e.g. by certain chemical modifications) or decreased (e.g. by using (a) certain protease(s)) by a certain value. It is therefore of note in context of the present invention that the molecular weight values given for certain OPA1 isoforms can change, dependent on the particular preparational/experimental conditions employed during the corresponding mass spectrometry experiment (or other methods for determining molecular weights). The skilled person is readily in the position to deduce whether certain changes/differences of given molecular weight values result from the particular preparational/experimental method employed or form a specific composition of the protein/peptide analyzed.

In context of the present invention, the term "isoform" of OPA1 means a certain form of the OPA1 protein. Without bound by theory, an OPA1 isoform derives from (a protein encoded by) any one of spliceforms 1 to 8 of OPA1, e.g. by posttranslational processing (e.g. proteolytical processing). Without bound by theory, said posttranslational processing (e.g. proteolytical processing) leads to a shortened N-terminus of OPA1, particularly of the spliceforms thereof, wherein the C-terminus remains complete. The "isoforms" of OPA1 to be scrutinized in context of the present invention are described herein in more detail. Accordingly, the term "corresponding" in context of OPA1 isoforms and OPA1 spliceforms, e.g. in the term "an OPA1 isoform having an apparent molecular weight calculated from amino acid sequences of the corresponding spliceform(s)", means that the respective OPA1 isoform can be related to or may be derived from said OPA1 spliceform(s). These spliceforms are also described herein below.

In context of the present invention, the term "spliceform" or "splice variant" of OPA1 means a form of OPA1 that emerges by alternative splicing of the primary transcript transcribed from the OPA1 gene. It is envisaged herein, that the term "spliceform" either refers to the mature transcript generated by alternative splicing, but also refers to the corresponding protein which has been translated from said mature transcript. Accordingly, the term "isoform being derived from (corresponding) spliceform" means that an OPA1 isoform originates from a protein that has been translated from a mature (alternatively spliced) transcript of the OPA1 gene. Thereby, posttranslational processing (e.g. proteolytical processing) of said protein that has been translated from a mature (alternatively spliced) transcript of the OPA1 gene may occur. However, an OPA1 isoform may also directly originate from said protein, without further posttranslational processing. In such specific case, said protein then is said OPA1 isoform.

At present, 8 spliceforms of OPA1 are known in the art, which emerge by alternative splicing of exon 4, exon 4b and/or exon 5. The corresponding amino acid sequences of these 8 spliceforms are given in SEQ ID NO: 2, 4, 6, 8, 10, 12, 14 and 16. Their corresponding nucleotide acid sequences are given in SEQ ID NO: 1, 3, 5, 7, 9, 11, 13 and 15.

Dependent whether exon 4, exon 4b and/or exon 5 is comprised, the OPA1 spliceforms can be defined by specific amino acid sequences, e.g. by one of the following amino acid sequences:

EYKWIVPDIVWEIDEYIDFGHKLVSEVIGASDLL-LLL (SEQ ID NO: 60) corresponds to the amino acid sequences from exon 3 to exon 4b (lack of exon 4) and is comprised in spliceforms 3 and 6.

EYKWIVPDIVWEIDEYIDFGSPEETAFRATDRGS-ESDKHFRK (SEQ ID NO: 61) corresponds to the amino acid sequences from exon 3 to exon 5 (lack of exon 4 and 4b) and is comprised in spliceforms 2 and 4.

EKIRKALPNSEDLVKLAPDFDKIVESLSLLKDFFT-SGSPEETAFRATDRGSESDKHFRK (SEQ ID NO: 62) corresponds to the amino acid sequences from exon 4 to exon 5 (lack of exon 4b) and is comprised in spliceforms 1 and 7.

GSPEETAFRATDRGSESDKHFRKVSDKEKIDQLQ-EELLHTQLKYQRILERLEKENKELRK (SEQ ID NO: 63) corresponds to the amino acid sequences from exon 5 to exon 6 (lack of exon 5b) and is comprised in spliceforms 1, 2, 3 and 5.

Other amino acid sequences specific for a certain OPA1 spliceform can be derived from the amino acid sequences of the OPA1 spliceforms given herein below.

Since an OPA1 isoform to be employed in context of the present invention may be derive from one particular OPA1 spliceform, the above mentioned amino acid sequences defining the different OPA1 spliceforms may also be used to determine the identity, amount and/or ratio (e.g. the presence or absence) of a given OPA1 isoform as defined herein. For example, since the present invention provides evidence that OPA1-L1 be derived from spliceform 7 and OPA1-L2 be derived from spliceform 1, OPA1-L1 may, e.g. be characterized in that it comprises the amino acid sequence EKIRKALPNSEDLVKLAPDFDKIVESLSLLKDFFTSG-SPEETAFRATDRGSESDKHFRK (SEQ ID NO: 62) and in that it not comprises the amino acid sequence. GSPEET-AFRATDRGSESDKHFRKVSDKEKIDQLQEELL-HTQLKYQRILERLEKENKELRK (SEQ ID NO: 63) and OPA1-L2 may, e.g. be characterized in that it comprises the amino acid sequence EKIRKALPNSEDLVKLAPDFD-KIVESLSLLKDFFTSGSPEETAFRATDRGSESDKHFRK (SEQ ID NO: 62) and GSPEETAFRATDRGSESDKHF-RKVSDKEKIDQLQEELLHTQLKYQRILERLEKEN-KELRK (SEQ ID NO: 63).

However, since the OPA1 isoforms to be employed in context of the present invention may derive from the OPA1 splicefroms by (proteolytical) processing, not the complete amino acid sequences as given above, but fragments or derivatives thereof, may be used to determine a certain OPA1 isoform.

The meaning of the term "Mass spectrometry" (MS) is, and corresponding methods, are known in the art. Particularly useful "mass spectrometry" methods to be employed in context of the present invention are MALDI-MS or LC-MS/MS. Further "mass spectrometry" methods are known in the art and can easily be adapted to the specific needs of the present invention by a person skilled in the art.

The term "molecular weights being determined by mass spectrometry" means that the apparent molecular weight of a certain OPA1 isoform is determined by performing mass spectrometry analysis on said OPA1 isoform and using the results of said mass spectrometry analysis to calculate said apparent molecular weight of said certain OPA1 isoform on the basis of the amino acid sequence of OPAL. Since eight alternative spliceforms exist of OPA1, having different amino acid sequences, the result of said calculation may vary, dependent on the spliceform, the amino acid sequence of which is used for said calculation.

It is of note that the so determined theoretical molecular weight may be further increased by the presence of a few further N-terminally located amino acid residues present in the (proteolytically) processed mature OPA1 isoform. The person skilled in the art is readily in the position to determine said slightly increased molecular weight, by taking advantage of the teaching of the present invention.

In context of the present invention, the large isoforms of OPA1 may comprise two isoforms (e.g. OPA1-L1 and OPA1-L2) and the small isoforms of OPA1 may comprise three isoforms (e.g. OPA1-S3, OPA1-S4 and OPA1-S5). However, it is also envisaged that further, possibly existing isoforms may be assigned as large or small isoforms in context of the present invention. For instance, it is evident for a skilled person that, e.g., single bands of an SDS-PAGE/Western-blot as exemplified herein, may represent not only one, but several different isoforms and/or that further isoforms, larger or smaller than the particular isoforms defined herein may be present. For example, particularly the band corresponding to OPA1-S4 as defined herein may correspond to (a) further OPA1 isoform(s). Again, the gist of the present invention is based on the fact the determination of "small" versus "large" isoforms is illustrative for mitochondrial dysfunction and corresponding related disorders/diseases. Therefore, further, possibly existing isoforms may, e.g., be detectable by alternative comparable methods known in the art and may also be taken into consideration in the herein provided methods and means. For example, such methods may be SDS-PAGEs taking advantage of gels having very low polyacrylamide concentrations (e.g. 1%, 2%, 3% or 4%) and/or Western-blots taking advantage of radionuclide labelling, e.g. radionucleotide labelling of (secondary) antibodies used in said Western-blots, or other labelling approaches known in the art, e.g. other very sensitive labelling approaches being suitable for the detection of proteins being present in low amount(s)/concentration(s). Moreover, such methods may be a two dimensional gelelectrophoresis methods. These and other alternative methods for detecting isoforms of certain proteins/genes, like OPA1, are known in the art. It is envisaged that such alternative methods may also be employed in context of the present invention.

However, it is preferred that each single band as evident from the SDS-PAGE analysis as employed and exemplified herein represents one single OPA1 isoform. Accordingly, in one embodiment of the present invention, the two large OPA1 isoforms as defined herein (e.g. OPA1-L1 and OPA1-L2) are represented by two single bands, and the three small OPA1 isoforms as defined herein (e.g. OPA1-S3, OPA1-S4 and OPA1-S5) are represented by three single bands occurring in an SDS-PAGE, e.g. an SDS-PAGE as exemplified herein (FIG. 1).

FIG. 1 shows an illustration of the 5 human OPA1 isoforms resolved by SDS-PAGE/Western-blot. Human HEK293T cells were harvested, solubilized in RIPA buffer, and separated utilizing an 8% Tris-Glycine Gel (Novex, ThermoFisher Scientific, CA). The large bands of OPA1 comprise two isoforms, OPA1-L1 and OPA1-L2, and the small bands of OPA1 comprise three isoforms, OPA1-S3, OPA1-S4 and OPA1-S5 (lane 1). Under conditions allowing OPA1 processing to occur, large OPA1 isoforms are proteolytically cleaved and convert into one or more of the small OPA1 isoforms. OPA1 processing was evoked in this particular non-limiting example by uncoupling of the oxidative phosphorylation through addition of 10 μMCCCP for 30 minutes at 37° C. (lane 2).

In context of the present invention, the two large OPA1 isoforms are indicated by numbers 1 and 2, namely 1 for the largest and 2 for the second largest OPA1 isoform. The three small OPA1 isoforms are indicated by numbers 3, 4 and 5, namely 3 for the largest of the three small isoforms, 4 for the second largest of the three small isoforms and 5 for the smallest isoform. The numbering of the OPA1 isoforms to be employed in context of the present invention is also given in FIG. 1. In accordance thereto the OPA1 isoforms as employed in context of the present invention are termed as follows: OPA1-L/l1, L/l-OPA1 #1, OPA1 #1 or L/11-OPA1 for the largest OPA1 isoform. OPA1-L/12, L/1-OPA1 #2, OPA1 #2 or L/12-OPA1 for the second largest OPA1 isoform. Large isoform(s) in context of the present invention is (are), e.g., OPA1-L1 and/or OPA1-L2. OPA1-S/s3, S/s-OPA1 #3, OPA1 #3 or S/s3-OPA1 for the largest of the three small OPA1 isoforms. OPA1-S/s4, S/s-OPA1 #4, OPA1 #4 or S/s4-OPA1 for the second largest of the three small isoforms. OPA1-S/s5, S/s-OPA1 #5, OPA1 #5 or S/s5-OPA1 for the smallest OPA1 isoform. Accordingly, small isoform(s) in context of the present invention is (are), e.g., OPA1-S3, OPA1-S4 and/or OPA1-S5.

It is of note that the specific numbering is indicative for the specific OPA1 isoform, and that the additional terming, like "1" for large; "s" for small or "OPA", "OPA1" or "OPA1 #" for OPA1 may slightly vary. However, the abbreviations "L" or "1" indicate large isoforms and "S" or "s" indicate small isoforms of OPAL.

In view of the teaching provided herein, also in the appended examples, the OPA1 isoforms employed in context of the present invention are defined as follows:

In one aspect of the present invention, the term "OPA1 isoform" means a protein encoded by the OPA1 gene, but particularly be derived from at least one of the different spliceforms of OPA1 (e.g. from at least one of spliceforms 1 to 8), e.g. by posttranslational (e.g. proteolytical) processing, wherein said proteins are distinguishable by their molecular weight and/or (a) certain amino acid sequence(s). From the above, it is, inter alia, evident that an "OPA1 isoform" as employed in context of the present invention comprises (an) amino acid stretche(s) which unambiguously characterize it as a polypeptide/protein derived from OPAL. In this context, "derived from OPA1" particularly means encoded by the OPA1 gene and/or generated from OPA1 by the herein described and defined OPA1 processing. Thus, an "OPA1 isoform" as employed can particularly be characterized by (a) certain amino acid stretch(es) of any one of SEQ ID NO: 2, 4, 6, 8, 10, 12, 14 or 16 or by (a) certain amino acid stretch(es) encoded by any one of SEQ ID NO: 1, 3, 5, 7, 9, 11, 13 or 15.

In context of the present invention, the term "molecular weight" may, inter alia, refer to the apparent molecular weight. Said apparent molecular weight can be determined by methods known in the art. E.g., said apparent molecular weight can be determined by SDS-PAGE, and, accordingly, also from Western-blots, or can be calculated from the amino acid sequence of OPA1, particularly from the amino acid sequence(s) of the corresponding spliceform(s) by taking advantage of mass spectrometry methods. Examples of the determination of the OPA1 isoforms by using these techniques are given in the appended examples.

As already mentioned above, in context of the present invention, certain given molecular weight values are apparent molecular weight values. It is envisaged, that the certain molecular weight values given herein may slightly vary, e.g. with respect to the molecular weight of the protein present in vivo. Said variation may by in the range of 5 kD, 4 kD, 3 kD, 2 kD, 1 kD, 0.5 kD, 0.4 kD, 0.3 kD, 0.2 kD or 0.1 kD, whereby the smaller variations are preferred over the larger variations. The definitions given for the term "about" with respect to molecular weight values herein above, apply here, mutatis mutandis.

In context of the present invention, large isoforms comprise an isoform having an apparent molecular weight of about 97 kD (96.8 kD) (defined as OPA1-L1) or an isoform having an apparent molecular weight of about 92 kD (92.3 kD) (defined as OPA1-L2), said molecular weights being determined by SDS-PAGE analysis. Moreover, in context of the present invention large isoforms comprise an isoform having an apparent molecular weight of about 104 kD (104.0 kD) or, preferably, of about 105 kD (105.1 kD) (defined as OPA1-L1) or an isoform having an apparent molecular weight of about 99 kD (99.2 kD) or, preferably, of about 100 kD (100.0 kD) (defined as OPA1-L2), said molecular weights being determined by mass spectrometry.

In context of the present invention, small isoforms comprise an isoform having an apparent molecular weight of about 88 kD (88.1 kD) (defined as OPA1-S3), an isoform having an apparent molecular weight of about 84 kD (84.4 kD) (defined as OPA1-S4) or an isoform having an apparent molecular weight of about 81 kD (80.9 kD) (defined as OPA1-S5), said molecular weights being determined by SDS-PAGE analysis. Moreover, in context of the present invention small isoforms comprise an isoform having an apparent molecular weight of about 92 kD (91.8 kD) or, preferably, of about 96 kD (95.9 kD) (defined as OPA1-S3), an isoform having an apparent molecular weight of about 89 kD (89.2 kD) or, preferably, of about 92 kD (91.8 kD) (defined as OPA1-S4) or an isoform having an apparent molecular weight of about 87 kD (86.8 kD) or, preferably, of about 87 kD (86.8 kD) (defined as OPA1-S5), said molecular weights being determined by mass spectrometry.

It is of note that the molecular weight values of the OPA1 isoforms scrutinized herein are given as averaged values corresponding to the molecular weight values of different isoform bands within an SDS-PAGE/Western-blot.

The term "derivatives" or "derivatives thereof" as well as "homologous" as defined herein above, also apply, mutatis mutandis, in context of the peptides shown above, e.g. the peptides comprised in the OPA1 isoforms or the peptides that characterize the OPA1 spliceforms. Moreover, the term "derivatives" or "derivatives thereof" also refers to (a) fragment(s), e.g. (a) fragment(s) of the peptides shown above, e.g. the peptides comprised in the OPA1 isoforms or the peptides that characterize the OPA1 spliceforms. The term "fragment(s)" means amino acid stretches of at least 3, 4, 5, 6, 7, 8, 9, 10, 11, 12, 13, 14, 15, 20, 30, 50, 100 or 150 amino acids. Also, amino acid stretches having other numbers of amino acids are envisaged.

In terms of the present invention the term "derivatives" or "derivatives thereof" also comprises homologies as well as conservative amino acid exchanges and further known modifications.

In a non-limiting example, it is envisaged in context of the present invention that the identity, amount and/or ratio of the large OPA1 isoforms as defined herein, namely OPA1-L1 and OPA1-L2, can be determined via specific detection of any amino acid stretch of the large OPA1 isoforms lying in N-terminal direction to the amino acid stretches corresponding to the N-terminal amino acids of the "most N-terminal peptide(s)" defined herein of the small OPA1 isoform(s), alternatively and preferred lying in N-terminal direction to the amino acid stretches corresponding to the N-terminal amino acid of the small OPA1 isoforms. In analogy to the above, said amino acid stretch to be detected may be any epitope-bearing portion, or, e.g. any other portion to which a binding molecule as defined herein can bind and said detection may be a detection method as defined and exemplified herein, e.g. a detection method taking advantage of corresponding OPA1 antibodies as defined and exemplified herein, or a detection method taking advantage of other corresponding OPA1 binding molecules as defined herein.

In another particular embodiment of this invention, it is envisaged to distinguish between various types of mitochondrial dysfunction(s)/disease(s). In particular, it is envisaged to differentiate between mitochondrial dysfunction(s)/disease(s) dependent on depletion of mitochondrial DNA and other types of mitochondrial dysfunction(s)/disease(s). Moreover, a quantitative measure of mitochondrial dysfunction and the employment of a corresponding adapted medical intervention is also envisaged.

In context of the present invention, it is intended that the identity, amount or ratio of large and/or small isoforms of OPA1 is determined by optical, spectrophotometric and/or densitometric measurements or analysis. Such determination methods are well known in the art. A particular choice of such methods is described in the appended examples. For instance, such methods comprise the SDS-PAGE analysis, Western blots, ELISA, RIA, CLIA, IRMA and/or EIA. These and further methods are known in the art and are, e.g., described in "Cell Biology: Laboratory manual 3rd edition" (2005, J. Celis, editor. Academic Press, New York).

It is also intended that the identity, amount or ratio of large and/or small isoforms of OPA1 is determined by peptide analysis. Again, such peptide analysis methods are well known in the art. For example, such peptide analysis methods comprise mass spectrometry methods, like MALDI-MS or LC-MS/MS. The use of these particular mass spectrometry methods are described in the appended examples.

As detailed herein one gist of the present invention is based on the finding that a determined reduction of large OPA1 isoforms as described herein (OPA1-L1 and/or -L2) and/or a determined increase of small OPA1 isoforms as described herein (OPA1-S3, OPA1-S4 and/or OPA1-S5) is indicative for the presence of or the susceptibility to a mitochondrial disease/disorder/dysfunction.

Ratios between large and small OPA1 isoforms can be deduced from the the activity of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof as defined herein.

It is understood that the ratios to be determined in context of the present invention may also differ from the ones exemplified above. As already mentioned above, examples that, in a non-limiting manner, describe the evaluation of such ratios are given herein below.

Inter alia, in context of the present invention, the term "ratio" or "density ratio", inter alia, refers to a comparison of density values of bands corresponding to OPA1 isoforms, as, e.g., derived from an SDS-PAGE/Western-blot. Methods how such density values can be obtained are known in the art and exemplified in the appended non-limiting examples.

It is to be understood that not only the comparison of small (OPA1-S3, -S4 and/or -S5) versus large isoforms of OPA1 (OPA1-L1 and/or -L2) or small or large versus other or all OPA1 isoforms derived from an individual patient sample or sample to be tested is of relevance with respect to a certain disorder or disease, but that also a comparison to a healthy control or a corresponding standard is of relevance and can, in accordance with the teachings provided herein, be obtained. This applies, mutatis mutandis, for all methods provided herein.

The person skilled in the art is readily in a position to determine the ratio of individual (or more) OPA1 isoforms as described herein by methods known in the art, like for example densitometric, spectrophotometric, luminescent, autoradiographic or fluorescent quantification methods. Also in this context, methods comprising tests with specific anti-OPA1 isoform antibodies (also specific antibodies against individual OPA1-isoforms as provided herein) are useful. Accordingly, methods, like Western-blot analysis or ELISA/RIA-tests may be employed to determine the OPA1 isoform ratio(s). Corresponding non-limiting examples are illustrated in the appended experimental part.

In context of the present invention, the amount or ratio of large and/or small isoforms of OPA1 can be, inter alia, derived from measurements of the enzymatic activity and/or the gene expression levels and/or the protein levels of OMA1 and/or an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof. In an embodiment, these different measurements can be integrated to determine the subject's prognosis based on said integration, wherein depending on the disorder or disease an increase and/or decrease of any of the aforementioned activities and/or levels indicates the subject has a favorable or unfavorable susceptibility for, predisposition for or the presence of the disorder or disease and therefore requires and/or responds to a treatment, prevention and/or amelioration of the disorder or disease. The term "biomarker" refers to such a prognostic method and is well known to the person skilled in the art.

As used herein, the term "subject" and "patient" are used interchangeably and refer to both human and non-human animals. The term "non-human animals" of the disclosure includes all vertebrates, e.g., mammals and non-mammals, such as nonhuman primates, sheep, dog, cat, horse, cow, chickens, rodents, amphibians, reptiles, and the like. Preferably, the subject is a human patient.

As used herein the term, "integration" refers to providing a probability based analysis of how a particular subject will develop a disorder or disease and/or how a particular subject will require or respond to a treatment. The prediction of responsiveness is not a guarantee or absolute, only a statistically probable indication of the responsiveness of the subject.

The prediction of responsiveness to a therapy may indicate that the subject is likely to be responsive to a therapy or alternatively may indicate that the subject is not likely to be responsive to a therapy. Alternatively, the prediction, may indicate that a method for the treatment, prevention and/or amelioration of a disorder or disease correlated with mitochondrial dysfunction or a mitochondrial disorder or disease, or a disorder or disease characterized by OPA1 alterations regime may be counter-productive and lead to a worse result for the subject than if no therapy was used or a placebo was used. Responsiveness includes but is not limited to, any measure of a likelihood of clinical benefit. For example, clinical benefits include an increase in overall survival, an increase in progression free survival, an increase in time to progression, increased response, decreased symptoms, or other quality of live benefits.

In one embodiment, the method includes determining the expression levels of the proteins or the RNA transcripts for the biomarkers in a sample from a patient with cancer or any other disorder or disease. Biomarker expression in some instances may be normalized against the expression levels of all proteins or RNA transcripts in the sample, or against a reference set of proteins or RNA transcripts in the sample. The level of expression of the biomarkers is indicative of the prognosis for the subject or predictive of the effectiveness of a particular treatment.

The methods of the present disclosure can also be used to assist in selecting appropriate courses of treatment and to identify patients that would benefit; from a particular course of therapy. Thus, the expression of the particular biomarkers described herein provides insight into which treatment regimens will be most effective for the patient. This information can be used, to generate treatment plans for the patient to prolong survival and minimize side effects or therapy related toxicity.

In some embodiments described herein, prognostic performance of the biomarkers and/or other clinical parameters was assessed by determining the threshold of OMA1 activation and/or the activation threshold of an oligomeric complex comprising OMA1 and/or HIDG1A and/or OPA1 and/or BNIP3 and/or YME1L1 and/or PHB and/or PHB2 and/or SAMM50 and/or IMMT or (a) variant(s) thereof upon induction of inner membrane permeabilization through addition of mitochondrial uncouplers, such as carbonyl cyanide m-chlorophenyl hydrazine (CCCP; CAS #555-60-2).

It is to be understood that any binding molecule capable of lowering or increasing the threshold levels is an agonist or antagonist in the context of the present invention and therefore administration of such a binding molecule to a patient in need of medical intervention is a method of treatment, prevention and/or amelioration of a disorder or disease correlated with mitochondrial dysfunction or a mitochondrial disorder or disease; or a disorder or disease characterized by OPA1 alterations.

"Sample" is intended to include a sampling of cells, tissues, or bodily fluids in which expression of a biomarker can be detected. Examples of such samples include, but are not limited to, biopsies, cerebrospinal fluid, blood, lymph, urine, saliva, or any other bodily secretion or derivative thereof. Blood can include whole blood, plasma (citrate, EDTA, heparin), serum, or any derivative of blood. Samples may be obtained from a patient by a variety of techniques available to those skilled in the art. Methods for collecting various samples are well known in the art.

Any methods available in the art for detecting expression of biomarkers are encompassed herein. The expression of a biomarker of the invention can be detected on a nucleic acid level (e.g., as an RNA transcript) or a protein level. By "detecting or determining expression" is intended determining the quantity or presence of a protein or its RNA transcript for any combination of at least two genes/proteins from the list compromising OMA1, HIGD1A, OPA1, BNIP3, YME1L1, PHB, SAMM50, IMMT or PHB2. Thus, "detecting expression" encompasses instances where a biomarker is determined not to be expressed, not to be detectably expressed, expressed at a low level, expressed at a normal level, or overexpressed.

Methods suitable for detecting or determining the expression levels of biomarkers are known to those of skill in the art and include, but are not limited to, ELISA, immunofluorescence, FACS analysis, Western blot, magnetic Immunoassays, and both antibody-based micro arrays and non-antibody-based microarrays. Methods for detecting expression of the biomarkers described herein are not limited to protein expression. Gene expression profiling including methods based on hybridization analysis of polynucleotides, methods based on sequencing of polynucleotides, immunohistochemistry methods, and proteomics-based methods may also be used. Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE) and gene expression analysis by massively parallel signature sequencing.

The term "probe" refers to any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Aspects of the Invention

Aspect 1. A method for the treatment, prevention and/or amelioration of

- (i) a disorder or disease correlated with mitochondrial dysfunction, or a mitochondrial disorder or disease; or
- (ii) a disorder or disease characterized by OPA1 alterations, wherein said method comprises the administration to a patient in need of medical intervention a pharmaceutically active amount of a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 2. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

- (a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.
- (b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
- (c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
- (d) a polypeptide comprising an amino acid sequence having at least 50% sequence identity to the polypeptide of any one of (a) to (c);
- (e) a polypeptide comprising an amino acid sequence encoded by a nucleic acid molecule having at least 50% sequence identity to the nucleic acid molecule as defined in any one of (a) to (c);
- (f) a polypeptide comprising an amino acid sequence encoded by a nucleic acid molecule hybridizing under stringent conditions to the complement stand of a nucleic acid molecule as defined in any one of (a) to (c); and
- (g) fragment of a polypeptide of any one of (a) to (f).

Aspect 3. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 4. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

- (a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.
- (b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
- (c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.
- (d) a polypeptide comprising an amino acid sequence having at least 50% sequence identity to the polypeptide of any one of (a) to (c);
- (e) a polypeptide comprising an amino acid sequence encoded by a nucleic acid molecule having at least 50% sequence identity to the nucleic acid molecule as defined in any one of (a) to (c);
- (f) a polypeptide comprising an amino acid sequence encoded by a nucleic acid molecule hybridizing under stringent conditions to the complement stand of a nucleic acid molecule as defined in any one of (a) to (c); and
- (g) fragment of a polypeptide of any one of (a) to (f).

Aspect 5. The method of aspect 1, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 6. The method of aspect 5, wherein said hetero-oligomeric complex comprises AFG311 and/or AFG312 and/or paraplegin and/or HIGD1a and/or OPA1 and/or BNIP3 and/or YME1L1 and/or PHB and/or PHB2 or a variant thereof.

Aspect 7. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a compound obtained by a method comprising the steps of:

(a) contacting OPA1 with OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

Aspect 8. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 9. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(a) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(b) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(c) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (d) a low molecular weight compound or a small molecule.

Aspect 10. The method of aspect 9, wherein said binding molecule is selected form the group consisting of antibodies, affybodies, trinectins, anticalins, aptamers, PNA, DNA or RNA.

Aspect 11. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(B) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(C) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (D) a low molecular weight compound or a small molecule, wherein said binding molecule is selected from the group consisting of:

(i) an antibody that binds to the polypeptide or the nucleic acid molecule selected from the group consisting of:

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (b) to (c);

(f) a polypeptide comprising an amino acid sequence encoded by a nucleic acid molecule hybridizing under stringent conditions to the complement stand of a nucleic acid molecule as defined in any one of (b) to (c); and (g) fragment of a polypeptide of any one of (b) to (f). or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(ii) an antisense nucleotide sequence that hybridizes to the nucleic acid molecule as defined in (i);

(iii) a siRNA that interacts with the nucleic acid molecule as defined in (i);

(iv) an aptamer that binds to the polypeptide or the nucleic acid molecule as defined in (i) or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant (s) thereof as defined in claim 1; and (v) ribozyme that interacts with the nucleic acid molecule as defined in (i).

Aspect 12. The method of any one of aspects 1 to 6, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a polypeptide as defined in (a)-(g) or a nucleotide sequence comprising a nucleic acid molecule as defined in (a)-(g);

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (b) to (c);

(f) a polypeptide comprising an amino acid sequence encoded by a nucleic acid molecule hybridizing under stringent conditions to the complement stand of a nucleic acid molecule as defined in any one of (b) to (c); and (g) fragment of a polypeptide of any one of (a) to (f), (B) a binding molecule as defined in any one of claims 9, 10, and 11 (*a*) and (*d*) being an agonistic binding molecule; and (C) a low molecular weight compound or a small molecule.

Aspect 13. The method of any one of aspects 1 to 6, wherein said compound is selected from thiorphan, phenanthroline, ARP100, glucosamine, micro-RNA miR-203. SB2K763, cuytokine CXCL4, and isoflurane.

Aspect 14. The method of aspects 1 to 6, wherein said compound is SB-3CT.

Aspect 15. The method of any one of aspects 1 to 14, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a protease activity.

Aspect 16. The method of any one of aspects 1 to 14, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is an AAA protease activity.

Aspect 17. The method of any one of aspects 1 to 14, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is proteolytic cleavage of OPAL.

Aspect 18. The method of aspect 17, wherein said proteolytic cleavage of OPA1 leads to OPA1 processing.

Aspect 19. The method of any one of aspects 1 to 18, wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard.

Aspect 20. The method of aspect 19, wherein said at least one small isoform of OPA1 is OPA1-S3, OPA1-S4 and/or OPA1-S5.

Aspect 21. The method of any one of aspec201 to 18, wherein said disorder or disease is selected from the group consisting of premature ageing, cardiomyopathy, a respiratory chain disorder, mtDNA depletion syndrome, myoclonus epilepsy, ragged-red fibers syndrome (MERRF), myopathy encephalopathy lactic acidosis, stroke-like episodes (MELAS) and optic atrophy, glaucoma, optic neuropathy, Parkinson's Disease, Alzheimer's Disease or any other form of neurodegenerative disease or aging-related disease, such as cancer or diseases related to ischemia.

Aspect 22. A method of screening for a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprising the steps of (a) contacting OPA1 with said OMA1 and/or oligomeric complex comprising OMA1 and/or HIGD1A and/or OPA1 and/or BNIP3 and/or YME1L1 and/or PHB and/or PHB2 and/or SAMM50 and/or IMMT or (a)

variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

Aspect 23. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

(a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (a) to (c);

(f) a polypeptide comprising an amino acid sequence encoded by a nucleic acid molecule hybridizing under stringent conditions to the complement stand of a nucleic acid molecule as defined in any one of (a) to (c); and (g) fragment of a polypeptide of any one of (a) to (f).

Aspect 24. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 25. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof comprises a polypeptide selected from the group consisting of:

(a) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(b) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (a) to (c);

(f) a polypeptide comprising an amino acid sequence encoded by a nucleic acid molecule hybridizing under stringent conditions to the complement stand of a nucleic acid molecule as defined in any one of (a) to (c); and (g) fragment of a polypeptide of any one of (a) to (f).

Aspect 26. The method of aspect 22, wherein OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a homo-oligomeric complex or a hetero-oligomeric complex.

Aspect 27. The method of aspect 26, wherein said hetero-oligomeric complex comprises AFG311 and/or AFG312 and/or paraplegin and/or HIGD1a and/or OPA1 and/or BNIP3 and/or YME1L1 and/or PHB and/or PHB2 or a variant thereof.

Aspect 28. The method of any one of aspects 22 to 27, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a compound obtained by a method comprising the steps of:

(a) contacting OPA1 with OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof in the presence of said compound to be screened for under conditions allowing OPA1 processing to occur; and (b) evaluating whether OPA1 processing is altered compared to a control, where OPA1 and OMA1 and/or said oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof are contacted in the absence of said compound to be screened for under conditions allowing OPA1 processing to occur.

Aspect 29. The method of any one of aspects 22 to 27, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 30. The method of any one of aspects 20 to 25, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(a) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(b) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(c) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (d) a low molecular weight compound or a small molecule.

Aspect 31. The method of aspect 30, wherein said binding molecule is selected form the group consisting of antibodies, affybodies, trinectins, anticalins, aptamers, PNA, DNA or RNA.

Aspect 32. The method of any one of aspects 20 to 25, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a binding molecule that binds to/interacts with OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 or binds to/interacts with a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(B) a nucleic acid molecule capable of introducing an insertion of a heterologous sequence or a mutation into a nucleic acid molecule encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 via in vivo mutagenesis;

(C) a nucleic acid molecule capable of reducing the expression of mRNA encoding ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1 by co-suppression; and (D) a low molecular weight compound or a small molecule, wherein said binding molecule is selected from the group consisting of:

(i) an antibody that binds to the polypeptide or the nucleic acid molecule selected from the group consisting of:

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (b) to (c);

(f) a polypeptide comprising an amino acid sequence encoded by a nucleic acid molecule hybridizing under stringent conditions to the complement stand of a nucleic acid molecule as defined in any one of (b) to (c); and (g) fragment of a polypeptide of any one of (b) to (f).

or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1;

(ii) an antisense nucleotide sequence that hybridizes to the nucleic acid molecule as defined in (i);

(iii) a siRNA that interacts with the nucleic acid molecule as defined in (i);

(iv) an aptamer that binds to the polypeptide or the nucleic acid molecule as defined in (i) or to ((a) subunit(s) of) OMA1 and/or the oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof as defined in claim 1; and (v) ribozyme that interacts with the nucleic acid molecule as defined in (i).

Aspect 33. The method of any one of aspects 22 to 27, wherein said compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is or comprises an agonist or antagonist of the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, wherein said agonist or antagonist is a molecule selected from the group consisting of:

(A) a polypeptide as defined in (a)-(g) or a nucleotide sequence comprising a nucleic acid molecule as defined in (a)-(g);

(a) a polypeptide comprising an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(b) a polypeptide comprising an amino acid sequence encoded by a nucleic acid molecule as depicted in SEQ ID NO 1; 3; 5; 7; 9; 11; 13; 15; 17; 19; 21; 23; 25; 27; 31; 33; 35; 37; 39; 41; 43 or 45.

(c) a polypeptide comprising an amino acid sequence encoded by a nucleic acid molecule encoding an amino acid sequence as depicted in SEQ ID NO 2; 4; 6; 8; 10; 12; 14; 16; 18; 20; 22; 24; 26; 28; 30; 32; 34; 36; 38; 40; 42; 44 or 46.

(d) a polypeptide comprising an amino acid sequence having at least 50% sequence identity to the polypeptide of any one of (a) to (c);

(e) a polypeptide comprising an amino acid sequence encoded by a nucleic acid molecule having at least 50% sequence identity to the nucleic acid molecule as defined in any one of (b) to (c);

(f) a polypeptide comprising an amino acid sequence encoded by a nucleic acid molecule hybridizing under stringent conditions to the complement stand of a nucleic acid molecule as defined in any one of (b) to (c); and (g) fragment of a polypeptide of any one of (a) to (f), (B) a binding molecule as defined in any one of claims 9, 10, and 11 (*a*) and (*d*) being an agonistic binding molecule; and (C) a low molecular weight compound or a small molecule.

Aspect 34. The method of any one of aspects 22 to 33, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a protease activity.

Aspect 35. The method of any one of aspects 22 to 33, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is an AAA protease activity.

Aspect 36. The method of any one of aspects 22 to 33, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is proteolytic cleavage of OPAL.

Aspect 37. The method of claim 36, wherein said proteolytic cleavage of OPA1 leads to OPA1 processing.

Aspect 38. The method of any one of aspects 22 to 37, wherein said OPA1 processing is characterized by (a decrease of) a certain amount of at least one large isoform of OPA1, (an increase of) a certain amount of at least one small isoform of OPA1 and/or (a decrease of) a certain ratio of at least one large versus at least one small isoform of OPA1 (compared to a control/standard).

Aspect 39. The method of aspect 38, whereby a large isoform of OPA1 has an apparent molecular weight of more than about 91 kD and whereby a small isoform of OPA1 has an apparent molecular weight of less than about 91 kD, said molecular weights being determined by SDS-PAGE analysis; and/or whereby a large isoform of OPA1 has an apparent molecular weight of more than about 95 kD and whereby a small isoform of OPA1 has an apparent molecular weight of less than about 95 kD, said molecular weights being determined by mass spectrometry.

Aspect 40. The method of aspect 39, wherein said SDS-PAGE is a 10% SDS-PAGE.

Aspect 41. The method of any one of aspects 39 to 40, wherein said mass spectrometry is MALDI-MS or LC-MS/MS.

Aspect 42. The method of any one of aspects 39 to 41, wherein said at least one large isoform of OPA1 is OPA1-L1 and/or OPA1-L2.

Aspect 43. The method of aspect 38, wherein said at least one large isoform of OPA1 comprises two isoforms (OPA1-L1 and OPA1-L2) and/or wherein said at least one small isoform of OPA1 comprises three isoforms (OPA1-S3, OPA1-S4 and OPA1-S5).

Aspect 44. The method of aspect 43, wherein said at least one large isoform of OPA1 comprises an isoform having an apparent molecular weight of about 97 kD (OPA1-L1) or an isoform having an apparent molecular weight of about 92 kD (OPA1-L2), said molecular weights being determined by SDS-PAGE analysis.

Aspect 45. The method of aspect 43, wherein said at least one small isoform of OPA1 comprises an isoform having an apparent molecular weight of about 88 kD (OPA1-S3), an isoform having an apparent molecular weight of about 84 kD (OPA1-S4) or an isoform having an apparent molecular weight of about 81 kD (OPA1-S5), said molecular weights being determined by SDS-PAGE analysis.

Aspect 46. The method of aspect 43, wherein said at least one large isoform of OPA1 comprises an isoform having an apparent molecular weight of about 104 kD (OPA1-L1) or an isoform having an apparent molecular weight of about 99 kD (OPA1-L2), said molecular weights being determined by mass spectrometry.

Aspect 47. The method of aspect 43, wherein said at least one small isoform of OPA1 comprises an isoform having an apparent molecular weight of about 92 kD (OPA1-S3), an isoform having an apparent molecular weight of about 89 kD (OPA1-S4) or an isoform having an apparent molecular weight of about 87 kD (OPA1-S5), said molecular weights being determined by mass spectrometry.

Aspect 48. The method of aspect 43, wherein, said OPA1-L1 has an apparent molecular weight of about 97 kD, said OPA1-L2 has an apparent molecular weight of about 92 kD, said OPA1-S3 has an apparent molecular weight of about 88 kD, said OPA1-S4 has an apparent molecular weight of about 84 kD, and/or said OPA1-S5 has an apparent molecular weight of about 81 kD, said molecular weights being determined by SDS-PAGE analysis; or wherein said OPA1-L1 has an apparent molecular weight of about 104 kD, said OPA1-L2 has an apparent molecular weight of about 99 kD, said OPA1-S3 has an apparent molecular weight of about 92 kD, said OPA1-S4 has an apparent molecular weight of about 89 kD, and/or said OPA1-S5 has an apparent molecular weight of about 87 kD, said molecular weights being determined by mass spectrometry.

Aspect 49. The method of aspect 43, wherein, (a) OPA1-L1 and OPA1-L2 are characterized by comprising amino acid stretches or amino acid peptides comprising one or more of the following sequences:

```
                              (SEQ ID NO: 47)
YLILGSAVGGGYTAK;

                              (SEQ ID NO: 48)
TFDQWK;

                              (SEQ ID NO: 49)
DMIPDLSEYK;

                              (SEQ ID NO: 50)
WIVPDIVWEIDEYIDFEK;

                              (SEQ ID NO: 51)
LAPDFDK;

                              (SEQ ID NO: 52)
IVESLSLLK;

                              (SEQ ID NO: 53)
ALPNSEDLVK;

                              (SEQ ID NO: 54)
DFFTSGSPEETAFR;

                              (SEQ ID NO: 55)
TRLLKLRYLILGS;
and

                              (SEQ ID NO: 56)
FWPARLATRLLKLRYLILGS;
```

or derivatives thereof;

(b) OPA1-S3 is characterized by comprising amino acid stretches or amino acid peptides comprising one or more of the following sequences:

```
                              (SEQ ID NO: 52)
IVESLSLLK;

                              (SEQ ID NO: 54)
DFFTSGSPEETAFR;

                              (SEQ ID NO: 57)
GLLGELILLQQQIQEHEEEAR;

                              (SEQ ID NO: 58)
AAGQYSTSYAQQK;
and

                              (SEQ ID NO: 59)
IDQLQEELLHTQLK;
```

or derivatives thereof;

(c) OPA1-S4 is characterized by comprising amino acid stretches or amino acid peptides comprising one or more of the following sequences:

```
                              (SEQ ID NO: 57)
GLLGELILLQQQIQEHEEEAR;

                              (SEQ ID NO: 58)
AAGQYSTSYAQQK;
and

                              (SEQ ID NO: 59)
IDQLQEELLHTQLK;
```

or derivatives thereof; and/or (d) OPA1-S5 is characterized by comprising amino acid stretches or amino acid peptides comprising the following sequence:

```
                              (SEQ ID NO: 59)
IDQLQEELLHTQLK;
```

or derivatives thereof.

Aspect 50. The method of aspect 43, wherein (a) OPA1-L2 is characterized by not comprising amino acid stretches or amino acid peptides comprising one or more of the following sequences:

```
                              (SEQ ID NO: 57)
GLLGELILLQQQIQEHEEEAR;
and

                              (SEQ ID NO: 58)
AAGQYSTSYAQQK;
```

or derivatives thereof; and/or (b) OPA1-S3 is characterized by not comprising amino acid stretches or amino acid peptides comprising one or more of the following sequences:

```
                              (SEQ ID NO: 47)
YLILGSAVGGGYTAK

                              (SEQ ID NO: 48)
TFDQWK;

                              (SEQ ID NO: 49)
DMIPDLSEYK;

                              (SEQ ID NO: 50)
WIVPDIVWEIDEYIDFEK;

                              (SEQ ID NO: 51)
LAPDFDK;

                              (SEQ ID NO: 52)
IVESLSLLK;

                              (SEQ ID NO: 53)
ALPNSEDLVK;

                              (SEQ ID NO: 55)
TRLLKLRYLILGS;
and

                              (SEQ ID NO: 56)
FWPARLATRLLKLRYLILGS;
```

or derivatives thereof;

(c) OPA1-S4 is characterized by not comprising amino acid stretches or amino acid peptides comprising one or more of the following sequences:

```
                              (SEQ ID NO: 47)
YLILGSAVGGGYTAK;

                              (SEQ ID NO: 48)
TFDQWK;

                              (SEQ ID NO: 49)
DMIPDLSEYK;

                              (SEQ ID NO: 50)
WIVPDIVWEIDEYIDFEK;

                              (SEQ ID NO: 51)
LAPDFDK;

                              (SEQ ID NO: 52)
IVESLSLLK;

                              (SEQ ID NO: 53)
ALPNSEDLVK;
```

-continued

```
                              (SEQ ID NO: 54)
DFFTSGSPEETAFR;

                              (SEQ ID NO: 55)
TRLLKLRYLILGS;
and

                              (SEQ ID NO: 56)
FWPARLATRLLKLRYLILGS;
```

or derivatives thereof; and/or (d) OPA1-S5 is characterized by not comprising amino acid stretches or amino acid peptides comprising one or more of the following sequences:

```
                              (SEQ ID NO: 47)
YLILGSAVGGGYTAK;

                              (SEQ ID NO: 48)
TFDQWK;

                              (SEQ ID NO: 49)
DMIPDLSEYK;

                              (SEQ ID NO: 50)
WIVPDIVWEIDEYIDFEK;

                              (SEQ ID NO: 51)
LAPDFDK;

                              (SEQ ID NO: 52)
IVESLSLLK;

                              (SEQ ID NO: 53)
ALPNSEDLVK;

                              (SEQ ID NO: 54)
DFFTSGSPEETAFR;

                              (SEQ ID NO: 55)
TRLLKLRYLILGS;
and

                              (SEQ ID NO: 57)
GLLGELILLQQQIQEHEEEAR;
and

                              (SEQ ID NO: 58)
AAGQYSTSYAQQK;
```

or derivatives thereof.

Aspect 51. A method for determining the susceptibility for, predisposition for or the presence of (i) a disorder or disease correlated with mitochondrial dysfunction or a mitochondrial disorder or disease; or (ii) a disorder or disease characterized by OPA1 alterations, wherein said method comprises the steps of (a) obtaining a sample from the subject and measuring the activity of OMA1 and/or YME1L1 or (a) combination(s) thereof in the sample, and/or measuring the gene expression levels of OMA1, HIGD1A, OPA1, BNIP3, YME1L1, PHB, SAMM50, IMMT and/or PHB2 or (a) combination(s) thereof in the sample, and/or measuring the protein levels of OMA1, HIGD1A, OPA1, BNIP3, YME1L1, PHB, SAMM50, IMMT and/or PHB2 or (a) combination(s) thereof in the sample;

(b) comparing the increase and/or decrease of measured activity and/or gene expression levels and/or protein levels of OMA1 and/or HIGD1A and/or OPA1 and/or BNIP3 and/or YME1L1 and/or PHB and/or SAMM50 and/or IMMT and/or PHB2 or (a) combination(s) thereof in the sample compared to a reference;

(c) integrating the results of these measurements through combination of 3 or more genes selected from the group of OMA1, HIGD1A, OPA1, BNIP3, YME1L1, PHB, SAMM50, IMMT and PHB2.

Aspect 52. The method of aspect 50, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is a protease activity.

Aspect 53. The method of aspect 50, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is an AAA protease activity.

Aspect 54. The method of aspect 50, wherein said activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof is proteolytic cleavage of OPAL.

Aspect 55. The method of aspect 54, wherein said proteolytic cleavage of OPA1 leads to OPA1 processing.

Aspect 56. The method of any one of aspects 50 to 55, wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard.

Aspect 57. The method of aspect 56, wherein said at least one small isoform of OPA1 is OPA1-S3, OPA1-S4 and/or OPA1-S5.

Aspect 58. The method of any one of aspects 50 to 57, wherein said disorder or disease is selected from the group consisting of premature ageing, cardiomyopathy, a respiratory chain disorder, mtDNA depletion syndrome, myoclonus epilepsy, ragged-red fibers syndrome (MERRF), myopathy encephalopathy lactic acidosis, stroke-like episodes (MELAS) and optic atrophy, glaucoma, optic neuropathy, Parkinson's Disease, Alzheimer's Disease or any other form of neurodegenerative disease or aging-related disease, such as cancer or diseases related to ischemia.

Aspect 59. The method of any one of aspects 50 to 58, wherein said method is utilized for determining whether a patient in need for medical intervention will benefit from administration of a pharmaceutically active amount of a compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Aspect 60. The method of any one of aspects 50 to 59, wherein said method is a biomarker for the predisposition of a disorder or disease, a biomarker for a disorder or disease or a biomarker for evaluating efficacy of a method for treatment, prevention and/or amelioration of a disorder or disease.

Aspect 61. The method of aspect 60, wherein said biomarker is informative for selecting medical interventions and/or therapies, monitoring medical interventions and/or therapies or predicting outcomes of medical interventions and/or therapies.

Aspect 62. The method of any one of aspects 50 to 61, wherein said method compromises the use of a kit comprising reagents for the quantification of the expression levels of OMA1 and/or HIGD1A and/or OPA1 and/or BNIP3 and/or YME1L1 and/or PHB and/or SAMM50 and/or IMMT and/or PHB2 or (a) functionally equivalent variant(s) thereof or of any combination of these molecules.

Aspect 63. The method of any one of aspects 50 to 61, wherein said method compromises the use of a kit comprising reagenis for the quanlificalion of the levels of OMA1 and/or HIGD1A and/or OPA1 and/or BNIP3 and/or YME1L1 and/or PHB and/or SAMM50 and/or IMMT and/or PHB2 or (a) functionally equivalent variant(s) thereof or of any combination of these molecules, wherein such quantification is performed by means of Western blot, imrnunohistochemistry or ELISA.

Aspect 64. A compound capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof for the treatment, prevention and/or amelioration of (i) a disorder or disease correlated with mitochondrial dysfunction or a mitochondrial disorder or disease; or (ii) a disorder or disease characterized by OPA1 alterations, wherein the compound is capable of modulating the activity of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof, and wherein said altered OPA1 processing is characterized by an altered (decrease of a) certain amount of at least one large isoform of OPA1, an altered (increase of a) certain amount of at least one small isoform of OPA1 and/or an altered (decrease of a) certain ratio of at least one large versus at least one small isoform of OPA1 compared to a control/standard, Aspect 65. A method of treating a disease or disorder in a patient comprising administering to a patient in need of such treatment a therapeutically effective amount of the compound of aspect 65.

Aspect 66. A pharmaceutical composition comprising the compound of aspect 65 and a pharmaceutically acceptable excipient.

Aspect 67. A method of treating a disease or disorder in a patient comprising administering to a patient in need of such treatment a therapeutically effective amount of the pharmaceutical composition of aspect 66.

Aspect 68. A combination of two or more methods according to aspects 1, 22, and 51 that result in a medical intervention individualized for one or more patients and that may be referred to as personalized medicine and/or precision medicine.

Mitochondria are dynamic organelles forming networks of interconnected tubules, which maintain their homeostasis by constantly fusing and dividing. Fragmented mitochondria thereby are more susceptible to apoptotic cell death.

OPA1 is an essential fusion protein, which is deactivated by the OMA1 protease under conditions of cell stress. OPA1 occurs in two forms, large L-OPA1 isoforms and small S-OPA1 isoforms. S-OPA1 is derived from L-OMA1 by proteolytic cleavage by the OMA1 protease and the YME1L1 protease, which is also known as i-AAA protease. OMA1 cleaves OPA1 and thereby generates S-OPA1 under conditions broadly defined as cell-stress, whereby OMA1 activation facilitates outer membrane permeabilization and cytochrome c release resulting in apoptotic cell death.

We identified compounds disclosed herein which are known in the arts as HIV-1 protease inhibitors. These compounds, as shown in the example provided below and in Appendix 1, surprisingly and quite unexpectedly activated the OMA1 protease. The disclosed compounds had also a dose-dependent antagonistic effect on OPA1. Low doses resulted in OPA1 cleavage. However, higher doses prevented OPA1 cleavage even under conditions that would otherwise result in OPA1 cleavage.

The OMA1 protease has a number of disease implications and is supported by epidemiological and genetic data from humans and animal disease models. And yet, there are still until now no OMA1 modulators disclosed in the arts although many have tried without much success to identify such molecules.

The meaning of the terms "OMA1" and "OPA1" and "YME1L1" are well known in the art and is, if not explicitly prescribed differentially, used accordingly in context of the present invention. In context of this invention, these terms are likewise used to refer to the corresponding nucleotide sequences (e.g. the genes) as well as to the corresponding polypeptides (e.g. the polypeptides encoded by said genes). It is to be understood that these terms are defined as broad as possible and shall include all natural and non-natural variants thereof from any and every species.

As shown herein and in the arts, mitochondrial dysfunction (or a corresponding mitochondrial disease or disorder) is not merely correlated with decrease of any one of OPA1 isoforms, but with a decrease of particularly the large isoforms. Referring to FIG. 1, the large isoforms of OPA1 (L-OPA1) may comprise two isoforms and the small isoforms of OPA1 (S-OPA1) may comprise three isoforms. However, it is also within the context of the present invention that additional, possibly existing OPA1 isoforms may be assigned as large or small isoforms.

In this context, it is to be understood that the OPA1 isoforms serve as proxy for protease activity, in particular for OMA1 protease activity. Therefore, the present invention is not limited to the modulation of OPA1 isoforms but encompasses also any and every other proxy for OMA1 activity, including other OMA1 substrates, such as DELE1, PGAM5, or PINK1. A person skilled in the art is also readily in a position to deduce (further) amino acid stretches/peptides that are (artificial) OMA1 substrates (see, for example, U.S. Ser. No. 16/101,134.)

Conversely, compounds of present disclosure may modulate the ratio of OPA1 isoforms by direct or indirect interaction with the OMA1 protease, for example by interacting with a protein complex comprising OMA1, or by interacting with other proteases, which may cleave OPA1 and/or OMA1, such as the i-AAA protease, or by interacting with OMA1-regulating enzymes, such as the m-AAA protease or prohibitin (see also Alavi M. V. "OMA1—An integral membrane protease"*Biochim Biophys Acta Proteins Proteom.* 2020 Oct. 29:140558.)

Clinical and/or pathological examples for diseases linked to OPA1 modulation in the context of the present invention are given in the list above.

However, these disorders or diseases are mere examples to be covered by this invention which is not strictly construed to the clinical and/or pathological situations described above.

Cancer is defined broadly and can refer to any and all forms of malignancy.

The singular forms "a", "an", and "the" as used herein and in the claims include plural reference unless the context dictates otherwise. For example, "a cell" means as well a plurality of cells, and so forth. The term "and/or" as used in the present specification and in the claims implies that the phrases before and after this term are to be considered either as alternatives or in combination.

The terms “agent”, “reagent”, “modulator”, “compound”, “molecule” and the like refer to any substance, chemical, composition or extract that have a positive or negative biological effect on a cell, tissue, body fluid, or within the context of any biological system, or any assay system.

The compounds of the present invention can be in any suitable form, without limitation. Forms suitable for oral use, include, but are not limited to, tablets, troches, lozenges, aqueous or oily suspensions, dispersible powders or granules, emulsions, hard or soft capsules, solutions, syrups and elixirs. Compositions intended for oral use may be prepared according to any method known to the art for the manufacture of pharmaceutical compositions.

The compounds can be formulated with other ingredients, e.g., “pharmaceutically acceptable carriers” or “excipients” to indicate they are combined with the active drug and can be administered safely to a subject for therapeutic purposes. These include, but are not limited to, antioxidants, preservatives, dyes, tablet-coating compositions, plasticizers, inert carriers, excipients, polymers, coating materials, osmotic barriers, devices and agents which slow or retard solubility, etc.

The compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Non-toxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

The compositions intended for oral use may contain lecithin as an emulsifier and solubilizing agent to achieve a high loading of the disclosed compounds. The amount of active ingredient in the emulsion formulations of the present invention may vary or be adjusted widely depending on the intended route of administration, ages of patients being treated, the severity of the retroviral infection and the required concentration. In preparing the emulsion formulations, the amount of active ingredient is not particularly restricted up to 200 mg/ml (20% by weight) for maintaining high oral bioavailability, but preferably ranges from about 1% to about 20%, and more preferably from about 2% to about 15%, by weight of the total composition.

The emulsion formulations may be administered orally, or parenterally at a dosage to obtain and maintain a concentration, that is, an amount, or blood-level of the active ingredient in the patients, which will be therapeutically effective. Generally, such therapeutically effective amount of active ingredient ranges from about 0.1 to about 300 mg/kg of body weight per day. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two or more times per day.

The term “oil component” refers to monoglyceride, diglyceride, triglyceride, or a mixture comprising at least two members of these three glycerides. Preferably, the oil component is triglyceride, a mixture of diglyceride and monoglyceride in a ratio of from about 9:1 to about 1:9 by weight, a mixture of diglyceride and triglyceride in a ratio of from about 9:1 to about 1:9 by weight, or a mixture of monoglyceride, diglyceride and triglyceride in a ratio of from about 1 to about 8 parts of diglyceride per 10 parts of the mixture, about 1 to 5 parts of monoglyceride per 10 parts of the mixture, and about 1 to about 8 parts of triglyceride per 10 parts of the mixture.

More preferably, the oil component is triglyceride, a mixture of diglyceride and monoglyceride in a ratio of about 8:2 (diglyceride:monoglyceride) by weight, a mixture of diglyceride and triglyceride in a ratio of about 2:8 (triglyceride:diglyceride) by weight.

Diglyceride (hereinafter DGO) of the present invention refers to a long chain fatty acid ester of glycerol having structural formula $HOCH_2—CH(O_2CR)—CH_2(O_2CR)$ or $(RCO_2)CH_2—CH(OH)—CH_2(O_2CR)$, wherein R is mono-unsaturated or di-unsaturated alkyl group having fifteen to twenty-one carbon atoms. The preferred diglyceride is diolein (R is mono-unsaturated alkyl group with seventeen carbon atoms), dilinoleate (R is di-unsaturated alkyl group with seventeen carbon atoms), or a mixture of diolein and dilinoleate. The most preferred diglyceride is diolein.

Monoglyceride (hereinafter GMO) of the present invention refers to a long chain fatty acid ester of glycerol having structural formula $HOCH_2—CH(OH)—CH_2(O_2CR)$ or $HOCH_2—CH(O_2CR)—CH_2OH$, wherein R is a mono-unsaturated or di-unsaturated alkyl group having fifteen to twenty-one carbon atoms. The preferred monoglyceride is monoolein (R is mono-unsaturated alkyl group with seventeen carbon atoms), monolinoleate (R is di-unsaturated alkyl group with seventeen carbon atoms), or a mixture of monoolein and monolinoleate. The most preferred monoglyceride is monoolein.

Triglyceride (hereinafter MCT) of the present invention refers to a medium chain fatty acid ester of glycerol having structural formula $R^1OCH_2$—$CH(O_2CR_2)$—$CH_2(O_2CR^1)$, wherein $R^1$ is a saturated alkyl group having five to eleven carbon atoms. The preferred triglyceride is under brand names Miglyol 810, Miglyol 812, Miglyol 829, etc. which refer to different grades of fractionated and purified coconut oil consisting mainly of medium chain triglycerides.

In preparing the emulsion of the present invention, the amount of the oil component is not particularly restricted, but preferably ranges from about 5% to about 40%, more preferably from about 10% to about 30%, and most preferably from about 10% to about 20%, by weight of the total composition.

An oil component which comprises the mixture of diglyceride, monoglyceride or triglyceride may be prepared by mixing individual oil in appropriate proportion or by partial hydrolysis of triglyceride, or transesterification reaction of triglycerides or diglycerides with glycerol.

All of the glycerides of the present invention are known and can be obtained by conventional methods from a broad spectrum of water-immiscible material, such as soybean oil, avocado oil, squalene oil, sesame oil, olive oil, canola oil, corn oil, rapeseed oil, safflower oil, sunflower oil, coconut oil or mixtures thereof.

The term "lecithin" used herein refers monoaminomonophospholipid, a group of substances having structure formula FACOO—$CH_2$—CH(OOCFA)-$CH_2$—$OPO_4$—$NR''_3$, wherein FA is a fatty acid, R" is an alkyl radical. Lecithin also refers to esters of oleic, steric, palmitic, or other fatty acids with glycerolphosphoric acid and choline. Lecithin may be, for instance, yolk lecithin and soybean lecithin, or synthetic nontoxic didecanoyl phosphatidycholine, dilauroyl phosphatidycholine, dimyristoyl phosphatidycholine, dipalmitoyl phosphatidycholine or a mixture thereof. Therefore, lecithin is not restricted to specific ones so far as they have compositions comprising the foregoing element. Lecithin is used as a emulsifying agent in the present invention. It also operates as a solubilizing agent.

In preparing the lipid emulsion of the present invention, the amount of lecithin to be used is not particularly restricted, but preferably ranges from about 0.5% to about 20%, more preferably from about 1% to about 10% and most preferably from about 2% to about 5%, by weight of the total composition.

Solvents of the present invention refer to propylene glycol, polyethylene glycol, glycerol, triacetin, dimethyl isosorbide, glycofurol, propylene carbonate, ethanol, water, dimethyl acetamide or a mixture thereof. The preferred solvent is propylene glycol, ethanol, water or a mixture thereof. The most preferred solvent is water.

If desired, the compositions may further comprise conventional pharmaceutical additives such as coloring agents, flavoring agents, thickening agents, stabilizers such as sodium deoxycholate, anti-oxidants such as BHT or vitamin E, and preserving agents such as methyl paraben, or propyl paraben.

The compositions may be prepared in a conventional manner, for example, (1) preparing an oil phase by dissolving an active ingredient in a mixture of an oil component, solvent(s), lecithin and optional water-immiscible excipients by heat, (2) preparing an aqueous phase by dissolving optional excipients in water, (3) combining the oil phase and the aqueous phase using a high energy homogenizer to achieve a submicron lipid emulsion.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example *arachis* oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal temperature or vaginal temperature and will therefore melt in the rectum or vagina to release the drug. Such materials include cocoa butter and polyethylene glycols.

The compounds of the invention may also be administered transdermally using methods known to those skilled in the art (see, for example: Chien; "Transdermal Controlled Systemic Medications"; Marcel Dekker, Inc.; 1987. Lipp et al. WO94/04157 3 Mar. 94). For example, a solution or suspension of a compound of formula XII in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of formula XII may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

Compositions comprising the compounds can also be formulated for controlled release, where release of the active ingredient is regulated or modulated to achieve a desired rate of delivery into the systemic circulation. A controlled release formulation can be pulsed, delayed, extended, slow, steady, immediate, rapid, fast, etc. It can comprise one or more release formulations, e.g. extended- and immediate-release components. Extended delivery systems can be utilized to achieve a dosing internal of once every 24 hours, once every 12 hours, once every 8 hours, once every 6 hours, etc. The dosage form/delivery system can be a tablet or a capsule suited for extended release, but a sustained release liquid or suspension can also be used. A controlled release pharmaceutical formulation can be produced which maintains the release of, and or peak blood plasma levels of a compound of the aspect 1 or 11 of the present invention.

Compounds of the invention may also be administered to the nasal mucosa thereby delivering the agent through the olfactory epithelium into or along olfactory neurons and the olfactory neural pathway to the brain of a mammal or preferentially a human subject. Compounds of the invention may also be administered to a central nervous system of a mammal by administering a composition comprising an effective amount of the compound to a tissue of the mammal innervated by the trigeminal nerve, the olfactory nerve, or a combination thereof, wherein the compound is absorbed through the tissue and transported into the central nervous system of the mammal in an amount effective to provide a diagnostic, protective, or therapeutic effect on a cell of the central nervous system.

Compounds of the invention may be combined with a pharmaceutically-acceptable carrier, or a transfer component, or a combination thereof; the composition containing the compound in an amount effective for treating or preventing a brain disease or disorder in the mammal. Suitable pharmaceutically-acceptable carrier are known in the arts. The composition can include, for example, any pharmaceutically acceptable additive, carrier, or adjuvant that is suitable for administering a compound to tissue innervated by the olfactory and/or trigeminal nerves. Preferably, the pharmaceutical composition can be employed in diagnosis, prevention, or treatment of a disease, disorder, or injury of the CNS, brain, and/or spinal cord. Preferably, the composition includes a compounds in combination with a pharmaceutical carrier, additive, and/or adjuvant that can promote the transfer of the compound within or through tissue innervated by the olfactory and/or trigeminal nerves. Alternatively, the compound may be combined with substances that may assist in transporting the compounds to sites of malignancy or nerve cell damage.

The composition typically contains a pharmaceutically acceptable carrier mixed with the compound and other components in the pharmaceutical composition. By "pharmaceutically acceptable carrier" is intended a carrier that is conventionally used in the art to facilitate the storage, administration, and/or the healing effect of the disclosed compounds. A carrier may also reduce any undesirable side effects of the compound. A suitable carrier should be stable, i.e., incapable of reacting with other ingredients in the formulation. It should not produce significant local or systemic adverse effect in recipients at the dosages and concentrations employed for treatment. Such carriers are generally known in the art.

Suitable carriers for this invention include those conventionally used for large stable macromolecules such as albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like.

Water, saline, aqueous dextrose, and glycols are preferred liquid carriers, particularly (when isotonic) for solutions. The carrier can be selected from various oils, including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing compounds, wetting, or emulsifying agents, salts for adjusting osmotic pressure, buffers, and the like.

A composition formulated for intranasal delivery may optionally comprise an odorant. An odorant agent is combined with the compounds of present invention to provide an odorliferous sensation, and/or to encourage inhalation of the intranasal preparation to enhance delivery of the active compound to the olfactory neuroepithelium. The odorliferous sensation provided by the odorant agent may be pleasant, obnoxious, or otherwise malodorous. The odorant receptor neurons are localized to the olfactory epithelium that, in humans, occupies only a few square centimeters in the upper part of the nasal cavity. The cilia of the olfactory neuronal dendrites which contain the receptors are fairly long (about 30-200 μm). A 10-30 μm layer of mucus envelops the cilia that the odorant agent must penetrate to reach the receptors. See Snyder et al. (1998) *J Biol. Chem.* 263:13972-13974. Use of a lipophillic odorant agent having moderate to high affinity for odorant binding protein (OBP) is preferred. OBP has an affinity for small lipophillic molecules found in nasal secretions and may act as a carrier to enhance the transport of a lipophillic odorant substance and compounds to the olfactory receptor neurons. It is also preferred that an odorant agent is capable of associating with lipophillic additives such as liposomes and micelles within the preparation to further enhance delivery of the compounds by means of OBP to the olfactory neuroepithelium. OBP may also bind directly to lipophillic agents to enhance transport of the compounds to olfactory neural receptors.

Suitable odorants having a high affinity for OBP include terpanoids such as cetralva and citronellol, aldehydes such as amyl clnnamaldehyde and hexyl cinnamaldehyde, esters such as octyl isovalerate, jasmines such as CIS-jasmine and jasmal, and musk 89. Other suitable odorant agents include those which may be capable of stimulating odorant-sensitive enzymes such as aderrylate cyclase and guanylate cyclase, or which may be capable of modifying ion channels within the olfactory system to enhance absorption of the compound.

Other acceptable components in the composition include, but are not limited to, pharmaceutically acceptable agents that modify isotonicity, including water, salts, sugars, polyols, amino acids and buffers, such as, phosphate, citrate, succinate, acetate, and other organic acids or their salts. Typically, the pharmaceutically acceptable carrier also includes one or more stabilizers, reducing agents, anti-oxidants and/or anti-oxidant chelating agents. The use of buffers, stabilizers, reducing agents, anti-oxidants and chelating agents in the preparation of protein based compositions, particularly pharmaceutical compositions, is well known in the art. See Wang et al. (1980) *J. Parent. Drug Assn.,* 34(6):452-462; Wang et al. (1988) *J. Parent. Sci. and Tech.* 42:S4-S26 (Supplement); Lachman, et al. (1968) *Drug and Cosmetic Industry,* 102(1): 36-38, 40 and 146-148; Akers, M. J. (1988) *J. Parent. Sci. and Tech.,* 36(5):222-228; and Colowick et al. *Methods in Enzymology*, Vol. XXV, p. 185-188.

Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. See Wang (1980) supra at page 455. Suitable salts and isotonicifiers include sodium chloride, dextrose, mannitol, sucrose, trehalose, or the like. Where the carrier is a liquid, it is preferred that the carrier is hypotonic or isotonic with oral, conjunctival or dermal fluids and have a pH within the range of 4.5-8.5. Where the carrier is in powdered form, it is preferred that the carrier is also within an acceptable non-toxic pH range.

Suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2-3); and thioglycerol at 0.1% to 0.5% (pH 3.5 to 7.0) and glutathione. See Akers (1988) supra at pages 225 to 226. Suitable antioxidants include sodium bisulfite, sodium sulfite, sodium metabisulfite, sodium thiosulfate, sodium formaldehyde sulfoxylate, and ascorbic acid. See Akers (1988) supra at pages 225. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See, e.g., Wang (1980) supra at pages 457-458 and 460-461, and Akers (1988) supra at pages 224-227.

The composition can include one or more preservatives such as phenol, cresol, p-aminobenzoic acid, BDSA, sorbitrate, chlorhexidine, benzalkonium chloride, or the like. Suitable stabilizers include carbohydrates such as trehalose or glycerol. The composition can include a stabilizer such as one or more of microcrystalline cellulose, magnesium stearate, mannitol, sucrose to stabilize, for example, the physical form of the composition; and one or more of glycine, arginine, hydrolyzed collagen, or protease inhibitors to stabilize, for example, the chemical structure of the composition. Suitable suspending additives include carboxymethyl cellulose, hydroxypropyl methylcellulose, hyaluronic acid, alginate, chondroitin sulfate, dextran, maltodextrin, dextran sulfate, or the like. The composition can include an emulsifier such as polysorbate 20, polysorbate 80, pluronic, triolein, soybean oil, lecithins, squalene and squalanes, sorbitan treioleate, or the like. The composition can include an antimicrobial such as phenylethyl alcohol, phenol, cresol, benzalkonium chloride, phenoxyethanol, chlorhexidine, thimerosol, or the like. Suitable thickeners include natural polysaccharides such as mannans, arabinans, alginate, hyaluronic acid, dextrose, or the like; and synthetic ones like the PEG hydrogels of low molecular weight and aforementioned suspending compounds.

The composition can include an adjuvant such as cetyl trimethyl ammonium bromide, BDSA, cholate, deoxycholate, polysorbate 20 and 80, fusidic acid, or the like, and a cationic lipid. Suitable sugars include glycerol, threose, glucose, galactose, mannitol, and sorbitol. A suitable protein is human serum albumin.

Preferred compositions include one or more of a solubility enhancing additive, preferably a cyclodextrin; a hydrophilic additive, preferably a monosaccharide or oligosaccharide; an absorption promoting additive, preferably a cholate, a deoxycholate, a fusidic acid, or a chitosan; a cationic surfactant, preferably a cetyl trimethyl ammonium bromide; a viscosity enhancing additive, preferably to promote residence time of the composition at the site of administration, preferably a carboxymethyl cellulose, a maltodextrin, an alginic acid, a hyaluronic acid, or a chondroitin sulfate; or a sustained release matrix, preferably a polyanhydride, a polyorthoester, a hydrogel, a particulate slow release depo system, preferably a polylactide co-glycolides (PLG), a depo foam, a starch microsphere, or a cellulose derived buccal system; a lipid-based carrier, preferably an emulsion, a liposome, a niosomes, or a micelles. The composition can include a bilayer destabilizing additive, preferably a phosphatidyl ethanolamine; a fusogenic additive, preferably a cholesterol hemisuccinate.

Other preferred compositions for sublingual administration including, for example, a bioadhesive to retain the compound sublingually; a spray, paint, or swab applied to the tongue; retaining a slow dissolving pill or lozenge under the tongue; or the like. Other preferred compositions for transdermal administration include a bioadhesive to retain the compound on or in the skin; a spray, paint, cosmetic, or swab applied to the skin; or the like.

These lists of carriers and additives is by no means complete and a worker skilled in the art can choose excipients from the GRAS (generally regarded as safe) list of chemicals allowed in the pharmaceutical preparations and those that are currently allowed in topical and parenteral formulations.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

Without further elaboration, it is believed that one skilled in the art can, using the preceding description and the information provided in the examples below, practice the present invention to its fullest extent.

EXAMPLES

Example 1

In view of the teaching provided herein, it is envisioned that measurements of OMA1, HIGD1A, OPA1, BNIP3, YME1L1, PHB, SAMM50, IMMT and/or PHB2 gene expression levels are utilized for determining the susceptibility for, predisposition for, or the presence of a disorder or disease correlated with mitochondrial dysfunction, or a mitochondrial disorder or disease; or a disorder or disease characterized by OPA1 alterations.

A non-limiting example for such a disorder or disease is Alzheimer's disease. It is known in the arts that mitochondrial damage and dysfunction are early features of Alzheimer's disease and other neurodegenerative diseases. Briefly, the two neuropathological hall marks of Alzheimer's disease are extracellular amyloid-β deposits and intracellular tau accumulation causing plaques and neurofibrillary tangles, respectively (Taylor et al. 2002). However, dysfunctional mitochondria also have been recognized for many years in brains from deceased patients with Alzheimer's disease suggesting a direct connection between mitochondrial homeostasis and Alzheimer's disease. (Parker et al. 1990; Smith et al. 1996; Gibson et al. 1998; Maurer et al. 2000; Butterfield et al. 2001; Devi et al. 2006). Different genetic mouse models (Aliev et al. 2003; Li et al. 2004; Lustbader et al. 2004; Reddy et al. 2004; Caspersen et al. 2005; Manczak et al. 2006; Eckert et al. 2008; Yao et al. 2009) and cellular models for Alzheimer's disease showed mitochondrial impairments as well (Butterfield et al. 2001; Cardoso et al. 2004; Diana et al. 2008; Eckert et al. 2008; Schmidt et al. 2008; Wang et al. 2008). Amyloid-$ overexpression in cell culture studies decreased levels of DRP1 and OPA1, two key regulators of the dynamic mitochondrial network (Wang et al. 2008). Subsequent studies revealed that both amyloid-β and tau can interact with DRP1 and OPA1 leading to altered OPA1 processing, impaired mitochondrial dynamics and function (Wang et al. 2008; Manczak et al. 2011; Manczak and Reddy 2012; Shields et al. 2015; Akhtar et al. 2016; Yang et al. 2017). Moreover, neuronal damage in Amyloid-$ and tau mouse models could be delayed by blocking DRP1-mediated mitochondrial fission or OMA1 knock-out (Merkwirth et al. 2008; Yan et al. 2015; Kandimalla et al. 2016; Korwitz et al. 2016; Manczak et al. 2016; Baek et al. 2017; Reddy et al. 2017).

We mined all gene expression data available through the NCBI GEO database (Edgar et al. 2002) for studies comparing human brain samples from patients with and without Alzheimer's disease. We obtained the data set from the Hisayama study (GEO accession number: GDS4758), which examined 88 autopsy samples from Hisayama residents obtained between 15 Dec. 2008 and 24 Feb. 2011 (Hokama et al. 2014). We also obtained the data set from a large-scale transcriptional analysis of postmortem brain samples from deceased patients with late-onset Alzheimer's disease provided by two tissue centers (Alzheimer's Disease Center, Oregon Health and Sciences University, and Human Brain and Spinal Fluid Resource Center; GEO accession number: GSE29378) (Miller et al. 2013). We then analyzed the gene expression levels of OMA1, OPA1, HIGD1A, BNIP3, SAMM50, IMMT, YME1L1, PHB and PHB2 in the different brain regions of patients with and without Alzheimer's disease. We calculated the differential expression with respect to region, disease, and sex. Differences were considered statistically significant for P-values of ≤0.05 using a Student's T-test.

We also mined the data repositories for FDA-approved drugs that modify the gene expression levels of OMA1, OPA1, HIGD1A, BNIP3, SAMM50, IMMT, YME1L1, PHB or PHB2. In addition, we searched for interventions that would modify the gene expression_levels of OMA1, OPA1, HIGD1A, BNIP3, SAMM50, IMMT, YME1L1, PHB or PHB2. We identified Ribavirin (CAS #: 36791-04-5) as OMA1 antagonist in a study of human hepatocytes (Huh7.5.1 cells; GEO accession number: GSE23031) (Thomas et al. 2011). Ribavirin is approved by the regulatory authorities for the use as antiviral for patients with hepatitis C.

In context of the present invention it was, inter alia, found that OMA1, OPA1, BNIP3, SAMM50, IMMT and HIGD1A gene expression levels are differentially regulated in Alzheimer's disease brains in a sex-specific manner. Therefore, susceptibility and/or presence of Alzheimer's disease as well as treatment selection can be predicted by integrating these sex-specific expression profiles.

In one particular embodiment, we found significant gene expression changes in postmortem brain tissue from patients pathologically diagnosed as having Alzheimer's disease. OMA1 expression was significantly reduced in the hippocampus and temporal cortex of male individuals without Alzheimer's disease (FIGS. 2A and 2B), while OPA1 was significantly reduced in the hippocampus and temporal cortex of female Alzheimer's disease patients (FIG. 2C and FIG. 2D). BNIP3 levels were significantly reduced in the hippocampus of both male and female Alzheimer's disease patients (FIG. 2E), but not in the temporal cortex (FIG. 2F).

Figure 2:
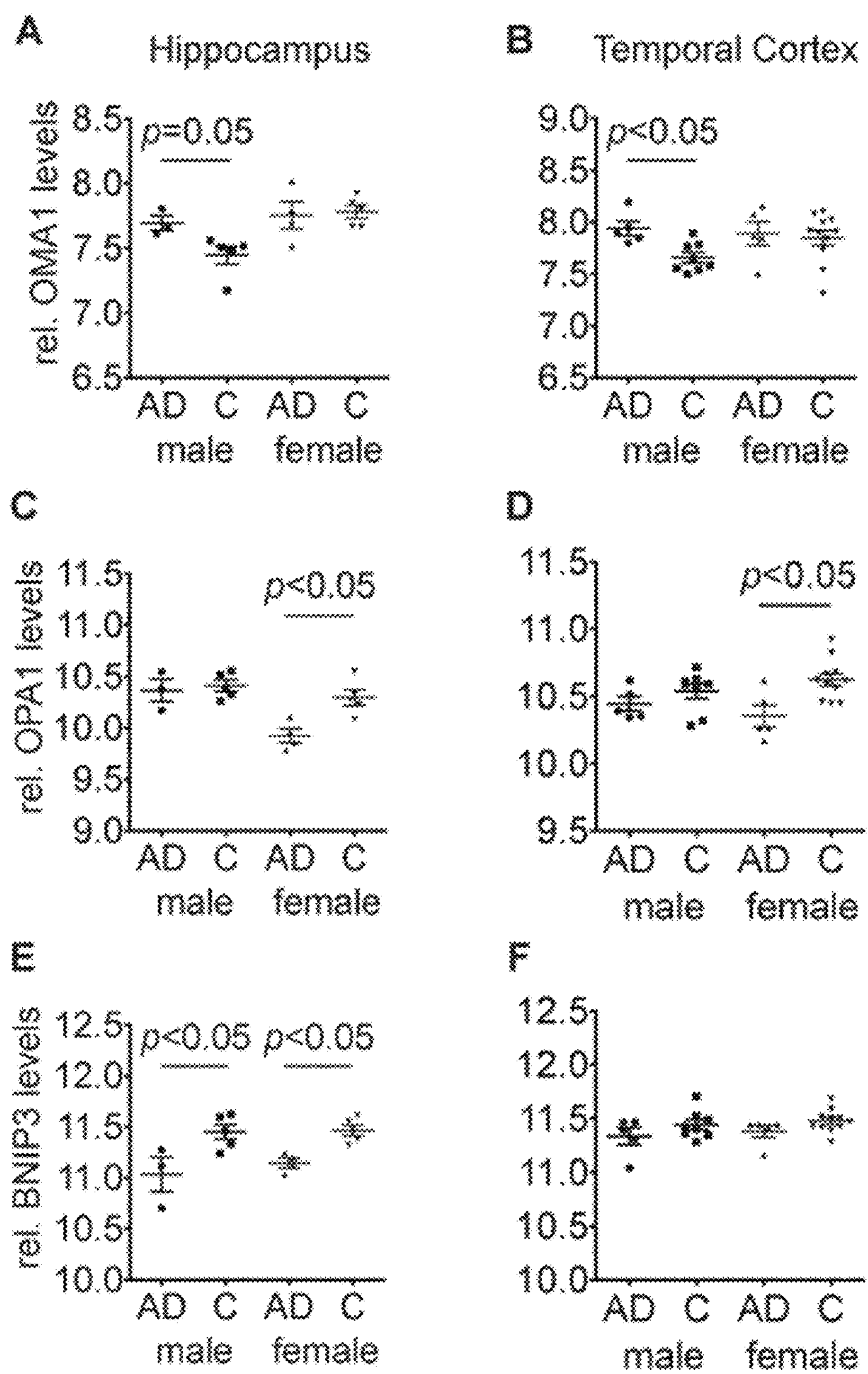
FIG. 2. (A) OMA1 gene expression levels in the hippocampus (AD: n=8; C: n=9) from post-mortem samples of patients with Alzheimer's disease (AD) and control subjects (C). (B) OMA1 gene expression levels in the temporal cortex (AD: n=13; C: n=16) from post-mortem samples of patients with Alzheimer's disease (AD) and control subjects (C). (C) OPA1 gene expression levels in the hippocampus (AD: n=8; C: n=9) from post-mortem samples of patients with Alzheimer's disease (AD) and control subjects (C). (D) OPA1 gene expression levels in the temporal cortex (AD: n=13; C: n=16) from post-mortem samples of patients with Alzheimer's disease (AD) and control subjects (C). (E) BNIP3 gene expression levels in the hippocampus (AD: n=8; C: n=9) from post-mortem samples of patients with Alzheimer's disease (AD) and control subjects (C). (F)

FIGS. 2A-2F show gene expression levels in the hippocampus (AD: n=8; C: n=9) and temporal cortex (AD: n=13; C: n=16) from post-mortem samples of patients with Alzheimer's disease (AD) and control subjects (C). OMA1 expression levels were significantly increased in males with Alzheimer's disease in the hippocampus by 3.3% (FIG. 2A) and the temporal cortex by 3.7% (FIG. 2B). Females appeared to have overall elevated OMA1 levels compared to males and there was no difference between Alzheimer's samples and controls. OPA1 levels were significantly reduced in the hippocampus of female patients with Alzheimer's by 3.7% (FIG. 2C) and the temporal cortex by 2.5% (FIG. 2C and FIG. 2D). BNIP3 levels were significantly reduced in the hippocampus from both male and female Alzheimer's patients by 3.7% and 2.8%, respectively (FIG. 2E), while there were no differences in the temporal cortex (FIG. 2F).

Expression of SAMM50 was significantly reduced in the hippocampus of female Alzheimer's disease patients (FIG. 3A) and the frontal cortex of male Alzheimer's disease patients (FIG. 3B). IMMT levels were significantly reduced in the hippocampus of female Alzheimer's disease patients (FIG. 3C) and in the frontal cortex of both male and female Alzheimer's disease patients (FIG. 3D). Expression of the endogenous OMA1 antagonist HIGD1A was also significantly reduced in the hippocampus of female Alzheimer's disease patients (FIG. 3E) and the frontal cortex of both male and female Alzheimer's disease patients (FIG. 3F).

FIGS. 3A-3F show gene expression levels in the hippocampus (AD: n=8; C: n=9) and frontal cortex (AD: n=16; C: n=17) from post-mortem samples of patients with Alzheimer's disease (AD) and control subjects C. SAMM50 expression levels appeared to be reduced in patients with Alzheimer's disease. They were significantly reduced by 3.0% in the hippocampus from Alzheimer's females (FIG. 3A) and by 2.4% in the frontal cortex from Alzheimer's males (FIG. 3B). IMMT levels were significantly reduced by 3.5% in the hippocampus from female subjects with Alzheimer's disease (FIG. 3C), while in the frontal cortex both males and females had significantly reduced IMMT levels by 2.0% and 1.0%, respectively (FIG. 3D). HIGD1A levels were significantly reduced by 6.6% in the hippocampus of female Alzheimer's patients (FIG. 3E). and in the frontal cortex of both male and female Alzheimer's patients by 3.3% and 3.6%, respectively (FIG. 3F).

In another embodiment, we found gene expression changes in the hippocampus from deceased late-onset Alzheimer's patients acquired at the Oregon Health and Sciences University (GEO accession number: GSE29378) (Miller et al. 2013). Again, OMA1 expression was significantly reduced in the hippocampus of non-Alzheimer's disease males (88.4%±15.1% S.D., p=0.05). We also found a trend for reduced HIGD1A levels in Alzheimer's brains at Oregon (86.3%±16.3% S.D., p=0.07), which agrees with the above data.

The specific changes in the gene expression of the genes OMA1, OPA1, BNIP3, SAMM50, IMMT and HIGD1A depends on the sex of a subject and the brain region. The specific expression profile and/or gene signature of these sex-dependent changes therefore represent a biomarker according to the definitions given above and is envisioned to be utilized, inter alia, for differentiation of Alzheimer's disease from other mitochondrial disorders or diseases, such as Parkinson's disease.

In view of the teaching provided herein, the means and methods of the present disclosure can also be used to inform selection and/or assist in selecting appropriate courses of treatment and/or medical interventions for patients in need of such interventions.

In one particular embodiment it was, inter alia, found that Ribavirin (CAS #: 36791-04-5) significantly decreases the gene expression levels of OMA1 by 15% to 17% (FIG. 4; Student's T-test: p≤0.05). Human hepatocytes (Huh7.5.1 cells) were cultured with or without 100 μg/mL Ribavirin (Thomas et al. 2011). Cells without Ribavirin (FIG. 4; PBS) expressed OMA1 at 7.89 (±0.21 S.D.; Spot ID: 226019_at) and 9.17 (±0.17 S.D. (FIG. 4A); Spot ID: 226020_s_at), while Ribavirin-treated cells had significantly reduced OMA1 levels at 6.52 (±0.22 S.D.; Spot ID: 226019_at) and 7.76 (±0.12 S.D.; Spot ID: 226020_s_at) (FIG. 4B), respectively.

Referring to FIGS. 4A and 4B, the antiviral Ribavirin (CAS #36791-04-5) represents an antagonist of OMA1. Ribavirin can significantly decrease the expression levels of OMA1 in human hepatocytes by 15% to 17%. Huh7.5.1 cells were cultured with either the addition of PBS or 100 μg/mL Ribavirin for 24 hours, after which mRNA was isolated and analyzed by gene expression microarrays. Vehicle treated cells (PBS) expressed OMA1 at 7.89 (±0.21 S.D.; Spot ID: 226019_at) and 9.17 (±0.17 S.D.; Spot ID: 226020_s_at) (FIG. 4A), while Ribavirin significantly reduced OMA1 levels to 6.52 (±0.22 S.D.; Spot ID: 226019_at) and 7.76 (±0.12 S.D.; Spot ID: 226020_s_at) (FIG. 4B), respectively.

Ribavirin is known in the arts as an antiviral agent that also possesses immunosuppressant activity. Neurotrophic activity of Ribavirin and analogs thereof are also known in the arts (WO 00/30656). However, the finding that Ribavirin can decrease OMA1 levels was unexpected and is non-obvious to a person skilled in the arts.

In context of the present invention Ribavirin thus represents an antagonist of OMA1. Accordingly, Ribavirin represent a medical intervention in particular for the treatment, of patients with Alzheimer's disease. Apovir is a combination drug of Ribavirin and Pleconaril that has been tested in a clinical study on patients with Alzheimer's disease (EudraCT number: 2013-002126-23) to investigate its effect on disease progression as assessed by the Alzheimer's Disease Assessment Scale-Cognitive Subscale [ADAS-cog]. Patients that received 600 mg Apovir per day (n=18) showed an improvement of −1.963 (±4.398 S.D.) points on the ADAS-cog. Subscale after 9 months, compared to placebo-treated patients (n=31), which showed worsening of 1.817 (±8.623 S.D.) points. Although these changes did not achieve statistical significance (P=0.1809), these results validate our method for the treatment of a mitochondrial disease, on the basis of Alzheimer's disease as an example for such a disease.

Example 2

Another non-limiting example for a disease correlated with altered OPA1 processing is Parkinson's disease for which there is strong evidence for mitochondrial dysfunction (Schapira et al. 1990; Keeney et al. 2006; Parker et al. 2008; Santos et al. 2015; Dolle et al. 2016). Briefly, familial forms of Parkinson's disease are associated with several proteins that directly impact mitochondrial fission and fusion. For example, α-synuclein can localize to mitochondria, and mitochondria associated ER membranes (Imaizumi et al. 2012*; Nakamura* 2013; Guardia-Laguarta et al. 2014; Ghio et al. 2016). Overexpression of mutant α-synuclein increased mitophagy in cortical neurons along with mitochondrial fragmentation and neuronal cell death by promoting OPA1 cleavage (Guardia-Laguarta et al. 2014). The adverse effects of mutant α-synuclein could be rescued in part by inhibiting mitophagy (Choubey et al. 2011; Nakamura et al. 2011). Pink1, Parkin and DJ-1 form an E3 ubiquitin-ligase complex on the mitochondrial surface that initiates mitophagy by ubiquitinating, among other proteins, DRP1 (Yang et al. 2008; Lutz et al. 2009; Wang et al. 2011). Mutations in any of the genes result in frustrated clearance and accumulation of damaged mitochondria leading to neuronal loss in the substantia nigra and other parts of the brain (Mukherjee et al. 2015). LRRK2 also resides on the mitochondrial outer membrane where it affects mitochondrial network dynamics through interactions with DRP1 and OPA1 (Stafa et al. 2014). As is the case for Alzheimer's disease, preventing mitochondrial fission through DRP1 inhibition also can attenuate neurotoxicity in animal models of Parkinson's disease (Rappold et al. 2014).

We mined all gene expression data available through the NCBI GEO database (Edgar et al. 2002) for studies comparing human brain samples from patients with and without Parkinson's disease. We obtained gene expression data from 16 patients with Parkinson's disease for which post mortem brain specimens were investigated. These patients were enrolled prospectively at the Department of Neurology of the Mayo Clinic in Rochester, MN, from June 1996 through May 2004 (GEO accession number: GDS2821) (Maraganore et al. 2005; Lesnick et al. 2007). We also obtained an independent second data set from postmortem brain tissue of 11 subjects diagnosed with neuropathologically confirmed Parkinson's disease. The tissue blocks were acquired from the University of Maryland Brain and Tissue Bank, the New York Brain Bank at Columbia University, the Human Brain and Spinal Fluid Resource Center at the West Los Angeles VA Medical Center, McLean Hospital of Harvard University, and the Miami Brain and Tissue Bank (GEO accession number: GSE20168) (Zhang et al. 2005). We then analyzed the gene expression levels of OMA1, OPA1, HIGD1A, BNIP3, SAMM50, IMMT, YME1L1, PHB and PHB2 in the different brain regions of patients with and without Parkinson's disease. We calculated the differential expression with respect to region, disease, and sex. Differences were considered statistically significant for P-values of ≤0.05 using a Student's T-test.

In one particular embodiment, we found significant gene expression changes in samples of the substantia nigra from postmortem brain tissue from patients with Parkinson's disease (GEO accession number: GDS2821). OMA1 gene expression levels were significantly increased in samples of the substantia nigra from female Parkinson's patients (FIG. 5A). OPA1 gene expression levels, on the other hand, were significantly decreased in Parkinson's samples from male subjects (FIG. 5B). Females had overall lower OPA1 expression levels and there was no significant difference between non-PD and PD samples (FIG. 5B). HIGD1A levels were also significantly decreased in males with Parkinson's, while females had overall lower HIGD1A levels and did not show any significant differences (FIG. 5C). IMMT levels were significantly decreased in male Parkinson's samples to about the levels of healthy females and females with Parkinson's (FIG. 5D). SAMM50 was decreased in Parkinson's samples; this difference was statistically significant for males, while females showed lower overall levels (FIG. 5E). PHB2 levels appeared to be reduced in Parkinson's samples, which was statistically significant for male subjects (FIG. 5F).

FIGS. 5A-5F show gene expression levels in post mortem samples of the substantia nigra from a cohort of healthy subjects (C; n=9) and patients with Parkinson's disease (PD; n=16) collected at Rochester, MN (GEO accession number: GDS2821). OMA1 gene expression levels appeared to be increased in Parkinson's samples; they were significantly increased by 27.6% in samples from female Parkinson's patients (FIG. 5A). OPA1 gene expression levels were significantly decreased by 50.3% in samples from male Parkinson's subjects (FIG. 5B). Females had overall lower OPA1 expression levels in the substantia nigra than males and there was no significant difference between C and PD samples (5B). HIGD1A levels were significantly decreased by 51.5% in males with Parkinson's (FIG. 5C). Again, females had overall lower HIGD1A levels and did not show any significant differences. IMMT levels were also significantly decreased in males with Parkinson's by 44.6%, while females had overall lower IMMT levels and no significant changes (FIG. 5D). SAMM50 levels appeared to be decreased in Parkinson's samples; this difference was statistically significant for males (29.9% reduction), while females again showed lower overall levels (FIG. 5E). PHB2 levels appeared to be reduced in Parkinson's samples as well, which was statistically significant for males (FIG. 5F; 15.5% reduction).

In another embodiment, we found significant gene expression changes in an independent set of samples from the substantia nigra of postmortem brain tissue from patients with Parkinson's disease (GEO accession number: GSE20292). In agreement with the data obtained from the first study, OPA1 gene expression levels were significantly decreased in Parkinson's samples from male subjects (FIG. 6A). Females had overall lower OPA1 expression levels and there was no significant difference between non-PD and PD samples (FIG. 6A). HIGD1A levels were overall lower in Parkinson's samples but did not reach statistical significance (FIG. 6B). BNIP3 gene expression levels were significantly reduced in male Parkinson's samples and females appear to have overall lower BNIP3 expression levels and there was no significant difference (FIG. 6C). Also, IMMT levels were significantly decreased in males with Parkinson's, while females had overall lower levels and did not show any significant differences (FIG. 6D). YME1L1 levels showed a small but significant decrease in male Parkinson's samples (FIG. 6E). SAMM50 was decreased in Parkinson's samples and this difference was statistically significant for males (FIG. 6F).

FIGS. 6A-6F show gene expression levels in post mortem samples of the substantia nigra from an independent cohort of healthy subjects (C; n=15) and patients with Parkinson's disease (PD; n=11) collected at Syracuse, NY (GEO accession number: GSE20292). OPA1 gene expression levels were significantly decreased by 9.1% in Parkinson's samples from male subjects (FIG. 6A). HIGD1A levels were overall lower in Parkinson's samples but did not reach statistical significance (FIG. 6B). BNIP3 gene expression levels were significantly reduced by 6.8% in male Parkinson's samples (FIG. 6C). Females appear to have overall lower BNIP3 expression levels and there was no significant difference. IMMT levels were significantly decreased by 10.1% in males with Parkinson's, while females had overall lower levels and again did not show any significant differences (FIG. 6D). YME1L1 levels were significantly reduced by 5.6% in male Parkinson's samples (FIG. 6E). Overall SAMM50 levels were decreased in Parkinson's samples; males had a significant reduction by 6.6% while the difference between female samples did not reach statistical significance (FIG. 6F).

In yet another embodiment, we found significant gene expression changes in post mortem samples of the prefrontal cortex from patients with Parkinson's disease (GEO accession number: GSE20168). OPA1 gene expression levels were also significantly decreased in the prefrontal cortex of male patients with Parkinson's (FIG. 7A). HIGD1A levels were significantly lower in male Parkinson's samples (FIG. 7B). BNIP3 gene expression levels were significantly reduced in male Parkinson's samples (FIG. 7C). IMMT levels appeared to be lower in Parkinson's samples and there was a statistically significant reduction in male samples (FIG. 7D). YME1L1 levels showed a small but significant reduction in Parkinson's samples when male and female samples were analyzed together (FIG. 7E). Females tended to have lower overall expression levels and did not show any significant changes for these genes. PHB showed a small but significant increase in the prefrontal cortex of males with Parkinson's (FIG. 7F).

FIGS. 7A-7F show gene expression levels in the prefrontal cortex from healthy subjects (C; n=15) and patients with Parkinson's disease (PD; n=11) from Syracuse, NY (GEO accession number: GSE20168). OPA1 gene expression levels were significantly decreased by 9.1% in Parkinson's samples from male subjects (FIG. 7A). HIGD1A levels were significantly reduced by 5.9% in male Parkinson's samples (FIG. 7B). BNIP3 gene expression levels were significantly reduced by 5.8% in male Parkinson's samples (FIG. 7C). IMMT levels appeared to be lower in Parkinson's samples and there was a statistically significant reduction by 6.2% in male samples (FIG. 7D). There was a 2.6% decrease of YME1L1 levels, in Parkinson's samples, which was significant when male and female samples were analyzed together (FIG. 7E). PHB was significantly increased in the prefrontal cortex from male Parkinson's patients by 2.3% (FIG. 7F).

We have demonstrated above that Parkinson's disease correlates with specific changes in the gene expression levels of OMA1, OPA1, HIGD1A, BNIP3, SAMM50, IMMT, YME1L1, PHB and PHB2. These changes depend on the sex of a subject and the brain region. In context of the present invention it is envisioned that measuring and integrating these gene expression changes can be utilized, inter alia, for determining the susceptibility for, predisposition for, or the presence of Parkinson's disease. These measurements also can be utilized for differentiation of Parkinson's disease from other disorders or diseases correlated with mitochondrial dysfunction, such as Alzheimer's disease. Moreover, this biomarker is envisioned to guide treatment selection.

Example 3

Yet another non-limiting example for a mitochondrial disorder or disease is cancer. Research over the past century or so has generated a complex and rich body of knowledge revealing cancer to be a disease correlated to mitochondrial dysfunction (Alirol and Martinou 2006; Frezza and Gottlieb 2009; Hanahan and Weinberg 2011; Wallace 2012; Vyas et al. 2016). Uncontrolled cell proliferation represents the essence of neoplastic disease and entails adjustments of energy metabolism in order to fuel cell growth and division. Aerobic glycolysis is an anomalous characteristic of cancer cell energy metabolism referred to as "Warburg effect": even in the presence of oxygen, cancer cells largely adopt glycolysis (Warburg 1956). The existence of this metabolic switch in cancer cells has been substantiated and other mitochondrial changes have been described in the ensuing decades (Alirol and Martinou 2006; Frezza and Gottlieb 2009; Hanahan and Weinberg 2011; Wallace 2012; Vyas et al. 2016). It is also known in the arts that changes in energy metabolism are tightly correlation with alterations in mitochondrial morphology (Hackenbrock 1966; Jakobs et al. 2003; Cogliati et al. 2013). Changes in OPA1 levels and OPA1 processing have been found in various cancers, accordingly (Zhao et al. 2013; Kong et al. 2014; Faccenda et al. 2017). These mitochondrial alterations might not be the primary cause for cancer. And yet, they are functionally important for the development and progression of many forms of human cancer. Therefore, mitochondrial dynamics can adjust chemoresistance in cancer (Kong et al. 2015) and regulate tumorogenesis, metastatic spread and overall survival of cancer cells.

We obtained gene-expression data paired with survival data for different tumor samples through public data repositories and conducted meta studies on 1764 patients with breast cancer (GEO accession numbers: E-MTAB-365, GSE12276, GSE16391, GSE16446, GSE17907, GSE19615, GSE20685, GSE20711, GSE21653, GSE42568, GSE9195), on 1145 patients with lung cancer (GEO accession numbers: GSE19188, GSE3141, GSE50081, GSE37745, GSE29013, GSE30219, GSE31210), on 631 patients with gastric cancer (GEO accession numbers: GSE22377, GSE15459, GSE51105, GSE62254, GSE62254), and on 1435 patients with ovarian cancer (GEO accession numbers: GSE51373, GSE9891, GSE15622, GSE26712, GSE26193, GSE63885, GSE65986, GSE30161, GSE14764, TCGA). We analyzed different gene signatures for their predictive value on patient survival. To this end we calculated the median gene-expression levels for OMA1, HIGD1A, OPA1, BNIP3, YME1L1, PHB, SAMM50, IMMT and/or PHB2 in the different datasets and defined two groups of patients, depending on whether a subject's expression levels were below (group "low") or above the median gene expression levels (group "high"). The minimum, maximum and median gene expression levels for OPA1, OMA1, HIGD1A, BNIP3, YME1L1, PHB, PHB2, SAMM50 and IMMT for each of the 4 investigated cancer types (i.e., breast cancer, lung cancer, gastric cancer, ovarian cancer) are given in the tables depicted in FIG. 8 and FIG. 9, respectively. Also, the data range for each group, "low" or "high", for each gene is depicted in FIG. 8 and FIG. 9. Based on these classifications we tested the predictive value of different combinations of at least 3 genes. We termed these groups of 3 or more combinations of gene expression groups "gene signatures" (e.g., OMA1: high, HIGD1A: high, BNIP3: low). We tested whether patients with particular gene signatures had an increased chance of overall survival using a Log-rank Test. Differences were considered statistically significant for P-values of $\leq 0.05$.

FIG. 8 shows data ranges for OPA1, OMA1, HIGD1A, BNIP3, YME1L1, PHB, PHB2, SAMM50 and IMMT gene expression levels in tissue samples from patients with breast cancer (top) and lung cancer (bottom). The median expression levels and the data range for the classification of patients, depending on whether a subject's expression levels were below (group "low") or above the median gene expression levels (group "high") are given as well.

FIG. 9 shows data ranges for OPA1, OMA1, HIGD1A, BNIP3, YME1L1, PHB, PHB2, SAMM50 and IMMT gene expression levels in tissue samples from patients with gastric cancer (top) and ovarian cancer (bottom). The median expression levels and the data range for the classification of patients, depending on whether a subject's expression levels were below (group "low") or above the median gene expression levels (group "high") are given as well.

In one particular embodiment we have invented a 3-gene expression signature particularly useful for the prognosis of survival of patients with cancer. This 3-gene signature comprises OMA1, HIGD1A and BNIP3, wherein OMA1 and HIGD1A expression levels are elevated and BNIP3 expression levels are reduced compared to the median expression levels. This particular 3-gene signature can stratify patients with breast cancer based on whether the expression levels of OMA1, HIGD1A and BNIP3 matched (positive; i.e., OMA1: high; HIGD1A: high; BNIP3 low) or did not match (negative; i.e., OMA1: low; HIGD1A: low;

BNIP3: high) the signature (FIG. 10). The median survival of patients with a negative gene signature was only 68 months, while patients with a positive signature had a significantly higher chance of survival (FIG. 10; Log-rank Test: p<0.0001; Chi square=65.60; df=2). This particular 3-gene signature has also been proven useful to stratify patients with lung cancer (FIG. 11) and gastric cancer (FIG. 12). Patients with lung cancer survived on average 78 months, while subjects with a negative signature survived only 52 months and subjects with a positive signature had significantly better chances of survival (FIG. 11; Log-rank Test: p<0.0001; Chi square=21.77; df=2). On the other hand, patients with gastric cancer had on average 53 months to survive, while subjects with a negative signature survived only 28 months and subjects with a positive signature had significantly better chances of survival (FIG. 12; Log-rank Test: p<0.0001; Chi square=24.12; df=2).

FIG. 10 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 3-gene signature based on OMA1, HIGD1A and BNIP3 expression levels (i.e., OMA1: high, HIGD1A: high, BNIP3: low). Patients whose signature matched all 3 genes (positive; black, solid line) had a 100% chance of survival, while patients whose signature was inverted (i.e., OMA1: low, HIGD1A: low, BNIP3: high; negative; light grey, dotted line) had only a 60% chance with a median survival of 42 months (Log-rank Test: p<0.0001; Chi square=65.60; df=2).

FIG. 11 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by the proprietary 3-gene signature (i.e., OMA1: high, HIGD1A: high, BNIP3: low). Patients whose signature matched all 3 genes (positive; black, solid line) had an 82% chance of survival, while patients whose signature was inverted (i.e., OMA1: low, HIGD1A: low, BNIP3: high; negative; light grey, dotted line) had only a 55% chance with a median survival of 25 months (Log-rank Test: p<0.0001; Chi square=21.77; df=2).

FIG. 12 shows Kaplan-Meier curves showing the overall survival of 631 patients with gastric cancer (average; dark grey, solid line; GEO accession numbers: GSE22377, GSE15459, GSE51105, GSE62254, GSE62254) stratified by the proprietary 3-gene signature (i.e., OMA1: high, HIGD1A: high, BNIP3: low). Patients whose signature matched all 3 genes (positive; black, solid line) had an 84% chance of survival, while patients whose whose signature was inverted (i.e., OMA1: low, HIGD1A: low, BNIP3: high; negative; light grey, dotted line) had only a 53% chance with a median survival of 25 months (Log-rank Test: p<0.0001; Chi square=24.12; df=2).

In another particular embodiment we have invented a more refined 6-gene expression signature particularly useful for the prognosis of survival of patients with breast cancer (FIG. 13). This 6-gene signature comprises OMA1, HIGD1A, BNIP3, OPA1, YME1L1 and IMMT, wherein OMA1 and HIGD1A expression levels are elevated and BNIP3, OPA1, YME1L1 and IMMT expression levels are reduced compared to the median expression levels (i.e., OMA1: high, HIGD1A: high, BNIP3: low, OPA1: low, YME1L1: low, IMMT: low). In a meta-study of 1764 patients with breast cancer, we were able to identify patients with 100% chance of survival provided that all 6 genes matched the 6-gene signature (FIG. 13, positive). Subjects whose gene expression profile did not match the 6-gene signature (negative; i.e., OMA1: low, HIGD1A: low, BNIP3: high, OPA1: high, YME1L1: high, IMMT: high) had only a 60.26% (±21.61 S.D.) chance of survival, and the median survival was 42 months (Log-rank Test: p<0.0001; Chi square=93.45; df=6). When the expression levels of 5 genes matched the 6-gene signature (5/6), patients had on average a chance of 87.19% (±7.188 S.D.). When 4 genes matched the 6-gene signature (4/6), the chance was 79.59% (±9.399 S.D.). When 3 genes matched the 6-gene signature (3/6), the chance was 73.12% (±12.70 S.D.). When 2 genes matched the 6-gene signature (2/6), the chance was 69.15% (±13.49 S.D.). And when only 1 gene matched the 6-gene signature (1/6), there was a 60.72% (±17.04 S.D.) chance of survival with a median survival of 73 months.

FIG. 13 shows Kaplan-Meier curves showing the overall survival of 1764 patients with breast cancer (average; dark grey, solid line; GEO accession numbers: E-MTAB-365, GSE12276, GSE16391, GSE16446, GSE17907, GSE19615, GSE20685, GSE20711, GSE21653, GSE42568, GSE9195) stratified by a proprietary 6-gene signature based on OMA1, HIGD1A, OPA1, BNIP3, YME1L1 and IMMT expression levels. Patients whose signature matched all 6 genes (positive; black, solid line) had a 100% chance of survival, while patients whose signature did not match any of the 6 genes (negative; light grey, dotted line) had only a 60% chance with a median survival of 42 months (Log-rank Test: p<0.0001; Chi square=93.45; df=6).

In another embodiment it was, inter alia, found that a proprietary 6-gene signature has proven useful for the prognosis of survival of patients with lung cancer (FIG. 14). The 6-gene signature comprises elevated levels of OMA1, HIGD1A, YME1L1, PHB and SAMM50 compared to the median expression levels, and reduced PHB2 levels compared to the median expression levels (i.e., OMA1: high, HIGD1A: high, YME1L1: high, PHB: high, SAMM50: high, PHB2: low). In a meta-study of 1145 patients with lung cancer, we were able to identify patients with an 81.73% (±7.114 S.D.) chance of survival provided that all 6 genes matched the 6-gene signature (FIG. 14, positive). Subjects whose gene expression profile did not match the 6-gene signature (negative; i.e., OMA1: low, HIGD1A: low, YME1L1: low, PHB: low, SAMM50: low, PHB2: high) had only a 54.67% (±25.63 S.D.) chance of survival, and the median survival was 25 months (Log-rank Test: p<0.0001; Chi square=85.40; df=6). When expression levels of 5 genes matched the 6-gene signature (5/6), there was a 69.72% (±16.07 S.D.) chance and the median survival was 110 months. When 4 genes matched the 6-gene signature (4/6), the chance was 62.50% (±19.47 S.D.) and the median survival was 89 months. When 3 genes matched the 6-gene signature (3/6), there was a 57.84% (±20.73 S.D.) chance and the median survival was 55 months. When 2 genes matched the 6-gene signature (2/6), there was a 58.82% (±22.90 S.D.) chance and the median survival was 57 months. When only 1 gene matched the 6-gene signature (1/6), there was a 58.11% (±21.49 S.D.) chance and a subject's median survival was 45 months.

FIG. 14 shows Kaplan-Meier curves showing the overall survival of 1145 patients with lung cancer (average; dark grey, solid line; GEO accession numbers: GSE19188, GSE3141, GSE50081, GSE37745, GSE29013, GSE30219, GSE31210) stratified by a proprietary 6-gene signature based on OMA1, HIGD1A, YME1L1, PHB, SAMM50 and PHB2 expression levels. Patients whose signature matched all 6 genes (positive; black, solid line) had an 82% chance of survival, while patients whose signature did not match any of the 6 genes (negative; light grey, dotted line) had only a 55% chance with a median survival of 25 months (Log-rank Test: p<0.0001; Chi square=85.40; df=6).

In yet another embodiment it was, inter alia, found that a proprietary 7-gene signature has proven useful for the prognosis of survival of patients with gastric cancer (FIG. 15). The 7-gene signature comprises OMA1, HIGD1A, OPA1, BNIP3, YME1L1, SAMM50 and IMMT, wherein expression levels of BNIP3 are elevated while OMA1, HIGD1A, OPA1, YME1L1, SAMM50 and IMMT levels are decreased compared to the median levels (i.e., OMA1: low, HIGD1A: low, OPA1: low, YME1L1: low, SAMM50: low, IMMT: low, BNIP3: high). In a meta-study of 631 patients with gastric cancer, we were able to identify patients with an 83.79% (±4.908 S.D.) chance of survival provided that all 7 genes matched the 7-gene signature (FIG. 15, positive). Subjects whose gene expression profile did not match the 7-gene signature (negative; i.e., OMA1: high, HIGD1A: high, OPA1: high, YME1L1: high, SAMM50: high, IMMT: high, BNIP3: low) had only a 52.53% (±29.71 S.D.) chance of survival, and the median survival was 25 months (Log-rank Test: p<0.0001; Chi square=50.81; df=7). When 6 genes matched the 7-gene signature (6/7), there was a 74.68% (±11.29 S.D.) chance of survival. When 5 genes matched the 7-gene signature (5/7), there was a 67.07% (±14.17 S.D.) chance of survival. When 4 genes matched the 7-gene signature (4/7), there was a 69.22% (±14.48 S.D.) chance of survival. When 3 genes matched the 7-gene signature (3/7), the likelihood to survive was 61.61% (21.79 S.D.) and the median survival was 38 months. When 2 genes matched the 7-gene signature (2/7), there was a 58.66% (±25.76 S.D.) chance and the median survival was 31 months. When only 1 gene matched the 7-gene signature (1/7), there was a 57.70% (±23.51 S.D.) chance and the median survival was 29 months.

FIG. 15 shows Kaplan-Meier curves showing the overall survival of 631 patients with gastric cancer (average; dark grey, solid line; GEO accession numbers: GSE22377, GSE15459, GSE51105, GSE62254, GSE62254) stratified by a proprietary 7-gene signature based on OMA1, HIGD1A, YME1L1, PHB, SAMM50 and PHB2 expression levels. Patients whose signature matched all 7 genes (positive; black, solid line) had an 84% chance of survival, while patients whose signature did not match any of the 7 genes (negative; light grey, dotted line) had only a 53% chance with a median survival of 25 months (Log-rank Test: p<0.0001; Chi square=50.81; df=7).

In yet another embodiment it was, inter alia, found that a proprietary 5-gene signature has proven useful for the prognosis of survival for patients with ovarian cancer (FIG. 16). The 5-gene expression signature comprises OPA1, BNIP3, YME1L1 and IMMT, which are reduced in their gene expression levels, and PHB, which has elevated levels compared to the median expression levels (i.e., OPA1: low, BNIP3: low, YME1L1: low, IMMT: low, PHB: high). In a meta-study of 1435 patients with ovarian cancer, we were able to identify patients with a 58.25% (±25.15 S.D) chance of survival provided that all 5 genes matched the 5-gene signature (FIG. 16, positive). These patients had a median survival of 43 months. When no gene matched the 5-gene signature (negative; i.e., OPA1: high, BNIP3: high, YME1L1: high, IMMT: high, PHB: low), there was a 56.81% (±28.46 S.D.) chance of survival and subjects had a median survival of 15 months (Log-rank Test: p<0.0001; Chi square=34.92; df=5). Patients had a 55.13% (±25.97 S.D.) chance of survival with a median survival of 24 months provided that 4 genes matched the 5-gene signature (4/5). When 3 genes matched the 5-gene signature (3/5), there was a 53.06% (±27.76 S.D.) chance and the median survival was 21 months. When 2 genes matched the 5-gene signature (2/5), there was a 57.53% (±28.81 S.D.) chance and the median survival was 19 months. When only 1 gene matched the 5-gene signature (1/5), there was a 60.48% (±28.47 S.D.) chance of survival and a subject's median survival was 19 months.

FIG. 16 shows Kaplan-Meier curves showing the overall survival of 1435 patients with ovarian cancer (average; dark grey, solid line; GEO accession numbers: GSE51373, GSE9891, GSE15622, GSE26712, GSE26193, GSE63885, GSE65986, GSE30161, GSE14764, TCGA) stratified by a proprietary 5-gene signature based on OPA1, BNIP3, YME1L1, IMMT, SAMM50 and PHB expression levels. Patients whose signature matched all 5 genes (positive; black, solid line) had a median survival of 43 months, while patients whose signature did not match any of the 5 genes (negative; light grey, dotted line) had only a median survival of 15 months (Log-rank Test: p<0.0001; Chi square=34.92; df=5).

It is known in the arts, and has been summarized above, that cancer also is a disorder correlated with mitochondrial dysfunction. In the context of the present invention it was, inter alia, found that measurements of OMA1, HIGD1A, OPA1, BNIP3, YME1L1, PHB, SAMM50, IMMT and/or PHB2 gene expression levels can be utilized for the prognosis of survival of a patient with cancer.

Cumulative evidence also exists for mitochondrial fusion/fission being necessary for normal cardiac function (Dorn 2013; Piquereau et al. 2013; Burke et al. 2015; Marin-Garcia and Akhmedov 2016; Ong et al. 2017). The first studies to investigate the role of OPA1 in the heart revealed reduced myocardial levels of OPA1 in ischemic heart failure patients and in a rat model of ischemic heart failure (Chen et al. 2009). OPA1 deficient mice show late onset cardiomyopathy with a decrease in cardiac output, reduced fractional shortening, and a blunted response to a β-adrenergic stimulus (Chen et al. 2012; Le Page et al. 2016). These findings were associated with mitochondrial fragmentation, impaired mitochondrial respiration, increased oxidative stress, attenuated calcium transients, and a reduction in mitochondrial DNA copy number (Chen et al. 2012). OPA1 deficient mice are also more susceptible to total aortic constriction, developing twice the extent of left ventricular hypertrophy, when compared to wild-type mice (Piquereau et al. 2012). These findings were associated with clustering of large mitochondria with abnormal cristae morphology, which were demonstrated to be resistant to calcium-induced mitochondrial permeability transition pore (MPTP) opening (Piquereau et al. 2012) Furthermore, cardiomyocytes from OPA1 deficient mice were more susceptible to cell death induced by ischemia/reperfusion injury (Chen et al. 2012; Le Page et al. 2016). Cardiac-specific ablation of YME1L1 in mice activated OMA1 and triggered OPA1 proteolysis, leading to a dilated cardiomyopathy and heart failure with mitochondrial fragmentation and altered cardiac metabolism (Wai et al. 2015). Genetic OMA1 deletion prevented OPA1 cleavage and cardio myopathy (Wai et al. 2015).

It is envisioned that comparable gene signatures can be developed based on the activity and/or expression of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof.

Example 4

The means and methods of the present disclosure can also be used to inform selection and/or assist in selecting appropriate courses of treatment and/or medical interventions for patients in need of such interventions.

We studied the OPA1 protein and its isoforms in fibroblast cell lines derived from patients that harbor a duplication of the exons 7 to 9 (c.678-984dup306) in the OPA1 gene (Fuhrmann et al. 2010). Exons 7 to 9 code for 102 amino acids in frame and one would expect a larger OPA1 protein. However, OPA1 protein levels were significantly reduced compared to healthy subjects and the ratios of the different OPA1 isoforms were altered. We could rule out nonsense mediated mRNA decay by qPCR analysis (Fuhrmann et al. 2010). Also mouse embryonic fibroblast cell lines with a splice-site mutation leading to skipping of Opal exon 10 (c.1065+5G>A) showed significantly reduced OPA1 protein levels despite no changes in the abundance of the mRNA (Alavi et al. 2007). These findings led us to the conclusion that OPA1 is regulated on protein levels and that only fully functional OPA1 is stable.

Co-culture experiments of mouse embryo fibroblasts from mutant OPA1 mice and wild-type control mice with epoxomycin, a specific inhibitor of the ubiquitin-proteasome degradation system, did not change OPA1 levels or the ratio of OPA1L to OPA1S isoforms, indicating that OPA1 is not regulated by the ubiquitin-proteasome pathway (Alavi et al. 2007). Phenanthroline is a chelator that sequesters divalent metal ions like zinc, which is crucial for the function of metallo-endopeptidases. When we cultured cells in the presence of phenantroline, we found an increase in the OPA1L isoform indicating that OPA1 is regulated by proteolytic turnover (Alavi et al. 2007). Indeed, when we investigated the OPA1 protein in pulse-chase experiments we found a degradation of OPA1L to OPA1S and changes in the protein half-life depending on single amino acid substitutions.

Stress-induced OPA1 cleavage caused cell death in different experimental paradigms (Olichon et al. 2003; Duvezin-Caubet et al. 2006; Ishihara et al. 2006; Griparic et al. 2007; Song et al. 2007; Merkwirth et al. 2008; Ehses et al. 2009; Head et al. 2009), and expression of non-cleavable OPA1 isoforms could prevent cell death in these experiments (Ishihara et al. 2006; Griparic et al. 2007; Song et al. 2007; Merkwirth et al. 2008). OMA1 knock-down or knock-out also can prevent cell death while prolonged activation of OMA1 will cause cell death. OMA1 is activated upon stress in pre-clinical disease models for ischemic kidney injury (Xiao et al. 2014), myocardial infarct (Piquereau et al. 2012; Wai et al. 2015), cancer (Kong et al. 2014), and neurodegeneration (Merkwirth et al. 2008; Korwitz et al. 2016). Knock-down or knock-out of OMA1 could prevent cell death in these models (Ehses et al. 2009; Head et al. 2009; Wai et al. 2015; Korwitz et al. 2016). We therefore screened for compounds that can modify OMA1 protease activity in a way that reduces OMA1 activity (i.e., OMA1 antagonists).

HEK293T cells were cultured and maintained in Dulbecco's Modified Eagle's Medium supplemented with 10% fetal bovine serum (FBS) and 2 mM 1-glutamine in a 95% air-5% $CO_2$ humidified atmosphere at 37° C. To test potential OMA1 antagonists, cells were seeded in 24-well plates and incubated over night to achieve around 90% confluency. For experiments the culture medium was replaced with Minimal Essential Medium and cells were pre-incubated with variable concentrations of the different test-compounds for 2 hours in a 95% air-5% $CO_2$ humidified atmosphere at 37° C. After 2 hours, OMA1 protease was activated through the addition of carbonyl cyanide m-chlorophenyl hydrazone (CCCP; 10 μM final concentration) for 30 min in the presence of different concentrations of compounds to be tested. After 30 minutes, cells were immediately placed on ice, the medium removed, and cells harvested through addition of 100 μl RIPA buffer supplemented with protease inhibitor cocktail. Samples were separated on 8% tris-glycine gels and transferred onto nitro-cellulose membranes by Wester blotting. Membranes were immunolabeled with anti-OPA1 Antibodies (1:1,000) and with goat-anti-mouse Alkaline Phosphatase conjugated secondary antibodies (1:5,000). OPA1 protein was visualized with NBT/BCIP between 5 and 15 minutes before the reaction was stopped with an excess of distilled water.

As illustrated in FIG. 1, lane 1, and described in more details above, 5 different OPA1 isoforms (i.e., OPA1-L1, OPA1-L2, OPA1-S3, OPA1-S4, OPA1-S5) can be detected in HEK293T cells under standard culture conditions. CCCP is a potent mitochondrial oxidative phosphorylation uncoupler that activates OMA1 and creates conditions that allow OPA1 cleavage to occur. As illustrated in FIG. 1, lane 2, 30 minutes of CCCP treatment resulted in cleavage of both large OPA1-L1 and OPA1-L2 isoforms so that only the small OPA1-S3, OPA1-S4 and OPA1-S5 isoforms were detectable.

In a non-limiting example it was, inter alia, found that Thiorphan (CAS #76721-89-6) can inhibit proteolytic cleavage of large OPA1 isoforms under conditions allowing OPA1 processing to occur (FIG. 17). As illustrated in FIG. 17, lanes 1, 2, 4 and 5, only the small OPA1 isoforms OPA1-S3, OPA1-S4 and OPA1-S5 were detectable by SDS-PAGE/Western-blotting upon treatment with 10 μM CCCP. In samples treated with 100 μM Thiorphan, however, all OPA1 isoforms including the two large OPA1-L1 and OPA1-L2 isoforms were readily detectable (FIG. 17, lane 3), which demonstrates that Thiorphan can affect proteolytic cleavage of OPA1 by OMA1 upon dissipation of the mitochondrial membrane potential. Thiorphan thus represent an antagonist of OMA1 and/or an oligomeric complex comprising OMA1.

Referring to FIG. 17, thiorphan (CAS #76721-89-6) is a non-limiting example of an OMA1 antagonists. In HEK293T cells, 10 μM CCCP could activate OMA1, which resulted in the cleavage of the OPA1-L1 and OPA1-L2 isoforms so that only the smaller three isoforms OPA1-S3, OPA1-S4 and OPA1-S5 were detectable by SDS-PAGE/Western-blot (lanes 1, 2, 4 and 5). The large OPA1-L1 and OPA1-L2 isoforms were still readily detectable when cells were treated with 100 μM Thiorphan (lane 3) for 2 hours prior OMA1 activation.

In another non-limiting example it was, inter alia, found that ARP100 (CAS #704888-90-4) can inhibit proteolytic cleavage of large OPA1 isoforms under conditions allowing OPA1 processing to occur (FIG. 18). Again, only the small OPA1 isoforms OPA1-S3, OPA1-S4 and OPA1-S5 were detectable by SDS-PAGE/Western-blotting upon CCCP treatment (FIG. 18, lanes 2, 3 and 6), while in samples treated with 70 μM ARP100 all OPA1 isoforms including the large OPA1-L1 and OPA1-L2 isoforms were readily detectable (FIG. 18, lane 4). This demonstrates that ARP100 can inhibit proteolytic cleavage of OPA1 by OMA1. ARP100 thus represent an antagonist of OMA1 and/or an oligomeric complex comprising OMA1.

Referring to FIG. 18, phenanthroline (CAS #66-71-7) and ARP100 (CAS #704888-90-4) are non-limiting examples of OMA1 antagonists. In HEK293T cells, 10 μM CCCP could activate OMA1, which resulted in the cleavage of the OPA1-L1 and OPA1-L2 isoforms so that only the smaller three isoforms OPA1-S3, OPA1-S4 and OPA1-S5 were detectable by SDS-PAGE/Western-blot (lanes 2, 3 and 6). The large OPA1-L1 and OPA1-L2 isoforms were still readily detectable when cells were treated with 500 μM phenanthroline (lane 1) or 70 μM ARP100 (lane 4) for 2 hours prior OMA1 activation.

We controlled the experiments with phenanthroline, a chelator with inhibitory effects on metallo-enzymes. As expected, 500 μM phenanthroline also inhibited proteolytic cleavage of OPA1 by OMA1 (FIG. 18, lane 1).

Thiorphan is a potent inhibitor of neprilysin, a membrane metallo-endopeptidase that cleaves peptide hormones, such as enkephalins, glucagon, and bradykinin (Eberlin et al. 2012). Thiorphan is known in the arts also for its neuroprotective activity against excitotoxic neuronal cell death (Medja et al. 2006), which supports the OMA1 protease as genuine target for neuroprotective therapies. Moreover, this validates our approach of developing means and methods for the development of therapies for patients with mitochondrial disease. ARP 100 is a biphenylsulfonamide that acts as a selective inhibitor of MMP-2 (Rossello et al. 2004; Tuccinardi et al. 2006). The antagonistic effects of ARP100 on OMA1 were not known and are non-obvious to a person skilled in the arts.

Example 5

Cancer is a non-limiting example for a mitochondrial disorder or disease characterized by OPA1 alterations. As laid out in more details above, alterations in OMA1 and/or a heterooligomeric complex compromising OMA1 have a prognostic value for patients with various types of cancer. Certain cancer types were characterized, inter alia, by a 3-gene signature of increased OMA1 and HIGD1A levels and decreased BNIP3 levels. Patients with increased with this particular 3-gene signature had a significantly better prognosis of overall survival than patients without this signature. Moreover, patients that would have an inverted 3-gene signature of reduced OMA1 and HIGD1A levels and increased BNIP3 levels had a significantly worse prognosis of overall survival. In accordance with our results are findings of a study that compared cancer cells that are resistant against platin-based therapies with cancer cells that are amenable to these therapies. Chemoresistant cancer cells show significantly reduced OMA1 activity, which correlated with tumorogenesis, metastatic spread and overall survival of the cancer cells (Kong et al. 2015). Taken together, these data demonstrate that certain mitochondrial disorders or diseases are characterized by decreased OMA1 and that OMA1 agonists represent genuine medical interventions for these diseases. We therefore also screened for compounds that can modify OMA1 protease activity in a way that increases OMA1 activity (i.e., OMA1 agonists).

HEK293T cells were cultured and maintained in Dulbecco's Modified Eagle's Medium supplemented with 10% fetal bovine serum (FBS) and 2 mM 1-glutamine in a 95% air-5% $CO_2$ humidified atmosphere at 37° C. To test potential OMA1 antagonists, cells were seeded in 24-well plates and incubated over night to achieve around 90% confluency. For experiments the culture medium was replaced with Minimal Essential Medium and cells were pre-incubated with 100 μM compounds to be tested for their effects on OMA1 protease for 2 hours in a 95% air-5% $CO_2$ humidified atmosphere at 37° C. After 2 hours, cells were treated with increasing concentrations of 0 μM, 3 μM, 5 μM or 7 μM CCCP for 20 minutes to determine the minimum CCCP concentration that would lead to OMA1 activation and OPA1 cleavage, and whether this threshold level could be modified by the compound at question. After 20 minutes, cells were immediately placed on ice, the medium removed, and cells harvested through addition of 100 μl RIPA buffer supplemented with protease inhibitor cocktail. Samples were separated on 8% tris-glycine gels and transferred onto nitro-cellulose membranes by Wester blotting. Membranes were immunolabeled with anti-OPA1 Antibodies (1:1,000) and with goat-anti-mouse Alkaline Phosphatase conjugated secondary antibodies (1:5,000). OPA1 protein was visualized with NBT/BCIP between 5 and 15 minutes before the reaction was stopped with an excess of distilled water.

In one particular embodiment it was, inter alia, found that SB-3CT (CAS #292605-14-2) reduced the threshold levels of OMA1 activation and allowed for proteolytic cleavage of large OPA1 isoforms to occur under conditions that otherwise would not allow for OPA1 cleavage to occur. HEK293T cells were cultured in MEM only or in MEM supplemented with increasing concentrations of 0 μM, 3 μM, 5 μM or 7 μM CCCP. As illustrated in FIG. 19, 0 μM, 3 μM and 5 μM CCCP had no effect on OPA1 processing in untreated cells (lanes 1, 2 and 3). In untreated cells OPA1 was cleaved only at the highest concentration of 7 μM CCCP (FIG. 19, lane 4). SB-3CT by itself had no effect on OPA1 under normal conditions that do not allow for OPA1 cleavage to occur, because cells that only were treated with 100 μM SB-3CT and that were not exposed to CCCP did not show OPA1 alterations (FIG. 19, lane 5). All 5 isoforms were readily detectable in these samples by SDS-PAGE/Western-blotting (FIG. 19, lane 5). To our surprise and against all expectations we found that 100 μM SB-3CT caused OPA1 cleavage to occur already at 3 μM and 5 μM CCCP (FIG. 19, lanes 6 and 7). As illustrated in FIG. 19, OPA1 cleavage in SB-3CT-treated cells, in particular at low CCCP concentrations, exceeded that of the control cells (FIG. 19, lanes 2 and 3, "vehicle-only".)

Referring to FIG. 19, SB-3CT (CAS #292605-14-2) represents an OMA1 agonist because SB-3CT reduces the threshold levels of OMA1 activation and allows for proteolytic cleavage of large OPA1 isoforms to occur under conditions that otherwise would not allow for OPA1 cleavage to occur. HEK293T cells were cultured with increasing concentrations of 0 μM, 3 μM, 5 μM and 7 μM CCCP (lanes 1-4 & 5-8). In "vehicle-only" treated cells (lanes 1-4), OMA1 was activated at the highest concentration of 7 μM CCCP (lane 4). In cells treated with 100 μM SB-3CT (lanes 5-8), OMA1 was already activated at lower concentrations of 3 μM and 5 μM CCCP (lanes 6 & 7). 100 μM SB-3CT did not induce OPA1 cleavage without CCCP (lane 5) demonstrating that SB-3CT acts through the stress-dependent modulation of the OMA1 complex.

SB-3CT is known in the arts for its inhibitory effects on proteases (US 2009/0209615 and US 2013/0052184) and the above-mentioned finding that SB-3CT can activate the OMA1 protease under conditions that otherwise would not allow for OPA1 cleavage to occur was surprising and against all expectations. In context of the present invention SB-3CT thus represents an agonist of OMA1 and/or an oligomeric complex comprising OMA1 as defined above. Accordingly, SB-3CT represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Example 6

An important aspect of the invention disclosed herein is that mitochondrial diseases or disorders or diseases can be characterized by alterations of OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof. Measurements of these alterations can support diagnosis and guide therapy selection. Moreover, compounds and/or interventions that can mitigate alterations in OMA1, HIGD1A, OPA1, BNIP3, YME1L1, PHB, PHB2, SAMM50 or IMMT present suitable medical interventions for patients suffering from such a disorder or disease.

In an in silico approach we aimed to identify compounds and/or interventions that affect OMA1 and/or a heterooligomeric complex compromising OMA1. To this end, we mined publicly available data repositories for compounds that can modulate OMA1, HIGD1A, OPA1, BNIP3, YME1L1, PHB, PHB2, SAMM50 or IMMT. The findings are summarized in the table depicted in FIG. 20, which provides a list of compounds and treatments that are suitable medical interventions for patients with a mitochondrial disease or disorder.

FIG. 20 shows a list of different drugs and compounds that can modify OMA1 and/or an oligomeric complex comprising OMA1 and/or HIGD1A and/or OPA1 and/or BNIP3 and/or YME1L1 and/or PHB and/or PHB2 and/or SAMM50 and/or IMMT or (a) variant(s) thereof. These drugs represent non-limiting examples for therapies and medical interventions for patients with mitochondrial disease or disorder.

In one embodiment it was, inter alia, found that glucosamine (CAS #3416-24-8) significantly decreases the gene expression levels of OMA1 by 8.5% (FIG. 21; Student's T-test: p<0.001). Human malignant lymphocytes (KMH2 cells) were cultured without or with 20 mM glucosamine (Carvalho et al. 2014). After 24 hours mRNA was isolated and analyzed by gene expression microarrays. Controls expressed OMA1 at 7.31 (±0.08 S.D.) and glucosamine treated cells expressed OMA1 at 6.69 (±0.06 S.D.). Glucosamine is a dietary supplement and its effects on mitochondria are known to a person skilled in the arts (Carvalho et al. 2014; Bond and Hanover 2015; Tan et al. 2017). However, the finding that glucosamine can significantly decrease OMA1 levels was unexpected and is non-obvious to a person skilled in the arts. In context of the present invention glucosamine thus represents an antagonist of OMA1 and/or an oligomeric complex comprising OMA1 as defined above. Accordingly, glucosamine represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIG. 21, the dietary supplement glucosamine (CAS #3416-24-8) represents an antagonist of OMA1. Glucosamine can significantly decrease the gene expression levels of OMA1 in human malignant lymphocytes by 8.5% (Student's T-test: p<0.001; GEO accession number: GDS5388). KMH2 cells were cultured for 24 hours without or with 20 mM glucosamine, after which mRNA was isolated and analyzed by gene expression microarrays. Controls expressed OMA1 at 7.31 (±0.08 S.D.) and glucosamine treated cells expressed OMA1 at 6.69 (±0.06 S.D.).

In another embodiment it was, inter alia, found that the micro-RNA miR-203 (NCBI Reference Sequence: NR_029620.1) significantly reduced the gene expression levels of OMA1 by 22% to 27% (FIGS. 22A and 22B); Student's T-test: p<0.05). miR-203 was overexpressed in the breast cancer cell line SUM159 using a retrovirus (Taube et al. 2013). SUM159 control cells expressed OMA1 at 1219.5 (±109.3 S.D.; Spot ID: 226019_at) and 718.4 (±50.0 S.D. (FIG. 22A); Spot ID: 226020_s_at), while SUM159 cells expressing miR-203 had significantly reduced OMA1 levels at 891.7 (±54.1 S.D.; Spot ID: 226019_at) and 557.8 (±59.1 S.D.; Spot ID: 226020_s_at) (FIG. 22B), respectively. A person skilled in the arts knows miR-203 for its role in the epithelial-mesenchymal transition (EMT). The finding that miR-203 can decrease OMA1 levels was unexpected and is non-obvious to a person skilled in the arts. In context of the present invention miR-203 thus represents an antagonist of OMA1 and/or an oligomeric complex comprising OMA1 as defined above. Accordingly, miR-203 represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIGS. 22A and 22B, the micro-RNA miR-203 (*NCBI Reference Sequence*: NR_029620.1) represents an antagonist of OMA1. miR-203 can significantly decrease the expression levels of OMA1 in human SUM159 mesenchymal-like breast cancer cells by 22% to 27% (Student's T-test: p<0.05; GEO accession number: GSE23031). SUM159 control cells expressed OMA1 at 1219.5 (±109.3 S.D.; Spot ID: 226019_at) and 718.4 (±50.0 S.D. (FIG. 22A); Spot ID: 226020_s_at), while SUM159 cells expressing miR-203 had significantly reduced OMA1 levels at 891.7 (±54.1 S.D.; Spot ID: 226019_at) and 557.8 (±59.1 S.D.; Spot ID: 226020_s_at) (FIG. 22B), respectively.

In another particular embodiment it was, inter alia, found that the GSK-3 inhibitor SB216763 (CAS #280744-09-4) significantly increased gene expression levels of OMA1 by 7.6% (FIG. 23; Student's T-test: p<0.05). Human MLL leukemia RS4.11 cells were cultured without or with 10 μM SB216763 for 20 hours (Wang et al. 2010). Gene expression analyses by microarrays demonstrated that controls expressed OMA1 at 8.10 (±0.01 S.D.), while cells treated with SB216763 expressed OMA1 at 8.7 (±0.18 S.D.). SB216763 is a kinase inhibitor and the finding that SB216763 can increase OMA1 levels was unexpected and is non-obvious to a person skilled in the arts. In context of the present invention SB216763 thus represents an agonist of OMA1 and/or an oligomeric complex comprising OMA1 as defined above. Accordingly, SB216763 represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIG. 23, the GSK-3 inhibitor SB216763 (CAS #280744-09-4) represents an agonist of OMA1. SB216763 can significantly increase OMA1 gene expression levels in human MLL leukemia cells (RS4.11 cells) by 7.6% (Student's T-test: p<0.05; GEO accession number: GDS4043). RS4.11 cells were cultured for 20 hours without or with 10 μM SB216763, after which mRNA was isolated and analyzed by gene expression microarrays. Controls expressed OMA1 at 8.10 (±0.01 S.D.) and SB216763 treated cells expressed OMA1 at 8.7 (±0.18 S.D.).

In one particular embodiment it was, inter alia, found that the cytokine CXCL4 (UniProt: P02776) significantly increased the gene expression levels of OMA1 in monocyte derived macrophages by 42% to 103% (FIGS. 24A and 24B; Student's T-test: p<0.05). Monocytes were cultured for 6 days without or with 1 μM CXCL4 (Gleissner et al. 2010). Controls expressed OMA1 at 279.0 (±30.9 S.D.; Spot ID:

226019_at) and 327.3 (±20.8 S.D.; Spot ID: 226020_s_at), while CXCL4 treated cells had significantly increased OMA1 levels at 566.8 (±94.5 S.D. (FIG. 24A); Spot ID: 226019_at) and 465.3 (+23.3 S.D.; Spot ID: 226020_s_at) (FIG. 24B), respectively. CXCL4 is a small cytokine belonging to the CXC chemokine family that is also known in the arts as platelet factor 4 (PF4). The finding that CXCL4 can increase OMA1 levels was unexpected and is non-obvious to a person skilled in the arts. In context of the present invention CXCL4 thus represents an agonist of OMA1 and/or an oligomeric complex comprising OMA1 as defined above. Accordingly, CXCL4 represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIGS. 24A and 24B, the small cytokine CXCL4 (UniProt: P02776) represents an agonist of OMA1. CXCL4 can significantly increase the gene expression levels of OMA1 in monocyte derived macrophages by 42% to 103% (Student's T-test: $p<0.05$; GEO accession number: GDS3787). Controls expressed OMA1 at 279.0 (±30.9 S.D.; Spot ID: 226019_at) and 327.3 (±20.8 S.D. (FIG. 24A); Spot ID: 226020_s_at), while CXCL4 treated cells had significantly increased OMA1 levels at 566.8 (±94.5 S.D.; Spot ID: 226019_at) and 465.3 (±23.3 S.D.; Spot ID: 226020_s_at) (FIG. 24B), respectively.

In another particular embodiment it was, inter alia, found that Isoflurane increased the gene expression levels of OMA1 in rat brains in a dose-dependent manner (FIG. 25). Rats were exposed to 1% Isoflurane for 90 minutes twice daily for a total of 5 or 10 exposures, after which animals were sacrificed and brain samples analyzed by gene expression micro-arrays (Pan et al. 2006). Control rats expressed OMA1 at 10.4 (±3.8 S.D.), while rats exposed to Isoflurane for 5-times expressed OMA1 at elevated levels of 19.1 (±3.4 S.D.). Rats exposed to Isoflurane for 10-times showed even higher OMA1 expression levels of 29.3 (±6.3 S.D.) The dose-dependent increase by 83% and 180%, respectively, was statistically significant (FIG. 25; Student's T-test: $p\leq0.05$). Isoflurane belongs to the halogenated ether family of medication and was approved for medical use in the United States in 1979. Isoflurane is a general anesthetic administered in conjunction with air and/or pure oxygen through inhalation. The exact mechanism of the action has not been clearly delineated. Isoflurane likely binds to GABA, glutamate and glycine receptors. It also binds to the D subunit of ATP synthase and NADH dehydrogenase. The finding that Isoflurane can increase OMA1 levels was unexpected and is non-obvious to a person skilled in the arts. In context of the present invention Isoflurane thus represents an agonist of OMA1 and/or an oligomeric complex comprising OMA1 as defined above. Accordingly, Isoflurane represents a medical intervention in particular for the treatment, prevention and/or amelioration of a disorder or disease correlated with mitochondrial stress or dysfunction, a mitochondrial disorder or disease, or a disorder or disease characterized by OPA1 alterations.

Referring to FIG. 25, isoflurane represents an agonist of OMA1. Isoflurane exposure can increase the gene expression levels of OMA1 in rat brains in a dose-dependent manner (GEO accession number: GDS364). Control rats expressed OMA1 at 10.4 (±3.8 S.D.), while rats exposed to Isoflurane for 5-times expressed OMA1 at elevated levels of 19.1 (±3.4 S.D.). Rats exposed to Isoflurane for 10-times showed even higher OMA1 expression levels of 29.3 (±6.3 S.D.). The dose-dependent increase of 183% and 280%, respectively, was statistically significant (Student's T-test: $p<0.05$).

In another non-limiting and merely illustrative example it was, inter alia, found that OPA1, PHB and YME1L1 gene expression levels were significantly elevated in tobacco smokers (FIGS. 26A-26F). Gene expression levels were determined in blood samples from tobacco smokers (n=6) and non-smokers (n=9) by micro array analysis (Philibert et al. 2007). OPA1 levels were highly significantly elevated by 85% in smokers (26.0±5.9 S.D.) compared to non-smokers (14.0±1.9 S.D.; FIG. 26A; Student's T-test: $p<0.001$). PHB levels were significantly elevated by 64% in smokers (27.1±8.3 S.D.) compared to non-smokers (16.6±6.3 S.D.; FIG. 26B; Student's T-test: $p<0.05$). And also YME1L1 levels were significantly increased by 32% in smokers (78.3±20.0 S.D.) compared to non-smokers (59.4±10.0 S.D.; FIG. 26C; Student's T-test: $p<0.05$). BNIP3 levels and PHB2 levels appeared to be reduced in smokers (FIGS. 26D and E), while OMA1 expression was not changed (FIG. 26F). In view of the teaching provided herein, it is envisioned that smoking, and more preferably one or more pharmaceutically active compound(s) contained in tobacco smoke, will be administered to a patient in need of medical intervention for the treatment, prevention and/or amelioration of a disorder or disease correlated with mitochondrial stress or dysfunction, a mitochondrial disorder or disease, or a disorder or disease characterized by OPA1 alterations.

Referring to FIGS. 26A-26F, tobacco smoking alters OPA1, PHB and YME1L1 gene expression. Smoking can increase the OPA1 (26A), PHB (26B) and YME1L1 gene expression levels (C) in blood samples by 85%, 64% and 32%, respectively (Student's T-test: $p<0.05$; GEO accession number: GDS2447). FIG. 26A: Non-smokers (NS) expressed OPA1 at 14.0 (±1.9 S.D.) and smokers (S) at 26.0 (±5.9 S.D.). FIG. 26B: Non-smokers expressed PHB at 16.6 (±6.3 S.D.) and smokers at 27.1 (±8.3 S.D.). FIG. 26C: And non-smokers expressed YME1L1 at 59.4 (±10.0 S.D.) and smokers at 78.3 (±20.0 S.D.). FIG. 26D: BNIP3 levels appeared to be reduced in smokers (12.6±10.0 S.D.) compared to non-smokers (29.4±19.5 S.D.) though the difference did not reach statistical significance. FIG. 26E: PHB2 levels also appeared to be reduced in smokers (13.0±5.6 S.D.) compared to non-smokers (17.6±4.0 S.D.). FIG. 26F: OMA1 levels were not changed (smokers: 17.4±10.3 S.D.; non-smokers: 16.8±4.9 S.D.).

Preferentially the susceptibility for, predisposition for, and/or presence of, such a disorder or disease has been determined by measurements of OMA1, HIGD1A, OPA1, BNIP3, YME1L1, PHB, SAMM50, IMMT and/or PHB2 levels as disclosed herein and the medical intervention has been selected based on these biomarkers. The skilled person is readily in the position to select the medical intervention for the patient in need of medical intervention based on these biomarkers.

Example 7. Tipranavir can inhibit OMA1. OMA1 is a $Zn^{2+}$-dependent metalloendopeptidase located in the mitochondrial inner membrane with the OPA1 protein as major substrate. The protease is classified according to the MEROPS database as M48 family member of metalloendopeptidases. The M48 family also encompasses the metallopeptidase STE24 (ZMPSTE24, also known as farnesylated-protein converting enzyme 1, FACE1). ZMPSTE24 is an integral membrane protein which cleaves the nuclear envelope protein prelaminin A.

As explained in the manuscript entitled "OMA1—An integral membrane protease?" (Alavi M V. *Biochim Biophys*

*Acta Proteins Proteom.* 2020 Oct. 29; 1869(2):140558), it is known in the arts that HIVi protease inhibitors can inhibit the ZMPSTE24 protease in the single-digit-micro molar range. We found—not unexpectedly and consistent with OMA1's homology with ZMPSTE24—that tipranavir, which is disclosed in present invention, appears to also inhibit OMA1 protease (see FIG. 27).

OMA1 shows little activity under physiological conditions. Experimentally, OMA1 can be activated in cellular assays by the mitochondrial uncoupler [(3-chlorophenyl) hydrazono]propanedinitrile (CCCP). This results in cleavage of the large L-OPA1 isoforms, which are a major OMA1 substrate. Referring to FIG. 27, all L-OPA1 isoforms are hydrolyzed upon CCCP treatment to the small, cleaved S-OPA1 isoforms. Tipranavir prevented this CCCP-dependent L-OPA1 hydrolysis at a concentration of 100 μM, from which can be deduced that tipranavir can inhibit OMA1 protease.

Example 8. Tipranavir has unexpected effects on OMA1 activity. I further investigated tipranavir's effect on OPA1 as described in Example 7. To this end, I incubated Hek293T cells with different tipranavir concentrations.

When I incubated Hek293T cells with 50 μM, 100 μM and 200 μM tipranavir for an hour, I found against all expectations and quite to my surprise that 50 μM tipranavir did not only not prevent OPA1 processing upon CCCP-treatment, which I observed at concentrations of 100 μM and 200 μM tipranavir, but resulted in OPA1 processing even in the absence of CCCP (see FIG. 28). This means tipranavir has an antagonistic effect on OMA1 depending on its dose: lower doses of about 50 μM can activate the enzyme and lead to OPA1 cleavage, while higher doses of about 100 μM inhibit the enzyme's activity and prevent OPA1 cleavage even in the presence of CCCP.

Example 9. Tipranavir can activate OMA1 at concentrations above 20 μM. To further determine tipranavir's effect on OPA1, I incubated Hek293T cells for an hour with low doses of 0 μM, 20 μM and 40 μM tipranavir (FIG. 29). I found OPA1 cleavage at 40 μM tipranavir without any CCCP, while 20 μM and 40 μM tipranavir were not sufficient to prevent CCCP-induced OPA1 cleavage.

Example 10. 100 μM tipranavir can inhibit OPA1 cleavage upon CCCP-treatment and upon sorafenib treatment. 30 μM sorafenib (SFB) activate OMA1 and lead to OPA1 cleavage similar to CCCP. To investigate whether 100 μM tipranavir can inhibit CCCP-induced OPA1-cleavage or OPA1-cleavage induced by other agents as well, I incubated Hek293T cells for an hour with low doses of 0 μM, 50 μM or 100 μM tipranavir before activating OMA1 with either 3 μM CCCP or 30 μM sorafenib (see FIG. 30). I observed OPA1 hydrolyzis at about 50 μM tipranavir irrespective of the presence or absence of CCCP or sorafenib. 100 μM tipranavir on the other hand prevented CCCP-induced OPA1 cleavage and sorafenib-induced OPA1 cleavage.

Example 11. Tipranavir has unexpected effects on the OMA1 protein itself. I examined the effects of tipranavir on the OMA1 protein. I incubated Hek293T cells for an hour with either 50 μM or 100 tipranavir (FIG. 31). I found OMA1 protein was reduced when cells were incubated with 100 μM tipranavir compared to 50 μM tipranavir. From this result the skilled artisan can deduce that tipranavir acts as a positive allosteric OMA1 modulator and that other compounds of the genus can act as OMA1 modulators as well.

It should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

REFERENCES

Akhtar, M. W., S. Sanz-Blasco, N. Dolatabadi, J. Parker, K. Chon, M. S. Lee, W. Soussou, S. R. McKercher, R. Ambasudhan, T. Nakamura and S. A. Lipton (2016). "Elevated glucose and oligomeric beta-amyloid disrupt synapses via a common pathway of aberrant protein S-nitrosylation." *Nat Commun* 7: 10242.

Alavi, M. V., S. Bette, S. Schimpf, F. Schuettauf, U. Schraermeyer, H. F. Wehrl, L. Ruttiger, S. C. Beck, F. Tonagel, B. J. Pichler, M. Knipper, T. Peters, J. Laufs and B. Wissinger (2007). "A splice site mutation in the murine Opal gene features pathology of autosomal dominant optic atrophy." *Brain* 130(Pt 4): 1029-1042.

Alavi, M. V. and N. Fuhrmann (2013). "Dominant optic atrophy, OPA1, and mitochondrial quality control: understanding mitochondrial network dynamics." *Mol Neurodegener* 8(1): 32.

Alexander, C., M. Votruba, U. E. Pesch, D. L. Thiselton, S. Mayer, A. Moore, M. Rodriguez, U. Kellner, B. Leo-Kottler, G. Auburger, S. S. Bhattacharya and B. Wissinger (2000). "OPA1, encoding a dynamin-related GTPase, is mutated in autosomal dominant optic atrophy linked to chromosome 3q28." *Nat Genet* 26(2): 211-215.

Aliev, G., D. Seyidova, B. T. Lamb, M. E. Obrenovich, S. L. Siedlak, H. V. Vinters, R. P. Friedland, J. C. LaManna, M. A. Smith and G. Perry (2003). "Mitochondria and vascular lesions as a central target for the development of Alzheimer's disease and Alzheimer disease-like pathology in transgenic mice." *Neurol Res* 25(6): 665-674.

Alirol, E. and J. C. Martinou (2006). "Mitochondria and cancer: is there a morphological connection?" *Oncogene* 25(34): 4706-4716.

Ameri, K., A. Jahangiri, A. M. Rajah, K. V. Tormos, R. Nagarajan, M. Pekmezci, V. Nguyen, M. L. Wheeler, M. P. Murphy, T. A. Sanders, S. S. Jeffrey, Y. Yeghiazarians, P. F. Rinaudo, J. F. Costello, M. K. Aghi and E. Maltepe (2015). "HIGD1A Regulates Oxygen Consumption, ROS Production, and AMPK Activity during Glucose Deprivation to Modulate Cell Survival and Tumor Growth." *Cell Rep.*

Ameri, K. and E. Maltepe (2015). "HIGD1A-mediated dormancy and tumor survival." *Mol Cell Oncol* 2(4): e1030537.

Ameri, K., A. M. Rajah, V. Nguyen, T. A. Sanders, A. Jahangiri, M. Delay, M. Donne, H. J. Choi, K. V. Tormos, Y. Yeghiazarians, S. S. Jeffrey, P. F. Rinaudo, D. H. Rowitch, M. Aghi and E. Maltepe (2013). "Nuclear localization of the mitochondrial factor HIGD1A during metabolic stress." *PLoS One* 8(4): e62758.

An, H. J., G. Cho, J. O. Lee, S. G. Paik, Y. S. Kim and H. Lee (2013). "Higd-1a interacts with Opal and is required for the morphological and functional integrity of mitochondria." *Proc Natl Acad Sci USA* 110(32): 13014-13019.

An, H. J., H. Shin, S. G. Jo, Y. J. Kim, J. O. Lee, S. G. Paik and H. Lee (2011). "The survival effect of mitochondrial Higd-1a is associated with suppression of cytochrome C release and prevention of caspase activation." *Biochim Biophys Acta* 1813(12): 2088-2098.

Baek, S. H., S. J. Park, J. I. Jeong, S. H. Kim, J. Han, J. W. Kyung, S. H. Baik, Y. Choi, B. Y. Choi, J. S. Park, G. Bahn, J. H. Shin, D. S. Jo, J. Y. Lee, C. G. Jang, T. V. Arumugam, J. Kim, J. W. Han, J. Y. Koh, D. H. Cho and D. G. Jo (2017). "Inhibition of Drp1 Ameliorates Synaptic Depression, Abeta Deposition, and Cognitive Impairment in an Alzheimer's Disease Model." *J Neurosci* 37(20): 5099-5110.

Barrera, M., S. Koob, D. Dikov, F. Vogel and A. S. Reichert (2016). "OPA1 functionally interacts with MIC60 but is dispensable for crista junction formation." *FEBS Lett* 590(19): 3309-3322.

Bohovych, I., S. Kastora, S. Christianson, D. Topil, H. Kim, T. Fangman, Y. J. Zhou, A. Barrientos, J. Lee, A. J. Brown and O. Khalimonchuk (2016). "Oma1 Links Mitochondrial Protein Quality Control and TOR Signaling To Modulate Physiological Plasticity and Cellular Stress Responses." *Mol Cell Biol* 36(17): 2300-2312.

Bond, M. R. and J. A. Hanover (2015). "A little sugar goes a long way: the cell biology of 0-GlcNAc." *J Cell Biol* 208(7): 869-880.

Bose, A. and M. F. Beal (2016). "Mitochondrial dysfunction in Parkinson's disease." *J Neurochem* 139 Suppl 1: 216-231.

Burke, N., A. R. Hall and D. J. Hausenloy (2015). "OPA1 in Cardiovascular Health and Disease." *Curr Drug Targets* 16(8): 912-920.

Burte, F., V. Carelli, P. F. Chinnery and P. Yu-Wai-Man (2015). "Disturbed mitochondrial dynamics and neurodegenerative disorders." *Nat Rev Neurol* 11(1): 11-24.

Butterfield, D. A., J. Drake, C. Pocernich and A. Castegna (2001). "Evidence of oxidative damage in Alzheimer's disease brain: central role for amyloid beta-peptide." *Trends Mol Med* 7(12): 548-554.

Cardoso, S. M., I. Santana, R. H. Swerdlow and C. R. Oliveira (2004). "Mitochondria dysfunction of Alzheimer's disease cybrids enhances Abeta toxicity." *J Neurochem* 89(6): 1417-1426.

Carelli, V., F. N. Ross-Cisneros and A. A. Sadun (2002). "Optic nerve degeneration and mitochondrial dysfunction: genetic and acquired optic neuropathies." *Neurochem Int* 40(6): 573-584.

Carelli, V., F. N. Ross-Cisneros and A. A. Sadun (2004). "Mitochondrial dysfunction as a cause of optic neuropathies." *Prog Retin Eye Res* 23(1): 53-89.

Carvalho, A. S., H. Ribeiro, P. Voabil, D. Penque, O. N. Jensen, H. Molina and R. Matthiesen (2014). "Global mass spectrometry and transcriptomics array based drug profiling provides novel insight into glucosamine induced endoplasmic reticulum stress." *Mol Cell Proteomics* 13(12): 3294-3307.

Caspersen, C., N. Wang, J. Yao, A. Sosunov, X. Chen, J. W. Lustbader, H. W. Xu, D. Stern, G. McKhann and S. D. Yan (2005). "Mitochondrial Abeta: a potential focal point for neuronal metabolic dysfunction in Alzheimer's disease." *FASEB J* 19(14): 2040-2041.

Chen, L., Q. Gong, J. P. Stice and A. A. Knowlton (2009). "Mitochondrial OPA1, apoptosis, and heart failure." *Cardiovasc Res* 84(1): 91-99.

Chen, L., T. Liu, A. Tran, X. Lu, A. A. Tomilov, V. Davies, G. Cortopassi, N. Chiamvimonvat, D. M. Bers, M. Votruba and A. A. Knowlton (2012). "OPA1 mutation and late-onset cardiomyopathy: mitochondrial dysfunction and mtDNA instability." *J Am Heart Assoc* 1(5): e003012.

Choubey, V., D. Safiulina, A. Vaarmann, M. Cagalinec, P. Wareski, M. Kuum, A. Zharkovsky and A. Kaasik (2011). "Mutant A53T alpha-synuclein induces neuronal death by increasing mitochondrial autophagy." *J Biol Chem* 286 (12): 10814-10824.

Chrysostomou, V., F. Rezania, I. A. Trounce and J. G. Crowston (2013). "Oxidative stress and mitochondrial dysfunction in glaucoma." *Curr Opin Pharmacol* 13(1): 12-15.

Cipolat, S., T. Rudka, D. Hartmann, V. Costa, L. Serneels, K. Craessaerts, K. Metzger, C. Frezza, W. Annaert, L. D'Adamio, C. Derks, T. Dejaegere, L. Pellegrini, R. D'Hooge, L. Scorrano and B. De Strooper (2006). "Mitochondrial rhomboid PARL regulates cytochrome c release during apoptosis via OPA1-dependent cristae remodeling." *Cell* 126(1): 163-175.

Cogliati, S., C. Frezza, M. E. Soriano, T. Varanita, R. *Quintana*-Cabrera, M. Corrado, S. Cipolat, V. Costa, A. Casarin, L. C. Gomes, E. Perales-Clemente, L. Salviati, P. Fernandez-Silva, J. A. Enriquez and L. Scorrano (2013). "Mitochondrial cristae shape determines respiratory chain supercomplexes assembly and respiratory efficiency." *Cell* 155(1): 160-171.

Coughlin, L., R. S. Morrison, P. J. Horner and D. M. Inman (2015). "Mitochondrial morphology differences and mitophagy deficit in murine glaucomatous optic nerve." *Invest Ophthalmol Vis Sci* 56(3): 1437-1446.

Daoud, H., P. N. Valdmanis, F. Gros-Louis, V. Belzil, D. Spiegelman, E. Henrion, O. Diallo, A. Desjarlais, J. Gauthier, W. Camu, P. A. Dion and G. A. Rouleau (2011). "Resequencing of 29 candidate genes in patients with familial and sporadic amyotrophic lateral sclerosis." *Arch Neurol* 68(5): 587-593.

Delettre, C., G. Lenaers, J. M. Griffoin, N. Gigarel, C. Lorenzo, P. Belenguer, L. Pelloquin, J. Grosgeorge, C. Turc-Carel, E. Perret, C. Astarie-Dequeker, L. Lasquellec, B. Arnaud, B. Ducommun, J. Kaplan and C. P. Hamel (2000). "Nuclear gene OPA1, encoding a mitochondrial dynamin-related protein, is mutated in dominant optic atrophy." *Nat Genet* 26(2): 207-210.

Devi, L., B. M. Prabhu, D. F. Galati, N. G. Avadhani and H. K. Anandatheerthavarada (2006). "Accumulation of amyloid precursor protein in the mitochondrial import channels of human Alzheimer's disease brain is associated with mitochondrial dysfunction." *J Neurosci* 26(35): 9057-9068.

Diana, A., G. Simic, E. Sinforiani, N. Orru, G. Pichiri and G. Bono (2008). "Mitochondria morphology and DNA content upon sublethal exposure to beta-amyloid(1-42) peptide."*Coll Antropol* 32 Suppl 1: 51-58.

Dolle, C., I. Flones, G. S. Nido, H. Miletic, N. Osuagwu, S. Kristoffersen, P. K. Lilleng, J. P. Larsen, O. B. Tysnes, K. Haugarvoll, L. A. Bindoff and C. Tzoulis (2016). "Defective mitochondrial DNA homeostasis in the substantia nigra in Parkinson disease." *Nat Commun* 7: 13548.

Dorn, G. W., 2nd (2013). "Mitochondrial dynamics in heart disease." *Biochim Biophys Acta* 1833(1): 233-241.

Duvezin-Caubet, S., R. Jagasia, J. Wagener, S. Hofmann, A. Trifunovic, A. Hansson, A. Chomyn, M. F. Bauer, G. Attardi, N. G. Larsson, W. Neupert and A. S. Reichert (2006). "Proteolytic processing of OPA1 links mitochondrial dysfunction to alterations in mitochondrial morphology." *J Biol Chem* 281(49): 37972-37979.

Eberlin, M., T. Muck and M. C. Michel (2012). "A comprehensive review of the pharmacodynamics, pharmacokinetics, and clinical effects of the neutral endopeptidase inhibitor racecadotril." *Front Pharmacol* 3: 93.

Eckert, A., S. Hauptmann, I. Scherping, V. Rhein, F. Muller-Spahn, J. Gotz and W. E. Muller (2008). "Soluble beta-amyloid leads to mitochondrial defects in amyloid precursor protein and tau transgenic mice." *Neurodegener Dis* 5(3-4): 157-159.

Edgar, R., M. Domrachev and A. E. Lash (2002). "Gene Expression Omnibus: NCBI gene expression and hybridization array data repository." *Nucleic Acids Res* 30(1): 207-210.

Ehses, S., I. Raschke, G. Mancuso, A. Bernacchia, S. Geimer, D. Tondera, J. C. Martinou, B. Westermann, E. I. Rugarli and T. Langer (2009). "Regulation of OPA1 processing and mitochondrial fusion by m-AAA protease isoenzymes and OMA1." *J Cell Biol* 187(7): 1023-1036.

Faccenda, D., J. Nakamura, G. Gorini, G. K. Dhoot, M. Piacentini, M. Yoshida and M. Campanella (2017). "Control of Mitochondrial Remodeling by the ATPase Inhibitory Factor 1 Unveils a Pro-survival Relay via OPAL." *Cell Rep* 18(8): 1869-1883.

Frezza, C., S. Cipolat, O. Martins de Brito, M. Micaroni, G. V. Beznoussenko, T. Rudka, D. Bartoli, R. S. Polishuck, N. N. Danial, B. De Strooper and L. Scorrano (2006). "OPA1 controls apoptotic cristae remodeling independently from mitochondrial fusion." *Cell* 126(1): 177-189.

Frezza, C. and E. Gottlieb (2009). "Mitochondria in cancer: not just innocent bystanders." *Semin Cancer Biol* 19(1): 4-11.

Fuhrmann, N., S. Schimpf, Y. Kamenisch, B. Leo-Kottler, C. Alexander, G. Auburger, E. Zrenner, B. Wissinger and M. V. Alavi (2010). "Solving a 50 year mystery of a missing OPA1 mutation: more insights from the first family diagnosed with autosomal dominant optic atrophy." *Mol Neurodegener* 5(1): 25.

Ghio, S., F. Kamp, R. Cauchi, A. Giese and N. Vassallo (2016). "Interaction of alpha-synuclein with biomembranes in Parkinson's disease—role of cardiolipin." *Prog Lipid Res* 61: 73-82.

Gibson, G. E., K. F. Sheu and J. P. Blass (1998). "Abnormalities of mitochondrial enzymes in Alzheimer disease." *J Neural Transm* (Vienna) 105(8-9): 855-870.

Gleissner, C. A., I. Shaked, K. M. Little and K. Ley (2010). "CXC chemokine ligand 4 induces a unique transcriptome in monocyte-derived macrophages." *J Immunol* 184(9): 4810-4818.

Glytsou, C., E. Calvo, S. Cogliati, A. Mehrotra, I. Anastasia, G. Rigoni, A. Raimondi, N. Shintani, M. Loureiro, J. Vazquez, L. Pellegrini, J. A. Enriquez, L. Scorrano and M. E. Soriano (2016). "Optic Atrophy 1 Is Epistatic to the Core MICOS Component MIC60 in Mitochondrial Cristae Shape Control." *Cell Rep* 17(11): 3024-3034.

Griparic, L., T. Kanazawa and A. M. van der Bliek (2007). "Regulation of the mitochondrial dynamin-like protein Opal by proteolytic cleavage." *J Cell Biol* 178(5): 757-764.

Guardia-Laguarta, C., E. Area-Gomez, C. Rub, Y. Liu, J. Magrane, D. Becker, W. Voos, E. A. Schon and S. Przedborski (2014). "alpha-Synuclein is localized to mitochondria-associated ER membranes." *J Neurosci* 34(1): 249-259.

Guo, Y., X. Chen, H. Zhang, N. Li, X. Yang, W. Cheng and K. Zhao (2012). "Association of OPA1 polymorphisms with NTG and HTG: a meta-analysis." *PLoS One* 7(8): e42387.

Hackenbrock, C. R. (1966). "Ultrastructural bases for metabolically linked mechanical activity in mitochondria. I. Reversible ultrastructural changes with change in metabolic steady state in isolated liver mitochondria." *J Cell Biol* 30(2): 269-297.

Hanahan, D. and R. A. Weinberg (2011). "Hallmarks of cancer: the next generation." *Cell* 144(5): 646-674.

Head, B., L. Griparic, M. Amiri, S. Gandre-Babbe and A. M. van der Bliek (2009). "Inducible proteolytic inactivation of OPA1 mediated by the OMA1 protease in mammalian cells." *J Cell Biol* 187(7): 959-966.

Hessenberger, M., R. M. Zerbes, H. Rampelt, S. Kunz, A. H. Xavier, B. Purfurst, H. Lilie, N. Pfanner, M. van der Laan and O. Daumke (2017). "Regulated membrane remodeling by Mic60 controls formation of mitochondrial crista junctions." *Nat Commun* 8: 15258.

Hokama, M., S. Oka, J. Leon, T. Ninomiya, H. Honda, K. Sasaki, T. Iwaki, T. Ohara, T. Sasaki, F. M. LaFerla, Y. Kiyohara and Y. Nakabeppu (2014). "Altered expression of diabetes-related genes in Alzheimer's disease brains: the Hisayama study." *Cereb Cortex* 24(9): 2476-2488.

Imaizumi, Y., Y. Okada, W. Akamatsu, M. Koike, N. Kuzumaki, H. Hayakawa, T. Nihira, T. Kobayashi, M. Ohyama, S. Sato, M. Takanashi, M. Funayama, A. Hirayama, T. Soga, T. Hishiki, M. Suematsu, T. Yagi, D. Ito, A. Kosakai, K. Hayashi, M. Shouji, A. Nakanishi, N. Suzuki, Y. Mizuno, N. Mizushima, M. Amagai, Y. Uchiyama, H. Mochizuki, N. Hattori and H. Okano (2012). "Mitochondrial dysfunction associated with increased oxidative stress and alpha-synuclein accumulation in PARK2 iPSC-derived neurons and postmortem brain tissue." *Mol Brain* 5: 35.

Ishihara, N., Y. Fujita, T. Oka and K. Mihara (2006). "Regulation of mitochondrial morphology through proteolytic cleavage of OPAL." *EMBO J* 25(13): 2966-2977.

Jakobs, S., N. Martini, A. C. Schauss, A. Egner, B. Westermann and S. W. Hell (2003). "Spatial and temporal dynamics of budding yeast mitochondria lacking the division component Fisip." *J Cell Sci* 116(Pt 10): 2005-2014.

Jiang, X., H. Jiang, Z. Shen and X. Wang (2014). "Activation of mitochondrial protease OMA1 by Bax and Bak promotes cytochrome c release during apoptosis." *Proc Natl Acad Sci USA.*

Ju, W. K., K. Y. Kim, J. D. Lindsey, M. Angert, K. X. Duong-Polk, R. T. Scott, J. J. Kim, I. Kukhmazov, M. H. Ellisman, G. A. Perkins and R. N. Weinreb (2008). "Intraocular pressure elevation induces mitochondrial fission and triggers OPA1 release in glaucomatous optic nerve." *Invest Ophthalmol Vis Sci* 49(11): 4903-4911.

Kandimalla, R., M. Manczak, D. Fry, Y. Suneetha, H. Sesaki and P. H. Reddy (2016). "Reduced dynamin-related protein 1 protects against phosphorylated Tau-induced mitochondrial dysfunction and synaptic damage in Alzheimer's disease." *Hum Mol Genet* 25(22): 4881-4897.

Kaser, M., M. Kambacheld, B. Kisters-Woike and T. Langer (2003). "Oma1, a novel membrane-bound metallopeptidase in mitochondria with activities overlapping with the m-AAA protease." *J Biol Chem* 278(47): 46414-46423.

Keeney, P. M., J. Xie, R. A. Capaldi and J. P. Bennett, Jr. (2006). "Parkinson's disease brain mitochondrial complex I has oxidatively damaged subunits and is functionally impaired and misassembled." *J Neurosci* 26(19): 5256-5264.

Kim, K. Y., G. A. Perkins, M. S. Shim, E. Bushong, N. Alcasid, S. Ju, M. H. Ellisman, R. N. Weinreb and W. K. Ju (2015). "DRP1 inhibition rescues retinal ganglion cells and their axons by preserving mitochondrial integrity in a mouse model of glaucoma." *Cell Death Dis* 6: e1839.

Kong, B., H. Tsuyoshi, M. Orisaka, D. B. Shieh, Y. Yoshida and B. K. Tsang (2015). "Mitochondrial dynamics regulating chemoresistance in gynecological cancers." *Ann N Y Acad Sci* 1350: 1-16.

Kong, B., Q. Wang, E. Fung, K. Xue and B. K. Tsang (2014). "p53 is required for cisplatin-induced processing of the mitochondrial fusion protein L-Opal that is mediated by the mitochondrial metallopeptidase Oma1 in gynecologic cancers." *J Biol Chem* 289(39): 27134-27145.

Kong, G. Y., N. J. Van Bergen, I. A. Trounce and J. G. Crowston (2009). "Mitochondrial dysfunction and glaucoma." *J Glaucoma* 18(2): 93-100.

Koob, S., M. Barrera, R. Anand and A. S. Reichert (2015). "The non-glycosylated isoform of MIC26 is a constituent of the mammalian MICOS complex and promotes formation of crista junctions." *Biochim Biophys Acta* 1853(7): 1551-1563.

Korwitz, A., C. Merkwirth, R. Richter-Dennerlein, S. E. Troder, H. G. Sprenger, P. M. Quiros, C. Lopez-Otin, E. I. Rugarli and T. Langer (2016). "Loss of OMA1 delays neurodegeneration by preventing stress-induced OPA1 processing in mitochondria." *J Cell Biol* 212(2): 157-166.

Landes, T., L. J. Emorine, D. Courilleau, M. Rojo, P. Belenguer and L. Arnaune-Pelloquin (2010). "The BH3-only Bnip3 binds to the dynamin Opal to promote mitochondrial fragmentation and apoptosis by distinct mechanisms." *EMBO Rep* 11(6): 459-465.

Le Page, S., M. Niro, J. Fauconnier, L. Cellier, S. Tamareille, A. Gharib, A. Chevrollier, L. Loufrani, C. Grenier, R. Kamel, E. Sarzi, A. Lacampagne, M. Ovize, D. Henrion, P. Reynier, G. Lenaers, D. Mirebeau-Prunier and F. Prunier (2016). "Increase in Cardiac Ischemia-Reperfusion Injuries in Opal+/− Mouse Model." *PLoS One* 11(10): e0164066.

Lee, S., N. J. Van Bergen, G. Y. Kong, V. Chrysostomou, H. S. Waugh, E. C. O'Neill, J. G. Crowston and I. A. Trounce (2011). "Mitochondrial dysfunction in glaucoma and emerging bioenergetic therapies." *Exp Eye Res* 93(2): 204-212.

Lenaers, G., P. Reynier, G. Elachouri, C. Soukkarieh, A. Olichon, P. Belenguer, L. Baricault, B. Ducommun, C. Hamel and C. Delettre (2009). "OPA1 functions in mitochondria and dysfunctions in optic nerve." *Int J Biochem Cell Biol* 41(10): 1866-1874.

Lesnick, T. G., S. Papapetropoulos, D. C. Mash, J. Ffrench-Mullen, L. Shehadeh, M. de Andrade, J. R. Henley, W. A. Rocca, J. E. Ahlskog and D. M. Maraganore (2007). "A genomic pathway approach to a complex disease: axon guidance and Parkinson disease." *PLoS Genet* 3(6): e98.

Li, F., N. Y. Calingasan, F. Yu, W. M. Mauck, M. Toidze, C. G. Almeida, R. H. Takahashi, G. A. Carlson, M. Flint Beal, M. T. Lin and G. K. Gouras (2004). "Increased plaque burden in brains of APP mutant MnSOD heterozygous knockout mice." *J Neurochem* 89(5): 1308-1312.

Lustbader, J. W., M. Cirilli, C. Lin, H. W. Xu, K. Takuma, N. Wang, C. Caspersen, X. Chen, S. Pollak, M. Chaney, F. Trinchese, S. Liu, F. Gunn-Moore, L. F. Lue, D. G. Walker, P. Kuppusamy, Z. L. Zewier, O. Arancio, D. Stern, S. S. Yan and H. Wu (2004). "ABAD directly links Abeta to mitochondrial toxicity in Alzheimer's disease." *Science* 304(5669): 448-452.

Lutz, A. K., N. Exner, M. E. Fett, J. S. Schlehe, K. Kloos, K. Lammermann, B. Brunner, A. Kurz-Drexler, F. Vogel, A. S. Reichert, L. Bouman, D. Vogt-Weisenhorn, W. Wurst, J. Tatzelt, C. Haass and K. F. Winklhofer (2009). "Loss of parkin or PINK1 function increases Drp1-dependent mitochondrial fragmentation." *J Biol Chem* 284 (34): 22938-22951.

Manczak, M., T. S. Anekonda, E. Henson, B. S. Park, J. Quinn and P. H. Reddy (2006). "Mitochondria are a direct site of A beta accumulation in Alzheimer's disease neurons: implications for free radical generation and oxidative damage in disease progression." *Hum Mol Genet* 15(9): 1437-1449.

Manczak, M., M. J. Calkins and P. H. Reddy (2011). "Impaired mitochondrial dynamics and abnormal interaction of amyloid beta with mitochondrial protein Drp1 in neurons from patients with Alzheimer's disease: implications for neuronal damage." *Hum Mol Genet* 20(13): 2495-2509.

Manczak, M., R. Kandimalla, D. Fry, H. Sesaki and P. H. Reddy (2016). "Protective effects of reduced dynamin-related protein 1 against amyloid beta-induced mitochondrial dysfunction and synaptic damage in Alzheimer's disease." *Hum Mol Genet* 25(23): 5148-5166.

Manczak, M. and P. H. Reddy (2012). "Abnormal interaction between the mitochondrial fission protein Drp1 and hyperphosphorylated tau in Alzheimer's disease neurons: implications for mitochondrial dysfunction and neuronal damage." *Hum Mol Genet* 21(11): 2538-2547.

Maraganore, D. M., M. de Andrade, T. G. Lesnick, K. J. Strain, M. J. Farrer, W. A. Rocca, P. V. Pant, K. A. Frazer, D. R. Cox and D. G. Ballinger (2005). "High-resolution whole-genome association study of Parkinson disease." *Am J Hum Genet* 77(5): 685-693.

Maresca, A., C. la Morgia, L. Caporali, M. L. Valentino and V. Carelli (2013). "The optic nerve: a "mito-window"on mitochondrial neurodegeneration." *Mol Cell Neurosci* 55: 62-76.

Marin-Garcia, J. and A. T. Akhmedov (2016). "Mitochondrial dynamics and cell death in heart failure." *Heart Fail Rev* 21(2): 123-136.

Maurer, I., S. Zierz and H. J. Moller (2000). "A selective defect of cytochrome c oxidase is present in brain of Alzheimer disease patients." *Neurobiol Aging* 21(3): 455-462.

Medja, F., V. Lelievre, R. H. Fontaine, F. Lebas, P. Leroux, T. Ouimet, A. Saria, C. Rougeot, P. Dournaud and P. Gressens (2006). "Thiorphan, a neutral endopeptidase inhibitor used for diarrhoea, is neuroprotective in newborn mice."*Brain* 129(Pt 12): 3209-3223.

Merkwirth, C., S. Dargazanli, T. Tatsuta, S. Geimer, B. Lower, F. T. Wunderlich, J. C. von Kleist-Retzow, A. Waisman, B. Westermann and T. Langer (2008). "Prohibitins control cell proliferation and apoptosis by regulating OPA1-dependent cristae morphogenesis in mitochondria." *Genes Dev* 22(4): 476-488.

Miller, J. A., R. L. Woltjer, J. M. Goodenbour, S. Horvath and D. H. Geschwind (2013). "Genes and pathways underlying regional and cell type changes in Alzheimer's disease." *Genome Med* 5(5): 48.

Mukherjee, U. A., S. B. Ong, S. G. Ong and D. J. Hausenloy (2015). "Parkinson's disease proteins: Novel mitochondrial targets for cardioprotection." *Pharmacol Ther* 156: 34-43.

Nakamura, K. (2013). "alpha-Synuclein and mitochondria: partners in crime?" *Neurotherapeutics* 10(3): 391-399.

Nakamura, K., V. M. Nemani, F. Azarbal, G. Skibinski, J. M. Levy, K. Egami, L. Munishkina, J. Zhang, B. Gardner, J. Wakabayashi, H. Sesaki, Y. Cheng, S. Finkbeiner, R. L. Nussbaum, E. Masliah and R. H. Edwards (2011). "Direct membrane association drives mitochondrial fission by the Parkinson disease-associated protein alpha-synuclein." *J Biol Chem* 286(23): 20710-20726.

Niemann, A., M. Ruegg, V. La Padula, A. Schenone and U. Suter (2005). "Ganglioside-induced differentiation associated protein 1 is a regulator of the mitochondrial network: new implications for Charcot-Marie-Tooth disease." *J Cell Biol* 170(7): 1067-1078.

Olichon, A., L. Baricault, N. Gas, E. Guillou, A. Valette, P. Belenguer and G. Lenaers (2003). "Loss of OPA1 perturbates the mitochondrial inner membrane structure and integrity, leading to cytochrome c release and apoptosis." *J Biol Chem* 278(10): 7743-7746.

Ong, S. B., S. B. Kalkhoran, S. Hernandez-Resendiz, P. Samangouei, S. G. Ong and D. J. Hausenloy (2017). "Mitochondrial-Shaping Proteins in Cardiac Health and Disease—the Long and the Short of It!" *Cardiovasc Drugs Ther* 31(1): 87-107.

Osborne, N. N. (2010). "Mitochondria: Their role in ganglion cell death and survival in primary open angle glaucoma." *Exp Eye Res* 90(6): 750-757.

Ott, C., E. Dorsch, M. Fraunholz, S. Straub and V. Kozjak-Pavlovic (2015). "Detailed analysis of the human mitochondrial contact site complex indicate a hierarchy of subunits." *PLoS One* 10(3): e0120213.

Pan, J. Z., H. Wei, J. G. Hecker, J. W. Tobias, R. G. Eckenhoff and M. F. Eckenhoff (2006). "Rat brain DNA transcript profile of halothane and isoflurane exposure." *Pharmacogenet Genomics* 16(3): 171-182.

Parker, W. D., Jr., C. M. Filley and J. K. Parks (1990). "Cytochrome oxidase deficiency in Alzheimer's disease." *Neurology* 40(8): 1302-1303.

Parker, W. D., Jr., J. K. Parks and R. H. Swerdlow (2008). "Complex I deficiency in Parkinson's disease frontal cortex." *Brain Res* 1189: 215-218.

Philibert, R. A., G. Y. Ryu, J. G. Yoon, H. Sandhu, N. Hollenbeck, T. Gunter, A. Barkhurst, W. Adams and A. Madan (2007). "Transcriptional profiling of subjects from the Iowa adoption studies." *Am J Med Genet B Neuropsychiatr Genet* 144B(5): 683-690.

Piquereau, J., F. Caffin, M. Novotova, C. Lemaire, V. Veksler, A. Garnier, R. Ventura-Clapier and F. Joubert (2013). "Mitochondrial dynamics in the adult cardiomyocytes: which roles for a highly specialized cell?" *Front Physiol* 4: 102.

Piquereau, J., F. Caffin, M. Novotova, A. Prola, A. Garnier, P. Mateo, D. Fortin, H. Huynh le, V. Nicolas, M. V. Alavi, C. Brenner, R. Ventura-Clapier, V. Veksler and F. Joubert (2012). "Down-regulation of OPA1 alters mouse mitochondrial morphology, PTP function, and cardiac adaptation to pressure overload." *Cardiovasc Res* 94(3): 408-417.

Rainbolt, T. K., J. Lebeau, C. Puchades and R. L. Wiseman (2016). "Reciprocal Degradation of YME1L and OMA1 Adapts Mitochondrial Proteolytic Activity during Stress." *Cell Rep* 14(9): 2041-2049.

Rappold, P. M., M. Cui, J. C. Grima, R. Z. Fan, K. L. de Mesy-Bentley, L. Chen, X. Zhuang, W. J. Bowers and K. Tieu (2014). "Drp1 inhibition attenuates neurotoxicity and dopamine release deficits in vivo." *Nat Commun* 5: 5244.

Reddy, P. H., M. Manczak and X. Yin (2017). "Mitochondria-Division Inhibitor 1 Protects Against Amyloid-beta induced Mitochondrial Fragmentation and Synaptic Damage in Alzheimer's Disease." *J Alzheimers Dis* 58(1): 147-162.

Reddy, P. H., S. McWeeney, B. S. Park, M. Manczak, R. V. Gutala, D. Partovi, Y. Jung, V. Yau, R. Searles, M. Mori and J. Quinn (2004). "Gene expression profiles of transcripts in amyloid precursor protein transgenic mice: up-regulation of mitochondrial metabolism and apoptotic genes is an early cellular change in Alzheimer's disease." *Hum Mol Genet* 13(12): 1225-1240.

Richter, U., T. Lahtinen, P. Marttinen, F. Suomi and B. J. Battersby (2015). "Quality control of mitochondrial protein synthesis is required for membrane integrity and cell fitness." *J Cell Biol* 211(2): 373-389.

Rossello, A., E. Nuti, E. Orlandini, P. Carelli, S. Rapposelli, M. Macchia, F. Minutolo, L. Carbonaro, A. Albini, R. Benelli, G. Cercignani, G. Murphy and A. Balsamo (2004). "New N-arylsulfonyl-N-alkoxyaminoacetohydroxamic acids as selective inhibitors of gelatinase A (MMP-2)." *Bioorg Med Chem* 12(9): 2441-2450.

Sadun, A. A. (2002). "Mitochondrial optic neuropathies." *J Neurol Neurosurg Psychiatry* 72(4): 423-425.

Salminen, A., A. Haapasalo, A. Kauppinen, K. Kaarniranta, H. Soininen and M. Hiltunen (2015). "Impaired mitochondrial energy metabolism in Alzheimer's disease: Impact on pathogenesis via disturbed epigenetic regulation of chromatin landscape." *Prog Neurobiol* 131: 1-20.

Santos, D., A. R. Esteves, D. F. Silva, C. Januario and S. M. Cardoso (2015). "The Impact of Mitochondrial Fusion and Fission Modulation in Sporadic Parkinson's Disease." *Mol Neurobiol* 52(1): 573-586.

Schapira, A. H., J. M. Cooper, D. Dexter, J. B. Clark, P. Jenner and C. D. Marsden (1990). "Mitochondrial complex I deficiency in Parkinson's disease." *J Neurochem* 54(3): 823-827.

Schmidt, C., E. Lepsverdize, S. L. Chi, A. M. Das, S. V. Pizzo, A. Dityatev and M. Schachner (2008). "Amyloid precursor protein and amyloid beta-peptide bind to ATP synthase and regulate its activity at the surface of neural cells." *Mol Psychiatry* 13(10): 953-969.

Shields, L. Y., H. Kim, L. Zhu, D. Haddad, A. Berthet, D. Pathak, M. Lam, R. Ponnusamy, L. G. Diaz-Ramirez, T. M. Gill, H. Sesaki, L. Mucke and K. Nakamura (2015). "Dynamin-related protein 1 is required for normal mitochondrial bioenergetic and synaptic function in CA1 hippocampal neurons." *Cell Death Dis* 6: e1725.

Sit, A. J. (2014). "Intraocular pressure variations: causes and clinical significance." *Can J Ophthalmol* 49(6): 484-488.

Smith, M. A., G. Perry, P. L. Richey, L. M. Sayre, V. E. Anderson, M. F. Beal and N. Kowall (1996). "Oxidative damage in Alzheimer's." *Nature* 382(6587): 120-121.

Song, Z., H. Chen, M. Fiket, C. Alexander and D. C. Chan (2007). "OPA1 processing controls mitochondrial fusion and is regulated by mRNA splicing, membrane potential, and Yme1L." *J Cell Biol* 178(5): 749-755.

Stafa, K., E. Tsika, R. Moser, A. Musso, L. Glauser, A. Jones, S. Biskup, Y. Xiong, R. Bandopadhyay, V. L. Dawson, T. M. Dawson and D. J. Moore (2014). "Functional interaction of Parkinson's disease-associated LRRK2 with members of the dynamin GTPase superfamily." *Hum Mol Genet* 23(8): 2055-2077.

Takihara, Y., M. Inatani, K. Eto, T. Inoue, A. Kreymerman, S. Miyake, S. Ueno, M. Nagaya, A. Nakanishi, K. Iwao, Y. Takamura, H. Sakamoto, K. Satoh, M. Kondo, T. Sakamoto, J. L. Goldberg, J. Nabekura and H. Tanihara (2015). "In vivo imaging of axonal transport of mitochondria in the diseased and aged mammalian CNS." *Proc Natl Acad Sci USA* 112(33): 10515-10520.

Tan, E. P., S. R. McGreal, S. Graw, R. Tessman, S. J. Koppel, P. Dhakal, Z. Zhang, M. Machacek, N. E. Zachara, D. C. Koestler, K. R. Peterson, J. P. Thyfault, R. H. Swerdlow, P. Krishnamurthy, L. DiTacchio, U. Apte and C. Slawson (2017). "Sustained O-GlcNAcylation reprograms mitochondrial function to regulate energy metabolism." *J Biol Chem* 292(36): 14940-14962.

Taube, J. H., G. G. Malouf, E. Lu, N. Sphyris, V. Vijay, P. P. Ramachandran, K. R. Ueno, S. Gaur, M. S. Nicoloso, S. Rossi, J. I. Herschkowitz, J. M. Rosen, J. P. Issa, G. A. Calin, J. T. Chang and S. A. Mani (2013). "Epigenetic silencing of microRNA-203 is required for EMT and cancer stem cell properties." *Sci Rep* 3: 2687.

Taylor, J. P., J. Hardy and K. H. Fischbeck (2002). "Toxic proteins in neurodegenerative disease." *Science* 296 (5575): 1991-1995.

Thomas, E., J. J. Feld, Q. Li, Z. Hu, M. W. Fried and T. J. Liang (2011). "Ribavirin potentiates interferon action by augmenting interferon-stimulated gene induction in hepatitis C virus cell culture models." *Hepatology* 53(1): 32-41.

Tuccinardi, T., A. Martinelli, E. Nuti, P. Carelli, F. Balzano, G. Uccello-Barretta, G. Murphy and A. Rossello (2006). "Amber force field implementation, molecular modelling study, synthesis and MMP-1/MMP-2 inhibition profile of (R)- and (S)—N-hydroxy-2-(N-isopropoxybiphenyl-4-ylsulfonamido)-3-methylbutanamides." *Bioorg Med Chem* 14(12): 4260-4276.

Voigt, A., L. A. Berlemann and K. F. Winklhofer (2016). "The mitochondrial kinase PINK1: functions beyond mitophagy." *J Neurochem* 139 Suppl 1: 232-239.

Vyas, S., E. Zaganjor and M. C. Haigis (2016). "Mitochondria and Cancer."*Cell* 166(3): 555-566.

Wai, T., J. Garcia-Prieto, M. J. Baker, C. Merkwirth, P. Benit, P. Rustin, F. J. Ruperez, C. Barbas, B. Ibanez and T. Langer (2015). "Imbalanced OPA1 processing and mitochondrial fragmentation cause heart failure in mice." *Science* 350(6265): aad0116.

Wai, T., S. Saita, H. Nolte, S. Muller, T. Konig, R. Richter-Dennerlein, H. G. Sprenger, J. Madrenas, M. Muhlmeister, U. Brandt, M. Kruger and T. Langer (2016). "The membrane scaffold SLP2 anchors a proteolytic hub in mitochondria containing PARL and the i-AAA protease YME1L." *EMBO Rep* 17(12): 1844-1856.

Wallace, D. C. (2012). "Mitochondria and cancer." *Nat Rev Cancer* 12(10): 685-698.

Wang, H., P. Song, L. Du, W. Tian, W. Yue, M. Liu, D. Li, B. Wang, Y. Zhu, C. Cao, J. Zhou and Q. Chen (2011). "Parkin ubiquitinates Drp1 for proteasome-dependent degradation: implication of dysregulated mitochondrial dynamics in Parkinson disease." *J Biol Chem* 286(13): 11649-11658.

Wang, X., B. Su, S. L. Siedlak, P. I. Moreira, H. Fujioka, Y. Wang, G. Casadesus and X. Zhu (2008). "Amyloid-beta overproduction causes abnormal mitochondrial dynamics via differential modulation of mitochondrial fission/fusion proteins." *Proc Natl Acad Sci USA* 105(49): 19318-19323.

Wang, Z., M. Iwasaki, F. Ficara, C. Lin, C. Matheny, S. H. Wong, K. S. Smith and M. L. Cleary (2010). "GSK-3 promotes conditional association of CREB and its coactivators with MEIS1 to facilitate HOX-mediated transcription and oncogenesis." *Cancer Cell* 17(6): 597-608.

Warburg, O. (1956). "On the origin of cancer cells." *Science* 123(3191): 309-314.

Xiao, X., Y. Hu, P. M. Quiros, Q. Wei, C. Lopez-Otin and Z. Dong (2014). "OMA1 mediates OPA1 proteolysis and mitochondrial fragmentation in experimental models of ischemic kidney injury." *Am J Physiol Renal Physiol* 306(11): F1318-1326.

Yan, J., X. H. Liu, M. Z. Han, Y. M. Wang, X. L. Sun, N. Yu, T. Li, B. Su and Z. Y. Chen (2015). "Blockage of GSK3beta-mediated Drp1 phosphorylation provides neuroprotection in neuronal and mouse models of Alzheimer's disease." *Neurobiol Aging* 36(1): 211-227.

Yang, X., Q. Shi, J. Sun, Y. Lv, Y. Ma, C. Chen, K. Xiao, W. Zhou and X. P. Dong (2017). "Aberrant Alterations of Mitochondrial Factors Drp1 and Opal in the Brains of Scrapie Experiment Rodents." *J Mol Neurosci* 61(3): 368-378.

Yang, Y., Y. Ouyang, L. Yang, M. F. Beal, A. McQuibban, H. Vogel and B. Lu (2008). "Pink1 regulates mitochondrial dynamics through interaction with the fission/fusion machinery." *Proc Natl Acad Sci USA* 105(19): 7070-7075.

Yao, J., R. W. Irwin, L. Zhao, J. Nilsen, R. T. Hamilton and R. D. Brinton (2009). "Mitochondrial bioenergetic deficit precedes Alzheimer's pathology in female mouse model of Alzheimer's disease." *Proc Natl Acad Sci USA* 106 (34): 14670-14675.

Zhang, T., L. Xue, L. Li, C. Tang, Z. Wan, R. Wang, J. Tan, Y. Tan, H. Han, R. Tian, T. R. Billiar, W. A. Tao and Z. Zhang (2016). "BNIP3 Protein Suppresses PINK1 Kinase Proteolytic Cleavage to Promote Mitophagy." *J Biol Chem* 291(41): 21616-21629.

Zhang, Y., M. James, F. A. Middleton and R. L. Davis (2005). "Transcriptional analysis of multiple brain regions in Parkinson's disease supports the involvement of specific protein processing, energy metabolism, and signaling pathways, and suggests novel disease mechanisms." *Am J Med Genet* B Neuropsychiatr Genet 137B (1): 5-16.

Zhao, X., C. Tian, W. M. Puszyk, O. O. Ogunwobi, M. Cao, T. Wang, R. Cabrera, D. R. Nelson and C. Liu (2013). "OPA1 downregulation is involved in sorafenib-induced apoptosis in hepatocellular carcinoma." *Lab Invest* 93(1): 8-19.

Zuchner, S., I. V. Mersiyanova, M. Muglia, N. Bissar-Tadmouri, J. Rochelle, E. L. Dadali, M. Zappia, E. Nelis, A. Patitucci, J. Senderek, Y. Parman, O. Evgrafov, P. D. Jonghe, Y. Takahashi, S. Tsuji, M. A. Pericak-Vance, A. Quattrone, E. Battaloglu, A. V. Polyakov, V. Timmerman, J. M. Schroder and J. M. Vance (2004). "Mutations in the mitochondrial GTPase mitofusin 2 cause Charcot-Marie-Tooth neuropathy type 2A." *Nat Genet* 36(5): 449-451.

PATENT CITATIONS

CN105769863B
CN110302199A
EP1712231A2
U.S. Pat. No. 5,852,195
U.S. Pat. No. 6,169,181
US20050020517A1
WO1995015972A1
WO2002036110A2
WO2004052831A2
WO2004087139A1
WO2008142090A1
WO2010033219A2
JP271816298
JP271819072
JP273710022
KR290283
KR513307
U.S. Ser. No. 15/296,2773
US224375049
U.S. Pat. No. 39,387,348
U.S. Pat. No. 39,444,655
U.S. Pat. No. 39,448,341
U.S. Pat. No. 39,464,492
U.S. Pat. No. 39,496,938
U.S. Pat. No. 39,508,105
U.S. Pat. No. 39,708,032
U.S. Pat. No. 39,828,430
U.S. Pat. No. 39,880,401
U.S. Pat. No. 39,914,181
U.S. Pat. No. 39,930,483

U.S. Pat. No. 39,977,358
U.S. Pat. No. 39,988,591
US40048676
US40076630
US40104645
US40108953
US40170483
US40244744
US40270458
US40274202
US40379080
US40454594
US40614434
US40680642
US40697127
US40923452
U.S. Pat. No. 41,144,813
U.S. Pat. No. 41,161,893
U.S. Pat. No. 41,207,728
U.S. Pat. No. 41,389,242
U.S. Pat. No. 41,412,787
U.S. Pat. No. 41,412,788
U.S. Pat. No. 41,429,131
U.S. Pat. No. 41,522,431
U.S. Pat. No. 41,646,456
U.S. Pat. No. 41,678,020
U.S. Pat. No. 41,682,212
U.S. Pat. No. 41,807,878
U.S. Pat. No. 41,838,863
U.S. Pat. No. 42,579,072
U.S. Pat. No. 42,983,588
U.S. Pat. No. 42,992,632
WO1995030670
WO1997021683
WO1997021685
WO1998022106
WO1999006024
WO1999006043
WO1999006044
WO2000055150
WO2001052821
WO2003090690
WO2004052831
WO2004052883
WO2004060370
WO2006055455
WO2006055660
WO2006060159
WO2006060175
WO2006060177
WO2007092802
WO2007103740
WO2007114978
WO2008112289
WO2008142090

NON-PATENT CITATIONS

APTIVUS (tipranavir) Label—FDA

*Remington's Pharmaceutical Sciences,* 17th ed. (1985)

Alavi M. V. (2020) "OMA1—An integral membrane protease" *Biochim Biophys Acta Proteins Proteom.* 2020 Oct. 29:140558.

Alavi, M. V. (2019). "Targeted OMA1 therapies for cancer." *Int J Cancer* 145(9): 2330-41.

Alavi M V & Fuhrmann N. (2013) "Dominant optic atrophy, OPA1, and mitochondrial quality control: understanding mitochondrial network dynamics."*Mol Neurodegener.* 25; 8:32.

Berge, S. M., et al. (1977). "Pharmaceutical Salts," *J. Pharm. Sci.,* 66: 1-19.

Head, B., et al. (2009). "Inducible proteolytic inactivation of OPA1 mediated by the OMA1 protease in mammalian cells." *J Cell Biol.* 187(7): 959-66.

Kong, B. Q., et. al. (2014). "p53 is required for cisplatin-induced processing of the mitochondrial fusion protein L-Opal that is mediated by the mitochondrial metallopeptidase Oma1 in gynecologic cancers." *J Biol Chem* 289(39): 27134-45.

Pal, H. C., et. al. (2017). "Cryptolepine inhibits melanoma cell growth through coordinated changes in mitochondrial biogenesis, dynamics and metabolic tumor suppressor AMPKalpha1/2-LKB1.*" Sci Rep* 7(1): 1498.

Rautio J, et al. (2008) "Prodrugs: design and clinical applications." *Nat Rev Drug Discov.* 7(3): 255-70.

Santin, G., et. al. (2013). "Mitochondrial fusion: a mechanism of cisplatin-induced resistance in neuroblastoma cells?" *Neurotoxicology* 34: 51-60.

Tang, Q., et. al. (2018). "Dynamin-related protein 1-mediated mitochondrial fission contributes to IR-783-induced apoptosis in human breast cancer cells." *J Cell Mol Med* 22(9): 4474-4485.

Zhao, X., et. al. (2013). "OPA1 downregulation is involved in sorafenib-induced apoptosis in hepatocellular carcinoma." *Lab Invest* 93(1): 8-19.

Akhtar, M. W., S. Sanz-Blasco, N. Dolatabadi, J. Parker, K. Chon, M. S. Lee, W. Soussou, S. R. McKercher, R. Ambasudhan, T. Nakamura and S. A. Lipton (2016). "Elevated glucose and oligomeric beta-amyloid disrupt synapses via a common pathway of aberrant protein S-nitrosylation. *Nat Commun* 7: 10242.

Alavi, M. V., S. Bette, S. Schimpf, F. Schuettauf, U. Schraermeyer, H. F. Wehrl, L. Ruttiger, S. C. Beck, F. Tonagel, B. J. Pichler, M. Knipper, T. Peters, J. Laufs and B. Wissinger (2007). "A splice site mutation in the murine Opal gene features pathology of autosomal dominant optic atrophy."*Brain* 130(Pt 4): 1029-1042.

Alavi, M. V. and N. Fuhrmann (2013). "Dominant optic atrophy, OPA1, and mitochondrial quality control: understanding mitochondrial network dynamics." *Mol Neurodegener* 8(1): 32.

Alexander, C., M. Votruba, U. E. Pesch, D. L. Thiselton, S. Mayer, A. Moore, M. Rodriguez, U. Kellner, B. Leo-Kottler, G. Auburger, S. S. Bhattacharya and B. Wissinger (2000). "OPA1, encoding a dynamin-related GTPase, is mutated in autosomal dominant optic atrophy linked to chromosome 3q28.*" Nat Genet* 26(2): 211-215.

Aliev, G., D. Seyidova, B. T. Lamb, M. E. Obrenovich, S. L. Siedlak, H. V. Vinters, R. P. Friedland, J. C. LaManna, M. A. Smith and G. Perry (2003). "Mitochondria and vascular lesions as a central target for the development of Alzheimer's disease and Alzheimer disease-like pathology in transgenic mice." *Neurol Res* 25(6): 665-674.

Alirol, E. and J. C. Martinou (2006). "Mitochondria and cancer: is there a morphological connection?" *Oncogene* 25(34): 4706-4716.

Ameri, K., A. Jahangiri, A. M. *Rajah*, K. V. Tormos, R. Nagarajan, M. Pekmezci, V. Nguyen, M. L. Wheeler, M. P. Murphy, T. A. Sanders, S. S. Jeffrey, Y. Yeghiazarians, P. F. Rinaudo, J. F. Costello, M. K. Aghi and E. Maltepe (2015). "HIGD1A Regulates Oxygen Consumption, ROS Production, and AMPK Activity during Glucose Deprivation to Modulate Cell Survival and Tumor Growth."*Cell Rep.*

Ameri, K. and E. Maltepe (2015). "HIGD1A-mediated dormancy and tumor survival." *Mol Cell Oncol* 2(4): e1030537.

Ameri, K., A. M. Rajah, V. Nguyen, T. A. Sanders, A. Jahangiri, M. Delay, M. Donne, H. J. Choi, K. V. Tormos, Y. Yeghiazarians, S. S. Jeffrey, P. F. Rinaudo, D. H. Rowitch, M. Aghi and E. Maltepe (2013). "Nuclear localization of the mitochondrial factor HIGD1A during metabolic stress." *PLoS One* 8(4): e62758.

An, H. J., G. Cho, J. O. Lee, S. G. Paik, Y. S. Kim and H. Lee (2013). "Higd-1a interacts with Opal and is required for the morphological and functional integrity of mitochondria." *Proc Natl Acad Sci USA* 110(32): 13014-13019.

An, H. J., H. Shin, S. G. Jo, Y. J. Kim, J. O. Lee, S. G. Paik and H. Lee (2011). "The survival effect of mitochondrial Higd-1a is associated with suppression of cytochrome C release and prevention of caspase activation." *Biochim Biophys Acta* 1813(12): 2088-2098.

Baek, S. H., S. J. Park, J. I. Jeong, S. H. Kim, J. Han, J. W. Kyung, S. H. Baik, Y. Choi, B. Y. Choi, J. S. Park, G. Bahn, J. H. Shin, D. S. Jo, J. Y. Lee, C. G. Jang, T. V. Arumugam, J. Kim, J. W. Han, J. Y. Koh, D. H. Cho and D. G. Jo (2017). "Inhibition of Drp1 Ameliorates Synaptic Depression, Abeta Deposition, and Cognitive Impairment in an Alzheimer's Disease Model." *J Neurosci* 37(20): 5099-5110.

Barrera, M., S. Koob, D. Dikov, F. Vogel and A. S. Reichert (2016). "OPA1 functionally interacts with MIC60 but is dispensable for crista junction formation." *FEBS Lett* 590(19): 3309-3322.

Bohovych, I., S. Kastora, S. Christianson, D. Topil, H. Kim, T. Fangman, Y. J. Zhou, A. Barrientos, J. Lee, A. J. Brown and O. Khalimonchuk (2016). "Oma1 Links Mitochondrial Protein Quality Control and TOR Signaling To Modulate Physiological Plasticity and Cellular Stress Responses." *Mol Cell Biol* 36(17): 2300-2312.

Bond, M. R. and J. A. Hanover (2015). "A little sugar goes a long way: the cell biology of O-GlcNAc." *J Cell Biol* 208(7): 869-880.

Bose, A. and M. F. Beal (2016). "Mitochondrial dysfunction in Parkinson's disease." *J Neurochem* 139 Suppl 1: 216-231.

Burke, N., A. R. Hall and D. J. Hausenloy (2015). "OPA1 in Cardiovascular Health and Disease." *Curr Drug Targets* 16(8): 912-920.

Burte, F., V. Carelli, P. F. Chinnery and P. Yu-Wai-Man (2015). "Disturbed mitochondrial dynamics and neurodegenerative disorders." *Nat Rev Neurol* 11(1): 11-24.

Butterfield, D. A., J. Drake, C. Pocernich and A. Castegna (2001). "Evidence of oxidative damage in Alzheimer's disease brain: central role for amyloid beta-peptide." *Trends Mol Med* 7(12): 548-554.

Cardoso, S. M., I. Santana, R. H. Swerdlow and C. R. Oliveira (2004). "Mitochondria dysfunction of Alzheimer's disease cybrids enhances Abeta toxicity." *J Neurochem* 89(6): 1417-1426.

Carelli, V., F. N. Ross-Cisneros and A. A. Sadun (2002). "Optic nerve degeneration and mitochondrial dysfunction: genetic and acquired optic neuropathies." *Neurochem Int* 40(6): 573-584.

Carelli, V., F. N. Ross-Cisneros and A. A. Sadun (2004). "Mitochondrial dysfunction as a cause of optic neuropathies." *Prog Retin Eye Res* 23(1): 53-89.

Carvalho, A. S., H. Ribeiro, P. Voabil, D. Penque, O. N. Jensen, H. Molina and R. Matthiesen (2014). "Global mass spectrometry and transcriptomics array based drug profiling provides novel insight into glucosamine induced endoplasmic reticulum stress." *Mol Cell Proteomics* 13(12): 3294-3307.

Caspersen, C., N. Wang, J. Yao, A. Sosunov, X. Chen, J. W. Lustbader, H. W. Xu, D. Stem, G. McKhann and S. D. Yan (2005). "Mitochondrial Abeta: a potential focal point for neuronal metabolic dysfunction in Alzheimer's disease." *FASEB J* 19(14): 2040-2041.

Chen, L., Q. Gong, J. P. Stice and A. A. Knowlton (2009). "Mitochondrial OPA1, apoptosis, and heart failure." *Cardiovasc Res* 84(1): 91-99.

Chen, L., T. Liu, A. Tran, X. Lu, A. A. Tomilov, V. Davies, G. Cortopassi, N. Chiamvimonvat, D. M. Bers, M. Votruba and A. A. Knowlton (2012). "OPA1 mutation and late-onset cardiomyopathy: mitochondrial dysfunction and mtDNA instability." *J Am Heart Assoc* 1(5): e003012.

Choubey, V., D. Safiulina, A. Vaarmann, M. Cagalinec, P. Wareski, M. Kuum, A. Zharkovsky and A. Kaasik (2011). "Mutant A53T alpha-synuclein induces neuronal death by increasing mitochondrial autophagy." *J Biol Chem* 286(12): 10814-10824.

Chrysostomou, V., F. Rezania, I. A. Trounce and J. G. Crowston (2013). "Oxidative stress and mitochondrial dysfunction in glaucoma." *Curr Opin Pharmacol* 13(1): 12-15.

Cipolat, S., T. Rudka, D. Hartmann, V. Costa, L. Serneels, K. Craessaerts, K. Metzger, C. Frezza, W. Annaert, L. D'Adamio, C. Derks, T. Dejaegere, L. Pellegrini, R. D'Hooge, L. Scorrano and B. De Strooper (2006). "Mitochondrial rhomboid PARL regulates cytochrome c release during apoptosis via OPA1-dependent cristae remodeling." *Cell* 126(1): 163-175.

Cogliati, S., C. Frezza, M. E. Soriano, T. Varanita, R. *Quintana*-Cabrera, M. Corrado, S. Cipolat, V. Costa, A. Casarin, L. C. Gomes, E. Perales-Clemente, L. Salviati, P. Fernandez-Silva, J. A. Enriquez and L. Scorrano (2013). "Mitochondrial cristae shape determines respiratory chain supercomplexes assembly and respiratory efficiency." *Cell* 155(1): 160-171.

Coughlin, L., R. S. Morrison, P. J. Horner and D. M. Inman (2015). "Mitochondrial morphology differences and mitophagy deficit in murine glaucomatous optic nerve." *Invest Ophthalmol Vis Sci* 56(3): 1437-1446.

Daoud, H., P. N. Valdmanis, F. Gros-Louis, V. Belzil, D. Spiegelman, E. Henrion, O. Diallo, A. Desjarlais, J. Gauthier, W. Camu, P. A. Dion and G. A. Rouleau (2011). "Resequencing of 29 candidate genes in patients with familial and sporadic amyotrophic lateral sclerosis." *Arch Neurol* 68(5): 587-593.

Delettre, C., G. Lenaers, J. M. Griffoin, N. Gigarel, C. Lorenzo, P. Belenguer, L. Pelloquin, J. Grosgeorge, C. Turc-Carel, E. Perret, C. Astarie-Dequeker, L. Lasquellec, B. Arnaud, B. Ducommun, J. Kaplan and C. P. Hamel (2000). "Nuclear gene OPA1, encoding a mitochondrial dynamin-related protein, is mutated in dominant optic atrophy." *Nat Genet* 26(2): 207-210.

Devi, L., B. M. Prabhu, D. F. Galati, N. G. Avadhani and H. K. Anandatheerthavarada (2006). "Accumulation of amyloid precursor protein in the mitochondrial import channels of human Alzheimer's disease brain is associated with mitochondrial dysfunction." *J Neurosci* 26(35): 9057-9068.

Diana, A., G. Simic, E. Sinforiani, N. Orru, G. Pichiri and G. Bono (2008). "Mitochondria morphology and DNA content upon sublethal exposure to beta-amyloid(1-42) peptide."*Coll Antropol* 32 Suppl 1: 51-58.

Dolle, C., I. Flones, G. S. Nido, H. Miletic, N. Osuagwu, S. Kristoffersen, P. K. Lilleng, J. P. Larsen, O. B. Tysnes, K. Haugarvoll, L. A. Bindoff and C. Tzoulis (2016). "Defective mitochondrial DNA homeostasis in the substantia nigra in Parkinson disease." *Nat Commun* 7: 13548.

Dorn, G. W., 2nd (2013). "Mitochondrial dynamics in heart disease." *Biochim Biophys Acta* 1833(1): 233-241.

Duvezin-Caubet, S., R. Jagasia, J. Wagener, S. Hofmann, A. Trifunovic, A. Hansson, A. Chomyn, M. F. Bauer, G. Attardi, N. G. Larsson, W. Neupert and A. S. Reichert (2006). "Proteolytic processing of OPA1 links mitochondrial dysfunction to alterations in mitochondrial morphology." *J Biol Chem* 281(49): 37972-37979.

Eberlin, M., T. Muck and M. C. Michel (2012). "A comprehensive review of the pharmacodynamics, pharmacokinetics, and clinical effects of the neutral endopeptidase inhibitor racecadotril." *Front Pharmacol* 3: 93.

Eckert, A., S. Hauptmann, I. Scherping, V. Rhein, F. Muller-Spahn, J. Gotz and W. E. Muller (2008). "Soluble beta-amyloid leads to mitochondrial defects in amyloid precursor protein and tau transgenic mice." *Neurodegener Dis* 5(3-4): 157-159.

Edgar, R., M. Domrachev and A. E. Lash (2002). "Gene Expression Omnibus: NCBI gene expression and hybridization array data repository." *Nucleic Acids Res* 30(1): 207-210.

Ehses, S., I. Raschke, G. Mancuso, A. Bernacchia, S. Geimer, D. Tondera, J. C. Martinou, B. Westermann, E. I. Rugarli and T. Langer (2009). "Regulation of OPA1 processing and mitochondrial fusion by m-AAA protease isoenzymes and OMA1." *J Cell Biol* 187(7): 1023-1036.

Faccenda, D., J. Nakamura, G. Gorini, G. K. Dhoot, M. Piacentini, M. Yoshida and M. Campanella (2017). "Control of Mitochondrial Remodeling by the ATPase Inhibitory Factor 1 Unveils a Pro-survival Relay via OPA1." *Cell Rep* 18(8): 1869-1883.

Frezza, C., S. Cipolat, O. Martins de Brito, M. Micaroni, G. V. Beznoussenko, T. Rudka, D. Bartoli, R. S. Polishuck, N. N. Danial, B. De Strooper and L. Scorrano (2006). "OPA1 controls apoptotic cristae remodeling independently from mitochondrial fusion." *Cell* 126 (1): 177-189.

Frezza, C. and E. Gottlieb (2009). "Mitochondria in cancer: not just innocent bystanders." *Semin Cancer Biol* 19(1): 4-11.

Fuhrmann, N., S. Schimpf, Y. Kamenisch, B. Leo-Kottler, C. Alexander, G. Auburger, E. Zrenner, B. Wissinger and M. V. Alavi (2010). "Solving a 50 year mystery of a missing OPA1 mutation: more insights from the first family diagnosed with autosomal dominant optic atrophy." *Mol Neurodegener* 5(1): 25.

Ghio, S., F. Kamp, R. Cauchi, A. Giese and N. Vassallo (2016). "Interaction of alpha-synuclein with biomembranes in Parkinson's disease—role of cardiolipin." *Prog Lipid Res* 61: 73-82.

Gibson, G. E., K. F. Sheu and J. P. Blass (1998). "Abnormalities of mitochondrial enzymes in Alzheimer disease." *J Neural Transm* (Vienna) 105(8-9): 855-870.

Gleissner, C. A., I. Shaked, K. M. Little and K. Ley (2010). "CXC chemokine ligand 4 induces a unique transcriptome in monocyte-derived macrophages." *J Immunol* 184(9): 4810-4818.

Glytsou, C., E. Calvo, S. Cogliati, A. Mehrotra, I. Anastasia, G. Rigoni, A. Raimondi, N. Shintani, M. Loureiro, J. Vazquez, L. Pellegrini, J. A. Enriquez, L. Scorrano and M. E. Soriano (2016). "Optic Atrophy 1 Is Epistatic to the Core MICOS Component MIC60 in Mitochondrial Cristae Shape Control." *Cell Rep* 17(11): 3024-3034.

Griparic, L., T. Kanazawa and A. M. van der Bliek (2007). "Regulation of the mitochondrial dynamin-like protein Opal by proteolytic cleavage." *J Cell Biol* 178(5): 757-764.

Guardia-Laguarta, C., E. Area-Gomez, C. Rub, Y. Liu, J. Magrane, D. Becker, W. Voos, E. A. Schon and S. Przedborski (2014). "alpha-Synuclein is localized to mitochondria-associated ER membranes." *J Neurosci* 34(1): 249-259.

Guo, Y., X. Chen, H. Zhang, N. Li, X. Yang, W. Cheng and K. Zhao (2012). "Association of OPA1 polymorphisms with NTG and HTG: a meta-analysis." *PLoS One* 7(8): e42387.

Hackenbrock, C. R. (1966). "Ultrastructural bases for metabolically linked mechanical activity in mitochondria. I. Reversible ultrastructural changes with change in metabolic steady state in isolated liver mitochondria." *J Cell Biol* 30(2): 269-297.

Hanahan, D. and R. A. Weinberg (2011). "Hallmarks of cancer: the next generation." *Cell* 144(5): 646-674.

Head, B., L. Griparic, M. Amiri, S. Gandre-Babbe and A. M. van der Bliek (2009). "Inducible proteolytic inactivation of OPA1 mediated by the OMA1 protease in mammalian cells." *J Cell Biol* 187(7): 959-966.

Hessenberger, M., R. M. Zerbes, H. Rampelt, S. Kunz, A. H. Xavier, B. Purfurst, H. Lilie, N. Pfanner, M. van der Laan and O. Daumke (2017). "Regulated membrane remodeling by Mic60 controls formation of mitochondrial crista junctions." *Nat Commun* 8: 15258.

Hokama, M., S. Oka, J. Leon, T. Ninomiya, H. Honda, K. Sasaki, T. Iwaki, T. Ohara, T. Sasaki, F. M. LaFerla, Y. Kiyohara and Y. Nakabeppu (2014). "Altered expression of diabetes-related genes in Alzheimer's disease brains: the Hisayama study." *Cereb Cortex* 24(9): 2476-2488.

Imaizumi, Y., Y. Okada, W. Akamatsu, M. Koike, N. Kuzumaki, H. Hayakawa, T. Nihira, T. Kobayashi, M. Ohyama, S. Sato, M. Takanashi, M. Funayama, A. Hirayama, T. Soga, T. Hishiki, M. Suematsu, T. Yagi, D. Ito, A. Kosakai, K. Hayashi, M. Shouji, A. Nakanishi, N. Suzuki, Y. Mizuno, N. Mizushima, M. Amagai, Y. Uchiyama, H. Mochizuki, N. Hattori and H. Okano (2012). "Mitochondrial dysfunction associated with increased oxidative stress and alpha-synuclein accumulation in PARK2 iPSC-derived neurons and postmortem brain tissue." *Mol Brain* 5: 35.

Ishihara, N., Y. Fujita, T. Oka and K. Mihara (2006). "Regulation of mitochondrial morphology through proteolytic cleavage of OPA1." *EMBO J* 25(13): 2966-2977.

Jakobs, S., N. Martini, A. C. Schauss, A. Egner, B. Westermann and S. W. Hell (2003). "Spatial and temporal dynamics of budding yeast mitochondria lacking the division component Fislp." *J Cell Sci* 116(Pt 10): 2005-2014.

Jiang, X., H. Jiang, Z. Shen and X. Wang (2014). "Activation of mitochondrial protease OMA1 by Bax and Bak promotes cytochrome c release during apoptosis." *Proc Natl Acad Sci USA.*

Ju, W. K., K. Y. Kim, J. D. Lindsey, M. Angert, K. X. Duong-Polk, R. T. Scott, J. J. Kim, I. Kukhmazov, M. H. Ellisman, G. A. Perkins and R. N. Weinreb (2008). "Intraocular pressure elevation induces mitochondrial fission and triggers OPA1 release in glaucomatous optic nerve." *Invest Ophthalmol Vis Sci* 49(11): 4903-4911.

Kandimalla, R., M. Manczak, D. Fry, Y. Suneetha, H. Sesaki and P. H. Reddy (2016). "Reduced dynamin-related protein 1 protects against phosphorylated Tau-induced mitochondrial dysfunction and synaptic damage in Alzheimer's disease." *Hum Mol Genet* 25(22): 4881-4897.

Kaser, M., M. Kambacheld, B. Kisters-Woike and T. Langer (2003). "Oma1, a novel membrane-bound metallopeptidase in mitochondria with activities overlapping with the m-AAA protease." *J Biol Chem* 278(47): 46414-46423.

Keeney, P. M., J. Xie, R. A. Capaldi and J. P. Bennett, Jr. (2006). "Parkinson's disease brain mitochondrial complex I has oxidatively damaged subunits and is functionally impaired and misassembled." *J Neurosci* 26(19): 5256-5264.

Kim, K. Y., G. A. Perkins, M. S. Shim, E. Bushong, N. Alcasid, S. Ju, M. H. Ellisman, R. N. Weinreb and W. K. Ju (2015). "DRP1 inhibition rescues retinal ganglion cells and their axons by preserving mitochondrial integrity in a mouse model of glaucoma." *Cell Death Dis* 6: e1839.

Kong, B., H. Tsuyoshi, M. Orisaka, D. B. Shieh, Y. Yoshida and B. K. Tsang (2015). "Mitochondrial dynamics regulating chemoresistance in gynecological cancers." *Ann N Y Acad Sci* 1350: 1-16.

Kong, B., Q. Wang, E. Fung, K. Xue and B. K. Tsang (2014). "p53 is required for cisplatin-induced processing of the mitochondrial fusion protein L-Opal that is mediated by the mitochondrial metallopeptidase Oma1 in gynecologic cancers." *J Biol Chem* 289(39): 27134-27145.

Kong, G. Y., N. J. Van Bergen, I. A. Trounce and J. G. Crowston (2009). "Mitochondrial dysfunction and glaucoma." *J Glaucoma* 18(2): 93-100.

Koob, S., M. Barrera, R. Anand and A. S. Reichert (2015). "The non-glycosylated isoform of MIC26 is a constituent of the mammalian MICOS complex and promotes formation of crista junctions." *Biochim Biophys Acta* 1853(7): 1551-1563.

Korwitz, A., C. Merkwirth, R. Richter-Dennerlein, S. E. Troder, H. G. Sprenger, P. M. Quiros, C. Lopez-Otin, E. I. Rugarli and T. Langer (2016). "Loss of OMA1 delays neurodegeneration by preventing stress-induced OPA1 processing in mitochondria." *J Cell Biol* 212(2): 157-166.

Landes, T., L. J. Emorine, D. Courilleau, M. Rojo, P. Belenguer and L. Arnaune-Pelloquin (2010). "The BH3-only Bnip3 binds to the dynamin Opal to promote mitochondrial fragmentation and apoptosis by distinct mechanisms." *EMBO Rep* 11(6): 459-465.

Le Page, S., M. Niro, J. Fauconnier, L. Cellier, S. Tamareille, A. Gharib, A. Chevrollier, L. Loufrani, C. Grenier, R. Kamel, E. Sarzi, A. Lacampagne, M. Ovize, D. Henrion, P. Reynier, G. Lenaers, D. Mirebeau-Prunier and F. Prunier (2016). "Increase in Cardiac Ischemia-Reperfusion Injuries in Opal+/− Mouse Model." *PLoS One* 11(10): e0164066.

Lee, S., N. J. Van Bergen, G. Y. Kong, V. Chrysostomou, H. S. Waugh, E. C. O'Neill, J. G. Crowston and I. A. Trounce (2011). "Mitochondrial dysfunction in glaucoma and emerging bioenergetic therapies." *Exp Eye Res* 93(2): 204-212.

Lenaers, G., P. Reynier, G. Elachouri, C. Soukkarieh, A. Olichon, P. Belenguer, L. Baricault, B. Ducommun, C. Hamel and C. Delettre (2009). "OPA1 functions in mitochondria and dysfunctions in optic nerve." *Int J Biochem Cell Biol* 41(10): 1866-1874.

Lesnick, T. G., S. Papapetropoulos, D. C. Mash, J. Ffrench-Mullen, L. Shehadeh, M. de Andrade, J. R. Henley, W. A. Rocca, J. E. Ahlskog and D. M. Maraganore (2007). "A genomic pathway approach to a complex disease: axon guidance and Parkinson disease." *PLoS Genet* 3(6): e98.

Li, F., N. Y. Calingasan, F. Yu, W. M. Mauck, M. Toidze, C. G. Almeida, R. H. Takahashi, G. A. Carlson, M. Flint Beal, M. T. Lin and G. K. Gouras (2004). "Increased plaque burden in brains of APP mutant MnSOD heterozygous knockout mice." *J Neurochem* 89(5): 1308-1312.

Lustbader, J. W., M. Cirilli, C. Lin, H. W. Xu, K. Takuma, N. Wang, C. Caspersen, X. Chen, S. Pollak, M. Chaney, F. Trinchese, S. Liu, F. Gunn-Moore, L. F. Lue, D. G. Walker, P. Kuppusamy, Z. L. Zewier, O. Arancio, D. Stem, S. S. Yan and H. Wu (2004). "ABAD directly links Abeta to mitochondrial toxicity in Alzheimer's disease." *Science* 304(5669): 448-452.

Lutz, A. K., N. Exner, M. E. Fett, J. S. Schlehe, K. Kloos, K. Lammermann, B. Brunner, A. Kurz-Drexler, F. Vogel, A. S. Reichert, L. Bouman, D. Vogt-Weisenhorn, W. Wurst, J. Tatzelt, C. Haass and K. F. Winklhofer (2009). "Loss of parkin or PINK1 function increases Drp1-dependent mitochondrial fragmentation." *J Biol Chem* 284(34): 22938-22951.

Manczak, M., T. S. Anekonda, E. Henson, B. S. Park, J. Quinn and P. H. Reddy (2006). "Mitochondria are a direct site of A beta accumulation in Alzheimer's disease neurons: implications for free radical generation and oxidative damage in disease progression." *Hum Mol Genet* 15(9): 1437-1449.

Manczak, M., M. J. Calkins and P. H. Reddy (2011). "Impaired mitochondrial dynamics and abnormal interaction of amyloid beta with mitochondrial protein Drp1 in neurons from patients with Alzheimer's disease: implications for neuronal damage." *Hum Mol Genet* 20(13): 2495-2509.

Manczak, M., R. Kandimalla, D. Fry, H. Sesaki and P. H. Reddy (2016). "Protective effects of reduced dynamin-related protein 1 against amyloid beta-induced mitochondrial dysfunction and synaptic damage in Alzheimer's disease." *Hum Mol Genet* 25(23): 5148-5166.

Manczak, M. and P. H. Reddy (2012). "Abnormal interaction between the mitochondrial fission protein Drp1 and hyperphosphorylated tau in Alzheimer's disease neurons: implications for mitochondrial dysfunction and neuronal damage." *Hum Mol Genet* 21(11): 2538-2547.

Maraganore, D. M., M. de Andrade, T. G. Lesnick, K. J. Strain, M. J. Farrer, W. A. Rocca, P. V. Pant, K. A. Frazer, D. R. Cox and D. G. Ballinger (2005). "High-resolution whole-genome association study of Parkinson disease." *Am J Hum Genet* 77(5): 685-693.

Maresca, A., C. la Morgia, L. Caporali, M. L. Valentino and V. Carelli (2013). "The optic nerve: a "mito-window"on mitochondrial neurodegeneration." *Mol Cell Neurosci* 55: 62-76.

Marin-Garcia, J. and A. T. Akhmedov (2016). "Mitochondrial dynamics and cell death in heart failure." *Heart Fail Rev* 21(2): 123-136.

Maurer, I., S. Zierz and H. J. Moller (2000). "A selective defect of cytochrome c oxidase is present in brain of Alzheimer disease patients." *Neurobiol Aging* 21(3): 455-462.

Medja, F., V. Lelievre, R. H. Fontaine, F. Lebas, P. Leroux, T. Ouimet, A. Saria, C. Rougeot, P. Dournaud and P. Gressens (2006). "Thiorphan, a neutral endopeptidase inhibitor used for diarrhoea, is neuroprotective in newborn mice."*Brain* 129(Pt 12): 3209-3223.

Merkwirth, C., S. Dargazanli, T. Tatsuta, S. Geimer, B. Lower, F. T. Wunderlich, J. C. von Kleist-Retzow, A. Waisman, B. Westermann and T. Langer (2008). "Prohibitins control cell proliferation and apoptosis by regulating OPA1-dependent cristae morphogenesis in mitochondria." *Genes Dev* 22(4): 476-488.

Miller, J. A., R. L. Woltjer, J. M. Goodenbour, S. Horvath and D. H. Geschwind (2013). "Genes and pathways underlying regional and cell type changes in Alzheimer's disease." *Genome Med* 5(5): 48.

Mukherjee, U. A., S. B. Ong, S. G. Ong and D. J. Hausenloy (2015). "Parkinson's disease proteins: Novel mitochondrial targets for cardioprotection." *Pharmacol Ther* 156: 34-43.

Nakamura, K. (2013). "alpha-Synuclein and mitochondria: partners in crime?"*Neurotherapeutics* 10(3): 391-399.

Nakamura, K., V. M. Nemani, F. Azarbal, G. Skibinski, J. M. Levy, K. Egami, L. Munishkina, J. Zhang, B. Gardner, J. Wakabayashi, H. Sesaki, Y. Cheng, S. Finkbeiner, R. L. Nussbaum, E. Masliah and R. H. Edwards (2011). "Direct membrane association drives mitochondrial fission by the Parkinson disease-associated protein alpha-synuclein." *J Biol Chem* 286(23): 20710-20726.

Niemann, A., M. Ruegg, V. La Padula, A. Schenone and U. Suter (2005). "Ganglioside-induced differentiation associated protein 1 is a regulator of the mitochondrial network: new implications for Charcot-Marie-Tooth disease." *J Cell Biol* 170(7): 1067-1078.

Olichon, A., L. Baricault, N. Gas, E. Guillou, A. Valette, P. Belenguer and G. Lenaers (2003). "Loss of OPA1 perturbates the mitochondrial inner membrane structure and integrity, leading to cytochrome c release and apoptosis." *J Biol Chem* 278(10): 7743-7746.

Ong, S. B., S. B. Kalkhoran, S. Hernandez-Resendiz, P. Samangouei, S. G. Ong and D. J. Hausenloy (2017). "Mitochondrial-Shaping Proteins in Cardiac Health and Disease—the Long and the Short of It!" *Cardiovasc Drugs Ther* 31(1): 87-107.

Osborne, N. N. (2010). "Mitochondria: Their role in ganglion cell death and survival in primary open angle glaucoma." *Exp Eye Res* 90(6): 750-757.

Ott, C., E. Dorsch, M. Fraunholz, S. Straub and V. Kozjak-Pavlovic (2015). "Detailed analysis of the human mitochondrial contact site complex indicate a hierarchy of subunits." *PLoS One* 10(3): e0120213.

Pan, J. Z., H. Wei, J. G. Hecker, J. W. Tobias, R. G. Eckenhoff and M. F. Eckenhoff (2006). "Rat brain DNA transcript profile of halothane and isoflurane exposure." *Pharmacogenet Genomics* 16(3): 171-182.

Parker, W. D., Jr., C. M. Filley and J. K. Parks (1990). "Cytochrome oxidase deficiency in Alzheimer's disease." *Neurology* 40(8): 1302-1303.

Parker, W. D., Jr., J. K. Parks and R. H. Swerdlow (2008). "Complex I deficiency in Parkinson's disease frontal cortex." *Brain Res* 1189: 215-218.

Philibert, R. A., G. Y. Ryu, J. G. Yoon, H. Sandhu, N. Hollenbeck, T. Gunter, A. Barkhurst, W. Adams and A. Madan (2007). "Transcriptional profiling of subjects from the Iowa adoption studies." *Am J Med Genet B Neuropsychiatr Genet* 144B(5): 683-690.

Piquereau, J., F. Caffin, M. Novotova, C. Lemaire, V. Veksler, A. Garnier, R. Ventura-Clapier and F. Joubert (2013). "Mitochondrial dynamics in the adult cardiomyocytes: which roles for a highly specialized cell?" *Front Physiol* 4: 102.

Piquereau, J., F. Caffin, M. Novotova, A. Prola, A. Garnier, P. Mateo, D. Fortin, H. Huynh le, V. Nicolas, M. V. Alavi, C. Brenner, R. Ventura-Clapier, V. Veksler and F. Joubert (2012). "Down-regulation of OPA1 alters mouse mitochondrial morphology, PTP function, and cardiac adaptation to pressure overload." *Cardiovasc Res* 94(3): 408-417.

Rainbolt, T. K., J. Lebeau, C. Puchades and R. L. Wiseman (2016). "Reciprocal Degradation of YME1L and OMA1 Adapts Mitochondrial Proteolytic Activity during Stress." *Cell Rep* 14(9): 2041-2049.

Rappold, P. M., M. Cui, J. C. Grima, R. Z. Fan, K. L. de Mesy-Bentley, L. Chen, X. Zhuang, W. J. Bowers and K. Tieu (2014). "Drp1 inhibition attenuates neurotoxicity and dopamine release deficits in vivo." *Nat Commun* 5: 5244.

Reddy, P. H., M. Manczak and X. Yin (2017). "Mitochondria-Division Inhibitor 1 Protects Against Amyloid-beta induced Mitochondrial Fragmentation and Synaptic Damage in Alzheimer's Disease." *J Alzheimers Dis* 58(1): 147-162.

Reddy, P. H., S. McWeeney, B. S. Park, M. Manczak, R. V. Gutala, D. Partovi, Y. Jung, V. Yau, R. Searles, M. Mori and J. Quinn (2004). "Gene expression profiles of transcripts in amyloid precursor protein transgenic mice: up-regulation of mitochondrial metabolism and apoptotic genes is an early cellular change in Alzheimer's disease." *Hum Mol Genet* 13(12): 1225-1240.

Richter, U., T. Lahtinen, P. Marttinen, F. Suomi and B. J. Battersby (2015). "Quality control of mitochondrial protein synthesis is required for membrane integrity and cell fitness." *J Cell Biol* 211(2): 373-389.

Rossello, A., E. Nuti, E. Orlandini, P. Carelli, S. Rapposelli, M. Macchia, F. Minutolo, L. Carbonaro, A. Albini, R. Benelli, G. Cercignani, G. Murphy and A. Balsamo (2004). "New N-arylsulfonyl-N-alkoxyaminoacetohydroxamic acids as selective inhibitors of gelatinase A (MMP-2)." *Bioorg Med Chem* 12(9): 2441-2450.

Sadun, A. A. (2002). "Mitochondrial optic neuropathies." *J Neurol Neurosurg Psychiatry* 72(4): 423-425.

Salminen, A., A. Haapasalo, A. Kauppinen, K. Kaarniranta, H. Soininen and M. Hiltunen (2015). "Impaired mitochondrial energy metabolism in Alzheimer's disease: Impact on pathogenesis via disturbed epigenetic regulation of chromatin landscape." *Prog Neurobiol* 131: 1-20.

Santos, D., A. R. Esteves, D. F. Silva, C. Januario and S. M. Cardoso (2015). "The Impact of Mitochondrial Fusion and Fission Modulation in Sporadic Parkinson's Disease." *Mol Neurobiol* 52(1): 573-586.

Schapira, A. H., J. M. Cooper, D. Dexter, J. B. Clark, P. Jenner and C. D. Marsden (1990). "Mitochondrial complex I deficiency in Parkinson's disease." *J Neurochem* 54(3): 823-827.

Schmidt, C., E. Lepsverdize, S. L. Chi, A. M. Das, S. V. Pizzo, A. Dityatev and M. Schachner (2008). "Amyloid precursor protein and amyloid beta-peptide bind to ATP synthase and regulate its activity at the surface of neural cells." *Mol Psychiatry* 13(10): 953-969.

Shields, L. Y., H. Kim, L. Zhu, D. Haddad, A. Berthet, D. Pathak, M. Lam, R. Ponnusamy, L. G. Diaz-Ramirez, T. M. Gill, H. Sesaki, L. Mucke and K. Nakamura (2015). "Dynamin-related protein 1 is required for normal mitochondrial bioenergetic and synaptic function in CA1 hippocampal neurons." *Cell Death Dis* 6: e1725.

Sit, A. J. (2014). "Intraocular pressure variations: causes and clinical significance." *Can J Ophthalmol* 49(6): 484-488.

Smith, M. A., G. Perry, P. L. Richey, L. M. Sayre, V. E. Anderson, M. F. Beal and N. Kowall (1996). "Oxidative damage in Alzheimer's." *Nature* 382(6587): 120-121.

Song, Z., H. Chen, M. Fiket, C. Alexander and D. C. Chan (2007). "OPA1 processing controls mitochondrial fusion and is regulated by mRNA splicing, membrane potential, and Yme1L." *J Cell Biol* 178(5): 749-755.

Stafa, K., E. Tsika, R. Moser, A. Musso, L. Glauser, A. Jones, S. Biskup, Y. Xiong, R. Bandopadhyay, V. L. Dawson, T. M. Dawson and D. J. Moore (2014). "Functional interaction of Parkinson's disease-associated LRRK2 with members of the dynamin GTPase superfamily." *Hum Mol Genet* 23(8): 2055-2077.

Takihara, Y., M. Inatani, K. Eto, T. Inoue, A. Kreymerman, S. Miyake, S. Ueno, M. Nagaya, A. Nakanishi, K. Iwao, Y. Takamura, H. Sakamoto, K. Satoh, M. Kondo, T. Sakamoto, J. L. Goldberg, J. Nabekura and H. Tanihara (2015). "In vivo imaging of axonal transport of mitochondria in the diseased and aged mammalian CNS." *Proc Natl Acad Sci USA* 112(33): 10515-10520.

Tan, E. P., S. R. McGreal, S. Graw, R. Tessman, S. J. Koppel, P. Dhakal, Z. Zhang, M. Machacek, N. E. Zachara, D. C. Koestler, K. R. Peterson, J. P. Thyfault, R. H. Swerdlow, P. Krishnamurthy, L. DiTacchio, U. Apte and C. Slawson (2017). "Sustained O-GlcNAcylation reprograms mitochondrial function to regulate energy metabolism." *J Biol Chem* 292(36): 14940-14962.

Taube, J. H., G. G. Malouf, E. Lu, N. Sphyris, V. Vijay, P. P. Ramachandran, K. R. Ueno, S. Gaur, M. S. Nicoloso, S. Rossi, J. I. Herschkowitz, J. M. Rosen, J. P. Issa, G. A. Calin, J. T. Chang and S. A. Mani (2013). "Epigenetic silencing of microRNA-203 is required for EMT and cancer stem cell properties." *Sci Rep* 3: 2687.

Taylor, J. P., J. Hardy and K. H. Fischbeck (2002). "Toxic proteins in neurodegenerative disease." *Science* 296 (5575): 1991-1995.

Thomas, E., J. J. Feld, Q. Li, Z. Hu, M. W. Fried and T. J. Liang (2011). "Ribavirin potentiates interferon action by augmenting interferon-stimulated gene induction in hepatitis C virus cell culture models." *Hepatology* 53(1): 32-41.

Tuccinardi, T., A. Martinelli, E. Nuti, P. Carelli, F. Balzano, G. Uccello-Barretta, G. Murphy and A. Rossello (2006). "Amber force field implementation, molecular modelling study, synthesis and MMP-1/MMP-2 inhibition profile of (R)- and (S)—N-hydroxy-2-(N-isopropoxybiphenyl-4-ylsulfonamido)-3-methylbutanamides." *Bioorg Med Chem* 14(12): 4260-4276.

Voigt, A., L. A. Berlemann and K. F. Winklhofer (2016). "The mitochondrial kinase PINK1: functions beyond mitophagy." *J Neurochem* 139 Suppl 1: 232-239.

Vyas, S., E. Zaganjor and M. C. Haigis (2016). "Mitochondria and Cancer." *Cell* 166(3): 555-566.

Wai, T., J. Garcia-Prieto, M. J. Baker, C. Merkwirth, P. Benit, P. Rustin, F. J. Ruperez, C. Barbas, B. Ibanez and T. Langer (2015). "Imbalanced OPA1 processing and mitochondrial fragmentation cause heart failure in mice." *Science* 350(6265): aad0116.

Wai, T., S. Saita, H. Nolte, S. Muller, T. Konig, R. Richter-Dennerlein, H. G. Sprenger, J. Madrenas, M. Muhlmeister, U. Brandt, M. Kruger and T. Langer (2016). "The membrane scaffold SLP2 anchors a proteolytic hub in mitochondria containing PARL and the i-AAA protease YME1L." *EMBO Rep* 17(12): 1844-1856.

Wallace, D. C. (2012). "Mitochondria and cancer." *Nat Rev Cancer* 12(10): 685-698.

Wang, H., P. Song, L. Du, W. Tian, W. Yue, M. Liu, D. Li, B. Wang, Y. Zhu, C. Cao, J. Zhou and Q. Chen (2011). "Parkin ubiquitinates Drp1 for proteasome-dependent degradation: implication of dysregulated mitochondrial dynamics in Parkinson disease." *J Biol Chem* 286(13): 11649-11658.

Wang, X., B. Su, S. L. Siedlak, P. I. Moreira, H. Fujioka, Y. Wang, G. Casadesus and X. Zhu (2008). "Amyloid-beta overproduction causes abnormal mitochondrial dynamics via differential modulation of mitochondrial fission/fusion proteins." *Proc Natl Acad Sci USA* 105 (49): 19318-19323.

Wang, Z., M. Iwasaki, F. Ficara, C. Lin, C. Matheny, S. H. Wong, K. S. Smith and M. L. Cleary (2010). "GSK-3 promotes conditional association of CREB and its coactivators with MEIS1 to facilitate HOX-mediated transcription and oncogenesis." *Cancer Cell* 17(6): 597-608.

Warburg, O. (1956). "On the origin of cancer cells." *Science* 123(3191): 309-314.

Xiao, X., Y. Hu, P. M. Quiros, Q. Wei, C. Lopez-Otin and Z. Dong (2014). "OMA1 mediates OPA1 proteolysis and mitochondrial fragmentation in experimental models of ischemic kidney injury." *Am J Physiol Renal Physiol* 306(11): F1318-1326.

Yan, J., X. H. Liu, M. Z. Han, Y. M. Wang, X. L. Sun, N. Yu, T. Li, B. Su and Z. Y. Chen (2015). "Blockage of GSK3beta-mediated Drp1 phosphorylation provides neuroprotection in neuronal and mouse models of Alzheimer's disease." *Neurobiol Aging* 36(1): 211-227.

Yang, X., Q. Shi, J. Sun, Y. Lv, Y. Ma, C. Chen, K. Xiao, W. Zhou and X. P. Dong (2017). "Aberrant Alterations of Mitochondrial Factors Drp1 and Opal in the Brains of Scrapie Experiment Rodents." *J Mol Neurosci* 61(3): 368-378.

Yang, Y., Y. Ouyang, L. Yang, M. F. Beal, A. McQuibban, H. Vogel and B. Lu (2008). "Pink1 regulates mitochondrial dynamics through interaction with the fission/fusion machinery." *Proc Natl Acad Sci USA* 105(19): 7070-7075.

Yao, J., R. W. Irwin, L. Zhao, J. Nilsen, R. T. Hamilton and R. D. Brinton (2009). "Mitochondrial bioenergetic deficit precedes Alzheimer's pathology in female mouse model of Alzheimer's disease." *Proc Natl Acad Sci USA* 106(34): 14670-14675.

Zhang, T., L. Xue, L. Li, C. Tang, Z. Wan, R. Wang, J. Tan, Y. Tan, H. Han, R. Tian, T. R. Billiar, W. A. Tao and Z. Zhang (2016). "BNIP3 Protein Suppresses PINK1 Kinase Proteolytic Cleavage to Promote Mitophagy." *J Biol Chem* 291(41): 21616-21629.

Zhang, Y., M. James, F. A. Middleton and R. L. Davis (2005). "Transcriptional analysis of multiple brain regions in Parkinson's disease supports the involvement of specific protein processing, energy metabolism, and signaling pathways, and suggests novel disease mechanisms." *Am J Med Genet B Neuropsychiatr Genet* 137B(1): 5-16.

Zhao, X., C. Tian, W. M. Puszyk, O. O. Ogunwobi, M. Cao, T. Wang, R. Cabrera, D. R. Nelson and C. Liu (2013). "OPA1 downregulation is involved in sorafenib-induced apoptosis in hepatocellular carcinoma." *Lab Invest* 93(1): 8-19.

Zuchner, S., I. V. Mersiyanova, M. Muglia, N. Bissar-Tadmouri, J. Rochelle, E. L. Dadali, M. Zappia, E. Nelis, A. Patitucci, J. Senderek, Y. Parman, O. Evgrafov, P. D. Jonghe, Y. Takahashi, S. Tsuji, M. A. Pericak-Vance, A. Quattrone, E. Battaloglu, A. V. Polyakov, V. Timmerman, J. M. Schroder and J. M. Vance (2004). "Mutations in the mitochondrial GTPase mitofusin 2 cause Charcot-Marie-Tooth neuropathy type 2A." *Nat Genet* 36(5): 449-451.

What is claimed is:

1. A compound of the formula I

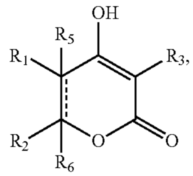

(I)

wherein $R_1$ is H—;

wherein $R_2$ is a) $C_3$-$C_5$ alkyl, b) phenyl-$(CH_2)_2$—, c) het-$SO_2NH$—$(CH_2)_2$—, d) cyclopropyl-$(CH_2)_2$—, e) F-phenyl-$(CH_2)_2$—, f) het-$SO_2NH$-phenyl-, or g) $F_3C$—$(CH_2)_2$—; or wherein $R_1$ and $R_2$ taken together are a double bond;

wherein $R_3$ is the moiety of formula II

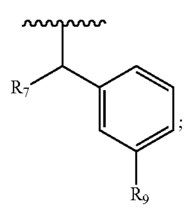

(II)

wherein $R_5$ and $R_6$ taken together are forming a 5-, 6- or 7-membered saturated or unsaturated ring;

wherein $R_7$ is a) cyclopropyl, b) $CH_3$—$CH_2$—, or c) t-butyl;

wherein $R_9$ is a) —$NR_{12}SO_2$-het, b) —$NR_{12}SO_2$-phenyl unsubstituted or substituted by one (1) $R_{11}$, c) —$CH_2$—$SO_2$-phenyl unsubstituted or substituted by one (1) $R_{11}$, or d) —$CH_2$—$SO_2$-het;

wherein het is a 5-, 6- or 7-membered saturated or unsaturated ring containing from one (1) to three (3) heteroatoms selected from the group consisting of nitrogen, oxygen and sulfur; or any bicyclic group in which any of the above heterocyclic rings is fused to a benzene ring or another heterocycle; unsubstituted or substituted by one (1) $R_{10}$;

wherein $R_{10}$ is a) —$CH_3$, b) —CN, c) —OH, d) —C(O)$OC_2H_5$, e) —$CF_3$, f) —$NH_2$, or g) —C(O)—$NH_2$;

wherein $R_{11}$ is a) —CN, b) —F, c) —OH, or d) —$NO_2$; and wherein $R_{12}$ is a) —H, or b) —$CH_3$;

or a stereochemically isomeric form thereof or a pharmaceutically acceptable salt thereof, wherein said compound is provided in an effective amount for the treatment of a mitochondrial disease characterized by OPA1 alterations, wherein the effective amount is obtained after detecting inhibition of OMA1 protease and/or OPA1 cleavage, wherein said compound is not tipranavir, and wherein said compound does not activate OMA1 protease.

2. The compound of claim 1, wherein $R_1$ is H—;

wherein $R_2$ is a) $C_3$-$C_5$ alkyl, b) phenyl-$(CH_2)_2$—, or c) het-$SO_2NH$—$(CH_2)_2$—; or wherein $R_1$ and $R_2$ taken together are a double bond;

or a stereochemically isomeric form thereof or a pharmaceutically acceptable salt thereof.

3. The compound of claim 2, wherein het in $R_2$ is the following, a) 2-pyridinyl, b) imidazol-2-yl, c) imidazol-4-yl, d) benzimidazol-2-yl, e) quinolin-8-yl, f) quinolin-2-yl, g) pyrimidin-2-yl, h) quinazolin-2-yl, i) purin-6-yl, j) thiazol-2-yl, k) thiazol-4-yl, 1) 2-pyrazolyl, m) 2-pyrazinyl, n) tetrahydropyran-4-yl, or o) tetrahydropyran-3-yl, unsubstituted or substituted by one (1) $R_{10}$.

4. The compound of claim 1, wherein the compound is selected from the group consisting of:

N-[3-[cyclopropyl(5,6,7,8,9,10-hexahydro-4-hydroxy-2-oxo-10-propyl-2H-cycloocta[b]pyran-3-yl)methyl]phenyl]benzenesulfonamide, 4-Cyano-N-[3-(R or S)-[cyclopropyl(5,6,7,8,9,10-hexahydro-4-hydroxy-2-oxo-(R or S)-10-propyl-2H-cycloocta[b]pyran-3-yl)methyl]phenyl]benzenesulfonamide, 4-Cyano-N-[3-(R or S)-[cyclopropyl(5,6,7,8,9,10-hexahydro-(R or S)-10-cyclopropylmethyl-4-hydroxy-2-oxo-2H-cycloocta[b]pyran-3-yl)methyl]phenyl]benzenesulfonamide, 4-Cyano-N-[3-(R or S)-[cyclopropyl(5,6,7,8,9,10-hexahydro-(R or S)-10-benzyl-4-hydroxy-2-oxo-2H-cycloocta[b]pyran-3-yl)methyl]phenyl]benzenesulfonamide, N-[3-(R or S)-[cyclopropyl(5,6,7,8,9,10-hexahydro-4-hydroxy-2-oxo-(R or S)-10-propyl-2H-cycloocta[b]pyran-3-yl)methyl]phenyl]-1-methyl-1H-imidazole-4-sulfonamide, N-[3-(R or S)-[cyclopropyl(5,6,7,8,9,10-hexahydro-(R or S)-10-cyclopropylmethyl-4-hydroxy-2-oxo-2H-cycloocta[b]pyran-3-yl)methyl]phenyl]-1-methyl-1H-imidazole-4-sulfonamide, N-[3-(R or S)-[cyclopropyl(5,6,7,8,9,10-hexahydro-(R or S)-10-benzyl-4-hydroxy-2-oxo-2H-cycloocta[b]pyran-3-yl)methyl]phenyl]-1-methyl-1H-imidazole-4-sulfonamide, (R or S)—N-[3-1-(5,6,7,8,9,10-Hexahydro-4-hydroxy-2-oxo-2H-cycloocta[b]pyran-3-yl)-3-methylbutyl]phenyl]-1-methyl-1H-imidazole-4-sulfonamide, 3-[Cyclopropyl[3-[(phenylsulfonyl)methyl]phenyl]methyl]-5,6,7,8,9,10-hexahydro-4-hydroxy-2H-Cycloocta[b]pyran-2-one, 3-[cyclopropyl[3-[(4-cyanophenylsulfonyl)methyl]phenyl]methyl]-5,6,7,8,9,10-hexahydro-4-hydroxy-2H-cycloocta[b]pyran-2-one, 3-[cyclopropyl[3-[(4-fluorophenylsulfonyl)methyl]phenyl]methyl]-5,6,7,8,9,10-hexahydro-4-hydroxy-2H-cycloocta[b]pyran-2-one, 3-[cyclopropyl[3-[(4-methylphenylsulfonyl)methyl]phenyl]methyl]-5,6,7,8,9,10-hexahydro-4-hydroxy-2H-cycloocta[b]pyran-2-one, 3-[cyclopropyl[3-[(4-carboxyphenylsulfonyl)methyl]phenyl]methyl]-5,6,7,8,9,10-hexahydro-4-hydroxy-2H-cycloocta[b]pyran-2-one, 3-[cyclopropyl[3-[(2-(1-methylimidazoyl)sulfonyl)methyl]phenyl]methyl]-5,6,7,8,9,10-hexahydro-4-hydroxy-2H-cycloocta[b]pyran-2-one, 3-[cyclopropyl[3-[(2-pyrimidinylsulfonyl)methyl]phenyl]methyl]-5,6,7,8,9,10-hexahydro-4-hydroxy-2H-cycloocta[b]pyran-2-one, 3-[cyclopropyl[3-[(2-pyridinylsulfonyl)methyl]phenyl]methyl]-5,6,7,8,9,10-hexahydro-4-hydroxy-2H-cycloocta[b]pyran-2-one, 3-[cyclopropyl[3-[(1-methyl-4-imidazolylsulfonyl)methyl]phenyl]methyl]-5,6,7,8,9,10-hexahydro-4-hydroxy-2H-cycloocta[b]pyran-2-one, 3-[cyclopropyl[3-[(5-cyano-2-pyridinylsulfonyl)methyl]phenyl]methyl]-5,6,7,8,9,10-hexahydro-4-hydroxy-2H-cycloocta[b]pyran-2-one, 3-[cyclopropyl[3-[(2-benzimidazolylsulfonyl)methyl]phenyl]methyl]-5,6,7,8,9,10-hexahydro-4-hydroxy-2H-cycloocta[b]pyran-2-one, 3-[cyclopropyl[3-[(2-quinolinylsulfonyl)methyl]phenyl]methyl]-5,6,7,8,9,10-hexahydro-4-hydroxy-2H-cycloocta[b]pyran-2-one, Disodium-4-cyano-N-[3-[cyclopropyl(5,6,7,8,9,10-hexahydro-4-hydroxy-2-oxo-2H-cycloocta[b]pyran-3-yl)methyl]phenyl]-benzenesulfonamide, 4-Cyano-N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide, 4-Fluoro-N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide, N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide, N-methyl-N-[3-[cyclopropyl(5,6,7,8,9,10-hexahydro-4-hydroxy-2-oxo-2H-cycloocta[b]pyran-3-yl)methyl]phenyl]-1H-Imidazole-1-methyl-sulfonamide, 5-cyano-N-[3-[cyclopropyl(5,6,7,8,9,10-hexahydro-4-hydroxy-2-oxo-2H-cycloocta[b]pyran-3-yl)methyl]phenyl]-2-pyridinesulfonamide, N-[3-[cyclopropyl(5,6,7,8,9,10-hexahydro-4-hydroxy-2-oxo-2H-cycloocta[b]pyran-3-yl)methyl]phenyl]-2-quinolinesulfonamide, N-[3-[cyclopropyl(5,6,7,8,9,10-hexahydro-4-hydroxy-2-oxo-2H-cycloocta[b]pyran-3-yl)methyl]phenyl]-2-imidazolesulfonamide, N-[3-[cyclopropyl(5,6,7,8,9,10-hexahydro-4-hydroxy-2-oxo-2H-cycloocta[b]pyran-3-yl)methyl]phenyl]-2-pyrimidinesulfonamide, N-[3-[cyclopropyl(5,6,7,8,9,10-hexahydro-4-hydroxy-2-oxo-2H-cycloocta[b]pyran-3-yl)methyl]phenyl]-2-benzimidazolesulfonamide, N-[3-[cyclopropyl(5,6,7,8,9,10-hexahydro-4-hydroxy-2-oxo-2H-cycloocta[b]pyran-3-yl)methyl]phenyl]-2-quinazolinesulfonamide, N-[3-[cyclopropyl(5,6,7,8,9,10-hexahydro-4-hydroxy-2-oxo-2H-cycloocta[b]pyran-3-yl)methyl]phenyl]-6-purinesulfonamide, 5-cyano-N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-quinolinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-imidazolesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-pyrimidinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-6-purinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-4-thiazolesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide, N-[4-[cyclopropyl(5,6,7,8,9,10-hexahydro-4-hydroxy-2-oxo-2H-cycloocta[b]pyran-3-yl)methyl]phenyl]-4-pyridylsulfonamide, N-[4-[cyclopropyl(5,6,7,8,9,10-hexahydro-4-hydroxy-2-oxo-2H-cycloocta[b]pyran-3-yl)methyl]phenyl]-5-cyanopyridin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-2-pyrazinylsulfonamide, N-[4-[cyclopropyl(5,6,7,8,9,10-hexahydro-4-hydroxy-2-oxo-2H-cycloocta[b]pyran-3-yl)methyl]phenyl]-2-pyrimidinylsulfonamide, N-[4-[cyclopropyl(5,6,7,8,9,10-hexahydro-4-hydroxy-2-oxo-2H-cycloocta[b]pyran-3-yl)methyl]phenyl]-4-6-dimethylpyrimidin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-4-methylpyrimidin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-2-pyridylsulfonamide 3-[cyclopropyl[3-[(4-cyanophenylsulfonyl)methyl]phenyl]methyl]-4-hydroxycoumarin, 3-[cyclopropyl[3-[(2-pyridinylsulfonyl)methyl]phenyl]methyl]-4-hydroxycoumarin, 3-[cyclopropyl[3-t(1-methyl-4-imidazolylsulfonyl)methyl]phenyl]methyl]-4-hydroxycoumarin, 3-[cyclopropyl[3-[(5-cyano-2-pyridinylsulfonyl)methyl]phenyl]methyl]-4-hydroxycoumarin, 3-[cyclopropyl[3-[(2-benzimidazolylsulfonyl)methyl]phenyl]methyl]-4-hydroxycoumarin, 3-[cyclopropyl[3-[(2-quinolinylsulfonyl)methyl]phenyl]methyl]-4-hydroxycoumarin, N-(3-{Cyclopropyl-[7-(2-(2-(2-methoxyethoxy)-ethoxy)ethoxy)-4-hydroxycoumarin-3-yl]-methyl}-phenyl)-1-methyl-1H-imidazole-4-sulfonamide, N-(3-{Cyclopropyl-[7-methoxy-4-hydroxycoumarin-3-yl]-methyl}-phenyl)-1-methyl-1H-imidazole-4-sulfonamide, N-(3-{Cyclopropyl-[7-(2-(2-(2-methoxyethoxy)-ethoxy)ethoxy)-4-hydroxycoumarin-3-yl]-methyl}-phenyl)-8-quinolinesulfonamide, N-(3-{Cyclopropyl-[7-(2-(2-(2-methoxyethoxy)-ethoxy)ethoxy)-4-hydroxycoumarin-3-yl]-methyl}-phenyl)-2-pyridinesulfonamide, N-(3-{Cyclopropyl-[4-hydroxycoumarin-3-yl]-methyl}-phenyl)-2-pyridinesulfonamide, N-(3-{Cyclopropyl-[4-hydroxycoumarin-3-yl]-methyl}-phenyl)-4-cyano-2-pyridinesulfonamide, N-(3-{Cyclopropyl-[4-hydroxycoumarin-3-yl]-methyl}-phenyl)-2-quinolinesulfonamide, N-(3-{Cyclopropyl-[4-hydroxycoumarin-3-yl]-methyl}-phenyl)-2-hydroxybenzenesulfonamide, N-(3-{Cyclopropyl-[4-hydroxycoumarin-3-yl]-methyl}-phenyl)-2-pyrazolesulfonamide, N-(3-{Cyclopropyl-[4-hydroxycoumarin-3-yl]-methyl}-phenyl)-2-quinazolinesulfonamide, N-(3-{Cyclopropyl-[4-hydroxycoumarin-3-yl]-methyl}-phenyl)-7H-purine-6-sulfonamide, N-(3-{Cyclopropyl-[4-hydroxycoumarin-3-yl]-methyl}-phenyl)-1H-imidazole-2-sulfonamide, N-(3-{Cyclopropyl-[4-hydroxycoumarin-3-yl]-methyl}-phenyl)-benzimidazole-2-sulfonamide, N-(3-{Cyclopropyl-[4-hydroxycoumarin-3-yl]-methyl}-phenyl)-thiazole-4-sulfonamide, N-(3-{Cyclopropyl-[4-hydroxycoumarin-3-yl]-methyl}-phenyl)-4-ethoxycarbonyl-1H-imidazole-2-sulfonamide, N-(3-{Cyclopropyl-[4-hydroxycoumarin-3-yl]-methyl}-phenyl)-3-hydroxy-2-pyridinesulfonamide, 5-cyano-N-[3-(1'-cyclopropylmethylphenyl)-4-hydroxycoumarin]-N-methyl-2-pyridinesulfonamide, N-[3-(1'-cyclopropylmethylphenyl)-4-hydroxycoumarin]-N-methyl-2-quinolinesulfonamide, N-[3-(1'-cyclopropylmethylphenyl)-4-hydroxycoumarin]-N-methyl-2-imidazolesulfonamide, N-[3-(1'-cyclopropylmethylphenyl)-4-hydroxycoumarin]-N-methyl-2-pyrimidinesulfonamide, N-[3-(1'-cyclopropylmethylphenyl)-4-hydroxycoumarin]-N-methyl-2-benzimidazolesulfonamide, N-[3-(1'-cyclopropylmethylphenyl)-4-hydroxycoumarin]-N-methyl-2-quinazolinesulfonamide, N-[3-(1'-cyclopropylmethylphenyl)-4-hydroxycoumarin]-N-methyl-6-purinesulfonamide, N-[3-(1'-cyclopropylmethylphenyl)-4-hydroxycoumarin]-N-methyl-4-thiazolesulfonamide, N-[3-(1'-cyclopropylmethylphenyl)-4-hydroxycoumarin]-N-methyl-2-pyridinesulfonamide, 5-Cyano-N-[3-{1-(4a,5,6,7,8,8a-hexahydro-4-hydroxy-2-oxo-2H-1-benzopyran-3-yl)propyl]}phenyl]-2-pyridinesulfonamide, 4-Cyano-N-[3-{1-(4a,5,6,7,8,8a-hexahydro-4-hydroxy-2-oxo-2H-1-benzopyran-3-yl)propyl]}phenyl]-benzenesulfonamide, 5-Cyano-N-[3-[1-(2,4a,5,6,7,8,9,9a-octahydro-4-hydroxy-2¬oxocyclohepta[b]pyran-3-yl)propyl]phenyl]-2-pyridinesulfonamide, and 5-Cyano-N-[3-[2,2-dimethyl-1-(4a,5,6,7,8,9,10,10a-octahydro-4-hydroxy-2-oxo-2H-cycloocta[b]pyran-3-yl)propyl]phenyl]-2-pyridinesulfonamide, or a stereochemically isomeric form thereof or a pharmaceutically acceptable salt thereof.

5. The compound of claim 1, wherein $R_5$ and $R_6$ form together a structure of formula VI:

(VI)

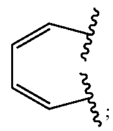

or a stereochemically isomeric form thereof or a pharmaceutically acceptable salt thereof.

6. The compound of claim 1, wherein $R_5$ and $R_6$ taken together are forming an unsaturated ring, or a stereochemically isomeric form thereof or a pharmaceutically acceptable salt thereof.

7. The compound of claim 1, wherein $R_1$ and $R_2$ taken together are a double bond;

wherein $R_5$ and $R_6$ taken together are forming an unsaturated ring;

wherein $R_7$ is cyclopropyl, wherein $R_9$ is —$CH_2$—$SO_2$-het; and wherein het is a 6-membered unsaturated ring containing one (1) nitrogen;

or a stereochemically isomeric form thereof or a pharmaceutically acceptable salt thereof.

8. The compound of claim 2, wherein $R_5$ and $R_6$ form together a structure of formula VI:

(VI)

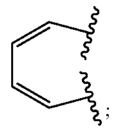

or a stereochemically isomeric form thereof or a pharmaceutically acceptable salt thereof.

9. A compound of the formula I (I)

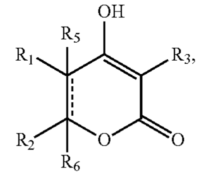

wherein $R_1$ and $R_2$ taken together are a double bond;

wherein $R_3$ is the moiety of formula II

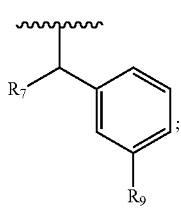

(II)

wherein $R_5$ and $R_6$ taken together are forming a 5-, 6- or 7-membered saturated or unsaturated ring;

wherein $R_7$ is a) cyclopropyl, b) $CH_3$—$CH_2$—, or c) t-butyl;

wherein $R_9$ is a) —$NR_{12}SO_2$-het, b) —$NR_{12}SO_2$-phenyl unsubstituted or substituted by one (1) $R_{11}$, c) —$CH_2$—$SO_2$-phenyl unsubstituted or substituted by one (1) $R_{11}$, or d) —$CH_2$—$SO_2$-het;

wherein het is a 5-, 6- or 7-membered saturated or unsaturated ring containing from one (1) to three (3) heteroatoms selected from the group consisting of nitrogen, oxygen and sulfur; or any bicyclic group in which any of the above heterocyclic rings is fused to a benzene ring or another heterocycle; unsubstituted or substituted by one (1) $R_{10}$;

wherein $R_{10}$ is a) —$CH_3$, b) —CN, c) —OH, d) —C(O)$OC_2H_5$, e) —$CF_3$, f) —$NH_2$, or g) —C(O)—$NH_2$;

wherein $R_{11}$ is a) —CN, b) —F, c) —OH, or d) —$NO_2$; and wherein $R_{12}$ is a) —H, or b) —$CH_3$;

or a stereochemically isomeric form thereof or a pharmaceutically acceptable salt thereof, wherein said compound is provided in an effective amount for the treatment of a mitochondrial disease characterized by OPA1 alterations, wherein the effective amount is obtained after detecting inhibition of OMA1 protease and/or OPA1 cleavage.

10. The compound of claim 9, wherein $R_5$ and $R_6$ form together a structure of formula VI:

(VI)

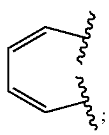

or a stereochemically isomeric form thereof or a pharmaceutically acceptable salt thereof.

11. The compound of claim 1, wherein the compound is selected from the group consisting of:

5-cyano-N-[3-[cyclopropyl(5,6,7,8,9,10-hexahydro-4-hydroxy-2-oxo-2H-cycloocta[b]pyran-3-yl)methyl]phenyl]-2-pyridinesulfonamide, 5-cyano-N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide, N-(3-{Cyclopropyl-[7-(2-(2-(2-methoxyethoxy)-ethoxy)ethoxy)-4-hydroxycoumarin-3-yl]-methyl}-phenyl)-2-pyridinesulfonamide, N-(3-{Cyclopropyl-[4-hydroxycoumarin-3-yl]-methyl}-phenyl)-2-pyridinesulfonamide, N-(3-{Cyclopropyl-[4-hydroxycoumarin-3-yl]-methyl}-phenyl)-4-cyano-2-pyridinesulfonamide, N-(3-{Cyclopropyl-[4-hydroxycoumarin-3-yl]-methyl}-phenyl)-3-hydroxy-2-pyridinesulfonamide, 5-cyano-N-[3-(1'-cyclopropylmethylphenyl)-4-hydroxy-coumarin]-N-methyl-2-pyridinesulfonamide, N-[3-(1'-cyclopropylmethylphenyl)-4-hydroxycoumarin]-N-methyl-2-pyridinesulfonamide, 5-Cyano-N-[3-{1-(4a,5,6,7,8,8a-hexahydro-4-hydroxy-2-oxo-2H-1-benzopyran-3-yl)propyl}phenyl]-2-pyridinesulfonamide, 5-Cyano-N-[3-[1-(2,4a,5,6,7,8,9,9a-octahydro-4-hydroxy-2¬oxocyclohepta[b]pyran-3-yl)propyl]phenyl]-2-pyridinesulfonamide, and 5-Cyano-N-[3-[2,2-dimethyl-1-(4a,5,6,7,8,9,10,10a-octahydro-4-hydroxy-2-oxo-2H-cycloocta[b]pyran-3-yl)propyl]phenyl]-2-pyridinesulfonamide, or a stereochemically isomeric form thereof or a pharmaceutically acceptable salt thereof.

12. The compound of claim 1, wherein the compound is selected from the group consisting of:

N-(3-{Cyclopropyl-[4-hydroxycoumarin-3-yl]-methyl}-phenyl)-2-pyridinesulfonamide, N-(3-{Cyclopropyl-[4-hydroxycoumarin-3-yl]-methyl}-phenyl)-4-cyano-2-pyridinesulfonamide, N-(3-{Cyclopropyl-[4-hydroxycoumarin-3-yl]-methyl}-phenyl)-2-quinolinesulfonamide, N-(3-{Cyclopropyl-[4-hydroxycoumarin-3-yl]-methyl}-phenyl)-2-hydroxybenzenesulfonamide, N-(3-{Cyclopropyl-[4-hydroxycoumarin-3-yl]-methyl}-phenyl)-2-pyrazolesulfonamide, N-(3-{Cyclopropyl-[4-hydroxycoumarin-3-yl]-methyl}-phenyl)-2-quinazolinesulfonamide, N-(3-{Cyclopropyl-[4-hydroxycoumarin-3-yl]-methyl}-phenyl)-7H-purine-6-sulfonamide, N-(3-{Cyclopropyl-[4-hydroxycoumarin-3-yl]-methyl}-phenyl)-1H-imidazole-2-sulfonamide, N-(3-{Cyclopropyl-[4-hydroxycoumarin-3-yl]-methyl}-phenyl)-benzimidazole-2-sulfonamide, N-(3-{Cyclopropyl-[4-hydroxycoumarin-3-yl]-methyl}-phenyl)-thiazole-4-sulfonamide, N-(3-{Cyclopropyl-[4-hydroxycoumarin-3-yl]-methyl}-phenyl)-4-ethoxycarbonyl-1H-imidazole-2-sulfonamide, and N-(3-{Cyclopropyl-[4-hydroxycoumarin-3-yl]-methyl}-phenyl)-3-hydroxy-2-pyridinesulfonamide, or a stereochemically isomeric form thereof or a pharmaceutically acceptable salt thereof.

13. The compound of claim 1, wherein $R_1$ and $R_2$ taken together are a double bond;

wherein $R_5$ and $R_6$ taken together are forming an unsaturated ring;

wherein $R_7$ is cyclopropyl;

wherein $R_9$ is —$CH_2$—$SO_2$-het; and wherein het is a 6-membered unsaturated ring containing one (1) nitrogen;

or a stereochemically isomeric form thereof or a pharmaceutically acceptable salt thereof.

14. The compound of claim 8, wherein $R_1$ and $R_2$ taken together are a double bond;

wherein $R_7$ is cyclopropyl;

wherein $R_9$ is —$CH_2$—$SO_2$-het; and wherein het is a 6-membered unsaturated ring containing one (1) nitrogen;

or a stereochemically isomeric form thereof or a pharmaceutically acceptable salt thereof.

15. The compound of claim 1, wherein said compound has the formula VII

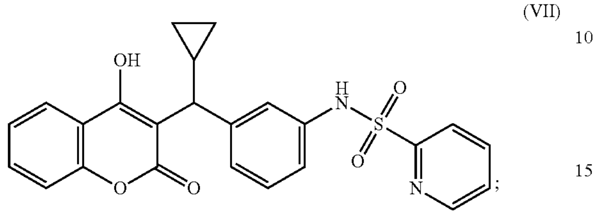

or a stereochemically isomeric form thereof or a pharmaceutically acceptable salt thereof.

16. The compound of claim 9, wherein $R_1$ and $R_2$ taken together are a double bond;

wherein $R_5$ and $R_6$ taken together are forming an unsaturated ring;

wherein $R_7$ is cyclopropyl;

wherein $R_9$ is —$CH_2$—$SO_2$-het; and wherein het is a 6-membered unsaturated ring containing one (1) nitrogen;

or a stereochemically isomeric form thereof or a pharmaceutically acceptable salt thereof.

17. The compound of claim 10, wherein $R_1$ and $R_2$ taken together are a double bond;

wherein $R_7$ is cyclopropyl;

wherein $R_9$ is —$CH_2$—$SO_2$-het; and wherein het is a 6-membered unsaturated ring containing one (1) nitrogen;

or a stereochemically isomeric form thereof or a pharmaceutically acceptable salt thereof.

18. The compound of claim 9, wherein said compound has the formula VII

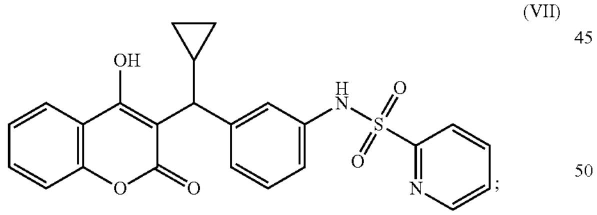

or a stereochemically isomeric form thereof or a pharmaceutically acceptable salt thereof.

19. A compound of the formula I

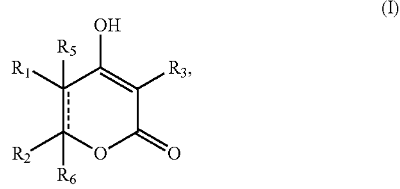

wherein $R_1$ is H—;

wherein $R_2$ is a) $C_3$-$C_5$ alkyl, b) phenyl-$(CH_2)_2$—, c) het-$SO_2NH$—$(CH_2)_2$—, d) cyclopropyl-$(CH_2)_2$—, e) F-phenyl-$(CH_2)_2$—, f) het-$SO_2NH$-phenyl-, or g) $F_3C$—$(CH_2)_2$—; or wherein $R_1$ and $R_2$ taken together are a double bond;

wherein $R_3$ is the moiety of formula II

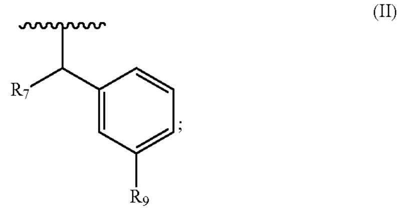

wherein $R_5$ and $R_6$ taken together are forming a 5-, 6- or 7-membered saturated or unsaturated ring;

wherein $R_7$ is a) cyclopropyl, b) $CH_3$—$CH_2$—, or c) t-butyl;

wherein $R_9$ is a) —$NR_{12}SO_2$-het, b) —$NR_{12}SO_2$-phenyl unsubstituted or substituted by one (1) $R_{11}$, c) —$CH_2$—$SO_2$-phenyl unsubstituted or substituted by one (1) $R_{11}$, or d) —$CH_2$—$SO_2$-het;

wherein het is a 5-, 6- or 7-membered saturated or unsaturated ring containing from one (1) to three (3) heteroatoms selected from the group consisting of nitrogen, oxygen and sulfur; or any bicyclic group in which any of the above heterocyclic rings is fused to a benzene ring or another heterocycle; unsubstituted or substituted by one (1) $R_{10}$;

wherein $R_{10}$ is a) —$CH_3$, b) —CN, c) —OH, d) —C(O)$OC_2H_5$, e) —$CF_3$, f) —$NH_2$, or g) —C(O)—$NH_2$;

wherein $R_{11}$ is a) —CN, b) —F, c) —OH, or d) —$NO_2$; and wherein $R_{12}$ is a) —H, or b) —$CH_3$;

or a stereochemically isomeric form thereof or a pharmaceutically acceptable salt thereof, wherein said compound does not activate OMA1 protease, and wherein said compound is provided in an effective amount for the treatment of a mitochondrial disease characterized by OPA1 alterations, wherein the effective amount is obtained after detecting inhibition of OMA1 protease and/or OPA1 cleavage.

20. The compound of claim 19, wherein the compound is selected from the group consisting of:

N-[3-[cyclopropyl(5,6,7,8,9,10-hexahydro-4-hydroxy-2-oxo-10-propyl-2H-cycloocta[b]pyran-3-yl)methyl]phenyl]benzenesulfonamide, 4-Cyano-N-[3-(R or S)-[cyclopropyl(5,6,7,8,9,10-hexahydro-4-hydroxy-2-oxo-(R or S)-10-propyl-2H-cycloocta[b]pyran-3-yl)methyl]phenyl]benzenesulfonamide, 4-Cyano-N-[3-(R or S)-[cyclopropyl(5,6,7,8,9,10-hexahydro-(R or S)-10-cyclopropylmethyl-4-hydroxy-2-oxo-2H-cycloocta[b]pyran-3-yl)methyl]phenyl]benzenesulfonamide, 4-Cyano-N-[3-(R or S)-[cyclopropyl(5,6,7,8,9,10-hexahydro-(R or S)-10-benzyl-4-hydroxy-2-oxo-2H-cycloocta[b]pyran-3-yl)methyl]phenyl]benzenesulfonamide, N-[3-(R or S)-[cyclopropyl(5,6,7,8,9,10-hexahydro-4-hydroxy-2-oxo-(R or S)-10-propyl-2H-cycloocta[b]pyran-3-yl)methyl]phenyl]-1-methyl-1H-imidazole-4-sulfonamide, N-[3-(R or S)-[cyclopropyl(5,6,7,8,9,10-hexahydro-(R or S)-10-cyclopropylmethyl-4-hydroxy-2-oxo-2H-cycloocta[b]pyran-3-yl)methyl]phenyl]-1-methyl-1H-imidazole-4-sulfonamide, N-[3-(R or S)-[cyclopropyl(5,6,7,8,9,10-hexahydro-(R or S)-10-benzyl-4-hydroxy-2-oxo-2H-cycloocta[b]pyran-3-yl)methyl]phenyl]-1-methyl-1H-imidazole-4-sulfonamide, (R or S)—N-[3-1-(5,6,7,8,9,10-Hexahydro-4-hydroxy-2-oxo-2H-cycloocta[b]pyran-3-yl)-3-methylbutyl]phenyl]-1-methyl-1H-imidazole-4-sulfonamide, (R or S)—N-[3-1-(5,6,7,8,9,10-Hexahydro-4-hydroxy-2-oxo-2H-cycloocta[b]pyran-3-yl)-3-methylbutyl]phenyl]-1-methyl-1H-imidazole-4-sulfonamide, 3-[Cyclopropyl[3-[(phenylsulfonyl)methyl]phenyl]methyl]-5,6,7,8,9,10-hexahydro-4-hydroxy-2H-Cycloocta[b]pyran-2-one, 3-[cyclopropyl[3-[(4-cyanophenylsulfonyl)methyl]phenyl]methyl]-5,6,7,8,9,10-hexahydro-4-hydroxy-2H-cycloocta[b]pyran-2-one, 3-[cyclopropyl[3-[(4-fluorophenylsulfonyl)methyl]phenyl]methyl]-5,6,7,8,9,10-hexahydro-4-hydroxy-2H-cycloocta[b]pyran-2-one, 3-[cyclopropyl[3-[(4-methylphenylsulfonyl)methyl]phenyl]methyl]-5,6,7,8,9,10-hexahydro-4-hydroxy-2H-cycloocta[b]pyran-2-one, 3-[cyclopropyl[3-[(4-carboxyphenylsulfonyl)methyl]phenyl]methyl]-5,6,7,8,9,10-hexahydro-4-hydroxy-2H-cycloocta[b]pyran-2-one, 3-[cyclopropyl[3-[(2-(1-methylimidazoyl)sulfonyl)methyl]phenyl]methyl]-5,6,7,8,9,10-hexahydro-4-hydroxy-2H-cycloocta[b]pyran-2-one, 3-[cyclopropyl[3-[(2-pyrimidinylsulfonyl)methyl]phenyl]methyl]-5,6,7,8,9,10-hexahydro-4-hydroxy-2H-cycloocta[b]pyran-2-one, 3-[cyclopropyl[3-[(2-pyridinylsulfonyl)methyl]phenyl]methyl]-5,6,7,8,9,10-hexahydro-4-hydroxy-2H-cycloocta[b]pyran-2-one, 3-[cyclopropyl[3-[(1-methyl-4-imidazolylsulfonyl)methyl]phenyl]methyl]-5,6,7,8,9,10-hexahydro-4-hydroxy-2H-cycloocta[b]pyran-2-one, 3-[cyclopropyl[3-[(5-cyano-2-pyridinylsulfonyl)methyl]phenyl]methyl]-5,6,7,8,9,10-hexahydro-4-hydroxy-2H-cycloocta[b]pyran-2-one, 3-[cyclopropyl[3-[(2-benzimidazolylsulfonyl)methyl]phenyl]methyl]-5,6,7,8,9,10-hexahydro-4-hydroxy-2H-cycloocta[b]pyran-2-one, 3-[cyclopropyl[3-[(2-quinolinylsulfonyl)methyl]phenyl]methyl]-5,6,7,8,9,10-hexahydro-4-hydroxy-2H-cycloocta[b]pyran-2-one, Disodium-4-cyano-N-[3-[cyclopropyl(5,6,7,8,9,10-hexahydro-4-hydroxy-2-oxo-2H-cycloocta[b]pyran-3-yl)methyl]phenyl]-benzenesulfonamide, 4-Cyano-N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide, 4-Fluoro-N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide, N-methyl-N-[3-[cyclopropyl(5,6,7,8,9,10-hexahydro-4-hydroxy-2-oxo-2H-cycloocta[b]pyran-3-yl)methyl]phenyl]-benzenesulfonamide, N-methyl-N-[3-[cyclopropyl(5,6,7,8,9,10-hexahydro-4-hydroxy-2-oxo-2H-cycloocta[b]pyran-3-yl)methyl]phenyl]-1H-Imidazole-1-methyl-sulfonamide, 5-cyano-N-[3-[cyclopropyl(5,6,7,8,9,10-hexahydro-4-hydroxy-2-oxo-2H-cycloocta[b]pyran-3-yl)methyl]phenyl]-2-pyridinesulfonamide, N-[3-[cyclopropyl(5,6,7,8,9,10-hexahydro-4-hydroxy-2-oxo-2H-cycloocta[b]pyran-3-yl)methyl]phenyl]-2-quinolinesulfonamide, N-[3-[cyclopropyl(5,6,7,8,9,10-hexahydro-4-hydroxy-2-oxo-2H-cycloocta[b]pyran-3-yl)methyl]phenyl]-2-imidazolesulfonamide, N-[3-[cyclopropyl(5,6,7,8,9,10-hexahydro-4-hydroxy-2-oxo-2H-cycloocta[b]pyran-3-yl)methyl]phenyl]-2-pyrimidinesulfonamide, N-[3-[cyclopropyl(5,6,7,8,9,10-hexahydro-4-hydroxy-2-oxo-2H-cycloocta[b]pyran-3-yl)methyl]phenyl]-2-benzimidazolesulfonamide, N-[3-[cyclopropyl(5,6,7,8,9,10-hexahydro-4-hydroxy-2-oxo-2H-cycloocta[b]pyran-3-yl)methyl]phenyl]-2-quinazolinesulfonamide, N-[3-[cyclopropyl(5,6,7,8,9,10-hexahydro-4-hydroxy-2-oxo-2H-cycloocta[b]pyran-3-yl)methyl]phenyl]-6-purinesulfonamide, 5-cyano-N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-quinolinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-imidazolesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-pyrimidinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-6-purinesulfonamide, N-[3-[cyclopropyl(5,6,7,8,9,10-hexahydro-4-hydroxy-2-oxo-2H-cycloocta[b]pyran-3-yl)methyl]phenyl]-N-methyl-4-thiazolesulfonamide, N-[3-[cyclopropyl(5,6,7,8,9,10-hexahydro-4-hydroxy-2-oxo-2H-cycloocta[b]pyran-3-yl)methyl]phenyl]-N-methyl-2-pyridinesulfonamide, N-[4-[cyclopropyl(5,6,7,8,9,10-hexahydro-4-hydroxy-2-oxo-2H-cycloocta[b]pyran-3-yl)methyl]phenyl]-4-pyridylsulfonamide, N-[4-[cyclopropyl(5,6,7,8,9,10-hexahydro-4-hydroxy-2-oxo-2H-cycloocta[b]pyran-3-yl)methyl]phenyl]-5-cyanopyridin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-2-pyrazinylsulfonamide, N-[4-[cyclopropyl(5,6,7,8,9,10-hexahydro-4-hydroxy-2-oxo-2H-cycloocta[b]pyran-3-yl)methyl]phenyl]-2-pyrimidinylsulfonamide, N-[4-[cyclopropyl(5,6,7,8,9,10-hexahydro-4-hydroxy-2-oxo-2H-cycloocta[b]pyran-3-yl)methyl]phenyl]-4-6-dimethylpyrimidin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-4-methylpyrimidin-2-yl-sulfonamide, N-[4-[cyclopropyl(5,6,7,8,9,10-hexahydro-4-hydroxy-2-oxo-2H-cycloocta[b]pyran-3-yl)methyl]phenyl]-2-pyridylsulfonamide 3-[cyclopropyl[3-[(4-cyanophenylsulfonyl)methyl]phenyl]methyl]-4-hydroxycoumarin,
3-[cyclopropyl[3-[(2-pyridinylsulfonyl)methyl]phenyl]methyl]-4-hydroxycoumarin,
3-[cyclopropyl[3-t(1-methyl-4-imidazolylsulfonyl)methyl]phenyl]methyl]-4-hydroxycoumarin,
3-[cyclopropyl[3-[(5-cyano-2-pyridinylsulfonyl)methyl]phenyl]methyl]-4-hydroxycoumarin,
3-[cyclopropyl[3-[(2-benzimidazolylsulfonyl)methyl]phenyl]methyl]-4-hydroxycoumarin,
3-[cyclopropyl[3-[(2-quinolinylsulfonyl)methyl]phenyl]methyl]-4-hydroxycoumarin,
N-(3-{Cyclopropyl-[7-(2-(2-(2-methoxyethoxy)-ethoxy)ethoxy)-4-hydroxycoumarin-3-yl]-methyl}-phenyl)-1-methyl-1H-imidazole-4-sulfonamide,
N-(3-{Cyclopropyl-[7-methoxy-4-hydroxycoumarin-3-yl]-methyl}-phenyl)-1-methyl-1H-imidazole-4-sulfonamide,
N-(3-{Cyclopropyl-[7-(2-(2-(2-methoxyethoxy)-ethoxy)ethoxy)-4-hydroxycoumarin-3-yl]-methyl}-phenyl)-8-quinolinesulfonamide,
N-(3-{Cyclopropyl-[7-(2-(2-(2-methoxyethoxy)-ethoxy)ethoxy)-4-hydroxycoumarin-3-yl]-methyl}-phenyl)-2-pyridinesulfonamide,
N-(3-{Cyclopropyl-[4-hydroxycoumarin-3-yl]-methyl}-phenyl)-2-pyridinesulfonamide,
N-(3-{Cyclopropyl-[4-hydroxycoumarin-3-yl]-methyl}-phenyl)-4-cyano-2-pyridinesulfonamide,
N-(3-{Cyclopropyl-[4-hydroxycoumarin-3-yl]-methyl}-phenyl)-2-quinolinesulfonamide,
N-(3-{Cyclopropyl-[4-hydroxycoumarin-3-yl]-methyl}-phenyl)-2-hydroxybenzenesulfonamide,
N-(3-{Cyclopropyl-[4-hydroxycoumarin-3-yl]-methyl}-phenyl)-2-pyrazolesulfonamide,
N-(3-{Cyclopropyl-[4-hydroxycoumarin-3-yl]-methyl}-phenyl)-2-quinazolinesulfonamide,
N-(3-{Cyclopropyl-[4-hydroxycoumarin-3-yl]-methyl}-phenyl)-7H-purine-6-sulfonamide,
N-(3-{Cyclopropyl-[4-hydroxycoumarin-3-yl]-methyl}-phenyl)-1H-imidazole-2-sulfonamide,
N-(3-{Cyclopropyl-[4-hydroxycoumarin-3-yl]-methyl}-phenyl)-benzimidazole-2-sulfonamide, N-(3-{Cyclopropyl-[4-hydroxycoumarin-3-yl]-methyl}-phenyl)-thiazole-4-sulfonamide,
N-(3-{Cyclopropyl-[4-hydroxycoumarin-3-yl]-methyl}-phenyl)-4-ethoxycarbonyl-1H-imidazole-2-sulfonamide,
N-(3-{Cyclopropyl-[4-hydroxycoumarin-3-yl]-methyl}-phenyl)-3-hydroxy-2-pyridinesulfonamide,
5-cyano-N-[3-(1'-cyclopropylmethylphenyl)-4-hydroxycoumarin]-N-methyl-2-pyridinesulfonamide,
N-[3-(1'-cyclopropylmethylphenyl)-4-hydroxycoumarin]-N-methyl-2-quinolinesulfonamide,
N-[3-(1'-cyclopropylmethylphenyl)-4-hydroxycoumarin]-N-methyl-2-imidazolesulfonamide,
N-[3-(1'-cyclopropylmethylphenyl)-4-hydroxycoumarin]-N-methyl-2-pyrimidinesulfonamide,
N-[3-(1'-cyclopropylmethylphenyl)-4-hydroxycoumarin]-N-methyl-2-benzimidazolesulfonamide,
N-[3-(1'-cyclopropylmethylphenyl)-4-hydroxycoumarin]-N-methyl-2-quinazolinesulfonamide,
N-[3-(1'-cyclopropylmethylphenyl)-4-hydroxycoumarin]-N-methyl-6-purinesulfonamide,
N-[3-(1'-cyclopropylmethylphenyl)-4-hydroxycoumarin]-N-methyl-4-thiazolesulfonamide,
N-[3-(1'-cyclopropylmethylphenyl)-4-hydroxycoumarin]-N-methyl-2-pyridinesulfonamide,
5-Cyano-N-[3-{1-(4a,5,6,7,8,8a-hexahydro-4-hydroxy-2-oxo-2H-1-benzopyran-3-yl)propyl}phenyl]-2-pyridinesulfonamide,
4-Cyano-N-[3-{1-(4a,5,6,7,8,8a-hexahydro-4-hydroxy-2-oxo-2H-1-benzopyran-3-yl)propyl}phenyl]-benzenesulfonamide,
5-Cyano-N-[3-[1-(2,4a,5,6,7,8,9,9a-octahydro-4-hydroxy-2¬oxocyclohepta[b]pyran-3-yl)propyl]phenyl]-2-pyridinesulfonamide,
5-Cyano-N-[3-[2,2-dimethyl-1-(4a,5,6,7,8,9,10,10a-octahydro-4-hydroxy-2-oxo-2H-cycloocta[b]pyran-3-yl)propyl]phenyl]-2-pyridinesulfonamide, or a stereochemically isomeric form thereof or a pharmaceutically acceptable salt thereof.

* * * * *